United States Patent
Young et al.

(10) Patent No.: US 12,234,263 B2
(45) Date of Patent: *Feb. 25, 2025

(54) INFLUENZA VACCINES

(71) Applicants: InvVax, Inc., Pasadena, CA (US); The Regents of the University of California, Oakland, CA (US)

(72) Inventors: Arthur Young, Cypress, CA (US); Ren Sun, Los Angeles, CA (US); Nicholas C. Wu, Los Angeles, CA (US)

(73) Assignees: InvVax, Inc., Pasadena, CA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/344,909

(22) Filed: Jun. 30, 2023

(65) Prior Publication Data

US 2023/0416311 A1    Dec. 28, 2023

Related U.S. Application Data

(63) Continuation of application No. 17/375,797, filed on Jul. 14, 2021, now Pat. No. 11,739,127, which is a continuation of application No. 15/857,436, filed on Dec. 28, 2017, now Pat. No. 11,111,277.

(60) Provisional application No. 62/550,167, filed on Aug. 25, 2017, provisional application No. 62/439,865, filed on Dec. 28, 2016.

(51) Int. Cl.
| | |
|---|---|
| *C12N 15/86* | (2006.01) |
| *A61K 39/12* | (2006.01) |
| *A61K 39/145* | (2006.01) |
| *A61P 31/16* | (2006.01) |
| *C07K 14/005* | (2006.01) |
| *C07K 14/075* | (2006.01) |
| *C07K 14/11* | (2006.01) |
| *A61K 39/00* | (2006.01) |

(52) U.S. Cl.
CPC ............ *C07K 14/11* (2013.01); *A61K 39/12* (2013.01); *A61K 39/145* (2013.01); *A61P 31/16* (2018.01); *C07K 14/005* (2013.01); *C07K 14/075* (2013.01); *C12N 15/86* (2013.01); *A61K 2039/5256* (2013.01); *A61K 2039/5258* (2013.01); *A61K 2039/53* (2013.01); *A61K 2039/543* (2013.01); *A61K 2039/545* (2013.01); *A61K 2039/55555* (2013.01); *A61K 2039/57* (2013.01); *A61K 2039/6018* (2013.01); *A61K 2039/70* (2013.01); *C12N 2710/10343* (2013.01); *C12N 2760/16134* (2013.01); *C12N 2760/16234* (2013.01); *C12N 2760/16334* (2013.01)

(58) Field of Classification Search
None
See application file for complete search history.

(56) References Cited

U.S. PATENT DOCUMENTS

| | | | |
|---|---|---|---|
| 6,083,716 A | 7/2000 | Wilson et al. | |
| 6,171,820 B1 | 1/2001 | Short | |
| 6,337,186 B1 | 1/2002 | Krebber | |
| 6,596,539 B1 | 7/2003 | Stemmer et al. | |
| 6,696,275 B2 | 2/2004 | Short et al. | |
| 6,713,279 B1 | 3/2004 | Short | |
| 6,740,325 B1 | 5/2004 | Arnon et al. | |
| 6,740,506 B2 | 5/2004 | Short et al. | |
| 6,773,900 B2 | 8/2004 | Short et al. | |
| 7,488,491 B2 | 2/2009 | Tsuji et al. | |
| 7,537,768 B2 | 5/2009 | Luke et al. | |
| 7,569,225 B2 | 8/2009 | Jackson et al. | |
| 7,785,603 B2 | 8/2010 | Luke et al. | |
| 7,790,374 B2 | 9/2010 | Schwaneberg | |
| 7,914,797 B2 | 3/2011 | Arnon et al. | |
| 8,128,938 B1 | 3/2012 | Luke et al. | |
| 8,444,995 B2 | 5/2013 | Soloff et al. | |
| 8,685,409 B2 | 4/2014 | Youn et al. | |
| 8,747,861 B2 | 6/2014 | Ben-Yedidia et al. | |
| 8,821,890 B2 | 9/2014 | Luke et al. | |
| 9,045,531 B2 | 6/2015 | Miyakawa et al. | |
| 9,205,144 B2 * | 12/2015 | Brusic | G01N 33/505 |
| 9,265,822 B2 | 2/2016 | Hoft | |
| 9,303,070 B2 | 4/2016 | Ben-Yedidia et al. | |

(Continued)

FOREIGN PATENT DOCUMENTS

| | | |
|---|---|---|
| CA | 2658559 A1 | 4/2008 |
| CA | 2566355 C | 4/2014 |

(Continued)

OTHER PUBLICATIONS

Alexander, Jeff et al. "Identification of broad binding class I HLA supertype epitopes to provide universal coverage of influenza A virus." Human immunology vol. 71, 5 (2010): 468-74. doi: 10.1016/j.humimm.2010.02.014.

Amabel C.L. Tan et al., "Precursor Frequency and Competition Dictate the HLA-A2-Restricted CD8+ T Cell Responses to Influenza A Infection and Vaccination in HLA-A2.1 Transgenic Mice", J Immunol Aug. 15, 2011,187 (4) 1895-1902; DOI: https://doi.org/10.4049/jimmunol.1100664.

Arts, E.J. et al. HIV-1 antiretroviral drug therapy. Cold Spring Harbor Perspec Med vol. 2, pp. a007161 (2012).

(Continued)

*Primary Examiner* — Agnieszka Boesen
(74) *Attorney, Agent, or Firm* — Mintz, Levin, Cohn, Ferris, Glovsky and Popeo, P.C.

(57) ABSTRACT

Provided herein are compositions related to vaccines, e.g., influenza vaccines, including, peptide based vaccines, nucleic acid based vaccines, recombinant virus based vaccines, antibody based vaccines, and virus based vaccines. Also provided herein are methods related to vaccines, e.g., influenza vaccines, including methods of identifying epitopes for the vaccines, producing, formulating, and administering the vaccines.

20 Claims, 6 Drawing Sheets

Specification includes a Sequence Listing.

(56) References Cited

U.S. PATENT DOCUMENTS

| | | | |
|---|---|---|---|
| 9,353,159 | B2 | 5/2016 | Ben-Yedidia et al. |
| 9,446,116 | B2 | 9/2016 | Stoloff et al. |
| 9,603,920 | B2 | 3/2017 | Diaz-Mitoma et al. |
| 9,889,191 | B2 | 2/2018 | Stoloff et al. |
| 10,030,231 | B2 | 7/2018 | Dormitzer et al. |
| 10,179,174 | B2 | 1/2019 | Zimmerman et al. |
| 10,238,747 | B2 | 3/2019 | Zimmerman |
| 10,400,011 | B2 | 9/2019 | Mahr et al. |
| 10,426,828 | B2 | 10/2019 | Uritski et al. |
| 11,111,277 | B2 | 9/2021 | Young et al. |
| 11,739,127 | B2 | 8/2023 | Young et al. |
| 2004/0116368 | A1 | 6/2004 | Wen et al. |
| 2006/0079453 | A1 | 4/2006 | Sidney et al. |
| 2007/0003576 | A1 | 1/2007 | Gambotto et al. |
| 2007/0066534 | A1 | 3/2007 | Jackson et al. |
| 2007/0122424 | A1 | 5/2007 | Arnon et al. |
| 2007/0122430 | A1 | 5/2007 | Shneider et al. |
| 2009/0191233 | A1 | 7/2009 | Bonnet et al. |
| 2011/0087005 | A1 | 4/2011 | Miyakawa et al. |
| 2014/0274806 | A1 | 9/2014 | O'Hagan et al. |
| 2015/0086579 | A1* | 3/2015 | Mayall .............. A61P 33/06 424/233.1 |
| 2015/0140065 | A1 | 5/2015 | Zimmerman et al. |
| 2017/0319671 | A1 | 11/2017 | Faulkner et al. |
| 2019/0201519 | A1 | 7/2019 | Stoloff et al. |

FOREIGN PATENT DOCUMENTS

| | | |
|---|---|---|
| EP | 1189624 A1 | 3/2002 |
| EP | 1578432 A2 | 9/2005 |
| EP | 1982992 B1 | 10/2010 |
| EP | 1917970 B1 | 6/2011 |
| EP | 2795321 A2 | 10/2014 |
| EP | 2173376 B1 | 3/2015 |
| EP | 2383284 B1 | 8/2016 |
| EP | 3263589 A2 | 1/2018 |
| WO | 9945954 A1 | 9/1999 |
| WO | 2002092780 A2 | 11/2002 |
| WO | 2004014956 A1 | 2/2004 |
| WO | 2006113214 A2 | 10/2006 |
| WO | 2007051036 A2 | 5/2007 |
| WO | 2009014919 A2 | 1/2009 |
| WO | 2009016639 A2 | 2/2009 |
| WO | 2009029686 A1 | 3/2009 |
| WO | 2009117134 A2 | 9/2009 |
| WO | 2010117786 A1 | 10/2010 |
| WO | 2011041490 A1 | 4/2011 |
| WO | 2013093512 A2 | 6/2013 |
| WO | 2015157189 A1 | 10/2015 |
| WO | 2018126060 A1 | 7/2018 |
| WO | 2019046901 A1 | 3/2019 |

OTHER PUBLICATIONS

Babon, Jenny Aurielle B et al. "Genome-wide screening of human T-cell epitopes in influenza A virus reveals a broad spectrum of CD4(+) T-cell responses to internal proteins, hemagglutinins, and neuraminidases." Human immunology vol. 70,9 (2009): 711-21. doi:10.1016/j.humimm.2 009.06.004.
Ben-Yedidia, T., et al. Intranasal administration of peptide vaccine protects human/mouse radiation chimera from influenza infection. International Immunology, 11(7), 1043-1055, 1999.
Berg, P. Co-chairman's remarks: reverse genetics: directed modification of DNA for functional analysis. Gene. Dec. 15, 1993; 135(1-2):261-4.
Bloom, J.D., An Experimentally Determined Evolutionary Model Dramatically Improves Phylogenetic Fit. Mol Biol Evol. Aug. 2014; 31(8): 1956-1978.
Boon, A C M et al. "The magnitude and specificity of influenza A virus-specific cytotoxic T-lymphocyte responses in humans is related to HLA-A and -B phenotype." Journal of virology vol. 76,2 (2002): 582-90. doi: 10.1128/jvi.76.2.582-590.
Breuer, et al. A cleavage enzyme-cytometric bead array provides biochemical profiling of resistance mutations in HIV-1 Gag and protease. Biochemistry. May 24, 2011;50(20):4371-81. doi: 10.1021/bi200031m. Epub Apr. 27, 2011.
Burnham, A.J. et al., Neuraminidase inhibitors for influenza B virus infection: efficacy and resistance. Antiviral Res. vol. 100 pp. 520-534 (2013).
Burton, D. R., et al. Broadly neutralizing antibodies present new prospects to counter highly antigenically diverse viruses. Science vol. 337, pp. 183-186 (2012).
Carreno BM et al., The peptide binding specificity of HLA class I molecules is largely allele-specific and non-overlapping, Mol Immunol. Sep. 1992; 29(9):1131-40.
Chaves, Francisco A et al., "The utility and limitations of current Web-available algorithms to predict peptides recognized by CD4 T cells in response to pathogen infection." Journal of Immunology, vol. 188, No. 9, pp. 4235-4248, 2012.
Chayama, K. & Hayes, C. N. Hepatitis C virus: How genetic variability affects pathobiology of disease. J Gastroenterol Hepatol vol. 1, pp. 83-95 (2011).
Chen, et al. Vaccine design of hemagglutinin glycoprotein against influenza. Trends Biotechnol. Sep. 2011;29 (9):426-34. doi: 10.1016/j.tibtech.2011.04.007.
Chen, Li et al. "Broad-Based CD4+ T Cell Responses to Influenza A Virus in a Healthy Individual Who Lacks Typical Immunodominance Hierarchy." Frontiers in immunology vol. 8 375.Apr. 3, 2017, doi: 10.3389/fimmu.2017.00375.
Cho et al. (Cancer Immunology Immunotherapy, 2012, p. 343-351).
Choi et al. Viral vectors for vaccine applications. Clin Exp Vaccine Res.Jul. 2013; 2(2): 97-105.
Coffin, J. et al. HIV pathogenesis: dynamics and genetics of viral populations and infected cells. Cold Spring Harbor Perspec Med vol. 3, p. a012526 (2013).
Coffin, J. M. HIV population dynamics in vivo: implications for genetic variation, pathogenesis, and therapy. Science vol. 267, pp. 483-489 (1995).
Currier JR et al., "A panel of MHC class I restricted viral peptides for use as a quality control for vaccine trial ELISPOT assays", J Immunol Methods. Feb. 1, 2002;260(1-2):157-72.
DeGroot, A. S. et al. Further progress on defining highly conserved immunogenic epitopes for a global HIV vaccine: HLA-A3-restricted GAIA vaccine epitopes. Hum. Vaccin. Immunother vol. 8, pp. 987-1000 (2012).
Di Mario, Giuseppina et al. "A heat-inactivated H7N3 vaccine induces cross-reactive cellular immunity in HLA-A2.1 transgenic mice." Virology journal vol. 13 56. Mar. 31, 2016, doi: 10.1186/s12985-016-0513-7.
Di Mario, Giuseppina et al. "Protective immunity against influenza in HLA-A2 transgenic mice by modified vaccinia virus Ankara vectored vaccines containing internal influenza proteins." Pathogens and global health vol. 111,2 (2017): 76-82. doi: 10.1080/20477724.2016.1275465.
Ekiert, et al. Antibody recognition of a highly conserved influenza virus epitope. Science. Apr. 10, 2009;324 (5924):246-51. doi: 10.1126/science.1171491. Epub Feb. 26, 2009.
Engelhardt, OG. Many ways to make an influenza virus-review of influenza virus reverse genetics methods. Influenza Other Respir Viruses. May 2013;7(3):249-56. doi: 10.1111/j.1750-2659.2012.00392.x. Epub Jun. 19, 2012.
Epstein, et al. Protection against multiple influenza A subtypes by vaccination with highly conserved nucleoprotein. Vaccine, 2005. 23(46-47): p. 5404-10.
Fijalkowska, Iwona et al. DNA replication fidelity in *Escherichia coli*: a multi-DNA polymerase affair. FEMS Microbial Rev vol. 36, pp. 1105-1121 (2012).
Fløe, Andreas et al. "Development of an epitope panel for consistent identification of antigen-specific T-cells in humans." Immunology vol. 152,2 (2017): 298-307. doi: 10.1111/imm.12769.
Fodor, et al. Rescue of influenza A virus from recombinant DNA. J Virol. Nov. 1999;73(11):9679-82.
Genesca, M. et al. With minimal systemic T-cell expansion, CD8+ T cells mediate protection of rhesus macaques immunized with

(56) References Cited

OTHER PUBLICATIONS attenuated simian-human immunodeficiency virus SHIV89.6 from vaginal challenge with simian immunodeficiency virus. J. Viral. 82:11181-11196 (2008).
Gerhard, W.et al. Prospects for universal influenza virus vaccine. Emerg. Infect. Dis. vol. 12, pp. 569-574 (2006).
Gianfrani C et al., "Human memory CTL response specific for influenza A virus is broad and multispecific", Human Immunology, vol. 61, Issue 5, May 2000, pp. 438-452.
Gilbert, S.C. Advances in the development of universal influenza vaccines. Influenza Other Respi. Viruses vol. 7, Issue 5, pp. 750-758. Sep. 2013. (Epub Sep. 24, 2012).
Girard, et al. A review of vaccine research and development: human acute respiratory infections. Vaccine. Dec. 30, 2005;23(50):5708-24. Epub Aug. 3, 2005.
Goodman et al. A Human Multi-Epitope Recombinant Vaccinia Virus as a Universal T Cell Vaccine Candidate against Influenza Virus. PLoS One, 2011, 6(10): e25938. https://doi.org/10.1371/journal.pone.0025938.
Gout, J-F. et al. Large-scale detection of in vivo transcription errors. Proc. Natl. Acad. Sci. USA 110:18584-18589 (2013).
Gray, Kevin A., et al. "Rapid Evolution of Reversible Denaturation and Elevated Melting Temperature in a Microbial Haloalkane Dehalogenase" Adv. Synth. Catal. vol. 343, No. 6-7, 2001.
Gschoesser C et al., "CD4+ and CD8+ mediated cellular immune response to recombinant influenza nucleoprotein", Vaccine. Nov. 1, 2002;20(31-32):3731-8.
Guan, et al. The emergence of pandemic influenza viruses. Protein Cell. Jan. 2010;1(1):9-13. doi: 10.1007/513238-010-0008-z. Epub Feb. 7, 2010.
Haut et al. A Partial E3 Deletion in Replication-Defective Adenoviral Vectors Allows for Stable Expression of Potentially Toxic Transgene Products. Hum Gene Ther Methods. Oct. 2016;27(5): 187-196.
He, et al. Crystal structure of the polymerase PA(C)-PB1(N) complex from an avian influenza H5N1 virus. Nature. Aug. 28, 2008;454(7208):1123-6. doi: 10.1038/nature07120. Epub Jul. 9, 2008.
Hedskog, et al. Dynamics of HIV-1 quasispecies during antiviral treatment dissected using ultra-deep pyrosequencing. PLoS One. Jul. 7, 2010;5(7):e11345. doi: 10.1371/journal.pone.0011345.
Henderson et al. Recombinant Vaccinia Virus Vaccines. Vaccines. 3rd edition. Philadelphia: Saunders. 5 pages. 1999.
Herrmann VL et al., "Cytotoxic T cell vaccination with PLGA microspheres interferes with influenza A virus replication in the lung and suppresses the infectious disease", J Control Release. Oct. 28, 2015;216:121-31. doi: 10.1016/j.jconrel.2015.08.019.
Hersperger, A. R. et al. Increased HIV-specific CD8+ T-cell cytotoxic potential in HIV elite controllers is associated with T-bet expression. Blood 117:3799-3808 (2011).
Hoffmann, E. et at. Rescue of influenza B virus from eight plasmids. Proc. Natl. Acad. Sci. USA vol. 99, pp. 11411-11416 (2002).
Hoffmann, et al. A DNA transfection system for generation of influenza A virus from eight plasmids. Proc Natl Acad Sci USA. vol. 97, Issue 11, pp. 6108-6113 (May 23, 2000).
Hoft, Daniel F et al. "Live and inactivated influenza vaccines induce similar humoral responses, but only live vaccines induce diverse T-cell responses in young children." The Journal of infectious diseases vol. 204,6 (2011): 845-53. doi:10.1093/infdis/jir436.
Homer, et al. BFAST: an alignment tool for large scale genome resequencing. PLoS One. Nov. 11, 2009;4(11):e7767. doi: 10.1371/journal.pone.0007767.
Scorza et al. Universal influenza vaccines: Shifting to better vaccines. Vaccine. vol. 34, Issue 26, Jun. 3, 2016, pp. 2926-2933.
Sedova et al. Recombinant Influenza Vaccines. Acta Naturae. Oct.-Dec. 2012; 4(4): 17-27.
Shacklett, B. L. & Ferre, A. L. Mucosal immunity in HIV controllers: the right place at the right time. Curr. Opin. HIV Aids 6:202-207 (2011).

Siloto, MP et al. Site Saturation mutagenesis: Methods and Applications in protein engineering. Biocatalysis and Agricultural Biotechnology vol. 1, pp. 181-189. 2012.
Soboleski et al. Cold-adapted influenza and recombinant adenovirus vaccines induce cross-protective immunity against pH1N1 challenge in mice. PLoS One. 2011;6(7):e21937.
Soema, Peter C et al. "Whole-Inactivated Influenza Virus is a Potent Adjuvant for Influenza Peptides Containing CD8+ T Cell Epitopes." Frontiers in immunology vol. 9 525. Mar. 14, 2018, doi: 10.3389/fimmu.2018.00525.
Souza et al. Recombinant viruses as vaccines against viral diseases. Braz J Med Biol Res. Apr. 2005;38(4):509-22.
Staneková et al. Conserved epitopes of influenza A virus inducing protective immunity and their prospects for universal vaccine development. Virology Journal, 2010, 7:351.
Steel, et al. Influenza virus vaccine based on the conserved hemagglutinin stalk domain. MBio. May 18, 2010;1(1). pii: e00018-10. doi: 10.1128/mBio.00018-10.
Stoloff et al. Synthetic multi-epitope peptides identified in silico induce protective immunity against multiple influenza serotypes. Eur. J. Immunol., 37: 2441-2449, (2007).
Strait, et al. The Shannon information entropy of protein sequences. Biophys J. Jul. 1996;71(1):148-55.
Subbarao et al. The prospects and challenges of universal vaccines for influenza. Cell Press. Trends in Microbiology. vol. 21, Issue 7, Jul. 2013, pp. 350-358.
Supplementary European Search Report dated Sep. 18, 2020 for Application Serial No. EP 17887439.2, (10 pages).
Taft, et al., Identification of mammalian-adapting mutations in the polymerase complex of an avian H5N1 influenza virus. Nat Commun. 2015; 6: 7491.
Takagi et al. Characterization of DNA polymerase from *Pyrococcus* sp. strain KOD1 and its application to PCR. Appl Environ Microbiol 63(11):4504-4510 (1997).
Tam, James P. Recent advances in multiple antigen peptides. J Immunol Methods. Sep. 13, 1996; 196(1):17-32.
Tan et al. The design and proof of concept for a CD8+ T cell-based vaccine inducing cross-subtype protection against influenza A virus. Immunology and Cell Biology (2013) 91, 96-104, (2013).
Tan, A. C. et al. Precursor frequency and competition dictate the HLA-A2-restricted CDS+ T cell responses to influenza A infection and vaccination in HLA-A2.1 transgenic mice. J Immunol. vol. 187, pp. 1895-1902 (2011).
Tang et al. Adenovirus as a carrier for the development of influenza virus-free avian influenza vaccines. Expert Rev Vaccines. Apr. 2009;8(4):469-81.
Tang et al. Recombinant adenovirus encoding the HA gene from swine H3N2 influenza virus partially protects mice from challenge with heterologous virus: A/HK/1/68 (H3N2). Arch Virol. Nov. 2002;147(11):2125-41.
Tarendeau, et al. Structure and nuclear import function of the C-terminal domain of influenza virus polymerase PB2 subunit. Nat Struct Mol Biol. Mar. 2007; 14(3):229-33. Epub Feb. 25, 2007.
Tatsis et al. Chimpanzee-origin adenovirus vectors as vaccine carriers. Gene Ther. Mar. 2006; 13(5):421-9.
Tompkins et al. Matrix Protein 2 Vaccination and Protection against Influenza Viruses, Including Subtype H5N1. Emerg Infect Dis. Mar. 2007; 13(3): 426-435.
Toussaint, N.C.et al. Universal peptide vaccines—optimal peptide vaccine design based on viral sequence conservation. Vaccine vol. 29, pp. 8745-8753 (2011).
Tripp et al. Virus-Vectored Influenza Virus Vaccines. Viruses. Aug. 2014; 6(8): 3055-3079.
Tsibris, A. M. et al. Quantitative deep sequencing reveals dynamic HIV-1 escape and large population shifts during CCR5 antagonist therapy in vivo. PLoS One 4:e5683 (2009).
Tungatt, Katie et al. "Induction of influenza-specific local CD8 T-cells in the respiratory tract after aerosol delivery of vaccine antigen or virus in the Babraham inbred pig." PLoS pathogens vol. 14,5 e1007017. May 17, 2018, doi: 10.1371/journal.ppat.1007017.
Uddback, et al. Combined local and systemic immunization is essential for durable T-cell mediated heterosubtypic immunity against

(56) References Cited

OTHER PUBLICATIONS influenza A virus. Scientific Reports 6, Article No. 20137. Published online: Feb. 1, 2016. doi:10.1038/srep20137.

Ura et al. Developments in Viral Vector-Based Vaccines. Vaccines (Basel). Sep. 2014; 2(3). 17 pages. 624-641.

Valkenburg, Sophie A et al. "Molecular basis for universal HLA-A*0201-restricted CD8+ T-cell immunity against influenza viruses." Proceedings of the National Academy of Sciences of the United States of America vol. 113,16 (2016): 4440-5. doi:10.1073/pnas.1603106113.

Vemula et al. Broadly protective adenovirus-based multivalent vaccines against highly pathogenic avian influenza viruses for pandemic preparedness. PLoS One. Apr. 30, 2013;8(4):e62496.

Vemula et al. Production of adenovirus vectors and their use as a delivery system for influenza vaccines. Expert Opin Biol Ther. Oct. 2010;10(10):1469-87.

Vitiello et al. Analysis of the HLA-restricted influenza-specific cytotoxic T lymphocyte response in transgenic mice carrying a chimeric human-mouse class I major histocompatibility complex. J Exp Med 173: 1007-1015 (1991).

Voeten, J T et al. "Antigen processing for MHC class I restricted presentation of exogenous influenza A virus nucleoprotein by B-lymphoblastoid cells." Clinical and experimental immunology vol. 125,3 (2001): 423-31. doi:10.1046/j.1365-2249.2001.01613.x.

Voeten, J T et al. "Antigenic drift in the influenza a virus (H3N2) nucleoprotein and escape from recognition by cytotoxic T lymphocytes." Journal of virology vol. 74,15 (2000): 6800-7. doi: 10.1128/jvi.74.15.6800-6807.2000.

Weaver et al. Low Seroprevalent Species D Adenovirus Vectors as Influenza Vaccines. PLoS One. 2013; 8(8): e73313.

Weber, et al. A classical bipartite nuclear localization signal on Thogoto and influenza A virus nucleoproteins. Virology. Oct. 10, 1998;250(1):9-18.

Wei, Huiling et al. "DNA-vaccine platform development against H1N1 subtype of swine influenza A viruses." Viral immunology vol. 25,4 (2012): 297-305. doi: 10.1089/vim.2011.0093.

Wesley et al. Protection of weaned pigs by vaccination with human adenovirus 5 recombinant viruses expressing the hemagglutinin and the nucleoprotein of H3N2 swine influenza virus. Vaccine. Sep. 3, 2004;22(25-26):3427-34.

Wilkinson TM et al., "Preexisting influenza-specific CD4+ T cells correlate with disease protection against influenza challenge in humans", Nat Med. Jan. 29, 2012;18(2):274-80. doi: 10.1038/nm.2612.

Wu, Chao et al. "Systematic identification of immunodominant CD8+ T-cell responses to influenza A virus in HLA-A2 individuals." Proceedings of the National Academy of Sciences of the United States of America vol. 108,22 (2011): 9178-83. doi:10.1073/pnas.1105624108.

Wu, et al. High-throughput functional annotation of influenza A virus genome at single-nucleotide resolution. 2014. http://dx.doi.org/10.1101/005702.

Wu, et al. High-throughput profiling of influenza A virus hemagglutinin gene at single-nucleotide resolution. Scientific Reports, vol. 4, pp. 4942 (2014).

Wu, et al. Systematic identification of H274Y compensatory mutations in influenza A virus neuraminidase by high-throughput screening. J Virol. Jan. 2013;87(2): 1193-9.

Y. Adar et al., A universal epitope-based influenza vaccine and its efficacy against H5N1, vol. 27, Issue 15, Mar. 26, 2009, pp. 2099-2107.

Yin, L. et al. High resolution deep sequencing reveals biodiversity, population structure, and persistence of HIV-1 quasispecies within host ecosystems. Retrovirology vol. 9, p. 108 (2012).

Yk Cheung et al., "Human immunogenic T cell epitopes in nucleoprotein of human influenza A (H5N1) virus", Hong Kong Med J 2012; 18(Suppl 2):S17-21.

Zhang, Jianfeng. Advances and Future Challenges in Recombinant Adenoviral Vectored H5N1 Influenza Vaccines. Viruses. Nov. 2012; 4(11): 2711-2735.

Zhang, Nianzhi et al. "Crystal structure of swine major histocompatibility complex class I SLA-1 0401 and identification of 2009 pandemic swine-origin influenza A H1N1 virus cytotoxic T lymphocyte epitope peptides." Journal of virology vol. 85,22 (2011): 11709-24. doi: 10.1128/JVI.05040-11.

Zhou et al. A Universal Influenza A Vaccine Based on Adenovirus Expressing Matrix-2 Ectodomain and Nucleoprotein Protects Mice From Lethal Challenge. Mol Ther. Dec. 2010; 18(12): 2182-2189.

Hoof, et al. NetMHCpan, a method for MHC class I binding prediction beyond humans. Immunogenetics. Jan. 2009;61 (1):1-13. doi: 10.1007/s00251-008-0341-z. Epub Nov. 12, 2008.

Hoppes, Rieuwert et al. "Altered peptide ligands revisited: vaccine design through chemically modified HLA-A2-restricted T cell epitopes." Journal of immunology (Baltimore, Md. : 1950) vol. 193, 10 (2014): 4803-13. doi: 10.4049/jimmunol.1400800.

Hwang, et al. Conserved herpesviral kinase promotes viral persistence by inhibiting the IRF-3-mediated type I interferon response. Cell Host Microbe. Feb. 19, 2009;5(2): 166-78. doi: 10.1016/j.chom.2008.12.013.

Influenza Virus Resource Website. Accessed Nov. 10, 2014. http://www.ncbi.nlm.nih.gov/genomes/FLU/FLU.html.

Jackson David C Et al: "A totally synthetic vaccine of generic structure that targets Toll-like receptor 2 on dendritic cells and promotes antibody or cytotoxic T cell responses", Proceedings of Thenational Academy of Sciences (PNAS), National Academy of Sciences, US, vol. 101, No. 43, Oct. 26, 2004 (Oct. 26, 2004), pp. 15440-15445,XP002340337, ISSN: 0027-8424, DOI: 10.1073/PNAS.0406740101.

Jin, X. et al. Dramatic rise in plasma viremia after CD8+ T cell depletion in simian immunodeficiency virus-infected macaques. J. Exp. Med. 189:991-998 (1999).

Kang, S. M., Song, J. M. & Compans, R. W. Novel vaccines against influenza viruses. Virus Res. vol. 162, pp. 31-38 (2011).

Keskin, Derin B et al. "Physical detection of influenza A epitopes identifies a stealth subset on human lung epithelium evading natural CD8 immunity." Proceedings of the National Academy of Sciences of the United States of America vol. 112,7 (2015): 2151-6. doi: 10.1073/pnas.1423482112.

Kiepiela, K. et al. CD8+ T-cell responses to different HIV proteins have discordant associations with viral load. Nature Med. 13:46-53 (2007).

Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.

Klinger, Mark et al. "Multiplex Identification of Antigen-Specific T Cell Receptors Using a Combination of Immune Assays and Immune Receptor Sequencing." PloS one vol. 10,10 e0141561. Oct. 28, 2015, doi: 10.1371/journal.pone.0141561.

Knapp, et al. In vitro selection of clinically relevant bevirimat resistance mutations revealed by "deep" sequencing of serially passaged, quasispecies-containing recombinant HIV-1. J Clin Microbiol. Jan. 2011;49(1):201-8. doi: 10.1128/JCM.01868-10. Epub Nov. 17, 2010.

Korber, Bet al. Evolutionary and immunological implications of contemporary HIV-1 variation. Br Med Bull vol. 58, pp. 19-42 (2001).

Kretz, Keith A., et al. "Gene Site Saturation Mutagenesis: A Comprehensive Mutagenesis Approach" Methods in enzymology, vol. 388, pp. 3-11 (2004).

Kuroda, et al. Characterization of quasispecies of pandemic 2009 influenza A virus (A/H1N1/2009) by de novo sequencing using a next-generation DNA sequencer. PLOS One. Apr. 23, 2010;5(4):e10256. doi: 10.1371/journal. pone.0010256.

Lambert, et al. Influenza vaccines for the future. New England Journal of Medicine. Nov. 18, 2010; vol. 363, Issue 21, pp. 2036-2044. doi: 10.1056/NEJMra1002842.

Lee, Jessica B et al. "Decline of influenza-specific CD8+ T cell repertoire in healthy geriatric donors." Immunity & ageing : I & A vol. 8 6. Aug. 16, 2011, doi: 10.1186/1742-4933-8-6.

Lee, Laurel Yong-Hwa et al. "Memory T cells established by seasonal human influenza A infection cross-react with avian influ-

(56) References Cited

OTHER PUBLICATIONS enza A (H5N1) in healthy individuals." The Journal of clinical investigation vol. 118, 10 (2008): 3478-90. doi:10.1172/JCI32460.
Levitz, L. et al. Conservation of HIV-1 T cell epitopes across time and clades: validation of immunogenic HLA-A2 epitopes selected for the GAIA HIV vaccine. Vaccine vol. 30, pp. 7547-7560 (2012).
Li et al. Recombinant protein comprising multi-neutralizing epitopes induced high titer of antibodies against Influenza A virus. Immunobiology. vol. 207, Issue 5, 2003, pp. 305-313.
Luytjes, et al. Amplification, expression, and packaging of foreign gene by influenza virus. Cell. Dec. 22, 1989;59 (6):1107-13.
Lynch, RM, et al. Appreciating HIV type 1 diversity: subtype differences in Env. AIDS Res Human Retroviruses vol. 25, pp. 237-248 (2009).
Maier, et al. Differential role of the influenza A virus polymerase PA subunit for vRNA and cRNA promoter binding. Virology. Jan. 5, 2008;370(1):194-204. Epub Oct. 1, 2007.
Middleton, D. et al., New allele frequency database: http://www.allelefrequencies.net Tissue Antigens, vol. 61, pp. 403-407 (2003).
Nayak, Jennifer L et al. "Analyses of the specificity of CD4 T cells during the primary immune response to influenza virus reveals dramatic MHC-linked asymmetries in reactivity to individual viral proteins." Viral immunology vol. 23,2 (2010): 169-80. doi:10.1089/vim.2009.0099.
Nayak, Jennifer L, and Andrea J Sant. "Loss in CD4 T-cell responses to multiple epitopes in influenza due to expression of one additional MHC class II molecule in the host." Immunology vol. 136,4 (2012): 425-36. doi: 10.1111/j.1365-2567.2012.03599.x.
Neumann, et al. Generation of influenza A viruses entirely from cloned cDNAs. Proc Natl Acad Sci U S A. Aug. 3, 1999;96(16):9345-50.
Neumann, et al. The first influenza pandemic of the new millennium. Influenza Other. Respi. Viruses. vol. 5, pp. 157-166. (2011).
Ng, et al. Structure and sequence analysis of influenza A virus nucleoprotein. Sci China C Life Sci. May 2009;52 (5):439-49. doi: 10.1007/s11427-009-0064-x. Epub May 27, 2009.
Nicholson, et al. "Influenza" Lancet. vol. 362, Issue 9397, pp. 1733-1745, Nov. 22, 2003.
Nielsen, M. et al. NetMHCpan, a method for quantitative predictions of peptide binding to any I-ILA-A and -B locus protein of known sequence. PLoS One vol. 2, p. 796 (2007).
Nobusawa, E. et al. Comparison of the mutation rates of human influenza A and B viruses. J Virol vol. 80, pp. 3675-3678 (2006).
O'Connell, R. J., et al., Human immunodeficiency virus vaccine trials. Cold Spring Harbor Perspec Med vol. 2, pp. a007351 (2012).
PCT/US2017/068800 International Search Report and Written Opinion dated May 8, 2018.
Peters, et al. Forward genetics and map-based cloning approaches. Trends Plant Sci. Oct. 2003;8(10):484-91.
Phillips, C. J. et al. Comparison of the effectiveness of trivalent inactivated influenza vaccine and live, attenuated influenza vaccine in preventing influenza-like illness among US military service members, 2006-2009. Clin. Infect. Dis. vol. 56, pp. 11-19 (2013).
Pica, et al. Toward a universal influenza virus vaccine: prospects and challenges. Ann. Rev. Med. vol. 64, pp. 189-202. (2013).
Poon, A. F. et al. Reconstructing the dynamics of HIV evolution within hosts from serial deep sequence data. PLoS Comput. Biol. 8:e1002753 (2012).
Price et al. Vaccination focusing immunity on conserved antigens protects mice and ferrets against virulent H1N1 and H5N1 influenza A viruses. Vaccine. Nov. 5, 2009;27(47):6512-21.
Quiñones-Parra, Sergio et al. "Preexisting CD8+ T-cell immunity to the H7N9 influenza A virus varies across ethnicities." Proceedings of the National Academy of Sciences of the United States of America vol. 111,3 (2014): 1049-54. doi:10.1073/pnas.1322229111.
Rao et al. Comparative Efficacy of Hemagglutinin, Nucleoprotein, and Matrix 2 Protein Gene-Based Vaccination against H5N1 Influenza in Mouse and Ferret. PLoS One. 2010; 5(3): e9812.
Regan, et al. Defective assembly of influenza A virus due to a mutation in the polymerase subunit PA. J Virol. Jan. 2006;80(1):252-61.
Richards, Katherine A et al. "Infection of HLA-DR1 transgenic mice with a human isolate of influenza a virus (H1N1) primes a diverse CD4 T-cell repertoire that includes CD4 T cells with heterosubtypic cross-reactivity to avian (H5N1) influenza virus." Journal of virology vol. 83,13 (2009): 6566-77. doi:10.1128/JVI.00302-09.
Rolland, M. et al. HIV-1 conserved elements vaccines: Relationship between sequence conservation and replicative capacity. J. Viral. Epub ahead of print (2013).
Rosendahl Huber, Sietske K et al. "Chemical Modification of Influenza CD8+ T-Cell Epitopes Enhances Their Immunogenicity Regardless of Immunodominance." PLoS one vol. 11,6 e0156462. Jun. 22, 2016, doi: 10.1371/journal.pone.0156462.
Roy et al. Rescue of chimeric adenoviral vectors to expand the serotype repertoire. J Virol Methods. Apr. 2007; 141(1): 14-21.
Samiji, T. Influenza A: understanding the viral life cycle. Yale J Biol Med. Dec. 2009;82(4):153-9.
Samson, et al. Influenza virus resistance to neuraminidase inhibitors. Antiviral Res. vol. 98, Issue 2, pp. 174-185. May 2013.
Schmitz, J. E. et al. Control of viremia in simian immunodeficiency virus infection by CD8+ lymphocytes. Science 283:857-860 (1999).
Schnell, et al. Structure and mechanism of the M2 proton channel of influenza A virus. Nature. Jan. 31, 2008;451 (7178):591-5. doi: 10.1038/nature06531.

\* cited by examiner

Fig. 1

```
┌─────────────────────────────────┐         ┌─────────────────────────────────┐
│ Mutation tolerance information for │   +    │ Immunogenicity information for  │
│ influenza virus proteins           │        │ influenza epitopes              │
└─────────────────────────────────┘         └─────────────────────────────────┘
                                    │
                                    ▼
                    ┌─────────────────────────────────┐
                    │ Identify influenza peptide sequences │
                    │ for use in vaccine              │
                    └─────────────────────────────────┘
                                    │
                                    ▼
                    ┌─────────────────────────────────┐
                    │ Generate vaccine                │
                    └─────────────────────────────────┘
                                    │
                                    ▼
                    ┌─────────────────────────────────┐
                    │ Administer vaccine to subject   │
                    └─────────────────────────────────┘
```

Fig. 2
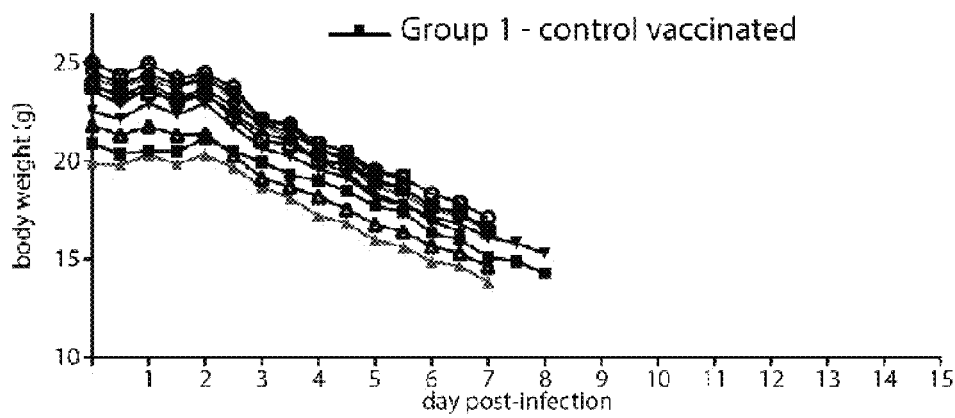
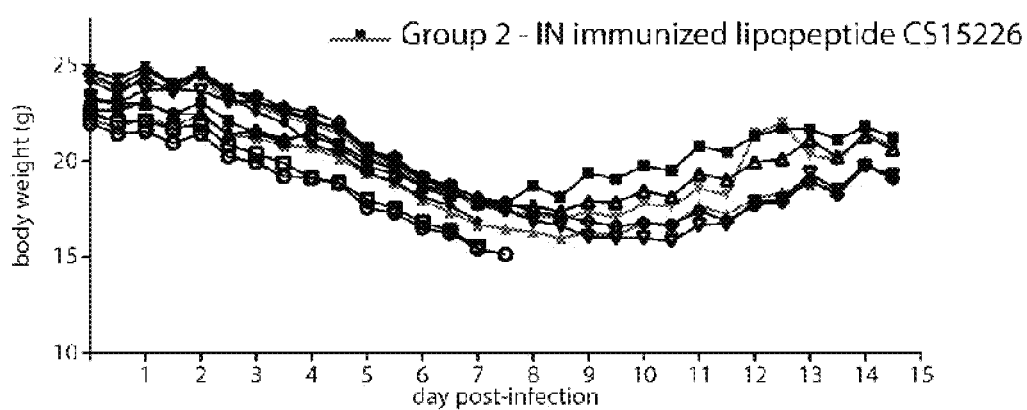
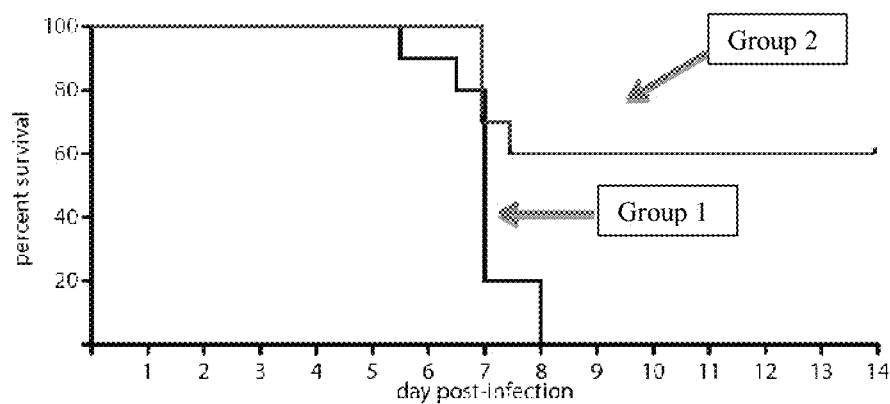

INFLUENZA VACCINES

CROSS-REFERENCE

This application is a continuation of U.S. patent application Ser. No. 17/375,797, filed on Jul. 14, 2021, which is a continuation of U.S. patent application Ser. No. 15/857,436, filed on Dec. 28, 2017, which issued as U.S. Pat. No. 11,111,277 on Sep. 7, 2021, which claims the benefit of U.S. provisional application No. 62/439,865, filed Dec. 28, 2016, and U.S. provisional application No. 62/550,167, filed Aug. 25, 2017, which are herein incorporated by reference in their entirety.

SEQUENCE LISTING

The instant application contains a Sequence Listing, which has been filed electronically in the XML format and is hereby incorporated by reference in its entirety. Said XML copy, created on Sep. 12, 2023, is named 121692-0013_SUBSEQ.XML and is 230,225 bytes in size.

BACKGROUND

Vaccines greatly promote human health by providing active adapted immunity to a particular disease. There is a need for improved vaccines, e.g., influenza vaccines. Improved vaccines may exhibit higher safety, increased immunogenicity, coverage of broader range of pathogens, or any combination thereof.

SUMMARY

One aspect of the present disclosure provides a polypeptide that comprises a first sequence selected from the group consisting of SEQ ID NOs: 2, 3, 8, 11, 12, 40, 41, 43, 51, 52, 58, 59, 61, 62, 84, and 92; and a second sequence selected from the group consisting of SEQ ID NOs: 17, 20, 21, 22, 24, 26, 29, 30, 32, 33, 34, 44, 45, 49, 53, 60, 70, 73, 74, 75, 76, 77, 78, 82, 83, 85, 86, 87, 88, 89, 90, 91, 93, and 94.

Another aspect of the present disclosure provides a polypeptide that comprises a first sequence selected from the group consisting of SEQ ID NOs: 2, 8, 11, 12, 40, 41, 43, 52, 58, 59, 61, 62, 84, and 92; and a second sequence selected from the group consisting of SEQ ID NOs: 17, 20, 21, 22, 24, 26, 29, 30, 31, 32, 33, 34, 44, 45, 49, 53, 60, 70, 73, 74, 75, 76, 77, 78, 82, 83, 85, 86, 87, 88, 89, 90, 91, 93, and 94.

Another aspect of the present disclosure provides a polypeptide that comprises: (a) a first sequence comprising at least 60%, at least 75%, at least 85%, or 100% sequence identity to at least 8 contiguous amino acids of SEQ ID NO: 8, 11, 12, 40, 41, 58, 59, 61, 62, 84, or 92, and a second sequence comprising at least 60%, at least 75%, at least 85%, or 100% sequence identity to at least 8 contiguous amino acids of SEQ ID NO: 2, 3, 17, 20, 21, 22, 24, 26, 29, 30, 31, 32, 33, 34, 43, 44, 45, 49, 51, 52, 53, 60, 70, 73, 74, 75, 76, 77, 78, 82, 83, 85, 86, 87, 88, 89, 90, 91, 93, or 94; or (b) a first sequence comprising at least 60%, at least 75%, at least 85%, or 100% sequence identity to at least 8 contiguous amino acids of SEQ ID NO: 2 or 43 and a second sequence comprising at least 60%, at least 75%, at least 85%, or 100% sequence identity to at least 8 contiguous amino acids of SEQ ID NO: 8, 11, 12, 17, 20, 21, 22, 24, 26, 29, 30, 31, 32, 33, 34, 40, 41, 44, 45, 49, 53, 58, 59, 60, 61, 62, 70, 73, 74, 75, 76, 77, 78, 82, 83, 84, 85, 86, 87, 88, 89, 90, 91, 92, 93, or 94; or (c) a first sequence comprising at least 60%, at least 75%, at least 85%, or 100% sequence identity to at least 8 contiguous amino acids of SEQ ID NO: 21, 22, 24, 26, 30, 32, 49, 53, 60, 70, 85, 86, 93, or 94, and a second sequence comprising at least 60%, at least 75%, at least 85%, or 100% sequence identity to at least 8 contiguous amino acids of SEQ ID NO: 2, 3, 8, 11, 12, 40, 41, 43, 51, 52, 58, 59, 61, 62, 84, or 92; or (d) a first sequence comprising at least 60%, at least 75%, at least 85%, or 100% sequence identity to at least 8 contiguous amino acids of SEQ ID NO: 17, 20, 29, 31, 33, 34, 44, 45, 73, 74, 75, 76, 77, 78, 82, 83, 87, 88, 89, 90, or 91 and a second sequence comprising at least 60%, at least 75%, at least 85%, or 100% sequence identity to at least 8 contiguous amino acids of SEQ ID NO: 2, 8, 11, 12, 40, 41, 43, 58, 59, 61, 62, 84, or 92; or (e) a first sequence comprising at least 60%, at least 75%, at least 85%, or 100% sequence identity to at least 8 contiguous amino acids of SEQ ID NO: 2 or 43 and a second sequence comprising at least 60%, at least 75%, at least 85%, or 100% sequence identity to at least 8 contiguous amino acids of SEQ ID NO: 8, 11, 12, 21, 22, 24, 26, 30, 32, 40, 41, 49, 53, 58, 59, 60, 61, 62, 70, 84, 85, 86, 92, 93, or 94; or (f) a first sequence comprising at least 60%, at least 75%, at least 85%, or 100% sequence identity to at least 8 contiguous amino acids of SEQ ID NO: 3, 51, or 52, and a second sequence comprising at least 60%, at least 75%, at least 85%, or 100% sequence identity to at least 8 contiguous amino acids of SEQ ID NO: 8, 11, 12, 21, 22, 24, 26, 30, 32, 40, 41, 49, 53, 58, 59, 60, 61, 62, 70, 84, 85, 86, 92, 93, 94; or (g) a first sequence comprising at least 60%, at least 75%, at least 85%, or 100% sequence identity to at least 8 contiguous amino acids of SEQ ID NO: 2, 8, 11, 12, 40, 41, 43, 58, 59, 61, 62, 84, or 92, and a second sequence comprising at least 60%, at least 75%, at least 85%, or 100% sequence identity to at least 8 contiguous amino acids of SEQ ID NO: 21, 22, 24, 26, 30, 32, 49, 53, 60, 70, 85, 86, 93, or 94; or (h) a first sequence comprising at least 60%, at least 75%, at least 85%, or 100% sequence identity to at least 8 contiguous amino acids of SEQ ID NO: 2, 8, 11, 12, 21, 22, 24, 26, 30, 32, 40, 41, 43, 49, 53, 58, 59, 60, 61, 62, 70, 84, 85, 86, 92, 93, or 94, and a second different sequence comprising at least 60%, at least 75%, at least 85%, or 100% sequence identity to at least 8 contiguous amino acids of SEQ ID NO: 2, 3, 8, 11, 12, 17, 20, 21, 22, 24, 26, 29, 30, 31, 32, 33, 34, 40, 41, 43, 44, 45, 49, 51, 52, 53, 58, 59, 60, 61, 62, 70, 73, 74, 75, 76, 77, 78, 82, 83, 84, 85, 86, 87, 88, 89, 90, 91, 92, 93, or 94, wherein a contiguous sequence comprising the first sequence and the second different sequence is not found in a PB1, PA, or NP.

Another aspect of the present disclosure provides a polypeptide that comprises a first sequence, second sequence, third sequence, fourth sequence, and a fifth sequence, wherein each of the first sequence, second sequence, third sequence, fourth sequence, and fifth sequence comprises at least 75% sequence identity to a different sequence selected from the group consisting of SEQ ID NOs: 2, 3, 8, 11, 12, 17, 20-22, 24, 26, 29-34, 40, 41, 43-45, 49, 51-53, 58-62, 70, 73-78, and 82-94, wherein the polypeptide is not naturally occurring.

In some cases, at least one of the first sequence, second sequence, third sequence, fourth sequence, and fifth sequence can comprise at least 75% sequence identity to a sequence selected from the group consisting of SEQ ID NOs: 17, 20-22, 24, 26, 29-34, 44, 45, 49, 53, 60, 70, 72-78, 82, 83, 85-91, 93, and 94. In some cases, at least one of the first sequence, second sequence, third sequence, fourth, and fifth sequence can comprise at least 75% sequence identity to a sequence selected from the group consisting of SEQ ID NOs: 2, 3, 43, 51, and 52. In some cases, at least one of the first sequence, second sequence, third sequence, fourth sequence, and fifth sequence can comprise at least 75% sequence identity to a sequence selected from the group consisting of SEQ ID NOs: 8, 11, 12, 40, 41, 58, 59, 61, 62, and 92.

A polypeptide provided herein can further comprise sequence with at least 50% sequence identity to at least 10% of the amino acid sequence of an NP protein of influenza B. A polypeptide provided herein can further comprise sequence with at least 50% sequence identity to at least 10% of the amino acid sequence of SEQ ID NO: 116, 117, or 118. In some cases, each sequence can be at most 10, 12, 15, 20, 25, 30, 35, 40, 45, or 50 amino acids in length. In some cases, the first sequence and second sequence can be directly linked. In some cases, the first sequence and the second sequence can be linked by a linker. In some cases, the linker can comprise a plurality of glycines, alanines, arginines, valines, or lysines. A linker can comprise the sequence RVKR (SEQ ID NO: 110). A polypeptide provided herein can further comprise sequence GALNNRFQIKGVELKSK (SEQ ID NO: 103). SEQ ID NO: 103 can be linked to an amino terminal portion of the polypeptide. A polypeptide provided herein can comprise SEQ ID NOs: 2, 3, 8, 11, 12, 17, 20, 21, 22, 24, 26, 29, 30, 31, 32, 33, 34, 40, 41, 43, 44, 45, 49, 51, 52, 53, 58, 59, 60, 61, 62, 70, 73, 74, 75, 76, 77, 78, 82, 83, 84, 85, 86, 87, 88, 89, 90, 91, 92, 93, and 94.

A polypeptide provided herein can be an isolated polypeptide.

Another aspect of the present disclosure provides a composition that comprises a polypeptide provided herein.

Another aspect of the present disclosure provides a polynucleotide encoding a polypeptide provided herein. A polynucleotide provided herein can be isolated.

Another aspect of the present disclosure provides a composition that comprises a polynucleotide provided herein.

Another aspect of the present disclosure provides a vector that comprises a polynucleotide provided herein. A vector provided herein can be a non-human primate vector. A vector provided herein can be an adenovirus vector. A vector provided herein can be a chimpanzee adenovirus vector. In some cases, the chimpanzee adenovirus vector can comprise at least 50% sequence identity to least 50% of the sequence of C68 (AdC68) (SEQ ID NO: 104), C7 (AdC7), C6 (AdC6) (SEQ ID NO: 105), Pan7, or Pan9.

A vector provided herein can be isolated.

Another aspect of the present disclosure provides a composition that comprises a vector provided herein.

Another aspect of the present disclosure provides a virus that comprises a polynucleotide provided herein.

Another aspect of the present disclosure provides a virus that comprises a vector provided herein.

A virus provided herein can be isolated. A virus can be an adenovirus.

Another aspect of the present disclosure provides a composition that comprises a virus provided herein.

Another aspect of the present disclosure provides a composition that comprises at least five different peptides, wherein each of the at least five different peptides comprises, consists of, or consists essentially of a sequence comprising at least 75% sequence identity to a sequence selected from the group consisting of SEQ ID NOs: 2, 3, 8, 11, 12, 17, 20-22, 24, 26, 29-34, 40, 41, 43-45, 49, 51-53, 58-62, 70, 73-78, and 82-94. In some cases of the composition, each peptide can be at most 10, 12, 15, 20, 25, 30, 35, 40, 45, or 50 amino acids in length. A composition provided herein can further comprise a peptide comprising a sequence with at least 50% sequence identity to at least 10% of the amino acid sequence of an NP protein of influenza B. A composition provided herein can further comprise a peptide comprising a sequence with at least 50% sequence identity to at least 10% of the amino acid sequence of SEQ ID NOs: 116, 117, or 118. A composition provided herein can further comprise a pharmaceutically acceptable excipient. A composition provided herein can be formulated for subcutaneous, intranasal, or intramuscular administration.

Another aspect of the present disclosure provides a method that comprises administering to a subject a composition provided herein. In some cases, the administration can be subcutaneous. In some cases, the administration can be intranasal. In some cases, the administration can be intramuscular. A method provided herein can further comprise administering the composition to the subject a second time.

In some cases, an immune response can be induced following the administration. The immune response can be a systemic immune response. In some cases, the subject can be a human. In some cases, the subject can be infected with a virus. The virus can be an influenza virus. The influenza virus can be influenza A virus, influenza B virus, or influenza C virus. In some cases, the influenza virus can be influenza A virus. In some cases, the composition when administered can induce cross-protection against one or more subtypes of influenza A strains in the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates a method for discovering vaccine epitopes.

FIG. 2 illustrates a result of an influenza challenge of vaccinated mice.

DETAILED DESCRIPTION

Figure 3A:
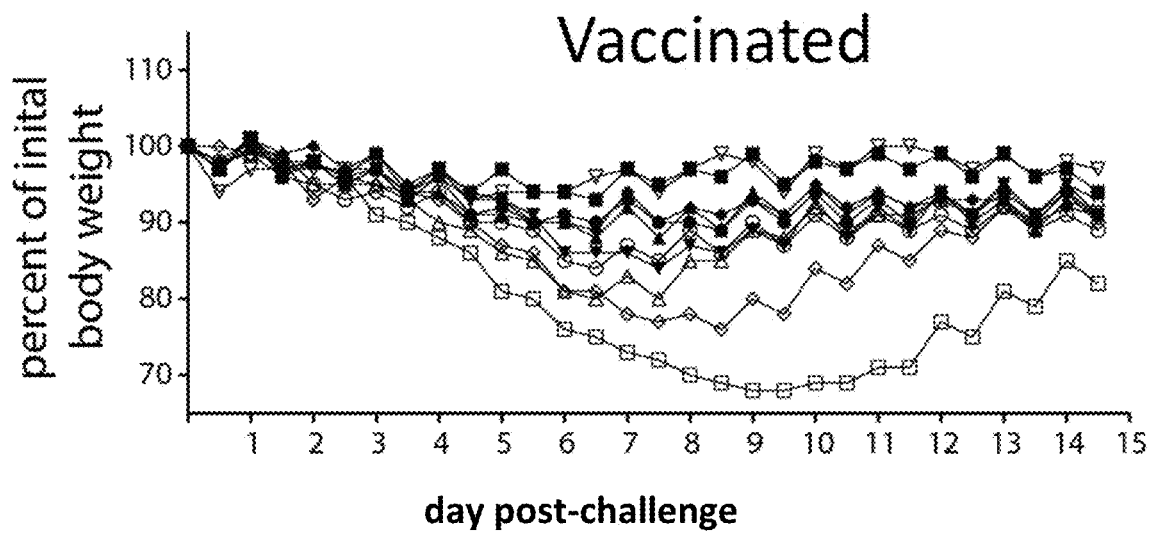
FIG. 3A illustrates the percent of initial body weight of vaccinated mice.

Provided herein are methods and compositions for forming vaccines, e.g., influenza vaccines.

The methods can comprise, e.g., making a recombinant viral vaccine, e.g., recombinant adenoviral vaccine, using sequence encoding one or more influenza epitopes, e.g., one or more influenza A epitopes, e.g., one or more influenza A peptide epitopes. The one or more epitopes can comprise an "invariant" sequence, e.g., a sequence with a low tolerance for mutations. The one or more epitopes can comprise an experimentally verified human CD8 T cell influenza A virus epitope. The recombinant adenovirus can express at least 1, 5, 8, 10, 25, 50, 100, or 1000 peptide epitopes. In some cases, the expressed epitopes are linked, e.g., through covalent bonds, e.g., in a single polypeptide. In some cases, the expressed epitopes are not linked, e.g., each epitope can be expressed from a separate promoter, separate nucleic acid, or separate virus. In some cases, the one or more epitopes are described in the Immune Epitope Database and Analysis Resource (worldwideweb.iedb.org). A single polypeptide comprising one or more epitopes can be linked to one, two, or more copies of a full-length viral protein (or at least 10%, 20%, 30%, 40%, 50%, 60%, 70%, 80%, 90%, or 95% of a full-length viral protein, or a sequence having at least 50%, 60%, 70%, 80%, 90%, 95%, or 100% sequence identity to such proteins) from, e.g., influenza A, influenza B, or influenza C.

Definitions

The terminology used herein is for the purpose of describing particular cases only and is not intended to be limiting. As used herein, the singular forms "a", "an" and "the" can include the plural forms as well, unless the context clearly indicates otherwise. Furthermore, to the extent that the terms "contains," "containing," "including," "includes," "having," "has," "with," or variants thereof are used in either the detailed description and/or the claims, such terms can be inclusive in a manner similar to the term "comprising."

The term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" can mean an acceptable error range for the particular value, such as +10% of the value modified by the term "about."

The term "polypeptide" and its grammatical equivalents, as used herein, can refer to a continuous and unbranched chain of amino acid monomers linked by peptide (amide) bonds, which can be covalent chemical bonds formed when the carboxyl group of one amino acid reacts with the amino group of another. Unless indicated otherwise, the terms "polypeptide" and "peptide" are interchangeable as used herein. The shortest polypeptide can be dipeptide with only two amino acids joined by a single peptide bond. For the purposes of the present disclosure, these terms should not to be construed as limiting with respect to an upper length. The terms can also encompass analogues of natural amino acids, as well as amino acids that are modified in the side chain, chirality, or properties.

The terms "nucleic acid," "polynucleotide," "polynucleic acid," and "oligonucleotide" and their grammatical equivalents can be used interchangeably and can refer to a deoxyribonucleotide or ribonucleotide polymer, in linear or circular conformation, and in either single- or double-stranded form. For the purposes of the present disclosure, these terms should not to be construed as limiting with respect to an upper length. The terms can also encompass analogues of natural nucleotides, as well as nucleotides that are modified in the base, sugar and/or phosphate moieties (e.g., phosphorothioate backbones). Modifications of the terms can also encompass demethylation, addition of CpG methylation, removal of bacterial methylation, and/or addition of mammalian methylation. In general, an analogue of a particular nucleotide can have the same base-pairing specificity, i.e., an analogue of A can base-pair with T.

The term "antigen" and its grammatical equivalents as used herein can refer to a molecule that contains one or more epitopes capable of being bound by one or more receptors. For example, an antigen can stimulate a host's immune system to make a cellular antigen-specific immune response when the antigen is presented, or a humoral antibody response. An antigen can also have the ability to elicit a cellular and/or humoral response by itself or when present in combination with another molecule. For example, an influenza A viral protein can be recognized by a TCR.

The term "epitope" and its grammatical equivalents as used herein can refer to a part of an antigen that can be recognized by antibodies, B cells, T cells or engineered cells. For example, an epitope can be an influenza A viral epitope that is recognized by a TCR. Multiple epitopes within an antigen can also be recognized. The epitope can also be mutated.

The term "mutation" and its grammatical equivalents, as used herein, can refer to a deletion, an insertion of a heterologous nucleic acid, an inversion or a substitution, including an open reading frame ablating mutation as commonly understood in the art.

The term "gene" and its grammatical equivalents, as used herein, can refer to a segment of nucleic acid that encodes an individual polypeptide, protein or RNA (also referred to as a "coding sequence" or "coding region"), optionally together with associated regulatory regions such as promoters, operators, terminators and the like, which can be located upstream or downstream of the coding sequence.

The term "naturally-occurring" and its grammatical equivalents, as used herein with reference to a virus, can indicate that the virus can be found in nature, i. e., it can be isolated from a source in nature and has not been intentionally modified.

The terms "inhibiting," "reducing" or "prevention," or any variation of these terms, referred to herein, can include any measurable decrease or complete inhibition to achieve a desired result.

A "promoter" and its grammatical equivalents, as used herein, can be a control sequence that is a region of a nucleic acid sequence at which initiation and rate of transcription are controlled. A promoter can contain genetic elements at which regulatory proteins and molecules can bind such as RNA polymerase and other transcription factors. The terms "operatively positioned," "operatively linked," "under control" and "under transcriptional control" can mean that a promoter is in a correct functional location and/or orientation in relation to a nucleic acid sequence to control transcriptional initiation and/or expression of that sequence. In some cases, a promoter may or may not be used in conjunction with an "enhancer," which can refer to a cis-acting regulatory sequence involved in the transcriptional activation of a nucleic acid sequence.

The term "subject" and its grammatical equivalents can refer to an animal, including, but not limited to, a primate (e.g., human), cow, sheep, goat, horse, dog, cat, rabbit, rat, or mouse. The terms "subject" and "patient" can be used interchangeably herein in reference, for example, to a mammalian subject, such as a human subject.

Methods of Identifying Epitopes for Use in a Vaccine

One aspect of the present disclosure provides methods of identifying epitopes for use in a vaccine. The methods can be used to identify an epitope sequence of a pathogen, e.g., a virus, e.g., an RNA virus, e.g., an influenza virus, e.g., an influenza A, influenza B, or influenza C virus. In some cases, the methods provided herein are used in connection with identification of epitope sequences of a pathogen, e.g., a virus, e.g., an RNA virus, e.g., an influenza virus, e.g., an influenza A influenza B, or influenza C virus, for use in a vaccine. The epitope sequences can be from one or more of, or have homology to one or more of, PB1, PB1-F2, PB2, PA, HA, NP, NA, M1, M2, NS1, or NEP/NS2.

Invariance, or invariant peptide regions, can be determined, e.g., as described in International PCT application publication WO/2015/157189, filed Apr. 6, 2015, which is herein incorporated by reference in its entirety. Invariance can describe the functional importance of an amino acid residue in the context of the fitness of a pathogen. Invariance can be a measurement of the fitness of a pathogen. At an amino acid residue level, invariance can be associated with how tolerant an amino acid residue is to a mutation and how adverse this mutation is to the ability of the pathogen to propagate, that is, fitness of the pathogen. Invariance can be correlated with the role of an amino acid residue in a pathogen's survival. For example, a mutation in a pathogen that exerts a deleterious effect on the proliferation of the pathogen can be considered a destructive mutation and would not be propagated within a pathogen population. An associated amino acid position correlated with the deleterious mutation can be characterized as invariant as its mutation would not be tolerated.

The methods can comprise generating a nucleic acid library. In some instances, the nucleic acid library can allow simulation of all possible mutations that can occur in a particular pathogen strain, for example, by generating a pool of mutant influenza A viruses or influenza B viruses. In some cases, the methods can further comprise introducing the library to cells to support production of a pool of pathogens, e.g. influenza A viruses. Sometimes, the methods can further comprise infection of cells with the pool of pathogens for a number of rounds (e.g., 1, 2, 3, 4, 5, 6, 7, 8, 9, 10 or more rounds), obtaining the resultant pool of pathogens, e.g. influenza A viruses, and generating a second sequencing library. The methods can further comprise obtaining the nucleic acid sequences of the second sequencing library. In some instances, the methods can further comprise comparing the sequences (e.g., comparing sequences from the library to sequences from the second library, or a library from the last round of infection) to obtain invariant sequence regions, e.g. invariant peptide regions. An invariant sequence region can have an average invariance ratio (frequency of mutant in final population/frequency in initial population) of $<0.05$, $<0.08$, $<0.1$, $<0.2$, $<0.3$, or $<0.4$ among all possible mutations in the stretch. The methods can further comprise evaluating the invariant sequence regions. In some cases, the methods can further comprise HLA affinity binding analysis of the invariant sequence regions, some additional immunogenicity analysis for vaccine development and treatment of patient, or any combination thereof. The term "immunogenicity," as used herein, can refer to the capability of a particular substance, e.g., antigen or epitope, to induce an immune response. In some cases, a first screen for epitope sequences for use in a vaccine comprises identifying immunogenicity peptide sequences and then evaluating the epitope sequences for sequence invariance.

HLA affinity binding analysis can be carried out using analysis programs such as NetMHCpan4.0 from the Center for Biological Sequences Analysis (CBS) at the Technical University of Denmark, HLA Peptide Binding Predictions server from the National Institute of Health, MHC-1 binding predictions server from the Immune Epitope Database (IEDB), and the like.

In some cases, candidate invariant sequences identified by a method provided herein can be further analyzed. For instance, the candidate invariant sequences can be compared against experimentally tested immunogenicity data of influenza virus epitopes, e.g., in various databases, such as Influenza Research Database (https://www.fludb.org). Upon the comparison, candidate invariant sequences with experimentally proven immunogenicity (e.g., deposited at https://fludb.org) can be identified and subject to either further analysis, or vaccine development. For instance, such candidate invariant sequences, or the variants thereof, can be chosen to be one of the constituent epitope sequences of a polypeptide as described herein, which can be expressed from a transgene as described herein, and the transgene can be part of a vector, e.g., a viral vector, for producing a virus-based vaccine, e.g., an adenoviral-based vaccine.

Additional Analysis

Additional analysis can be carried out to select candidate invariant sequences or peptides for vaccine development and for administration of the vaccine to a patient for treatment or prevention of a condition, e.g., influenza. These additional analysis or screenings can involve analysis of an immune response based on immunological assays. In some cases, test animals are first immunized (prime) with or without a second immunization (boost) following weeks after the prime and blood or tissue samples are collected, for example, two to four weeks after the last immunization. These studies can allow measurement of immune parameters that correlate to protective immunity, such as induction of specific antibodies (e.g., IgA, IgD, IgE, IgG, or IgM) and induction of specific T lymphocyte responses, in addition to determining whether an antigen or pools of antigens provides protective immunity.

Spleen cells, lung cells. cells from mediastinal lymph nodes, or peripheral blood mononuclear cells can be isolated from immunized test animals and measured for the presence of antigen-specific T cells and induction of cytokine synthesis. ELISA, ELISPOT, or cytoplasmic cytokine staining, alone or combined with flow cytometry, can provide such information on a single-cell level.

Immunological tests that can be used to identify the efficacy of immunization include antibody measurements, neutralization assays and analysis of activation levels or frequencies of antigen presenting cells or lymphocytes that are specific for the antigen or pathogen. The test animals that can be used in such studies include mice, rats, guinea pigs, hamsters, rabbits, cats, dogs, pigs, monkeys, or humans.

Monkey can be a useful test animal, e.g., due to the similarities of the MHC molecules between monkeys and humans. Virus neutralization assays can be useful for detection of antibodies that not only specifically bind to a pathogen, but also neutralize the function of the pathogen (e.g., virus). These can be based on detection of antibodies in the sera of immunized animal and analysis of these antibodies for their capacity to inhibit pathogen (e.g., virus) growth in tissue culture cells. Such assays are known to those skilled in the art. Virus neutralization assays can be used to screen for antigens that also provide protective immunity.

Polypeptides

One aspect of the present disclosure provides polypeptides that comprise, consist of, or consist essentially of, one or more influenza virus epitope sequences, for example, influenza A virus epitope sequences.

As used herein, a peptide or polypeptide that "comprises" a sequence according to a specified sequence or formula can be a peptide or polypeptide that can include additional amino acid residues, amino acid isomers, and/or amino acid analogs at its N-terminus, C-terminus, or both. The additional residues may or may not change its activity or function, e.g., increase or decrease the activity of the peptide as compared to the activity of a peptide consisting solely of the specified sequence or formula. As used herein, a peptide that "consists essentially of" a specified sequence or formula can mean that the peptide can include additional amino acid residues, amino acid isomers, and/or amino acid analogs at its N-terminus, C-terminus, or both, so long as the additional residues do not materially change its activity or function, e.g., increase or decrease the activity of the peptide as compared to the activity of a peptide consisting solely of the specified sequence or formula. As used herein, a peptide that "consists of" a specified sequence or formula can mean that the peptide does not include additional amino acid residues, amino acid isomers, and/or amino acid analogs at both its N-terminus and C-terminus.

The polypeptide can comprise, consist of, or consist essentially of, epitope sequences identified by the exemplary methods provided by the present disclosure. For instance, the polypeptide can comprise, consist of, or consist essentially of, one or more epitope sequences selected from the group consisting of: SEQ ID NOs: 1-94, or one or more epitope sequences selected from Table 1, Table 2, or Table 3. Tables 1, 2, and 3 below list epitope sequences, and viral proteins, which the epitope sequences are derived from, or variations of. Each of the polypeptides described herein can be chemically synthesized, or expressed in vivo, or in vitro. The polypeptide can be encoded by a nucleic acid, and the nucleic acid can be within a vector, e.g., viral vector, e.g., adenoviral vector. The vector, e.g. adenoviral vector, can be used to generate a recombinant virus, e.g. a recombinant adenovirus. Any of the polypeptides herein can be different than a full length viral protein. A polypeptide provided herein can be non-naturally occurring. A "non-naturally occurring polypeptide," as the term is used herein, can refer to a polypeptide whose primary sequence does not occur in nature, e.g., cannot be found in a single molecule in nature.

TABLE 1

| Protein | SEQ ID NO: | Sequences |
|---|---|---|
| PB1 | SEQ ID NO: 1 | GPATAQMAL |
| PB1 | SEQ ID NO: 2 | GTFEFTSFFY |
| PB1 | SEQ ID NO: 3 | YSHGTGTGY |
| PB1 | SEQ ID NO: 4 | GLPVGGNEKKAKLANVVR |
| PB1 | SEQ ID NO: 5 | GMMMGMFNMLSTVLGVS |
| PB1 | SEQ ID NO: 6 | LQLFIKDYRYTYRCHRG |
| PB1 | SEQ ID NO: 7 | RRAIATPGM |
| PA | SEQ ID NO: 8 | FMYSDFHFI |
| PA | SEQ ID NO: 9 | MRRNYFTAEVSHCRATEY |
| PA | SEQ ID NO: 10 | QLMWALGENMA |
| PA | SEQ ID NO: 11 | DVVNFVSMEFSLTDPRL |
| PA | SEQ ID NO: 12 | KWGMEMRRCLLQSLQQI |
| NP | SEQ ID NO: 13 | AEIEDLIFLA |
| NP | SEQ ID NO: 14 | CTELKLSDY |
| NP | SEQ ID NO: 15 | CTELKLTDQ |
| NP | SEQ ID NO: 16 | CTELKLTDY |
| NP | SEQ ID NO: 17 | ELRSRYWAIRTRSG |
| NP | SEQ ID NO: 18 | ELKSRYWAIRTRSG |
| NP | SEQ ID NO: 19 | GMDPRMCSL |
| NP | SEQ ID NO: 20 | ILKGKFQTA |
| NP | SEQ ID NO: 21 | ILRGSIAHK |
| NP | SEQ ID NO: 22 | ILRGSVAHK |
| NP | SEQ ID NO: 23 | LELRSRYWAI |
| NP | SEQ ID NO: 24 | LIFLARSAL |
| NP | SEQ ID NO: 25 | RGINDRNFW |
| NP | SEQ ID NO: 26 | FLARSALILRGSVAHK |
| NP | SEQ ID NO: 27 | RMVLSAFDER |
| NP | SEQ ID NO: 28 | TLELRSGYWAIRTRSGGN |
| NP | SEQ ID NO: 29 | IAYERMCNILKGKFQTAA |
| NP | SEQ ID NO: 30 | FLARSALILRGSVAHKS |
| NP | SEQ ID NO: 31 | FQGRGVFEL |
| NP | SEQ ID NO: 32 | GQISIQPTFS |
| NP | SEQ ID NO: 33 | WHSNLNDATYQRTRALVRTGMDPRM |
| NP | SEQ ID NO: 34 | WHSNLNDTTYQRTRALVRTGMDPRM |
| NA | SEQ ID NO: 35 | CVNGSCFTV |
| M1 | SEQ ID NO: 36 | RMVLASTTAK |

TABLE 2

| SEQ ID NO: | Peptide | Protein | HLA (Experimentally Validated) | Additional HLA (NetMHCpan3.0 prediction) | Inv. Ratio |
|---|---|---|---|---|---|
| 35 | CVNGSCFTV | NA | A2 | | 0.044 |
| 38 | CVNGSCYTV | NA | | | |
| 17 | ELRSRYWAIRTRSG | NP | B27 | A3, A26, B8 | 0.053 |

TABLE 2-continued

| SEQ ID NO: | Peptide | Protein | HLA (Experimentally Validated) | Additional HLA (NetMHCpan3.0 prediction) | Inv. Ratio |
|---|---|---|---|---|---|
| 39 | ELKSRYWAIRTRSG | NP | | | |
| 8 | FMYSDFHFI | PA | A2 | A24, B8, B39, B15 | 0.05 |
| 40 | FMYSDLHFI | PA | | | |
| 41 | FMYTDFHFI | PA | | | |
| 19 | GMDPRMCSL | NP | A2 | B39 | 0.052 |
| 42 | GRDPRMCSL | NP | | | |
| 2 | GTFEFTSFFY | PB1 | A3 | A1, A24, A26, B58, B15 | 0.04 |
| 43 | GTFEFTSYFY | PB1 | | | |
| 20 | ILKGKFQTA | NP | B8 | | 0.056 |
| 44 | IIKGKFQTA | NP | | | |
| 45 | ILKGKFQIA | NP | | | |
| 21 | ILRGSIAHK | NP | A3 | | 0.03 |
| 46 | ILRGSVAHK | NP | | | |
| 47 | LQLRSRYWAI | NP | | B8 | |
| 48 | LELRSRHWAI | NP | | | |
| 24 | LIFLARSAL | NP | A2 | B7, B8, B15 | 0.056 |
| 49 | LVFLARSAL | NP | | | |
| 50 | RWINDRNFW | NP | | | |
| 3 | YSHGTGTGY | PB1 | A1 | A26, B15 | 0.055 |
| 51 | YSHWTGTGY | PB1 | | | |
| 52 | YSHGSGTGY | PB1 | | | |
| 26 | FLARSALILRGSVAHK | NP | | A2, A3, B7, B27, B8, B39, B15 | 0.033 |
| 53 | FLARSALVLRGSVAHK | NP | | | |
| 29 | IAYERMCNILKGKFQTAA | NP | B40 | A3, A24, B8, B27, B15 | 0.058 |
| 54 | IAYERMCNIIKGKFQTAA | NP | | | |
| 55 | IAYERMCNILKVKFQTAA | NP | | | |
| 56 | IAYERMCNILKGKFKTAA | NP | | | |
| 57 | IAYERMCNILKGKFQIAA | NP | | | |
| 11 | DVVNFVSMEFSLTDPRL | PA | | A1, A3, A24, A26, B8, B39, B40, B58, B15 | 0.021 |
| 58 | DVVNFVSMEFSLTYPRL | PA | | | |
| 59 | DVVNFVSMEFSLTDQRL | PA | | | |
| 30 | FLARSALILRGSVAHKS | NP | A3 | A2, B7, B8, B27, B39, B15 | 0.049 |

TABLE 2-continued

| SEQ ID NO: | Peptide | Protein | HLA (Experimentally Validated) | Additional HLA (NetMHCpan3.0 prediction) | Inv. Ratio |
|---|---|---|---|---|---|
| 60 | FLARSALVLRGSVAHKS | NP | | | |
| 12 | KWGMEMRRCLLQSLQQI | PA | | A2, A24, B7, B8, B27, B39, B40 | 0.031 |
| 61 | KLGMEMRRCLLQSLQQI | PA | | | |
| 62 | KWGMEMRRCLLQSLQQV | PA | | | |
| 6 | LQLFIKDYRYTYRCHRG | PB1 | | A26, B27, B15 | 0.05 |
| 63 | LQLFIKDFRYTYRCHRG | PB1 | | | |
| 64 | LQLFIKDYRYTYRCLRG | PB1 | | | |
| 65 | LQLFIKDYRYTYRCPRG | PB1 | | | |
| 66 | LQLFIKDYRYTYRCHRV | PB1 | | | |
| 31 | FQGRGVFEL | NP | A2 | B39, B40 | 0.04 |
| 67 | FQGPGVFEL | NP | | | |
| 32 | GQISIQPTFS | NP | | B40, B15 | 0.053 |
| 68 | SQISIQPTFS | NP | | | |
| 69 | GQVSIQPTFS | NP | | | |
| 70 | GQISVQPTFS | NP | | | |
| 71 | GQNSIQPTFS | NP | | | |
| 33 | WHSNLNDATYQRTRALVRTGMDPRM | NP | B27 | A1, A3, A24, A26, B7, B8, B39, B58, B15 | N/A |
| 72 | WHSNLNDTTYQRTRALVRTGMDPRM | NP | | | |
| 73 | WHSNLNDSTYQRTRALVRTGMDPRM | NP | | | |
| 74 | WHSNLNDATYQRKRALVRTGMDPRM | NP | | | |
| 75 | WHSNLNDATYQRTRSLVRTGMDPRM | NP | | | |
| 76 | WHSNLNDATYQRTRAIVRTGMDPRM | NP | | | |
| 77 | WHSNLNDATYQRTRALVRSGMDPRM | NP | | | |
| 78 | WHSNLNDATYQRTRALVRTGRDPRM | NP | | | |

TABLE 3

| SEQ ID NO: | Peptide | Protein | HLA (Experimentally Validated) | Additional HLA (NetMHCpan3.0 prediction) |
|---|---|---|---|---|
| 17 | ELRSRYWAIRTRSG | NP | B27 | B8 |
| 82 | ELRSRHWAIRTRSG | NP | B27 | B8 |
| 83 | ELRSRYWASRTRSG | NP | | |
| 8 | FMYSDFHFI | PA | A2 | A24, B8, B39, B15 |
| 40 | FMYSDLHFI | PA | A2 | B8 4.00 pctl, A26 1.9 pctl |
| 41 | FMYTDFHFI | PA | A2 | A26 3.5 pctl, A24, B8, B39, B15 |
| 84 | FMFSDFHFI | PA | | |
| 2 | GTFEFTSFFY | PB1 | A3 | A1, A24, A26, B58, B15 |
| 43 | GTFEFTSYFY | PB1 | A3 | A1, A24, A26, B58, B15 |
| 20 | ILKGKFQTA | NP | B8 | |
| 44 | IIKGKFQTA | NP | B8 | |
| 45 | ILKGKFQIA | NP | B8 | |
| 21 | ILRGSIAHK | NP | A3 | |
| 22 | ILRGSVAHK | NP | A3 | |
| 85 | VLRGSIAHK | NP | | |
| 24 | LIFLARSAL | NP | A2 (negative on NetMHC) | B7, B8, B15 |
| 49 | LVFLARSAL | NP | | B7, B8, B15, B39 1.9 pctl |
| 86 | LTFLARSAL | NP | | |
| 3 | YSHGTGTGY | PB1 | A1 | A26, B15 |
| 51 | YSHWTGTGY | PB1 | A1 | A26, B15 |
| 52 | YSHGSGTGY | PB1 | A1 | A26, B15 |
| 26 | FLARSALILRGSVAHK | NP | | A2, A3, B7, B8, B39, B15 |
| 53 | FLARSALVLRGSVAHK | NP | | A2, A3, B7, B8, B39, B15 |
| 29 | IAYERMCNILKGKFQTAA | NP | B40 | A3, A24, B8, B27 |
| 87 | VAYERMCNILKGKFQTAA | NP | | |
| 88 | VAYERMCNIIKGKFQTAA | NP | B40 | A3, A24, B8, B27 |
| 89 | VAYERMCNILKGKFKTAA | NP | B40 | A3, A24, B8, B27 |
| 90 | VAYERMCNILKGKFQIAA | NP | B40 | A3, A24, B8, B27 |
| 91 | VAYERMCNILKGKFQTAV | NP | | |
| 11 | DVVNFVSMEFSLTDPRL | PA | | A1, A3, A24, A26, B8, B39, B40, B58, B15 |
| 58 | DVVNFVSMEFSLTYPRL | PA | | A1, A3, A24, A26, B8, B39, B40, B58, B15 |
| 59 | DVVNFVSMEFSLTDQRL | PA | | A3 2.5 pctl |

TABLE 3-continued

| SEQ ID NO: | Peptide | Protein | HLA (Experimentally Validated) | Additional HLA (NetMHCpan3.0 prediction) |
|---|---|---|---|---|
| 30 | FLARSALILRGSVAHKS | NP | A3 | A2, B7, B8, B39, B15 |
| 60 | FLARSALVLRGSVAHKS | NP | A3 | A2, B7, B8, B39, B15 |
| 12 | KWGMEMRRCLLQSLQQI | PA | | A2, B8, B27, B39 |
| 61 | KLGMEMRRCLLQSLQI | PA | | A2, B8, B27, B39 |
| 62 | KWGMEMRRCLLQSLQQV | PA | | A2, B8, B27, B39 |
| 92 | KWGMELRRCLLQSLQI | PA | | |
| 31 | FQGRGVFEL | NP | A2 | B39, B40 |
| 32 | GQISIQPTFS | NP | | B40, B15 |
| 93 | SQISVQPTFS | NP | | B39, B40, A24 (WB), B39 (WB) |
| 94 | GQVSVQPTFS | NP | | B39, B40 |
| 70 | GQISVQPTFS | NP | | B39, B40 |
| 33 | WHSNLNDATYQRTRALVRTGMDPRM | NP | B27 | A1, A3, A24, A26, B7, B8, B39, B58, B15 |
| 34 | WHSNLNDTTYQRTRALVRTGMDPRM | NP | B27 | A1, A3, A24, A26, B7, B8, B39, B58, B15 |
| 73 | WHSNLNDSTYQRTRALVRTGMDPRM | NP | B27 | A1, A3, A24, A26, B7, B8, B39, B58, B15 |
| 74 | WHSNLNDATYQRKRALVRTGMDPRM | NP | B27 | A1, A3, A24, A26, B7, B8, B39, B58, B15 |
| 75 | WHSNLNDATYQRTRSLVRTGMDPRM | NP | B27 | A1, A3, A24, A26, B7, B8, B39, B58, B15 |
| 76 | WHSNLNDATYQRTRAIVRTGMDPRM | NP | B27 | A3 2.5 pctl |
| 77 | WHSNLNDATYQRTRALVRSGMDPRM | NP | B27 | A1, A3, A24, A26, B7, B8, B39, B58, B15 |
| 78 | WHSNLNDATYQRTRALVRTGRDPRM | NP | B27 | A1, A3, A24, A26, B7, B8, B39, B58, B15 |

A polypeptide as described herein can comprise, consist of, or consist essentially of one or more epitope sequences. Sometimes, a polypeptide as described herein can comprise, consist of, or consist essentially of, more than one epitope sequence, among which some of the epitope sequences are the same, while others of the epitope sequences are different, or all the epitope sequences are the same, or all the epitope sequences are different. In some cases, one or more epitope sequences are repeated in a polypeptide, e.g., about, at least, or at most 2, 3, 4, 5, 6, 7, 8, 9, 10, 15, or 20 times. Sometimes, the polypeptide can comprise, consist of, or consist essentially of, one or more different epitope sequences. The polypeptide can comprise, consist of, or consist essentially of only one epitope sequence, and the one epitope sequence can be present in the polypeptide about, at least, or at most 1, 2, 3, 4, 5, 6, 7, 8, 9, 10, 15, or 20 times.

In some cases, a polypeptide can comprise, consist of, or consist essentially of one or more different epitope sequences, each of the one or more different epitope sequences comprising at least 70% sequence identity to at least 8 contiguous amino acids of a sequence selected from the group consisting of SEQ ID NOs: 1-94. A polypeptide provided herein can comprise, consist of, or consist essentially of one or more different epitope sequences, each of the one or more different epitope sequences comprising at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100% sequence identity to at least 8 contiguous amino acids of a sequence selected from the group consisting of SEQ ID NOs: 1-94. In some embodiments, the polypeptide comprises, consists of, or consists essentially of one or more different epitope sequences, each of the one or more different epitope sequences comprising at least 70% sequence identity to at least 4, at least 5, at least 6, at least 7, at least 8, at least 9, at least 10, at least 12, at least 14, at least 16, at least 18, at least 20, at least 22, at least 24, or at least 25 contiguous amino acids of a sequence selected from the group consisting of SEQ ID NOs: 1-94. A polypeptide can comprise, consist of, or consist essentially of one or more different epitope sequences, each of the one or more different epitope sequences comprising at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100% sequence identity to at least 4, at least 5, at least 6, at least 7, at least 8, at least 9, at least 10, at least 12, at least 14, at least 16, at least 18, at least 20, at least 22, at least 24, or at least 25 contiguous amino acids of a sequence selected from the group consisting of SEQ ID NOs: 1-94.

In some cases, a polypeptide can comprise, consist of, or consist essentially of one or more different epitope sequences, each of the one or more different epitope sequences comprises at least 70% sequence identity to at least 8 contiguous amino acids of a sequence selected from Table 1, Table 2, Table 3, or any combination thereof. A polypeptide provided herein can comprise, consist of, or consist essentially of one or more different epitope sequences, each of the one or more different epitope sequences comprising at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100% sequence identity to at least 8 contiguous amino acids of a sequence selected from Table 1, Table 2, Table 3, or any combination thereof. The polypeptide can comprise, consist of, or consist essentially of one or more different epitope sequences, each of the one or more different epitope sequences comprising at least 70% sequence identity to at least 4, at least 5, at least 6, at least 7, at least 8, at least 9, at least 10, at least 12, at least 14, at least 16, at least 18, at least 20, at least 22, at least 24, or at least 25 contiguous amino acids of a sequence selected from Table 1, Table 2, Table 3, or any combination thereof. A polypeptide can comprise, consist of, or consist essentially of one or more different epitope sequences, each of the one or more different epitope sequences comprising at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100% sequence identity to at least 4, at least 5, at least 6, at least 7, at least 8, at least 9, at least 10, at least 12, at least 14, at least 16, at least 18, at least 20, at least 22, at least 24, or at least 25 contiguous amino acids of a sequence selected from Table 1, Table 2, Table 3, or any combination thereof.

A polypeptide can comprise, consist of, or consist essentially of at least two different epitope sequences, each of the at least two different epitope sequences comprises at least 70% sequence identity to at least 8 contiguous amino acids of a sequence selected from the group consisting of SEQ ID NOs: 1-94 or of a sequence selected from Table 1, Table 2, or Table 3. The polypeptide can comprise, consist of, or consist essentially of at least three different epitope sequences, each of the at least three different epitope sequences comprising at least 70% sequence identity to at least 8 contiguous amino acids of SEQ ID NOs: 1-94 or of a sequence selected from Table 1, Table 2, or Table 3. The polypeptide can comprise, consist of, or consist essentially of at least four different epitope sequences, each of the at least four different epitope sequences comprising at least 70% sequence identity to at least 8 contiguous amino acids of SEQ ID NOs: 1-94 or of a sequence selected from Table 1, Table 2, or Table 3. The polypeptide can comprise, consist of, or consist essentially of, at least five different epitope sequences, each of the at least five different epitope sequences comprises at least 70% sequence identity to at least 8 contiguous amino acids of SEQ ID NOs: 1-94 or of a sequence selected from Table 1, Table 2, or Table 3. The polypeptide can comprise, consist of, or consist essentially of at least 2, at least 3, at least 4, at least 5, at least 6, at least 7, at least 8, at least 9, at least 10, at least 15, at least 20, at least 25, at least 30, at least 35, at least 40, at least 50, or at least 51 different epitope sequences, each of the different epitope sequences comprising at least 70% sequence identity to at least 8 contiguous amino acids of SEQ ID NOs: 1-94 or of a sequence selected from Table 1, Table 2, or Table 3.

One non-limiting example relates to a polypeptide that comprises, consists of, or consists essentially of, at least 51 different epitope sequences, each of the 51 different epitope sequences comprises at least 70% sequence identity to at least 8 contiguous amino acids of a different sequence selected from Table 3. Sometimes, a polypeptide can comprise, consist of, or consist essentially of, at least 51 different epitope sequences, each of the 51 different epitope sequences comprises at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100% sequence identity to at least 4, at least 5, at least 6, at least 7, at least 8, at least 9, at least 10, at least 12, at least 14, at least 16, at least 18, at least 20, at least 22, at least 24, or at least 25 contiguous amino acids of a different sequence selected from Table 3. In some cases, a polypeptide comprises, consists of, or consists essentially of each sequence from Table 3.

In some cases, the polypeptide comprises at least 8 amino acids. The polypeptide can comprise at least 8, at least 9, at least 10, at least 15, at least 20, at least 25, at least 30, at least 35, at least 40, at least 50, at least 60, at least 70, at least 80, at least 90, at least 100, at least 120, at least 140, at least 160, at least 180, at least 200, at least 250, at least 300, at least 400, at least 500, at least 1000, at least 1500, at least 2000, at least 2500, at least 3000, at least 4000, at least 5000, or more amino acids. In some cases, the polypeptide comprises, or consists of, at most 20, at most 30, at most 40, at most 50, at most 60, at most 70, at most 80, at most 90, at most 100, at most 150, at most 200, at most 250, at most 300, at most 500, at most 800, at most 1000, at most 1500, at most 2000, at most 2500, at most 3000, at most 4000, or at most 5000 amino acids. The polypeptide can comprise, consist of, or consist essentially of about 8 to about 5000 amino acids, about 8 to about 4000 amino acids, about 8 to about 3000 amino acids, about 8 to about 2000 amino acids, about 8 to about 1000 amino acids, about 8 to about 500 amino acids, about 100 to about 5000 amino acids, about 100 to about 2500 amino acids, about 100 to about 1000 amino acids, about 1500 to about 3000 amino acids, about 1000 to about 3000 amino acids, or about 1000 to about 2500 amino acids. The polypeptide can consist of less than 5000, 4000, 3000, 2900, 2800, 2700, 2600, 2500, 2400, 2300, 2200, 2100, 2000, 1900, 1800, 1700, 1600 1500, 1400, 1300, 1200, 1100, 1000, 750, 500, 250, or 100 amino acids, e.g., when synthesized or initially expressed, e.g., in a cell.

Provided herein is an engineered polypeptide that comprises, consists of, or consists essentially of one or more different epitope sequences that can be derived from, or variants of, or fragments of, at least a portion of a viral protein, e.g., an influenza virus protein, e.g. an influenza A virus protein. In some embodiments, the influenza A virus protein can be PB1, PB1-F2, PB2, PA, HA, NP, NA, M1, M2, NS1, or NEP/NS2. PB2 can be a part of an RNA-dependent RNA polymerase complex, which can facilitate "cap-snatching" from host pre-mRNA molecules to initiate transcription, and can be conducive for replication. In certain situations, PB1 can be a RNA-dependent RNA polymerase, which can bind to terminal ends of vRNA and cRNA for initiation of transcription and replication and can catalyze the sequential addition of nucleotides during RNA chain elongation. PA can be used for viral transcription and replication and can have endonuclease activity. In some instances, PA does not correlate with polymerase activity. HA can bind sialic acid on cell surface for attachment, and can undergo conformational change with low pH exposing fusion peptide which can interact with the endosomal membrane, forming a pore through which the viral RNPs can be released into the cytoplasm. NP can coat viral RNA to form viral ribonucleoprotein (vRNP) complex, which can be critical for the trafficking of vRNPs into the nucleus. NA can be needed for the final release of virus through cleavage of the HA-sialic acid bond which can anchor virus to cell membrane. NA can also prevent virus particles from aggregating. M1 can form intermediate core of a virion and tether NP w/vRNPs, and can drive budding of virus from the cell membrane. M2 can have ion channel activity, and can conduct protons from acidified endosomes into viral particle resulting in pH dependent dissociation of vRNP from the remainder of viral components. NS1 can inhibit cellular antiviral Type 1 Interferon response, and can be dependent on binding to dsRNA. NEP/NS2 can be necessary for nuclear export of vRNP through recruitment of cellular export machinery. The influenza A virus protein can be NP, PB1, or PA.

One non-limiting example of the polypeptide provided herein comprises, consists of, or consists essentially of one or more different epitope sequences having at least 70%, 75%, 80%, 85%, 90%, or 100% sequence identity to at least 8 contiguous amino acids of a sequence derived from or variants of PB1 protein, such as, but not limited to a sequence selected from the group consisting of SEQ ID NOs: 1-7, 43, 51, 52, and 63-66, or a sequence selected from the group consisting of SEQ ID Nos: 2, 3, 43, 51, and 52. In some cases, the polypeptide further comprises one or more different epitope sequences having at least 70%, 75%, 80%, 85%, 90%, or 100% sequence identity to at least 8 contiguous amino acids of a sequence selected from the group consisting of SEQ ID NOs: 8-42, 44-50, 53-62, 67-80, and 82-94. The polypeptide can comprise, consist of, or consist essentially of SEQ ID NOs: 2, 3, 8, 11, 12, 17, 20-22, 24, 26, 29-34, 40, 41, 43-45, 49, 51-53, 58-62, 70, 73-78, and 82-94. In some cases, the polypeptide does not comprise full-length PB1 sequence.

Another non-limiting example of the polypeptide provided herein comprises, consists of, or consists essentially of one or more different epitope sequences having at least 70% sequence identity to at least 8 contiguous amino acids of a sequence derived from or variants of PA protein, such as, but limited to a sequence selected from the group consisting of SEQ ID NOs: 8-12, 40, 41, 58, 59, 61, 62, 84, and 92, or a sequence selected from the group consisting of SEQ ID NOs: 8, 11, 12, 40, 41, 58, 59, 61, 62, 84, and 92. Sometimes, the polypeptide can further comprise one or more different epitope sequences having at least 70% sequence identity to at least 8 contiguous amino acids of a sequence selected from the group consisting of SEQ ID NOs: 1-7, 13-39, 42-57, 60, 63-80, 82, 83, 85-91, and 94. The polypeptide can comprise, consist of, or consist essentially of SEQ ID NOs: 2, 3, 8, 11, 12, 17, 20-22, 24, 26, 29-34, 40, 41, 43-45, 49, 51-53, 58-62, 70, 73-78, and 82-94. In some cases, the polypeptide does not comprise full-length PA sequence.

Another non-limiting example of the polypeptide provided herein comprises, consists of, or consists essentially of, one or more different epitope sequences having at least 70%, 75%, 80%, 85%, 90%, or 100% sequence identity to at least 8 contiguous amino acids of a sequence derived from or variants of NP protein, such as, but not limited to a sequence selected from the group consisting of SEQ ID NOs: 13-34, 37, 39, 42, 44-50, 53-57, 60, 67-80, 82, 83, 85-91, 93, and 94, or a sequence from the group consisting of SEQ ID NOs: 17, 20-22, 24, 26, 29-34, 44, 45, 49, 53, 60, 70, 73-78, 82, 83, 85-91, 93, and 94. Sometimes, the polypeptide can further comprise one or more different epitope sequences having at least 70%, 75%, 80%, 85%, 90%, or 100% sequence identity to at least 8 contiguous amino acids of a sequence selected from the group consisting of SEQ ID NOs: 1-12, 35, 36, 38, 43, 51, 52, 58, 59, 61-66, 84, and 92. The polypeptide can comprise, consist of, or consist essentially of SEQ ID NOs: 2, 3, 8, 11, 12, 17, 20-22, 24, 26, 29-34, 40, 41, 43-45, 49, 51-53, 58-62, 70, 73-78, and 82-94. In some cases, the polypeptide does not comprise full-length NP sequence.

Another non-limiting example of the polypeptide provided herein comprises, consists of, or consists essentially of one or more different epitope sequences having at least 70%, 75%, 80%, 85%, 90%, or 100% sequence identity to at least 8 contiguous amino acids of a sequence derived from or variants of NA protein, such as, but not limited to, a sequence selected from SEQ ID NOs: 35 and 38. Sometimes, the polypeptide can further comprise one or more different epitope sequences having at least 70%, 75%, 80%, 85%, 90%, or 100% sequence identity to at least 8 contiguous amino acids of a sequence selected from the group consisting of SEQ ID NOs: 1-34, 36, 37, 39-80, and 82-94. The polypeptide can comprise, consist of, or consist essentially of SEQ ID NOs: 2, 3, 8, 11, 12, 17, 20-22, 24, 26, 29-34, 40, 41, 43-45, 49, 51-53, 58-62, 70, 73-78, and 82-94. In some cases, the polypeptide does not comprise full-length NA sequence.

Another non-limiting example of the polypeptide provided herein comprises, consists of, or consists essentially of, one or more different epitope sequences having at least 70%, 75%, 80%, 85%, 90%, or 100% sequence identity to at least 8 contiguous amino acids of a sequence derived from or variants of M1 protein, such as, but not limited to SEQ ID NOs: 36. Sometimes, the polypeptide further comprises one or more different epitope sequences having at least 70%, 75%, 80%, 85%, 90%, or 100% sequence identity to at least 8 contiguous amino acids of a sequence selected from the group consisting of SEQ ID NOs: 1-35, 37-80, and 82-94. The polypeptide can comprise, consist of, or consist essentially of SEQ ID NOs: 2, 3, 8, 11, 12, 17, 20-22, 24, 26, 29-34, 40, 41, 43-45, 49, 51-53, 58-62, 70, 73-78, and 82-94. In some cases, the polypeptide does not comprise full-length M1 sequence.

One non-limiting example of a polypeptide provided herein can comprise, consist of, or consist essentially of a first sequence selected from the group consisting of SEQ ID NOs: 2, 3, 8, 11, 12, 40, 41, 43, 51, 52, 58, 59, 61, 62, 84, and 92; and a second sequence selected from the group consisting of SEQ ID NOs: 17, 20, 21, 22, 24, 26, 29, 30, 32, 33, 34, 44, 45, 49, 53, 60, 70, 73, 74, 75, 76, 77, 78, 82, 83, 85, 86, 87, 88, 89, 90, 91, 93, and 94.

Another non-limiting example of a polypeptide provided herein can comprise, consist of, or consist essentially of a first sequence selected from the group consisting of SEQ ID NOs: 2, 8, 11, 12, 40, 41, 43, 52, 58, 59, 61, 62, 84, and 92; and a second sequence selected from the group consisting of SEQ ID NOs: 17, 20, 21, 22, 24, 26, 29, 30, 31, 32, 33, 34, 44, 45, 49, 53, 60, 70, 73, 74, 75, 76, 77, 78, 82, 83, 85, 86, 87, 88, 89, 90, 91, 93, and 94.

Another non-limiting example of a polypeptide provided herein can comprise, consist of, or consist essentially of (a) a first sequence comprising at least 60%, at least 75%, at least 85%, or 100% sequence identity to at least 8 contiguous amino acids of SEQ ID NO: 8, 11, 12, 40, 41, 58, 59, 61, 62, 84, or 92, and a second sequence comprising at least 60%, at least 75%, at least 85%, or 100% sequence identity to at least 8 contiguous amino acids of SEQ ID NO: 2, 3, 17, 20, 21, 22, 24, 26, 29, 30, 31, 32, 33, 34, 43, 44, 45, 49, 51, 52, 53, 60, 70, 73, 74, 75, 76, 77, 78, 82, 83, 85, 86, 87, 88, 89, 90, 91, 93, or 94; or (b) a first sequence comprising at least 60%, at least 75%, at least 85%, or 100% sequence identity to at least 8 contiguous amino acids of SEQ ID NO: 2 or 43 and a second sequence comprising at least 60%, at least 75%, at least 85%, or 100% sequence identity to at least 8 contiguous amino acids of SEQ ID NO: 8, 11, 12, 17, 20, 21, 22, 24, 26, 29, 30, 31, 32, 33, 34, 40, 41, 44, 45, 49, 53, 58, 59, 60, 61, 62, 70, 73, 74, 75, 76, 77, 78, 82, 83, 84, 85, 86, 87, 88, 89, 90, 91, 92, 93, or 94; or (c) a first sequence comprising at least 60%, at least 75%, at least 85%, or 100% sequence identity to at least 8 contiguous amino acids of SEQ ID NO: 21, 22, 24, 26, 30, 32, 49, 53, 60, 70, 85, 86, 93, or 94, and a second sequence comprising at least 60%, at least 75%, at least 85%, or 100% sequence identity to at least 8 contiguous amino acids of SEQ ID NO: 2, 3, 8, 11, 12, 40, 41, 43, 51, 52, 58, 59, 61, 62, 84, or 92; or (d) a first sequence comprising at least 60%, at least 75%, at least 85%, or 100% sequence identity to at least 8 contiguous amino acids of SEQ ID NO: 17, 20, 29, 31, 33, 34, 44, 45, 73, 74, 75, 76, 77, 78, 82, 83, 87, 88, 89, 90, or 91 and a second sequence comprising at least 60%, at least 75%, at least 85%, or 100% sequence identity to at least 8 contiguous amino acids of SEQ ID NO: 2, 8, 11, 12, 40, 41, 43, 58, 59, 61, 62, 84, or 92; or (e) a first sequence comprising at least 60%, at least 75%, at least 85%, or 100% sequence identity to at least 8 contiguous amino acids of SEQ ID NO: 2 or 43 and a second sequence comprising at least 60%, at least 75%, at least 85%, or 100% sequence identity to at least 8 contiguous amino acids of SEQ ID NO: 8, 11, 12, 21, 22, 24, 26, 30, 32, 40, 41, 49, 53, 58, 59, 60, 61, 62, 70, 84, 85, 86, 92, 93, or 94; or (f) a first sequence comprising at least 60%, at least 75%, at least 85%, or 100% sequence identity to at least 8 contiguous amino acids of SEQ ID NO: 3, 51, or 52, and a second sequence comprising at least 60%, at least 75%, at least 85%, or 100% sequence identity to at least 8 contiguous amino acids of SEQ ID NO: 8, 11, 12, 21, 22, 24, 26, 30, 32, 40, 41, 49, 53, 58, 59, 60, 61, 62, 70, 84, 85, 86, 92, 93, 94; or (g) a first sequence comprising at least 60%, at least 75%, at least 85%, or 100% sequence identity to at least 8 contiguous amino acids of SEQ ID NO: 2, 8, 11, 12, 40, 41, 43, 58, 59, 61, 62, 84, or 92, and a second sequence comprising at least 60%, at least 75%, at least 85%, or 100% sequence identity to at least 8 contiguous amino acids of SEQ ID NO: 21, 22, 24, 26, 30, 32, 49, 53, 60, 70, 85, 86, 93, or 94; or (h) a first sequence comprising at least 60%, at least 75%, at least 85%, or 100% sequence identity to at least 8 contiguous amino acids of SEQ ID NO: 2, 8, 11, 12, 21, 22, 24, 26, 30, 32, 40, 41, 43, 49, 53, 58, 59, 60, 61, 62, 70, 84, 85, 86, 92, 93, or 94, and a second different sequence comprising at least 60%, at least 75%, at least 85%, or 100% sequence identity to at least 8 contiguous amino acids of SEQ ID NO: 2, 3, 8, 11, 12, 17, 20, 21, 22, 24, 26, 29, 30, 31, 32, 33, 34, 40, 41, 43, 44, 45, 49, 51, 52, 53, 58, 59, 60, 61, 62, 70, 73, 74, 75, 76, 77, 78, 82, 83, 84, 85, 86, 87, 88, 89, 90, 91, 92, 93, or 94, wherein a contiguous sequence comprising the first sequence and the second different sequence is not found in a PB1, PA, or NP.

Another non-limiting example of a polypeptide provided herein can comprise, consist of, or consist essentially of a sequence selected from at least two of the following groups: (a) a sequence comprising at least 60%, at least 75%, at least 85%, or 100% sequence identity to at least 8 contiguous amino acids of SEQ ID NO: 8, 40, 41, or 84; (b) a sequence comprising at least 60%, at least 75%, at least 85%, or 100% sequence identity to at least 8 contiguous amino acids SEQ ID NO: 11, 58, or 59; (c) a sequence comprising at least 60%, at least 75%, at least 85%, or 100% sequence identity to at least 8 contiguous amino acids SEQ ID NO: 12, 61, 62, or 92; (d) a sequence comprising at least 75%, at least 85%, or 100% sequence identity to at least 8 contiguous amino acids of SEQ ID NO: 2 or 43; (e) a sequence comprising at least 60%, at least 75%, at least 85%, or 100% sequence identity to at least 8 contiguous amino acids of SEQ ID NO: 3, 51, or 52; (f) a sequence comprising at least 60%, at least 75%, at least 85%, or 100% sequence identity to at least 8 contiguous amino acids of SEQ ID NO: 32, 93, 94, or 70; (g) a sequence comprising at least 60%, at least 75%, at least 85%, or 100% sequence identity to at least 8 contiguous amino acids of SEQ ID NO: 21, 22, or 85; (h) a sequence comprising at least 60%, at least 75%, at least 85%, or 100% sequence identity to at least 8 contiguous amino acids of SEQ ID NO: 24, 49, or 86; (i) a sequence comprising at least 60%, at least 75%, at least 85%, or 100% sequence identity to at least 8 contiguous amino acids of SEQ ID NO: 26, 53, 30, or 60; (j) a sequence comprising at least 60%, at least 75%, at least 85%, or 100% sequence identity to at least 8 contiguous amino acids of SEQ ID NO: 17, 82, or 83; (k) a sequence comprising at least 60%, at least 75%, at least 85%, or 100% sequence identity to at least 8 contiguous amino acids SEQ ID NO: 20, 44, or 45; (l) a sequence comprising at least 60%, at least 75%, at least 85%, or 100% sequence identity to at least 8 contiguous amino acids of SEQ ID NO: 29, 87, 88, 89, 90, or 91; (m) a sequence comprising at least 60%, at least 75%, at least 85%, or 100% sequence identity to at least 8 contiguous amino acids of SEQ ID NO: 31; and (n) a sequence comprising at least 60%, at least 75%, at least 85%, or 100% sequence identity to at least 8 contiguous amino acids of SEQ ID NO: 33, 34, 73, 74, 75, 76, 77, or 78; wherein at least one sequence is selected from groups (a)-(d) and at least one sequence is selected from groups (f)-(n).

Another non-limiting example of a polypeptide provided herein can comprise, consist of, or consist essentially of: (o) at least 1, 2, 3, or 4 sequences, each comprising at least 60%, at least 75%, at least 85%, or 100% sequence identity to at least 8 contiguous amino acids of any of SEQ ID NOs: 8, 40, 41, or 84, or at least 1, 2, 3, or 4 sequences, each comprising at least 55%, at least 66%, at least 77%, at least 88%, or 100% sequence identity to any of SEQ ID NOs: 8, 40, 41, or 84; (p) at least 1, 2, or 3 sequences, each comprising at least 60%, at least 75%, at least 85%, or 100% sequence identity to at least 8 contiguous amino acids of any of SEQ ID NOs: 11, 58, or 59, or at least 1, 2, or 3 sequences, each comprising at least 52%, at least 58%, at least 64%, at least 70%, and least 76%, at least 82%, at least 88%, at least 94%, or 100% sequence identity to at least 9, 10, 11, 12, 13, 14, 15, 16, or 17 contiguous amino acids of any of SEQ ID NOs: 11, 58, or 59; (q) at least 1, 2, 3, or 4 sequences, each comprising at least 60%, at least 75%, at least 85%, or 100% sequence identity to at least 8 contiguous amino acids of SEQ ID NOs: 12, 61, 62, or 92, or at least 1, 2, 3, or 4 sequences, each comprising at least 52%, at least 58%, at least 64%, at least 70%, and least 76%, at least 82%, at least 88%, at least 94%, or 100% sequence identity to at least 9, 10, 11, 12, 13, 14, 15, 16, or 17 contiguous amino acids of any of SEQ ID NOs: 12, 61, 62, or 92; (r) at least 1 or 2 sequences, each comprising at least 60%, at least 75%, at least 85%, or 100% sequence identity to at least 8 contiguous amino acids of any of SEQ ID NOs: 2 or 43, or at least 1 or 2 sequences, each comprising at least 60%, at least 70%, at least 80%, at least 90%, or 100% sequence identity to at least 9 or 10 contiguous amino acids of any of SEQ ID NOs: 2 or 43; (s) at least 1, 2, or 3 sequences, each comprising at least 60%, at least 75%, at least 85%, or 100% sequence identity to at least 8 contiguous amino acids of any of SEQ ID NOs: 3, 51, or 52, or at least 1, 2, or 3 sequences, each comprising at least 55%, at least 66%, at least 77%, at least 88%, or 100% sequence identity to at least 9 or 10 contiguous amino acids of any of SEQ ID NOs: 3, 51, or 52; (t) at least 1, 2, 3, or 4 sequences, each comprising at least 60%, at least 75%, at least 85%, or 100% sequence identity to at least 8 contiguous amino acids to any of SEQ ID NOs: 32, 93, 94, or 70, or at least 1, 2, 3, or 4 sequences, each comprising at least 60%, 70%, 80%, 90%, or 100% sequence identity to 9 or 10 contiguous amino acids of any of SEQ ID NOs: 32, 93, 94, or 70; (u) at least 1, 2, or 3 sequences, each comprising at least 60%, at least 75%, at least 85%, or 100% sequence identity to at least 8 contiguous amino acids any of SEQ ID NOs: 21, 22, or 85, or at least 1, 2, 3, or 4 sequences, each comprising at least 55%, at least 66%, at least 77%, at least 88%, or 100% sequence identity to 9 contiguous amino acids of any of SEQ ID NOs: 21, 22, or 85; (v) at least 1, 2 or 3 sequences, each comprising at least 60%, at least 75%, at least 85%, or 100% sequence identity to at least 8 contiguous amino acids of any of SEQ ID NOs: 24, 49, or 86, or at least 55%, at least 66%, at least 77%, at least 88%, or 100% sequence identity to 9 contiguous amino acids of any of SEQ ID NOs: 24, 49, or 86; (w) at least 1, 2, 3, or 4 sequences, each comprising at least 60%, at least 75%, at least 85%, or 100% sequence identity to at least 8 contiguous amino acids of any of SEQ ID NOs: 26, 53, 30, or 60, or at least 1, 2, 3, or 4 sequences, each comprising at least 50%, at least 56%, at least 62%, at least 68%, at least 75%, at least 81%, at least 87%, at least 93%, or at least 100% sequence identity to at least 9, 10, 11, 12, 13, 14, 15, or 16 contiguous amino acids of any of SEQ ID NOs: 26, 53, 30, or 60, or at least 9, 10, 11, 12, 13, 14, 15, 16, or 17 contiguous amino acids of any of SEQ ID NOs: 30 or 60; (x) at least 1, 2, or 3 sequences, each comprising at least 60%, at least 75%, at least 85%, or 100% sequence identity to at least 8 contiguous amino acids of any of SEQ ID NOs: 17, 82, or 83, or at least 1, 2, or 3 sequences, each comprising at least 50%, at least 57%, at least 60%, at least 71%, at least 78%, at least 85%, at least 92%, or 100% sequence identity to at least 9, 10, 11, 12, 13, or 14 contiguous amino acids of any of SEQ ID NOs: 17, 82, or 83; (y) at least 1, 2, or 3 sequences, each comprising at least 60%, at least 75%, at least 85%, or 100% sequence identity to at least 8 contiguous amino acids of any of SEQ ID NOs: 20, 44, or 45 or at least 1, 2, or 3 sequences, each comprising at least 55%, at least 66%, at least 77%, at least 88%, or 100% sequence identity to 9 contiguous amino acids of any of SEQ ID NOs: 20, 44, or 45; (z) at least 1, 2, 3, 4, 5, or 6 sequences, each comprising at least 60%, at least 75%, at least 85%, or 100% sequence identity to at least 8 contiguous amino acids of any of SEQ ID NOs: 29, 87, 88, 89, 90, or 91, or at least 1, 2, 3, 4, 5, or 6 sequences, each comprising at least 50%, at least 55%, at least 61%, at least 66%, at least 72%, at least 83%, at least 88%, at least 94%, or 100% sequence identity to at least 9, 10, 11, 12, 13, 14, 15, 16, 17, or 18 contiguous amino acids of any of SEQ ID NOs: 29, 87, 88, 89, 90, or 91; (aa) a sequence comprising at least 60%, at least 75%, at least 85%, or 100% sequence identity to at least 8 contiguous amino acids of SEQ ID NO: 31, or a sequence comprising at least 55%, at least 66%, at least 77%, at least 88%, or 100% sequence identity to 9 contiguous amino acids of SEQ ID NO: 31; (bb) at least 1, 2, 3, 4, 5, 6, 7, or 8 sequences, each comprising at least 60%, at least 75%, at least 85%, or 100% sequence identity to at least 8 contiguous amino acids of any of SEQ ID NOs: 33, 34, 73, 74, 75, 76, 77, or 78, or at least 1, 2, 3, 4, 5, 6, 7, or 8 sequences, each comprising at least 52%, at least 56%, at least 60%, at least 64%, at least 68%, at least 72%, at least 76%, at least 80%, at least 84%, at least 88%, at least 92%, at least 96%, or 100% sequence identity to at least 9, 10, 11, 12, 13, 14, 15, 16, 17, 18, 19, 20, 21, 22, 23, 24, or 25 contiguous amino acids of any of SEQ ID NOs: 33, 34, 73, 74, 75, 76, 77, or 78; or any combination of (o)-(bb).

Another non-limiting example of a polypeptide provided herein can comprise, consist of, consist essentially of: (cc) at least two sequences from the group consisting of SEQ ID NOs: 8, 40, 41, and 84; (dd) at least two sequences from the group consisting of SEQ ID NOs: 11, 58, and 59; (ee) at least two sequences from the group consisting of SEQ ID NO: 12, 61, 62, and 92; (ff) at least two sequences from the group consisting of SEQ ID NOs: 2 and 43; (gg) at least three sequences from the group consisting of SEQ ID NOs: 3, 51, and 52; (hh) at least two sequences from the group consisting of SEQ ID NOs: 32, 93, 94, and 70; (ii) at least two sequences from the group consisting of SEQ ID NOs: 21, 22, and 85; (jj) at least two sequences from the group consisting of SEQ ID NOs: 24, 49, and 86; (kk) at least two sequences from the group consisting of SEQ ID NOs: 26, 53, 30, and 60; (ll) at least two sequences from the group consisting of SEQ ID NOs: 17, 82, and 83; (mm) at least two sequences from the group consisting of SEQ ID NOs: 20, 44, and 45; (nn) at least two sequences from the group consisting of SEQ ID NOs: 29, 87, 88, 89, 90, and 91; or (oo) at least two sequences from the group consisting of SEQ ID NOs: 33, 34, 73, 74, 75, 76, 77, and 78.

In some cases, a polypeptide provided herein can further comprise a full-length amino acid sequence (or at least 20%, 30%, 40%, 50%, 60%, 70%, 80%, 90%, or 95% of the full-length sequence) of one or more (e.g., 1, 2, 3, 4, 5, 6, 7, 8, 9, or 10) virus proteins, e.g., one or more influenza virus proteins, e.g., one or more influenza A, influenza B, or influenza C virus proteins, e.g., PB1, PB1-F2, PB2, PA, HA, NP, NA, M1, M2, NS1, or NEP/NS2 from influenza A, influenza B, or influenza C. In some cases, a vaccine provided herein comprises a polypeptide comprising a full-length amino acid sequence (or at least 10%, 20%, 30%, 40%, 50%, 60%, 70%, 80%, 90%, or 95% of the full-length sequence) of one or more (e.g., 1, 2, 3, 4, 5, 6, 7, 8, 9, or 10) virus proteins, e.g., one or more influenza virus proteins, e.g., one or more influenza A, influenza B, or influenza C virus proteins, e.g., PB1, PB1-F2, PB2, PA, HA, NP, NA, M1, M2, NS1, or NEP/NS2 from influenza A, influenza B, or influenza C, e.g., or the polypeptide is expressed from a separate nucleic acid or virus in the vaccine, e.g., an adenovirus, A polypeptide provided herein can comprise 1, 2, 3, 4, or 5 or more copies of a sequence of a full-length amino acid sequence (or at least 50%, 60%, 70%, 80%, 90%, or 95% of the full-length sequence) of the viral protein. The full-length amino acid sequence (or at least 10%, 20%, 30%, 40%, 50%, 60%, 70%, 80%, 90%, or 95% of the full-length sequence) can be at the N-terminus of the polypeptide, the C-terminus of the polypeptide, internal in the polypeptide, or, e.g., if multiple copies are present, the N-terminus and C-terminus of the polypeptide. For example, a polypeptide can comprise at least 5, 10, 20, 30, 40, 50, or 51 sequences from Table 1, Table 2, or Table 3 (e.g., each sequence is from one of Table 1, Table 2, or Table 3), each sequence separated or not by a linker, and 1, 2, or 3 copies of a full-length amino acid sequence (or at least 10%, 20%, 30%, 40%, 50%, 60%, 70%, 80%, 90%, or 95% of the full-length sequence) of one or more (e.g., 1, 2, 3, 4, 5, 6, 7, 8, 9, or 10) virus proteins, e.g., one or more influenza virus proteins, e.g., one or more influenza A, influenza B, or influenza C virus proteins, e.g., PB1, PB1-F2, PB2, PA, HA, NP, NA, M1, M2, NS1, or NEP/NS2 from influenza A, influenza B, or influenza C.

In some cases, a polypeptide provided herein can further comprise a full length amino acid sequence (or at least 10%, 20%, 30%, 40%, 50%, 60%, 70%, 80%, 90%, or 95% of the full-length sequence) of NP protein of influenza, e.g., influenza A, or Influenza B, influenza C. In some cases, NP protein sequence (or at least 10%, 20%, 30%, 40%, 50%, 60%, 70%, 80%, 90%, or 95% of the full-length sequence of NP) can be from any appropriate strain of Influenza B. For instance, the sequence can be selected based the prevalent strain, or expected prevalent strain, for an influenza season. A strain of Influenza B from which an NP sequence is chosen can be chosen randomly. For instance, a polypeptide can comprise amino acid sequence of NP protein sequence (or at least 10%, 20%, 30%, 40%, 50%, 60%, 70%, 80%, 90%, or 95% of the full-length sequence of NP) from a particular strain of Influenza B, like B/Brisbane/60/2008-like that belong to B/Victoria lineage or B/Phuket/3073/2013-like or B/Pennsylvania/49/2015 that belongs to B/Yamagata lineage. A derivative (or fragment) of a full length amino acid sequence of NP protein of Influenza B can comprise at least 60% identity, at least 75% identity, at least 80% identity, at least 85% identity, at least 90% identity, at least 95% identity, at least 96% identity, at least 97% identity, at least 98% identity, at least 99% identity, at least 99.5% identity, at least 99.8% identity, at least 99.9% identity, at least 99.99% identity to the full length amino acid sequence of NP protein (or at least 10%, 20%, 30%, 40% 50%, 60%, 70%, 80%, 90%, or 95% of the full-length sequence of NP) of Influenza B. A derivative (or fragment) of a full length amino acid sequence of NP protein of Influenza B can comprise or consist of at most 100 amino acids, at most 80 amino acids, at most 60 amino acids, at most 50 amino acids, at most 40 amino acids, at most 30 amino acids, at most 20 amino acids, at most 15 amino acids, at most 10 amino acids, at most 9 amino acids, at most 8 amino acids, at most 7 amino acids, at most 6 amino acids, at most 5 amino acids, at most 4 amino acids, at most 3 amino acids, at most 2 amino acids, or only 1 amino acid different than the full length amino acid sequence of NP protein of Influenza B. A polypeptide can comprise all of the sequences in Table 1, with or without a linker between each sequence, and one or two copies of a full-length protein (or at least 10%, 20%, 30%, 40%, 50%, 60%, 70%, 80%, 90%, or 95% of the full-length sequence of the protein), e.g., NP protein from an influenza B strain. A polypeptide can comprise all of the sequences in Table 2, with or without a linker between each sequence, and one or two copies of a full-length protein (or at least 10%, 20%, 30%, 40%, 50%, 60%, 70%, 80%, 90%, or 95% of the full-length sequence of a protein), e.g., NP protein from an influenza B strain. A polypeptide can comprise all of the sequences in Table 3, with or without a linker between each sequence, and one or two copies of a full-length protein (or at least 10%, 20%, 30%, 40%, 50%, 60%, 70%, 80%, 90%, or 95% of the full-length sequence of a protein), e.g., NP protein from an influenza B strain.

In some cases, a polypeptide can comprise amino acid sequence (full-length or fragment) of NP protein from a virus that belongs to B/Victoria lineage. For example, a polypeptide can comprise amino acid sequence with at least 50%, 60%, 70%, 80%, 90%, 95%, or 100% sequence identity to full-length, or fragment, e.g., comprising amino acids 1 to 560, 38-557, 50 to 500, 100 to 500, 200 to 400, 1 to 100, 100 to 200, 200 to 300, 300 to 400, or 500 to 560, of NP protein (Accession NO.: AGK63064.1, SEQ ID NO: 116) from Influenza B/Brisbane/60/2008. In some cases, a polypeptide can comprise amino acid sequence (full-length or fragment) of NP protein from a virus that belongs to B/Yamagata lineage. For example, a polypeptide can comprise amino acid sequence with at least 50%, 60%, 70%, 80%, 90%, 95%, or 100% sequence identity to full-length, or fragment, e.g., comprising amino acids 1 to 560, 2 to 560, 50 to 500, 100 to 500, 200 to 400, 1 to 100, 2 to 100, 100 to 200, 200 to 300, 300 to 400, or 500 to 560, of NP protein (Accession NO.: ABL77260.1, SEQ ID NO: 117) from Influenza B/Yamagata/16/1988, or NP protein (Accession NO.: AOZ82278.1, SEQ ID NO: 118) from Influenza B/Pennsylvania/49/2015. In some cases, a polypeptide can comprise both an amino acid sequence (full-length or fragment) of NP protein from a virus that belongs to B/Victoria lineage, or a derivative thereof, and an amino acid sequence (full-length or fragment) of NP protein from a virus that belongs to B/Yamagata lineage, or a derivative thereof.

A polypeptide provided herein can comprise, consist of, or consist essentially of, one or more epitope sequences arranged in order. In some cases, epitope sequences are arranged in a particular order with the consideration of promoting immunogenicity, increasing expression, facilitating polypeptide stability, increasing polypeptide solubility, facilitating the in vivo cleavage of the polypeptide chain, or any other factors that may affect the vaccine performance, or any combination thereof. It is also possible to manipulate the order of the epitope sequences in the polypeptide in order to finely tune certain aspects of a vaccine, either upregulating or downregulating one or more certain parameters as one skilled in the art would be able to achieve.

In some embodiments, the polypeptide comprises more than one epitope sequence that are linked together directly, e.g., "back-to-back". Alternatively, the polypeptide can comprise, consist of, or consist essentially of, more than one epitope sequence, at least two neighboring epitope sequences among which are linked with a linker sequence. The polypeptide can comprise a single type of linker sequence throughout. The polypeptide can comprise more than one different type of linker sequence. The choice of linker sequence can vary depending on the selection of peptide sequences, the specific requirement for a number of different parameters, such as, but not limited to, expression level, folding and stability, solubility, cellular and subcellular targeting, immunogenicity, half-life in vitro and in vivo.

Linkers can be short amino acid sequences to separate multiple domains in a single polypeptide. In some cases, the linker sequence can comprise 3, 4, 5, 6, 7, 8, 9, 10, or more amino acids. The linker sequence can comprise at least 3, at least 4, at least 5, at least 6, at least 7, at least 8, at least 9, at least 10, at least 15, at least 20, or at least 50 amino acids. The linker sequence can comprise at most 4, at most 5, at most 6, at most 7, at most 8, at most 9, at most 10, at most 11, at most 12, at most 15, at most 20, at most 30, at most 40, at most 50, or at most 100 amino acids.

The linker sequence can comprise sequences occurring in natural multi-domain proteins that link the domains therein. The linker sequence can comprise an artificially created linker. The linker can also be a joined product of both a natural linker protein and an artificially created sequence. In some cases, specific linker sequences can be selected for in vivo cleavability of the polypeptide. For example, it can be desirable to cleave between certain epitope sequences, rendering the separated two or more parts of the polypeptide presented to the antigen-presenting cells separately. A linker can comprise a plurality of glycines, alanines, or any combinations thereof. A linker can comprise a plurality of arginines, valines, lysines, or any combinations thereof. Under such exemplary circumstances, linker sequences such as, LEAGCKNFFPRSFTSCGSLE (SEQ ID NO: 95), CRRRRRREAEAC (SEQ ID NO: 96), can be chosen. Sometimes, it can be desirable to use flexible linker sequences, such as, but not limited to, stretches of Gly and Ser residues ("GS" linker) like $(GGGGS)_n$ (n=1 to 10) (SEQ ID NO: 107), $(Gly)_8$ (SEQ ID NO: 97), GSAGSAAGSGEF (SEQ ID NO: 98), $(GGGGS)_4$ (SEQ ID NO: 99). In some cases, it can be desirable to use rigid linker sequences, such as, but not limited to, $(EAAAK)_n$ (SEQ ID NO: 108), Pro-rich sequences like $(XP)_n$ (SEQ ID NO: 109), with X designating any amino acid can be used (n=1 to 20). In some cases, the linker sequence RVKR (SEQ ID NO: 110) can be chosen. The linker sequence RVKR (SEQ ID NO: 110) can be immunostimulatory in some situations. The polypeptide can comprise, consist of, or consist essentially of, each sequence from Table 1, Table 2, or Table 3, wherein each sequence is separated by a linker. The polypeptide can comprise, consist of, or consist essentially of, each sequence from Table 1, Table 2, or Table 3, wherein each sequence is not separated by a linker. The polypeptide can comprise, consist of, or consist essentially of, each sequence from Table 1, Table 2, or Table 3, wherein some of the sequences are separated by a linker and some are not separated by a linker.

In certain aspects of the present disclosure, a polypeptide provided herein further comprises a CD4+ (helper) T cell epitope that is connected to one or more of the epitope sequences described above. A "connection" can be, e.g., a direct or indirect covalent linkage, or a direct or indirect non-covalent linkage. The CD4+ (helper) T cell epitope can be ISQAVHAAHAEINEAGR (SEQ ID NO: 100). In some cases, the CD4+ (helper) T cell epitope is AKFVAAWTL-KAAA (HLA DR-binding Epitope, PADRE) (SEQ ID NO: 101), or a non-natural amino acid derivative of the PADRE sequence, AKXVAAWTLKAAAZC (SEQ ID NO: 102), wherein X is L-cyclohexylalanine and Z is aminocaproic acid. In some cases, the CD4+ (helper) T cell epitope can be GALNNRFQIKGVELKSK (SEQ ID NO: 103). In some embodiments, the C-terminus of a polypeptide provided herein, e.g., a polypeptide comprising a sequence selected from SEQ ID NOs: 1-94 or a sequence selected from Table 1, Table 2, or Table 3, is attached to a lysine and the lysine is attached to the N-terminus of a CD4+ T cell epitope. The C-terminus of a CD4+ (helper) T cell epitope can be attached to a lysine and the lysine can be attached to the N-terminus of a peptide comprising a sequence selected from SEQ ID NOs: 1-94 or a sequence selected from Table 1, Table 2, or Table 3.

A polypeptide can be linked to a full length viral protein, e.g. full length PB1, PB1-F2, PB2, PA, HA, NP, NA, M1, M2, NS1, or NEP/NS2 protein, or the polypeptide can be link to a protein with at least 50%, 60%, 70%, 80%, 90%, 95%, or 100% sequence identity to at least 10%, 20%, 30%, 40%, 50%, 60%, 70%, 80%, 90%, or 95% of the full-length sequence of any of these proteins, from, e.g., influenza A, influenza B, or influenza C, e.g., via a linker described herein, or the connection can be without a linker.

A polypeptide provided herein can comprise one or more natural amino acids, unnatural amino acids, or a combination thereof. An amino acid residue can be a molecule containing both an amino group and a carboxyl group. Suitable amino acids for use in the peptides described include, without limitation, both the D- and L-isomers (amino acid isomer) of the naturally-occurring amino acids, as well as non-naturally occurring amino acids prepared by organic synthesis or other metabolic routes. An amino acid can be an α-amino acid, β-amino acid, natural amino acid, non-natural amino acid, or amino acid analog. An α-amino acid can be molecule containing both an amino group and a carboxyl group bound to a carbon which is designated the α-carbon. A α-amino acid can be a molecule containing both an amino group and a carboxyl group in a β configuration. A naturally occurring amino acid can be any one of the twenty amino acids commonly found in peptides synthesized in nature, and known by the one letter abbreviations A, R, N, C, D, Q, E, G, H, I, L, K, M, F, P, S, T, W, Y and V.

A polypeptide provided herein can comprise one or more hydrophobic, hydrophilic, polar, or charged amino acids. A hydrophobic amino acid can include small hydrophobic amino acids and large hydrophobic amino acids. A small hydrophobic amino acid can be glycine, alanine, proline, and analogs and isomers thereof. A large hydrophobic amino acid can be a valine, leucine, isoleucine, phenylalanine, methionine, tryptophan, and analogs and isomers thereof. A polar amino acid can be a serine, threonine, asparagine, glutamine, cysteine, tyrosine, and analogs and isomers thereof. A charged amino acid can be a lysine, arginine, histidine, aspartate, glutamate, or analog thereof.

A polypeptide as provided herein can comprise one or more amino acid analogs. An amino acid analog can be a molecule which is structurally similar to an amino acid and which can be substituted for an amino acid in the formation of a peptidomimetic macrocycle. Amino acid analogs include β-amino acids and amino acids where the amino or carboxyl group is substituted by a similarly reactive group (e.g., substitution of the primary amine with a secondary or tertiary amine, or substitution of the carboxyl group with an ester).

A polypeptide provided herein can comprise one or more non-natural amino acids. A non-natural amino acid can be an amino acid which is not one of the twenty amino acids commonly found in peptides synthesized in nature, and known by the one letter abbreviations A, R, N, C, D, Q, E, G, H, I, L, K, M, F, P, S, T, W, Y and V.

Amino acid analogs can include β-amino acid analogs. Amino acid analogs can include analogs of alanine, valine, glycine, leucine, arginine, lysine, aspartic acids, glutamic acids, cysteine, methionine, phenylalanine, tyrosine, proline, serine, threonine, and/or tryptophan.

Amino acid analogs can be racemic. In some embodiments, the D isomer of the amino acid analog is used. In some cases, the L isomer of the amino acid analog is used. In some embodiments, the amino acid analog comprises chiral centers that are in the R or S configuration. Sometimes, the amino group(s) of a β-amino acid analog is substituted with a protecting group, e.g., tert-butyloxycarbonyl (BOC group), 9-fluorenylmethyloxycarbonyl (FMOC), tosyl, and the like. Sometimes, the carboxylic acid functional group of a β-amino acid analog is protected, e.g., as its ester derivative. In some cases, the salt of the amino acid analog is used.

A polypeptide provided herein can comprise a non-essential amino acid. A non-essential amino acid residue can be a residue that can be altered from the wild-type sequence of a peptide without abolishing or substantially altering its essential biological or biochemical activity (e.g., receptor binding or activation). A peptide provided herein can comprise an essential amino acid. An essential amino acid residue can be a residue that, when altered from the wild-type sequence of the peptide, results in abolishing or substantially abolishing the peptide's essential biological or biochemical activity.

A polypeptide provided herein can comprise a conservative amino acid substitution. A conservative amino acid substitution can be one in which the amino acid residue is replaced with an amino acid residue having a similar side chain. Families of amino acid residues having similar side chains have been defined in the art. These families can include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a peptide, for example, can be replaced with another amino acid residue from the same side chain family. Other examples of acceptable substitutions can be substitutions based on isosteric considerations (e.g., norleucine for methionine) or other properties (e.g., 2-thienylalanine for phenylalanine, or 6-Cl-tryptophan for tryptophan).

Vaccine Compositions

Individual epitope sequences provided herein, polypeptides in which individual epitope sequences are linked, as provided herein, nucleic acid expressing individual epitope sequences or polypeptides provided herein, vectors comprising nucleic acid expressing individual epitope sequences or polypeptides provided herein, or viruses comprises such nucleic acid or vectors, can be formulated as vaccines. Vaccines provided herein can be any substance used to stimulate the production of antibodies and provide immunity against one or more diseases, e.g., influenza. The vaccines can be prepared from live pathogens, live attenuated pathogens, or inactivated pathogens that have been inactivated by e.g., chemicals, heat, or radiation. The vaccines can contain subunits or portions of a pathogen, in which these subunits can be optionally conjugated. The vaccine can also be prepared as a peptide-based vaccine, a nucleic acid-based vaccine, a viral vector-based vaccine, an antibody based vaccine, or an antigen-presenting cell based vaccine.

The vaccines can protect against pathogens, for example. A pathogen can be any infectious organism, including bacteria, fungi, viruses, protozoa, and others. The vaccines can also include tumor or cancer vaccines. A composition, e.g., a vaccine, provided herein can induce a systemic immune response, when administered into a subject body, e.g. human body. A composition, e.g., a vaccine, provided herein can induce a mucosal immune response, e.g., in the respiratory tract, in addition to systemic immune response, when administered into a subject body, e.g. human body.

The vaccines can be a traditional vaccine or a universal vaccine. A traditional vaccine can be a vaccine that can target a specific pathogen. Measles vaccine is one example of a traditional vaccine. It can target epitopes present on the hemagglutinin (H) protein of the Measles virus that have remained conserved over 50 years.

Seasonal vaccines can be another type of traditional vaccine. For example, an influenza vaccine can be modified annually and is tailored to the population of influenza viruses present at a given year. In some cases, an influenza vaccine is generated as a trivalent vaccine, which can include two subtypes of the influenza A virus, H1N1 and H3N2, and one strain of the influenza B virus. Sometimes, the influenza vaccine is generated as a quadrivalent vaccine, which can include two subtypes of influenza A virus and two strains of influenza B virus. The specific strains of the influenza A and B viruses can be chosen based on surveillance-based forecasts that can predict the pathogenicity of the circulating strains each year and can vary from country to country.

A universal vaccine can be a vaccine that offers broad-based protection against multiple strains of a pathogen, and/or against multiple pathogens within the same family. Exemplary universal vaccines include SynCon® influenza vaccines from Inovio Pharmaceuticals, M-001 from BiondVax, and FP-01 from Immune Targeting Systems. These universal vaccines can target conserved regions or epitopes that exist within the influenza viral proteins. Conserved regions or epitopes can exhibit at least 70%, 80%, 90%, 95%, 99% sequence homology or sequence identity.

Vaccine compositions can be formulated using one or more physiologically acceptable carriers including excipients and auxiliaries which facilitate processing of one or more active agents, such as one or more peptides, nucleic acids, proteins (e.g., antibodies or fragments thereof), APCs, or viruses described herein, into preparations which can be used pharmaceutically. Proper formulation can be dependent upon the route of administration chosen.

In some cases, the vaccine composition is formulated as a peptide-based vaccine, a nucleic acid-based vaccine, an antibody based vaccine, a cell based vaccine, or a virus-based vaccine. For example, a vaccine composition can include naked cDNA in cationic lipid formulations; lipopeptides (see e.g., Vitiello, A. et al, J. Clin. Invest. 95:341, 1995), naked cDNA or peptides, encapsulated e.g., in poly (DL-lactide-co-glycolide) ("PLG") microspheres (see, e.g., Eldridge, et al, Molec. Immunol. 28:287-294, 1991: Alonso et al, Vaccine 12:299-306, 1994; Jones et al, Vaccine 13:675-681, 1995); peptide composition contained in immune stimulating complexes (ISCOMS) (see, e.g. Takahashi et al, Nature 344:873-875, 1990; Hu et al, Clin Exp Immunol. 113:235-243, 1998); or multiple antigen peptide systems (MAPs) (see e.g., Tarn, J. P., Proc. Natl Acad. Sci. U.S.A. 85:5409-5413, 1988; Tarn, J. P., J. Immunol. Methods 196: 17-32, 1996). Sometimes, a vaccine is formulated as a peptide-based vaccine, or nucleic acid based vaccine in which the nucleic acid encodes the peptides. Sometimes, a vaccine is formulated as an antibody based vaccine. Sometimes, a vaccine is formulated as a cell based vaccine.

Vaccine compositions can be formulated using one or more physiologically acceptable carriers including excipients and auxiliaries which facilitate processing of one or more active agents, such as one or more peptides, nucleic acids, proteins (e.g., antibodies or fragments thereof), APCs, or viruses described herein, into preparations which can be used pharmaceutically. Proper formulation can be dependent upon the route of administration chosen.

Peptide-Based Vaccine

Provided herein is a peptide-based vaccine that comprises one or more epitope sequences or one or more polypeptides described herein. For instance, the polypeptide can comprise, consist of, or consist essentially of, one or more epitope sequences selected from the group consisting of:

SEQ ID NOs: 1-94, or one or more epitope sequences selected from Table 1, Table 2, or Table 3. The peptide-based vaccine can comprise one polypeptide. The peptide-based vaccine can comprises at least 2, 3, 4, 5, 6, 7, 8, 9, 10, 15, 20, 25, 30, 35, 40, 45, 50, 51, or more different peptide sequences, e.g., each peptide can have at least 70%, 75%, 80%, 85%, 90%, 95%, or 100% sequence identity to at least 8, 9, 10, 14, 16, 17, 18, or 25 amino acids of SEQ ID NOs: 2, 3, 8, 11, 12, 17, 20, 21, 22, 24, 26, 29, 30, 31, 32, 33, 34, 40, 41, 43, 44, 45, 49, 51, 52, 53, 58, 59, 60, 61, 62, 70, 73, 74, 75, 76, 77, 78, 82, 83, 84, 85, 86, 87, 88, 89, 90, 91, 92, 93, or 94. The peptide-based vaccine can be used to treat or prevent an influenza infection.

In some embodiments, a composition comprises, consists essentially of, or consists of one or more peptides or polypeptides, which may or may not be purified peptides or polypeptides as described herein. As used herein, a composition "comprising" one or more peptides or polypeptides as described herein can mean that the composition can contain other compounds, including one or more proteins that are not described herein. As used herein, a composition "consisting essentially of" one or more peptides or polypeptides can mean that the composition can comprise other compounds in addition to the peptides or polypeptides described herein so long as the additional compounds do not materially change the activity or function of the one or more peptides or polypeptides that are contained in the composition. As used herein, a composition "consisting of" one or more peptides or polypeptides as described herein can mean that the composition does not contain other proteins in addition to the one or more peptides or polypeptides described herein. Compositions consisting of one or more peptides or polypeptides described herein can comprise ingredients other than proteins, e.g., pharmaceutically acceptable carriers, surfactants, preservatives, etc. In some embodiments, compositions consisting of one or more peptides or polypeptides described herein can contain insignificant amounts of contaminants, which can include peptide or polypeptide contaminants, e.g., smaller fragments of the one or more peptides or polypeptides described herein, which can result from, for example, the synthesis of the one or more peptides or polypeptides described herein, subsequent processing, storage conditions, and/or protein degradation.

Peptide-based vaccine can be formulated using techniques, carriers, and excipients as suitable. The peptide-based vaccines can be formulated to improve their biological half-life, stability, efficacy, bioavailability, bioactivity, or a combination thereof.

Sometimes, a vaccine can comprises a cocktail of multiple polypeptides described herein containing the same sequence, or a cocktail of multiple copies of different polypeptides described herein. The polypeptides can be modified, such as by lipidation, or attachment to a carrier protein. Lipidation can be the covalent attachment of a lipid group to a polypeptide. Lipidated polypeptides can stabilize structures and can enhance efficacy of the vaccine treatment.

Lipidation can be classified into several different types, such as N-myristoylation, palmitoylation, GPI-anchor addition, prenylation, and several additional types of modifications. N-myristoylation can be the covalent attachment of myristate, a C14 saturated acid, to a glycine residue. Palmitoylation can be thioester linkage of long-chain fatty acids (CI 6) to cysteine residues. GPI-anchor addition can be glycosyl-phosphatidylinositol (GPI) linkage via amide bond. Prenylation can be the thioether linkage of an isoprenoid lipid (e.g., farnesyl (C-15), geranylgeranyl (C-20)) to cysteine residues. Additional types of modifications can include attachment of S-diacylglycerol by a sulfur atom of cysteines, 0-octanoyl conjugation via serine or threonine residues, S-archaeol conjugation to cysteine residues, and cholesterol attachment.

Fatty acids for generating a lipidated polypeptide can include C2 to C30 saturated, monounsaturated, or polyunsaturated fatty acyl groups. Exemplary fatty acids can include palmitoyl, myristoyl, stearoyl, and decanoyl groups.

In some embodiments, a lipid moiety that has adjuvant property is attached to a peptide of interest to elicit or enhance immunogenicity in the absence of an extrinsic adjuvant. A lipidated peptide or lipopeptide can be referred to as a self-adjuvant lipopeptide.

Any of the fatty acids described above and elsewhere herein can elicit or enhance immunogenicity of a peptide of interest. A fatty acid that can elicit or enhance immunogenicity can include palmitoyl, myristoyl, stearoyl, lauroyl, octanoyl, and decanoyl groups. In some cases, a fatty acid that can elicit or enhance immunogenicity can include palmitoyl groups. Non-limiting examples of palmitoyl group include $Pam_2Cys$, $Pam_3Cys$, or $Pam_3OH$.

$Pam_2Cys$, also known as dipalmitoyl-S-glyceryl-cysteine or S-[2,3 bis(palmitoyloxy) propyl]cysteine, corresponds to the lipid moiety of MALP-2, a macrophage-activating lipopeptide isolated from *Mycoplasma fermentans*.

$Pam_3Cys$, also known as $Pam_3OH$ or N-palmitoyl-S-[2,3-bis(palmitoyloxy)propyl]cysteine, is a synthetic version of the N-terminal moiety of Braun's lipoprotein that spans the inner and outer membranes of Gram negative bacteria.

Other fatty acid groups contemplated for use include Set2Cys (also known as S-(2,3-bis(stearoyloxy)propyl) cysteine or distearoyl-S-glyceryl-cysteine), Lau2Cys (also known as S-[2,3-bis(lauroyloxy) propyl]cysteine or dilauroyl-S-glyceryl-cysteine); and Oct2Cys (also known as S-[2,3-bis(octanoyloxy)propyl]cysteine or dioctanoyl-S-glyceryl-cysteine).

Additional suitable fatty acid groups include synthetic triacylated and diacylated lipopeptides, FSL-I (a synthetic lipoprotein derived from *Mycoplasma salivarium* I), $Pam_3Cys$ (tripaltnitoyl-S-glyceryl cysteine) and S-[2,3-bis(palmitoyloxy)-(2RS)-propyl]-N-palmitoyl-(R)-cysteine, where "$Pam_3$" is "tripalmitoyl-S-glyceryl". Derivatives of $Pam_3Cys$ are also suitable for use, in which derivatives include S-[2,3-bis(palmitoyloxy)-(2-R,S)-propyl]-N-palmitoyl-(R)-Cys-(S)-Ser-(Lys)4-hydroxytrihydrochloride ("(R)-Cys-(S)-Ser-(Lys)4" disclosed as SEQ ID NO: 111); Pam3Cys-Ser-Ser-Asn-Ala (SEQ ID NO: 112); PaM3Cys-Ser-(Lys)4 (SEQ ID NO: 113); Pam3Cys-Ala-Gly; PamsCys-Ser-Gly; Pam3Cys-Ser; PaM3CyS-OMe; Pam3Cys-OH; PamCAG, palmitoyl-Cys((RS)-2,3-di(palmitoyloxy)-propyl)-Ala-Gly-OH; and the like. Another non-limiting examples include Pam2CSK4 (SEQ ID NO: 114) (dipalmitoyl-S-glyceryl cysteine-serine-(lysine)4; or Pam2Cys-Ser-(Lys)4 (SEQ ID NO: 114)).

Peptides such as naked peptides or lipidated peptides can be incorporated into a liposome. For example, the lipid portion of the lipidated peptide can spontaneously integrate into the lipid bilayer of a liposome. Thus, a lipopeptide can be presented on the "surface" of a liposome. A lipidated peptide can be a peptide that is encapsulated within a liposome.

Exemplary liposomes suitable for incorporation in the formulations include, and are not limited to, multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV).

Depending on the method of preparation, liposomes can be unilamellar or multilamellar, and can vary in size with diameters ranging from about 0.02 µm to greater than about 10 µm. Sometimes, the liposomes can be small unilamellar vesicles (25-50 nm), large unilamellar vesicles (100-200 nm), giant unilamellar vesicles (1-2 µm), and multilamellar vesicles (MLV; 1 µm-2 µm). The peptides being delivered can be either encapsulated into liposomes or adsorbed on the surface. The size and surface properties of liposomes can be optimized for a desired result. For example, unilamellar and multilamellar liposomes provide sustained release from several hours to days after intravascular administration. The prolonged drug release can be achieved by multivesicular liposomes, also known as DepoFoam® technology. Unlike ULV and MLV, multivesicular liposomes are composed of nonconcentric multiple aqueous chambers surrounded by a network of lipid layers which confers an increased level of stability and longer duration of drug release. The liposomes can be further modified to achieve a desired result. For example, the liposomes can be PEGylated or have other surface modifications in order to interfere with recognition and uptake by the reticuloendothelial system and provide increased circulation times.

Liposomes can adsorb many types of cells and then release an incorporated agent (e.g., a polypeptide described herein). In some cases, the liposomes fuse with the target cell, whereby the contents of the liposome then empty into the target cell. A liposome can be endocytosed by cells that are phagocytic. Endocytosis can be followed by intralysosomal degradation of liposomal lipids and release of the encapsulated agents.

The liposomes provided herein can also comprise carrier lipids. In some embodiments the carrier lipids are phospholipids. Carrier lipids capable of forming liposomes include, but are not limited to dipalmitoylphosphatidylcholme (DPPC), phosphatidylcholine (PC; lecithin), phosphatidic acid (PA), phosphatidylglycerol (PG), phosphatidylethanolamine (PE), phosphatidylserine (PS). Other suitable phospholipids further include distearoylphosphatidylcholine (DSPC), dimyristoylphosphatidylcholine (DMPC), dipalmitoylphosphatidyglycerol (DPPG), distearoylphosphatidyglycerol (DSPG), dimyristoylphosphatidylglycerol (DMPG), dipalmitoylphosphatidic acid (DPPA); dimyristoylphosphatidic acid (DMPA), distearoylphosphatidic acid (DSP A), dipalmitoylphosphatidylserine (DPPS), dimyristoylphosphatidylserine (DMPS), distearoylphosphatidylserine (DSPS), dipalmitoylphosphatidyethanolamine (DPPE), dimyristoylphosphatidyletanolamine (DMPE), distearoylphosphatidylethanolamine (DSPE) and the like, or combinations thereof. In some embodiments, the liposomes further comprise a sterol (e.g., cholesterol) which modulates liposome formation. The carrier lipids can be any known non-phosphate polar lipids.

A polypeptide as described herein can also be attached to a carrier protein for delivery as a vaccine. The carrier protein can be an immunogenic carrier element and can be attached by any recombinant technology. Exemplary carrier proteins include Mariculture keyhole limpet hemocyanin (mcKLH), PEGylated mcKLH, Blue Carrier® Proteins, bovine serum albumin (BSA), cationized BSA, ovalbumin, and bacterial proteins such as tetanus toxoid (TT).

A polypeptide as described herein can also be prepared as multiple antigenic peptides (MAPs). Polypeptides can be attached at the N-terminus or the C-terminus to small non-immunogenic cores. Polypeptides built upon this core can offer highly localized peptide density. The core can be a dendritic core residue or matrix composed of bifunctional units. Suitable core molecules for constructing MAPs can include ammonia, ethylenediamine, aspartic acid, glutamic acid, and lysine. For example, a lysine core molecule can be attached via peptide bonds through each of its amino groups to two additional lysines. This second generation molecule has four free amino groups, each of which can be covalently linked to an additional lysine to form a third generation molecule with 8 free amino groups. A polypeptide can be attached via its C-terminus to each of these free groups to form an octavalent multiple antigenic peptide (also referred to as a "MAP8" structure). The second generation molecule having four free amino groups can be used to form a tetravalent or tetrameric MAP, e.g., a MAP having four peptides covalently linked to the core (also referred to as a "MAP4" structure). The carboxyl group of the first lysine residue can be left free, amidated, or coupled to β-alanine or another blocking compound. As used herein, the "linear portion or molecule" of a MAP system structure can refer to antigenic peptides that are linked to the core matrix. Thus, a cluster of antigenic epitopes can form the surface of a MAP and a small matrix forms its core. The dendritic core, and the entire MAP can be synthesized on a solid resin using a classic Merrifield synthesis procedure.

The polypeptides used for MAP preparation can be identical or can comprise multiple different sequences and lengths. The polypeptides can be derived from a bacterium, a virus, or a fungus. The peptides can be derived from a virus, such as influenza A virus, influenza B virus, influenza C virus, hepatitis B virus, hepatitis C virus, or HIV.

Sometimes, a polypeptide as described herein can be subjected to cyclization to result in a cyclic peptide which is resistant to proteolytic degradation. Cyclization can be carried out between side chains or ends of the peptide sequences through disulfide bonds, lanthionine, dicarba, hydrazine, or lactam bridges using methods known in the art.

In some embodiments, the polypeptide as described herein are conjugated to a molecule such as vitamin B12, a lipid, or an ethylene oxide compound, e.g., polyethylene glycol (PEG), polyethylene oxide (PEO), and polyoxyethylene (POE), methoxypolyethylene glycol (MPEG), monomethoxy PEG (mPEG), and the like. The ethylene oxide compound can be further functionalized with, for example, amine binding terminal functional groups such as N-hydroxysuccinimide esters, N-hydroxysuccinimide carbonates, and aliphatic aldehyde, or thiol binding groups such as maleimide, pyridyl disulphides, and vinyl sulfonates. Since amino groups (a-amino and ε-lysine amino) and cysteine residues are well suited for conjugation, the peptides provided herein can further include one or more amino acid residues for conjugation to an ethylene oxide molecule or a carrier compound known in the art. The pharmacokinetic and pharmacodynamic properties of a conjugated peptide can be further modified by the use of a particular linker. For example, propyl and amyl linkers can be used to provide a conjugate having a loose conformation whereas a phenyl linker can be used to provide a denser conformation as well as shield domains adjacent to the C-terminus. In some instances, dense conformations can be more efficient in maintaining bioactivity, prolonging plasma half-life, lowering proteolytic sensitivity, and immunogenicity relative to loose conformations.

In some embodiments, the polypeptides as described herein can be hyperglycosylated using methods known in the art, e.g., in situ chemical reactions or site-directed mutagenesis. Hyperglycosylation can result in either N-linked or O-linked protein glycosylation. The clearance rate of a given peptide can be optimized by the selection of the particular saccharide. For example, polysialic acid (PSA) is available in different sizes and its clearance depends on type and molecular size of the polymer. Thus, for example, PSAs having high molecular weights can be suitable for the delivery of low-molecular-weight peptides, and PSAs having low molecular weights can be suitable for the delivery of peptides having high molecular weights. The type of saccharide can be used to target the peptide to a particular tissue or cell. For example, polypeptides conjugated with mannose can be recognized by mannose-specific lectins, e.g., mannose receptors and mannose binding proteins, and are taken up by the liver. In some embodiments, the polypeptides can be hyperglycosylated to improve their physical and chemical stability under different environmental conditions, e.g., to inhibit inactivation under stress conditions and reduce aggregation resulting from production and storage conditions.

In some embodiments, a drug delivery system, such as microparticles, nanoparticles (particles having sizes ranging from 10 to 1000 nm), nanoemulsions, liposomes, and the like, can be used to provide protection of sensitive proteins, prolong release, reduce administration frequency, increase patient compliance, and control plasma levels. Various natural or synthetic microparticles and nanoparticles, which can be biodegradable and/or biocompatible polymers, can be used. Microparticles and nanoparticles can be fabricated from lipids, polymers, and/or metal. Polymeric microparticles and nanoparticles can be fabricated from natural or synthetic polymers, such as starch, alginate, collagen, chitosan, polycaprolactones (PCL), polylactic acid (PLA), poly (lactide-co-glycolide) (PLGA), and the like. In some embodiments, the nanoparticles are solid lipid nanoparticles (SLNs), carbon nanotubes, nanospheres, nanocapules, and the like. In some embodiments, the polymers are hydrophilic. In some embodiments, the polymers are thiolated polymers.

Since the rate and extent of drug release from microparticles and nanoparticles can depend on the composition of polymer and fabrication methods one can select a given composition and fabrication method, e.g., spray drying, lyophilization, microextrusion, and double emulsion, to confer a desired drug release profile. Since peptides incorporated in or on microparticles or nanoparticles can be prone to denaturation at aqueous-organic interface during formulation development, different stabilizing excipients and compositions can be used to prevent aggregation and denaturation. For example, PEG and sugars, e.g., PEG (MW 5000) and maltose with a-chymotrypsin, can be added to the composition to reduce aggregation and denaturation. Additionally, chemically modified peptides, e.g., conjugated peptides and hyperglycosylated peptides, as described herein, can be employed.

Protein stability can also be achieved by the selected fabrication method. For example, to prevent degradation at aqueous-organic interface, non-aqueous methodology called ProLease® technology can be used. Peptides in solid state can also be encapsulated using solid-in-oil-in-water (s/o/w) methods, e.g., spray- or spray-freeze-dried peptides or peptide-loaded solid nanoparticles can be encapsulated in microspheres using s/o/w methods.

Hydrophobic ion-pairing (HIP) complexation can be used to enhance protein stability and increase encapsulation efficiency into microparticles and nanoparticles. In hydrophobic ion-pairing (HIP) complexation, ionizable functional groups of a peptide are complexed with ion-pairing agents (e.g., surfactant or polymer) containing oppositely charged functional groups leading to formation of HIP complex where hydrophilic protein molecules exist in a hydrophobic complex form.

A polypeptide described herein can be chemically synthesized, or recombinantly expressed in a cell system or a cell-free system. A polypeptide can be synthesized, such as by a liquid-phase synthesis, a solid-phase synthesis, or by microwave assisted peptide synthesis. A polypeptide as described herein can be modified, such as by acylation, alkylation, amidation, arginylation, polyglutamylation, polyglycylation, butyrylation, gamma-carboxylation, glycosylation, malonylation, hydroxylation, iodination, nucleotide addition (e.g., ADP-ribosylation), oxidation, phosphorylation, adenylylation, propionylation, S-glutathionylation, S-nitrosylation, succinylation, sulfation, glycation, palmitoylation, myristoylation, isoprenylation or prenylation (e.g., farnesylation or geranylgeranylation), glypiation, lipoylation, attachement of flavin moiety (e.g., FMN or FAD), attachment of heme C, phosphopantetheinylation, retinylidene Schiff base formation, diphthamide formation, ethanolamine phosphoglycerol attachment, hypusine formuation, biotinylation, pegylation, ISGylation, SUMOylation, ubiquitination, Neddylation, Pupylation, citrullination, deamidation, eliminylation, carbamylation, or a combination thereof.

After generation of a polypeptide, the polypeptide can be subjected to one or more rounds of purification steps to remove impurities. The purification step can be a chromatographic step utilizing separation methods such as affinity-based, size-exclusion based, ion-exchange based, or the like. In some cases, the peptide is at most 30%, 40%, 50%, 60%, 70%, 80%, 90%, 95%, 99%, 99.9%, or 100% pure or without the presence of impurities. In some cases, the peptide is at least 30%, 40%, 50%, 60%, 70%, 80%, 90%, 95%, 99%, 99.9%, or 100% pure or without the presence of impurities. In some cases, the amount of the peptides in the peptide composition is at least 30%, 40%, 50%, 60%, 70%, 80%, 90%, 95%, 99%, 99.9%, or 100% by weight of the total composition. As used herein, a "purified" peptide of polypeptide can mean that an amount of the macromolecular components that are naturally associated with the peptide have been removed from the peptide. As used herein, a composition comprising, consisting essentially of, or consisting of one or more purified peptides of the present invention can mean that the composition does not contain an amount of the macromolecular components that are naturally associated with the one or more peptides or polypeptides and/or the reagents used to synthesize the peptides or polypeptides. In some embodiments, the compositions described herein consist solely of one or more peptides or polypeptides described herein, e.g., one or more peptides or polypeptides in a solid or crystalized form.

In some embodiments, the peptides or polypeptides or nucleic acid molecules of described herein can be isolated. As used herein, an "isolated" compound (e.g., peptide, polypeptide, nucleic acid molecule) can refer to a compound which is isolated from its native environment. For example, an isolated peptide or polypeptide can be one which does not have its native amino acids which correspond to the full length polypeptide, flanking the N-terminus, C-terminus, or both. As another example, an isolated peptide can be one which is immobilized to a substrate with which the peptide is not naturally associated. As a further example, an isolated peptide or polypeptide can be one which is linked to another molecule, e.g., a PEG compound, with which the peptide is not naturally associated. Similarly, an "isolated" nucleic acid molecule can be one which does not have its native nucleic acid basses which correspond to the full length nucleic acid molecule, flanking its 5' end, 3' end, or both. As another example, an isolated nucleic acid molecule can be one which is bound to a substrate or a compound, e.g., a label such as a fluorescent tag, with which the nucleic acid molecule is not naturally associated. As a further example, with respect to nucleic acid molecules, the term isolated can mean that it is separated from the nucleic acid and cell in which it naturally occurs.

A peptide-based vaccine can comprise about, at least, or at most 1, 2, 3, 4, 5, 6, 7, 8, 9, 10, 15, 20, 25, 30, 35, 40, 45, 50, 51, 55, 60, 65, 70, of 75 different peptide sequences. The different peptide sequences can include any polypeptide described herein.

Nucleic Acid-Based Vaccine

Provided herein is a nucleic acid-based vaccine that codes for about, at least, or at most 1, 2, 3, 4, 5, 6, 7, 8, 9, 10, 15, 20, 25, 30, 35, 40, 45, 50, 51, 55, 60, 65, 70, of 75 polypeptides as described herein. The nucleic acid-based vaccine can be used to treat or prevent an influenza infection.

A nucleic acid-based vaccine can be formulated using techniques, carriers, and excipients as suitable. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods. The vaccine can be a DNA-based vaccine, an RNA-based vaccine, a hybrid DNA/RNA based vaccine, or a hybrid nucleic acid/peptide based vaccine. The peptide can be a polypeptide that has a sequence with at least 40%, 50%, 60%, 70%, 80%, 90%, 95%, or 100% sequence homology or identity to a peptide selected from the group consisting of SEQ ID NOs: 1-94 or of a sequence selected from Table 1, Table 2, or Table 3. The peptide can be a polypeptide that has a sequence with at most 40%, 50%, 60%, 70%, 80%, 90%, 95%, or 100% sequence homology or identity to a peptide selected from the group consisting of SEQ ID NOs: 1-94 or of a sequence selected from Table 1, Table 2, or Table 3.

Nucleic acid molecules can refer to at least two nucleotides covalently linked together. A nucleic acid described herein can contain phosphodiester bonds, although in some cases, as outlined below (for example in the construction of primers and probes such as label probes), nucleic acid analogs are included that can have alternate backbones, comprising, for example, phosphoramide, phosphorothioate, phosphorodithioate, O-methylphosphoroamidite linkages, and peptide nucleic acid (also referred to herein as "PNA") backbones and linkages. Other analog nucleic acids include those with bicyclic structures including locked nucleic acids (also referred to herein as "LNA"); positive backbones; non-ionic backbones and non-ribose backbones. Nucleic acids containing one or more carbocyclic sugars are also included within the definition of nucleic acids (see e.g., Jenkins et al, Chem. Soc. Rev. (1995) pp 169 176). Several nucleic acid analogs are described, e.g., in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2-0 atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some embodiments. The target nucleic acids can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

Provided herein is a vector that comprises a polynucleotide that codes for a polypeptide as described herein. In some cases, the vector can be used to treat or prevent influenza infection. In some cases, the vector can be used to produce one or more of the polypeptides described herein.

A polynucleotide encoding a polypeptide provided herein can be codon optimized for a target subject, such as human being, mouse, pig, or dog. For example, a polynucleotide provided herein can be codon optimized for mice for pre-clinical animal experiments. In some cases, the subject matter may find use in preventing influenza for agriculture, for example, for preventing swine flu, or avian flu. This type of optimization can entail the mutation of foreign-derived (e.g., recombinant) DNA to mimic the codon preferences of the intended host organism or cell while encoding the same protein.

The vector can be a circular plasmid or a linear nucleic acid. The circular plasmid or linear nucleic acid can be capable of directing expression of a particular nucleotide sequence in an appropriate subject cell. The vector can have a promoter operably linked to the peptide-encoding nucleotide sequence, which can be operably linked to termination signals. The vector can also contain sequences required for proper translation of the nucleotide sequence. The vector comprising the nucleotide sequence of interest can be chimeric, meaning that at least one of its components is heterologous with respect to at least one of its other components. The expression of the nucleotide sequence in the expression cassette can be under the control of a constitutive promoter or of an inducible promoter, which can initiate transcription only when the host cell is exposed to some particular external stimulus.

The vector can be a plasmid. The plasmid can be useful for transfecting cells with nucleic acid encoding the peptide, which the transformed host cells can be cultured and maintained under conditions wherein expression of the peptide takes place.

The plasmid can comprise a nucleic acid sequence that encodes one or more of the various polypeptides disclosed herein. A single plasmid can contain coding sequence for a single polypeptide, or coding sequence for more than one polypeptide. Sometimes, the plasmid can further comprise coding sequence that encodes an adjuvant, such as an immune stimulating molecule, such as a cytokine.

The plasmid can further comprise an initiation codon, which can be upstream of the coding sequence, and a stop codon, which can be downstream of the coding sequence. The initiation and termination codon can be in frame with the coding sequence. The plasmid can also comprise a promoter that is operably linked to the coding sequence, and an enhancer upstream of the coding sequence. The enhancer can be human actin, human myosin, human hemoglobin, human muscle creatine, or a viral enhancer such as one from CMV, FMDV, RSV, or EBV.

The plasmid can also comprise a mammalian origin of replication in order to maintain the plasmid extrachromosomally and produce multiple copies of the plasmid in a cell. The plasmid can be pVAXI, pCEP4, or pREP4 from Invitrogen (San Diego, CA).

The plasmid can also comprise a regulatory sequence, which can be well suited for gene expression in a cell into which the plasmid is administered. The coding sequence can comprise a codon that can allow more efficient transcription of the coding sequence in the host cell.

The plasmid can be pSE420 (Invitrogen, San Diego, CA), pYES2 (Invitrogen, San Diego, CA), MAXBAC™ complete baculovirus expression system (Invitrogen, San Diego, CA), pcDNA I or pcDNA3 (Invitrogen, San Diego, CA).

The vector can be circular plasmid, which can transform a target cell by integration into the cellular genome or exist extrachromosomally (e.g., autonomous replicating plasmid with an origin of replication). Exemplary vectors include pVAX, pcDNA3.0, or provax, or any other expression vector capable of expressing DNA encoding the antigen and enabling a cell to translate the sequence to an antigen that is recognized by the immune system.

The nucleic acid based vaccine can also be a linear nucleic acid vaccine, or linear expression cassette ("LEC"), that can be efficiently delivered to a subject via electroporation and expressing one or more peptides disclosed herein. The LEC can be any linear DNA devoid of any phosphate backbone. The DNA can encode one or more peptides disclosed herein. The LEC can contain a promoter, an intron, a stop codon, and/or a polyadenylation signal. The expression of the peptide can be controlled by the promoter. It is also possible that the LEC does not contain any antibiotic resistance genes and/or a phosphate backbone. The LEC cannot contain other nucleic acid sequences unrelated to the polypeptide expression.

The LEC can be derived from any plasmid capable of being linearized. The plasmid can express the peptide. Exemplary plasmids include: pNP (Puerto Rico/34), pM2 (New Caledonia/99), WLV009, pVAX, pcDNA3.0, provax, or any other expression vector capable of expressing DNA encoding the antigen and enabling a cell to translate the sequence to an antigen that is recognized by the immune system.

The nucleic acid based vaccine can be delivered to a subject through a parenteral delivery method. A parenteral delivery can include intravenous, transdermal, oral, intrabiliary, intraparenchymal, intra-hepatic artery, intra-portal vein, intratumoral, or transvenous delivery. Sometimes, a parenteral delivery can utilize a needle (e.g., a hypodermic needle) for delivery of the nucleic acid based vaccine. The nucleic acid based vaccine can be formulated in an aqueous solution, e.g., saline. The delivery can be further assisted by electroporation. Sometimes, a parenteral delivery can utilize a gene gun as a delivery method. The nucleic acid based vaccine can be formulated as a DNA-coated microparticle, e.g., a DNA-coated gold or tungsten bead. The gene gun delivery method can use a ballistical delivery method to accelerate nucleic acid into target cells. Sometimes, a parenteral delivery can utilize a pneumatic injection as a delivery method. The nucleic acid based vaccine can be formulated as an aqueous solution.

The nucleic acid based vaccine can also be delivered to a subject through a topical delivery method. Topical nucleic acid based vaccine can be formulated as aerosol instillation of naked DNA to be delivered onto mucosal surfaces, such as the nasal and lung mucosa, ocular administration, or vaginal mucosa.

The nucleic acid based vaccine can further be delivered to a subject through a lipid-mediated delivery method. Sometimes, the lipid-mediated delivery method can be a cytofectin-mediated delivery method. Cytofectin can be cationic lipids that can bind and transport nucleic acid molecules across cell membranes. The nucleic acid can be incorporated by cytofectin-based liposomes. Sometimes, the lipid-mediated delivery method can be a neutral lipid-mediated delivery method.

A composition provided herein, e.g., a vaccine, can comprise at least 5, 10, 25, 50, 100, or 1000 different nucleic acids.

Recombinant Virus-Based Vaccine

Provided herein is a recombinant virus-based vaccine.

A vector as described above can be a viral vector, e.g. a recombinant viral vector. In some cases, a nucleic acid-based vaccine as described above can be in the form of a recombinant virus. The recombinant virus can comprise a recombinant viral vector as described herein that is encapsulated by a capsid protein, typically derived from the viral vector and from other viral origin than influenza virus.

The viral vector can be based on a range of different viruses, such as, but not limited to, adenoviruses, adeno-associated viruses (AAV), alphaviruses, baculoviruses, Newcastle Disease viruses (NDV), poxviruses, Parainfluenza Virus 5 (PIV5), and Vesicular Stomatitis Viruses (VSV). In some cases, the vector can be a recombinant viral vector that comprises polynucleotide that codes for one or more (e.g., 1, 2, 3, 4, 5, 6, 7, 8, 9, 10) of the polypeptides described herein and polynucleotide sequences that code for viral proteins from viruses other than influenza virus. A vaccine can comprise one or more (e.g., 2, 3, 4, 5, 6, 7, 8, 9, 10) different viral vectors, each vector expressing a polypeptide with a different sequence.

An adenovirus based vaccine can infect broad range of hosts. In some cases, an adenovirus vaccine can induce high levels of transgene expression without the potential of viral genes being integrated into the host genome. Due to their ability to grow in high titers in cell culture, an adenovirus vaccine described herein can be manufactured safely and inexpensively. In some cases, adenoviral vectors that are used for a vaccine provided herein can inherently stimulate innate immune responses via Toll-like receptor-dependent and Toll-like receptor-independent pathways. In some cases, an adenovirus vaccine can also infect dendritic cells (DCs), thereby leading to more effective antigen presentation to immune cells, through e.g., up-regulation of co-stimulatory molecules, increased cytokine and chemokine production by the infected DCs, or both.

An adenoviral vector described herein can be generated in two different forms: replication-defective or replication-competent. Replication-defective adenoviral vectors can be rendered by deletion of the E1 genes, which can be essential for replication. Sometimes, replication-defective adenoviral vectors can be rendered to lack E3 genes as well in order to create more space for foreign gene inserts. An expression cassette with desired transgene, e.g., a polynucleotide that encodes one or more polypeptide described herein, can be inserted. Replication-competent adenoviral vectors can be rendered with the deletion of E3 genes. Sometimes, replication-competent Ad-vectors can mimic the natural viral infection, thereby a potent adjuvant effect can be exerted due to the inherent stimulation of various elements of innate and adaptive immunity.

In some embodiments of the present disclosure, the vector can be an adenoviral vector. In some instances, the vector is a non-human adenoviral vector. In some cases, the vector can be a non-human primate adenoviral vector. In some cases, the vector can be a chimpanzee adenoviral vector.

In certain embodiments, Chimpanzee adenovirus vector can be used for expressing one or more polypeptides, such as C68 (AdC68) (SEQ ID NO: 104), e.g., that is disclosed in U.S. Pat. No. 6,083,716, C7 (AdC7), e.g., that is disclosed in Tatsis, et al., "Chimpanzee-origin adenovirus vectors as vaccine carriers," Gene Therapy 13: 421-429 (2006), C6(AdC6) (SEQ ID NO: 105) that is disclosed in Haut et al., "A Partial E3 Deletion in Replication-Defective Adenoviral Vectors Allows for Stable Expression of Potentially Toxic Transgene Products", Human Gene Therapy Methods DOI: 10.1089/hgtb.2016.044 (2016), Pan7 and Pan9, which are both disclosed in Roy, et al., "Rescue of chimeric adenoviral vectors to expand the serotype repertoire," J Virol Methods 141(a): 14-21 (2007).

Alternatively, the vector can be based on AAV. Recombination AAV can have broad tropism infecting a variety of hosts, tissues, and proliferating and non-proliferating cell types. AAVs that can be used in connection with the present disclosure can include, but not limited to, AAV serotype 2 (AAV2), AAV5, AAV7, AAV1, and AAV6.

The vector can also be based on a baculovirus. Baculoviruses that can be used as vector for the vaccine provided herein, e.g., influenza vaccine, can include, but not limited to, alphabaculoviruses, betabaculoviruses, gammabaculoviruses, and deltabaculoviruses.

Alternatively, the vector can be based on a poxvirus. Poxviruses can be double-stranded DNA viruses. Poxvirus genome can be very large; mammalian poxviruses can possess a genome of approximately 130 kb, and avian poxvirus genome is even larger at approximately 300 kb. Such large genome size can enable the insertion of more than 10 kb of foreign DNA without compromising the infectivity or other essential viral functions. Poxviruses can have their own transcription machinery, viral DNA-dependent RNA polymerase and post-transcriptional modifying enzymes, thereby allowing self-sufficient cytoplasmic replication. As a result, inserted transgene products can be expressed at high levels, resulting in potent cellular immune responses.

Recombinant vaccinia virus can be created to express the polypeptide as described herein. Non-replicating poxviral vectors that can be used in connection with the present disclosure include, but not limited to, modified vaccinia virus Ankara (MVA), NYVAC, and ALVAC strains. MVA was rendered replication-deficient by loss of approximately 15% of its original genome resulting from repetitive passaging in chick embryo fibroblasts. NYVAC strain, derived from the Copenhagen strain of vaccinia, was rendered replication-defective by deletion of 18 different open reading frames from the original viral genome. ALVAC is a canarypoxviral vector that does not replicate in human cells with further attenuation induced via over 200 passages in chicken embryo fibroblasts.

Alternatively, the vector can be based on an alphavirus. Alphaviruses can be single-stranded positive-sense RNA viruses that can replicate in the cytoplasm of infected cells. Alphaviruses that can be used in connection with the present disclosure include, but are not limited to, Venezuelan equine encephalitis virus (VEE), Sindbis virus (SIN), Semliki forest virus (SFV), and VEE-SIN chimeras.

Alphaviral vectors can be designed with the deletion of genes encoding structural proteins. Such alphavirus vectors are known as "replicons". Alphavirus vectors can potentially target antigen presenting cells, such as dendritic cells, in the draining lymph nodes, which can lead to the efficient generation of antigen-specific immune responses. Also, alphavirus vectors can create a proper environment for the cross-priming of vaccine antigen by inducing apoptosis in some cells. Vaccine immunity can also be further enhanced by the alphavirus vector itself.

VEE can be pathogenic in humans, but SIN is not. VEE/SIN chimeras can be used to avoid safety concerns when human is the vaccination subject. In a VEE/SIN chimera, VEE can function as the replicon component and SIN as the structural and packaging components.

Other RNA viruses that can be used as a vector for producing a vaccine as described herein can include, but not limited to, NDV, PIV5, and VSV.

Figure 5:
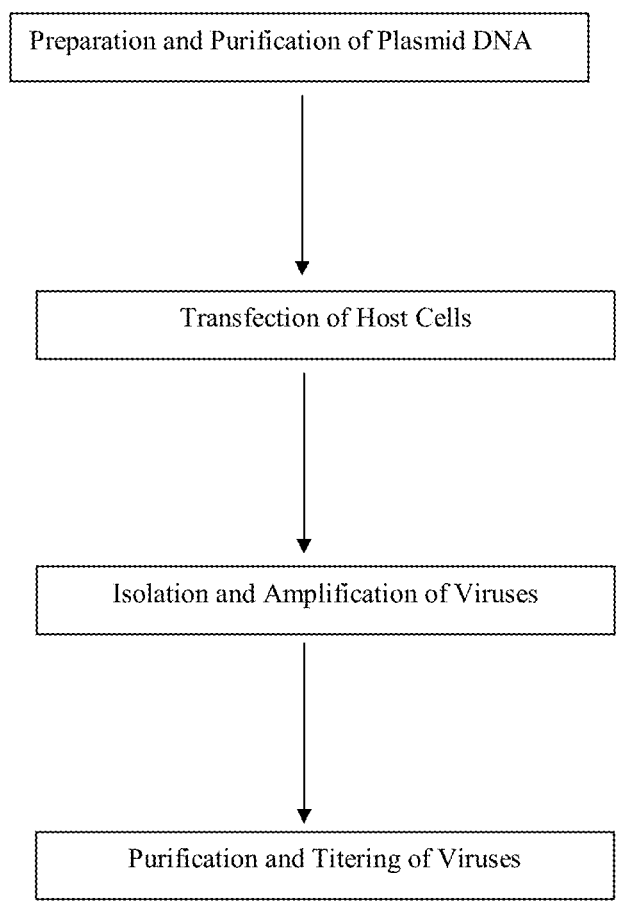
FIG. 5 illustrates a method of producing an adenovirus-based vaccine provided herein.

An adenoviral vector or an adenovirus based vaccine as described herein can be produced by a method provided herein, e.g., in accordance with procedures depicted in FIG. 5.

A method of producing an adenovirus based vaccine can comprise preparation and purification of plasmid DNA. The plasmid DNA herein can be a recombinant adenoviral vector DNA that comprises a polynucleotide encoding a polypeptide that comprises one or more epitope sequences as described herein. As discussed above, a recombinant adenoviral vector can lack E region genes, e.g. E1, E3, E5, or a combination thereof. The deletion of the endogenous viral genes can offer genomic space for insertion of gene of interest, e.g., polynucleotide expressing the polypeptide described herein. An E1-deleted Recombinant Adenoviral vector, as an example, can be constructed either by an in vitro ligation method or a homologous recombination method.

The in vitro ligation method can use whole adenoviral DNA genomes and a plasmid containing the left end of Ad with the right inverted terminal repeat (ITR), the packaging signal and E1A enhancer sequence. After the gene of interest, e.g., the polynucleotide encoding the polypeptide as described herein, can be inserted into the downstream of the viral sequence of the plasmid, the fragment containing viral sequence and gene of interest can be excised and ligated to a restriction site, replacing a portion of the viral E1 region, thereby producing a recombinant adenoviral DNA vector.

Alternatively, recombinant adenoviral vector can also be made by using homologous recombination method. Two or more plasmids with overlapping fragments that recombine in vivo can be used. An exemplary first plasmid can contain the entire Adenoviral genome with a deletion of the DNA packaging region and E1 region. An exemplary second plasmid (shuttle vector) can contain right ITR, packaging signal, overlapping sequence with the first plasmid. After the gene of interest, e.g. polynucleotide expressing a polypeptide described herein, can be introduced into the second plasmid, the two plasmids can be co-transfected into recombination cells. In the cells, homologous recombination can take place between the first and second plasmids, thereby producing a recombinant adenoviral vector. Non-limiting examples of cells for homologous recombination can include yeast, bacteria, and mammalian cell lines, such as, 293 cells, 293T cells, Hela cells. In some case, the recombinant adenoviral vector can be purified from the recombination cells. Alternatively, the recombination process can be conducted in vitro.

A method of producing an adenovirus based vaccine can further comprise transfection of host cells with the purified DNA plasmid. In some embodiments, the DNA plasmid, e.g. the recombinant adenoviral vector, is linearized before the transfection. In some cases, the transfection can generate adenoviral plaques.

In some cases, the recombinant adenoviral vector lack E1 gene, which can mediate the replication of adenovirus. Therefore, in some cases, it is necessary to supplement the E1 gene for the recombinant adenovirus to replicate. In some cases, 293 cell line, which have been generated using adenoviral infection and has E1 gene in the genome, can be used. Other cell lines that are engineered to produce E1 gene product can also be used for this purpose. In some cases, DNA fragments containing other viral genomic elements or one or more helper viruses can also be used for the production of recombinant adenovirus. For example, a helper virus can provide packaging signal for virus packaging, while the recombinant viral vector can lack the packaging signal. Alternatively, DNA fragment that contains the packaging signal can be co-transfected into the host cells for the production of the recombinant adenovirus. One or more plasmid vectors or helper virus used herein that contribute genomic materials for the production of the recombinant adenoviral vector can comprise reporter genes, selection markers, or any other genes that may be useful for the viral production.

Cell transfection can be performed using any transfection approach available to one skilled in the art. The transfection approach can include, but not limited to, electroporation, microinjection, calcium phosphate precipitation, cationic polymers, dendrimers, liposome, microprojectile bombardment, fugene, direct sonic loading, cell squeezing, optical transfection, protoplast fusion, impalefection, magnetofection, nucleofection, or any combination thereof.

A method of producing adenovirus based vaccine can further comprise isolation and amplification of viruses. Isolation of viruses can comprise isolating adenoviral plaques, which can be followed by screening of plaques. In some cases, the screening can be conducted by sequencing of the viral nucleic acids. In some cases, the plaques can be screened for the full, unaltered transgene sequence. A correct plaque can be further amplified by infection of successively larger number of cells. A method can further comprise isolating, and optionally lysing, the infected cells, which can be followed by purification of viral particles. The purification can be performed via various approaches, such as, but not limited to, ultracentrifugation and dialysis. A method can further comprise determining infectious titer, by e.g., plaque assay. A method can further comprise determining viral particle concentration, by e.g., ultraviolet absorbance measurement.

The recombinant virus based vaccine can be delivered to a subject through a parenteral delivery method. A parenteral delivery can include intravenous, transdermal, oral, intrabiliary, intraparenchymal, intra-hepatic artery, intra-portal vein, intratumoral, or transvenous delivery. Sometimes, a parenteral delivery can utilize a needle (e.g., a hypodermic needle) for delivery of the recombinant virus based vaccine. The recombinant virus based vaccine can be formulated in an aqueous solution, e.g., saline. Sometimes, a parenteral delivery can utilize a pneumatic injection as a delivery method. The nucleic acid based vaccine can be formulated as an aqueous solution.

The recombinant virus based vaccine can also be delivered to a subject through a topical delivery method. The vaccine can be applied directly onto an infected area, e.g., the nasal cavity.

Antibody Based Vaccine

Provided herein is an antibody based vaccine that can comprise an entity that binds a peptide or polypeptide sequence described herein. The antibody based vaccine can be used against influenza infection. The entity can be an antibody.

Antibody-based vaccine can be formulated using any techniques, carriers, and excipients as suitable. The antibody can be a natural antibody, a chimeric antibody, a humanized antibody, or can be an antibody fragment. The antibody can recognize one or more of the epitope sequences described herein. The antibody can recognize one or more sequences selected from SEQ ID NOs: 1-94 or a sequence selected from Table 1, Table 2, or Table 3. The antibody can recognize a sequence that has at most 40%, 50%, 60%, 70%, 80%, 90%, 95%, or 100% sequence homology or identity to a sequence selected from the group consisting of SEQ ID NOs: 1-94 or a sequence selected from Table 1, Table 2, or Table 3. The antibody can recognize a sequence with at least 40%, 50%, 60%, 70%, 80%, 90%, 95%, or 100% sequence homology or identity to a sequence selected from the group consisting of SEQ ID NOs: 1-94 or a sequence selected from Table 1, Table 2, or Table 3. The antibody can recognize a sequence length at least 30%, 40%, 50%, 60%, 70%, 80%, 90%, 95%, or 100%, or more of a sequence length of a sequence selected from the group consisting of SEQ ID NOs: 1-94 or a sequence selected from Table 1, Table 2, or Table 3. The antibody can recognize a sequence length at most 30%, 40%, 50%, 60%, 70%, 80%, 90%, 95%, or 100% the sequence length of a sequence selected from the group consisting of SEQ ID NOs: 1-94 or a sequence selected from Table 1, Table 2, or Table 3. In some embodiments, the antibody recognizes epitopes from multiple strains of influenza virus, such as influenza A virus, influenza B virus, influenza C virus.

An antibody can include fully assembled antibodies, antibody fragments that can bind antigen (e.g., Fab, F(ab')$_2$, Fv, single chain antibodies, diabodies, antibody chimeras, hybrid antibodies, bispecific antibodies, humanized antibodies, and the like), and recombinant peptides comprising the foregoing.

An antibody can be a monoclonal antibody. The preparation of monoclonal antibodies is known in the art and can be accomplished by fusing spleen cells from a host sensitized to the antigen with myeloma cells in accordance with known techniques or by transforming the spleen cells with an appropriate transforming vector to immortalize the cells. The cells can be cultured in a selective medium, cloned, and screened to select monoclonal antibodies that bind the designated antigens. Numerous references can be found on the preparation of monoclonal and polyclonal antibodies.

A native antibody (native immunoglobulin) can be heterotetrameric glycoproteins of about 150,000 daltons, composed of two identical light (L) chains and two identical heavy (H) chains. Each light chain can be linked to a heavy chain by one covalent disulfide bond, while the number of disulfide linkages can vary among the heavy chains of different immunoglobulin isotypes. Each heavy and light chain can also have regularly spaced intrachain disulfide bridges. Each heavy chain has at one end a variable domain (VH) followed by a number of constant domains. Each light chain can have a variable domain at one end (VL) and a constant domain at its other end; the constant domain of the light chain can be aligned with the first constant domain of the heavy chain, and the light chain variable domain can be aligned with the variable domain of the heavy chain. Particular amino acid residues can form an interface between the light and heavy-chain variable domains.

Variable regions can confer antigen-binding specificity. In some cases, the variability is not evenly distributed throughout the variable domains of antibodies. Variability can be concentrated in three segments called complementarity determining regions (CDRs) or hypervariable regions, both in the light chain and the heavy-chain variable domains. The more highly conserved portions of variable domains can be located in the framework (FR) regions. The variable domains of native heavy and light chains each can comprise four FR regions, largely adopting a β-pleated-sheet configuration, connected by three CDRs, which form loops connecting, and in some cases forming part of, the β-pleated-sheet structure. The CDRs in each chain can be held together in close proximity by the FR regions and, with the CDRs from the other chain, contribute to the formation of the antigen-binding site of antibodies. In some cases, the constant domains cannot be involved directly in binding an antibody to an antigen, but can exhibit various effector functions, such as Fc receptor (FcR) binding, participation of the antibody in antibody-dependent cellular toxicity, initiation of complement dependent cytotoxicity, and mast cell degranulation.

A hypervariable region can refer to the amino acid residues of an antibody that are responsible for antigen-binding. The hypervariable region can comprise amino acid residues from a complementarily determining region or CDR and/or those residues from a "hypervariable loop." Framework or FR residues can be those variable domain residues other than the hypervariable region residues, as herein deemed.

Antibody fragments can comprise a portion of an intact antibody, e.g., the antigen-binding or variable region of the intact antibody. Examples of antibody fragments include Fab, Fab, F(ab')2, and Fv fragments; diabodies; minibodies; linear antibodies; single-chain antibody molecules; and multispecific antibodies formed from antibody fragments. Papain digestion of antibodies can produce two identical antigen-binding fragments, called Fab fragments, each with a single antigen-binding site, and a residual Fc fragment, whose name reflects its ability to crystallize readily. Pepsin treatment yields an F(ab')2 fragment that has two antigen-combining sites and is still capable of cross-linking antigen.

Fv can be the minimum antibody fragment that contains a complete antigen recognition and binding site. This region can consist of a dimer of one heavy- and one light-chain variable domain in tight, non-covalent association. It is in this configuration that the three CDRs of each variable domain can interact to define an antigen-binding site on the surface of the VH-VL dimer. Collectively, the six CDRs can confer antigen-binding specificity to the antibody. However, even a single variable domain (or half of an Fv comprising only three CDRs specific for an antigen) can have the ability to recognize and bind antigen, although at a lower affinity than the entire binding site.

The Fab fragment can contain the constant domain of the light chain and the first constant domain (CHI) of the heavy chain. Fab fragment can differ from Fab' fragments by the addition of a few residues at the carboxy terminus of the heavy chain CHI domain including one or more cysteines from the antibody hinge region. Fab'-SH can be used herein for Fab' in which the cysteine residue(s) of the constant domains bear a free thiol group. Fab' fragments can be produced by reducing the F(ab')2 fragment's heavy chain disulfide bridge. Other chemical couplings of antibody fragments are also known.

The light chains of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. Five major classes of human immunoglobulins include: IgA, IgD, IgE, IgG, and IgM, and several of these can be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes can have different effector functions. For example, human IgG1 and IgG3 isotypes have ADCC (antibody dependent cell-mediated cytotoxicity) activity.

Monoclonal antibodies can be obtained from any suitable species e.g., murine, rabbit, sheep, goat, or human monoclonal antibodies.

A composition, e.g., vaccine, can comprise at about or at least or at most 5, 10, 25, 50 or 100 different antibodies.

Antigen Presenting Cell (APC) Based Vaccine

Provided herein is an APC based vaccine that presents a polypeptide described herein. The APC based vaccine can be used against influenza infection. The APC based vaccine can be formulated using any of the known techniques, carriers, and excipients as suitable and as understood in the art. APCs may include monocytes, monocyte-derived cells, macrophages, and dendritic cells. Sometimes, APC based vaccine can be a dendritic cell-based vaccine.

A dendritic cell (DC)-based vaccine can be prepared by any methods known in the art. In some cases, dendritic cell-based vaccines can be prepared through an ex vivo or in vivo method. The ex vivo method can comprise the use of autologous DCs pulsed ex vivo with the polypeptides described herein, to activate or load the DCs prior to administration into the patient. The in vivo method can comprise targeting specific DC receptors using antibodies coupled with the peptides described herein. The DC-based vaccine can further comprise DC activators such as TLR3, TLR-7-8, and CD40 agonists. The DC-based vaccine can further comprise adjuvants, and a pharmaceutically acceptable carrier.

Virus-Based Vaccine

A virus-based vaccine can be generated based on live virus or on inactivated virus. Viruses can be engineered to express one or more proteins that comprise any of the sequences described herein. Vaccines based on live virus can use an attenuated virus, or a virus that can be cold-adapted. Vaccines based on inactivated virus can comprise whole virion, split virion, or purified surface antigens (e.g., HA and/or N from influenza A virus). Chemical means for inactivating a virus can include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as UV light, heat inactivation, or gamma irradiation.

Virions can be harvested from virus-containing fluids by various methods. For example, a purification process can involve zonal centrifugation using a linear sucrose gradient solution that includes detergent to disrupt the virions. Antigens can be purified, after optional dilution, by diafiltration.

Split virions can be obtained by treating purified virions with detergents (e.g., ethyl ether, polysorbate 80, deoxycholate, tri-N-butyl phosphate, Triton X-100, Triton N101, cetyltrimethylammonium bromide, Tergitol NP9, etc.) to produce subvirion preparations, including the "Tween-ether" splitting process. Methods of splitting influenza viruses are well known in the art. Splitting of the virus can be carried out by disrupting or fragmenting whole virus, whether infectious or non-infectious with a disrupting concentration of a splitting agent. The disruption can result in a full or partial solubilization of the virus proteins, altering the integrity of the virus. Splitting agents can be non-ionic or ionic (e.g., cationic) surfactants e.g., alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g., the Triton surfactants, such as Triton X-100 or Triton N101), polyoxyethylene sorbitan esters (the Tween surfactants), polyoxyethylene ethers, polyoxyethlene esters, etc. One exemplary splitting procedure can use the consecutive effects of sodium deoxycholate and formaldehyde, and splitting can take place during initial virion purification (e.g., in a sucrose density gradient solution). Thus a splitting process can involve clarification of the virion-containing material (to remove non-virion material), concentration of the harvested virions (e.g., using an adsorption method, such as CaHP04 adsorption), separation of whole virions from non-virion material, splitting of virions using a splitting agent in a density gradient centrifugation step (e.g., using a sucrose gradient that contains a splitting agent such as sodium deoxycholate), and then filtration (e.g., ultrafiltration) to remove undesired materials. Split virions can usefully be resuspended in sodium phosphate-buffered isotonic sodium chloride solution. The BEGRIVAC™, FLUARIX™, FLUZONE™, and FLUSHIELD™ products are split vaccines.

Purified surface antigen vaccines can comprise the influenza surface antigens haemagglutinin and, typically, also neuraminidase. Processes for preparing these proteins in purified form are well known in the art. The FLUVIRIN™, AGRIPPAL™, and INFLUVAC™ products are examples.

Vaccine based on inactivated virus can include the virosome (nucleic acid free viral-like liposomal particles). Virosomes can be prepared by solubilization of influenza virus with a detergent followed by removal of the nucleocapsid and reconstitution of the membrane containing the viral glycoproteins. Virosomes can also be prepared by adding viral membrane glycoproteins to excess amounts of phospholipids, to yield liposomes with viral proteins in their membrane.

Pharmaceutical Composition and Administration

Provided herein is a pharmaceutical composition that can be used to provide immunity against influenza virus infection. In certain aspects of the disclosure, the pharmaceutical composition can be a vaccine.

A composition can comprise one or more polypeptides, nucleic acids, proteins (e.g., antibodies or fragments thereof), APCs, or viruses described herein, or a combination thereof, and a pharmaceutically acceptable excipient. In some embodiments, a composition can further comprise carriers for the polypeptide, polynucleotide, or vector. A composition can further comprise a preservative. In some cases, a composition can further comprise other reagents to maintain appropriate physical or chemical properties, such as, but not limited to, salt concentration, osmolality, pH, hydrophobicity/hydrophility, and solubility. A composition can further comprise appropriate penetration enhancer for enhanced delivery. A composition can further comprise appropriate adjuvant(s) that can enhance the immunogenicity of the polypeptide, polynucleotide, or vector.

Formulations

A composition provided herein, e.g., a vaccine, can be formulated based, in part, on the intended route of administration of the composition. The composition, e.g., vaccine, can comprise one or more active agents, such as one or more peptides, nucleic acids, proteins (e.g., antibodies or fragments thereof), APCs, viruses described herein, or a combination thereof. A composition comprising one or more active agents in combination with one or more adjuvants can be formulated in conventional manner using one or more physiologically acceptable carriers, comprising excipients, diluents, and/or auxiliaries, e.g., which facilitate processing of the one or more active agents into preparations that can be administered. The one or more active agents described herein can be delivered to a subject using a number of routes or modes of administration described herein, e.g., oral, buccal, topical, rectal, transdermal, transmucosal, subcutaneous, intravenous, and intramuscular applications, as well as by inhalation.

A composition described herein, e.g., a vaccine, can be a liquid preparation such as a suspension, syrup, or elixir. The composition, e.g., vaccine, can also be a preparation for parenteral, subcutaneous, intradermal, intramuscular, or intravenous administration (e.g., injectable administration), such as a sterile suspension or emulsion. In some cases, aqueous solutions can be packaged for use as is, or lyophilized, and the lyophilized preparation being combined with a sterile solution prior to administration. The composition, e.g., vaccine, can be delivered as a solution or as a suspension. In general, formulations such as jellies, creams, lotions, suppositories and ointments can provide an area with more extended exposure to one or more active agents, while formulations in solution, e.g., sprays, can provide more immediate, short-term exposure.

Formulations for Inhalation (e.g., Nasal Administration or Oral Inhalation)

A composition described herein, e.g., a vaccine, can be formulated for administration via the nasal passages of a subject. Formulations suitable for nasal administration, wherein the carrier is a solid, can include a coarse powder having a particle size, for example, in the range of about 10 to about 500 microns which can be administered in the manner in which snuff is taken, e.g., by rapid inhalation through the nasal passage from a container of the powder held close up to the nose. The formulation can be a nasal spray, nasal drops, or by aerosol administration by nebulizer. The formulation can include aqueous or oily solutions of the vaccine.

A composition provided herein, e.g., a vaccine, can be formulated as an aerosol formulation. The aerosol formulation can be, e.g., an aerosol solution, suspension or dry powder. The aerosol can be administered through the respiratory system or nasal passages. For example, the composition can be suspended or dissolved in an appropriate carrier, e.g., a pharmaceutically acceptable propellant, and administered directly into the lungs using a nasal spray or inhalant. For example, an aerosol formulation comprising one or more active agents can be dissolved, suspended or emulsified in a propellant or a mixture of solvent and propellant, e.g., for administration as a nasal spray or inhalant. The aerosol formulation can contain any acceptable propellant under pressure, such as a cosmetically or dermatologically or pharmaceutically acceptable propellant.

An aerosol formulation for nasal administration can be an aqueous solution designed to be administered to the nasal passages in drops or sprays. Nasal solutions can be similar to nasal secretions in that they can be isotonic and slightly buffered to maintain a pH of about 5.5 to about 6.5. In some cases, pH values outside of this range can be used. Antimicrobial agents or preservatives can also be included in the formulation.

An aerosol formulation for inhalation can be designed so that one or more active agents are carried into the respiratory system of the subject when administered by the nasal or oral respiratory route. Inhalation solutions can be administered, for example, by a nebulizer. Inhalations or insufflations, comprising finely powdered or liquid drugs, can be delivered to the respiratory system as a pharmaceutical aerosol of a solution or suspension of the agent or combination of agents in a propellant, e.g., to aid in disbursement. Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants can include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Hydrocarbon propellants can include, for example, propane, isobutane, n-butane, pentane, isopentane, and neopentane. A blend of hydrocarbons can also be used as a propellant. Ether propellants include, for example, dimethyl ether as well as ethers. An aerosol formulation can also comprise more than one propellant. For example, the aerosol formulation can comprise more than one propellant from the same class, such as two or more fluorocarbons; or more than one, more than two, more than three propellants from different classes, such as a fluorohydrocarbon and a hydrocarbon. A composition described herein, e.g., vaccine, can also be dispensed with a compressed gas, e.g., an inert gas such as carbon dioxide, nitrous oxide, or nitrogen.

The aerosol formulation can also include other components, for example, ethanol, isopropanol, propylene glycol, as well as surfactants or other components, such as oils and detergents. These components can serve to stabilize the formulation and/or lubricate valve components.

The aerosol formulation can be packaged under pressure and can be formulated as an aerosol using solutions, suspensions, emulsions, powders, and semisolid preparations. For example, a solution aerosol formulation can comprise a solution of an active agent such in (substantially) pure propellant or as a mixture of propellant and solvent. The solvent can be used to dissolve one or more active agents and/or retard the evaporation of the propellant. Solvents can include, for example, water, ethanol, and glycols. Any combination of suitable solvents can be use, optionally combined with preservatives, antioxidants, and/or other aerosol components.

An aerosol formulation can be a dispersion or suspension. A suspension aerosol formulation can comprise a suspension of one or more active agents, e.g., peptides, and a dispersing agent. Dispersing agents can include, for example, sorbitan trioleate, oleyl alcohol, oleic acid, lecithin, and corn oil. A suspension aerosol formulation can also include lubricants, preservatives, antioxidant, and/or other aerosol components.

An aerosol formulation can similarly be formulated as an emulsion. An emulsion aerosol formulation can include, for example, an alcohol such as ethanol, a surfactant, water, and a propellant, as well as an active agent or combination of active agents, e.g., one or more peptides. The surfactant used can be nonionic, anionic, or cationic. One example of an emulsion aerosol formulation comprises, for example, ethanol, surfactant, water, and propellant. Another example of an emulsion aerosol formulation comprises, for example, vegetable oil, glyceryl monostearate, and propane.

Formulations for Parenteral Administration

A composition, e.g., vaccine, comprising one or more active agents can be formulated for parenteral administration and can be presented in unit dose form in ampoules, pre-filled syringes, small volume infusion or in multi-dose containers with an added preservative. The composition can take such forms as suspensions, solutions, or emulsions in oily or aqueous vehicles, for example solutions in aqueous polyethylene glycol.

For injectable formulations, a vehicle can be chosen from those known in the art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of active agent in injection grade water, liposomes, and vehicles suitable for lipophilic substances and those known in the art.

Parenteral injection can include subcutaneous, intramuscular, intravenous, intraperitoneal, and intracardiac administration. A subcutaneous administration can be administered as a bolus into the subcutis. Subcutaneous injection sites on a human subject can include the outer area of the upper arm, abdomen, the front of the thigh, the upper back, the upper area of the buttock. Intramuscular administration can be an injection directly into muscle. Intramuscular injection sites can include deltoid, dorsogluteal, rectus femoris, vastus lateralis and ventrogluteal muscles. Intravenous administration can be delivery of a liquid formulation directly into a vein. Intravenous administration can be applied on a peripheral vein (e.g. the veins in the arms, hands, legs, and feet) or a central vein (e.g. superior vena cava, inferior vena cava, and the right atrium of the heart). Intraperitoneal administration can be injection into the peritoneum. Intracardiac administration can be injection directly into heart muscles or ventricles.

Sometimes, the composition, e.g., vaccine, can be formulated for intravenous administration to mammalian subjects, like human beings. The composition, e.g., vaccine, for intravenous administration can be a solution in sterile isotonic aqueous buffer. In some cases, the composition, e.g., vaccine, can include a solubilizing agent and a local anesthetic such as lidocaine to ease pain at the site of the injection. The ingredients can be supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

When administration is by injection, a composition, e.g., vaccine, comprising one or more active agents can be formulated in aqueous solutions, specifically in physiologically compatible buffers such as Hanks solution, Ringer's solution, or physiological saline buffer. The solution can contain formulatory agents such as suspending, stabilizing, and/or dispersing agents. Alternatively, the one or more active agents can be in powder form for constitution with a suitable vehicle, e.g., sterile pyrogen-free water, before use. In another embodiment, the composition, e.g., vaccine, does not comprise an adjuvant or any other substance added to enhance the immune response stimulated by the active agent. In another embodiment, the composition, e.g., vaccine, can comprise a substance that inhibits an immune response to the one or more active agents.

In some embodiments, one or more active agents are formulated as a depot preparation. Such long acting formulations can be administered by implantation or transcutaneous delivery (e.g., subcutaneously or intramuscularly), intramuscular injection or use of a transdermal patch. Thus, for example, one or more active agents can be formulated with suitable polymeric or hydrophobic materials (e.g., as an emulsion in an acceptable oil) or ion exchange resins, or as sparingly soluble derivatives, for example, as a sparingly soluble salt.

Formulations for Topical Administration

In certain aspects of the disclosure, a composition provided herein, e.g., a vaccine, can comprise one or more agents that exert local and regional effects when administered topically or injected at or near particular sites of infection. Direct topical application, e.g., of a viscous liquid, solution, suspension, dimethylsulfoxide (DMSO)-based solutions, liposomal formulations, gel, jelly, cream, lotion, ointment, suppository, foam, or aerosol spray, can be used for local administration, to produce for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations can also include preservatives (e.g., p-hydroxybenzoic acid esters) and/or antioxidants (e.g., ascorbic acid and tocopherol). In some embodiments, local/topical formulations comprising one or more active agents are used to treat epidermal or mucosal viral infections.

A composition provided herein, e.g., a vaccine, can contain a dermatologically acceptable carrier. Such carriers are compatible with skin, nails, mucous membranes, tissues, and/or hair, and can include any dermatological carrier meeting these requirements. Such carriers can be readily selected by one of ordinary skill in the art. In formulating skin ointments, one or more agents can be formulated in an oleaginous hydrocarbon base, an anhydrous absorption base, a water-in-oil absorption base, an oil-in-water water-removable base and/or a water-soluble base. Examples of such carriers and excipients include humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Ointments and creams can, for example, be formulated with an aqueous or oily base with the addition of suitable thickening and/or gelling agents. Lotions can be formulated with an aqueous or oily base and will in general also containing one or more emulsifying agents, stabilizing agents, dispersing agents, suspending agents, thickening agents, or coloring agents. The construction and use of transdermal patches for the delivery of pharmaceutical agents is known in the art. Such patches can be constructed for continuous, pulsatile, or on demand delivery of pharmaceutical agents.

Lubricants which can be used to form compositions and dosage forms can include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the composition.

A composition provided herein, e.g., a vaccine, can be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. Other than the one or more active agents, the amounts of the various constituents of the compositions provided herein can be those used in the art. These compositions can constitute protection, treatment or care creams, milks, lotions, gels or foams for the face, for the hands, for the body and/or for the mucous membranes, or for cleansing the skin. The compositions can also consist of solid preparations constituting soaps or cleansing bars.

A composition provided herein, e.g., a vaccine, for local/topical application can include one or more antimicrobial preservatives such as quaternary ammonium compounds, organic mercurials, p-hydroxy benzoates, aromatic alcohols, chlorobutanol, and the like.

Formulations for Oral Administration

Sometimes, a composition provided herein, e.g., a vaccine, can be formulated for oral administration.

For oral administration, a composition as provided herein can be formulated readily by combining the one or more active agents with pharmaceutically acceptable carriers known in the art. Such carriers enable active agents to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. A solid carrier can be one or more substances which can also act as diluents, flavoring agents, solubilizers, lubricants, suspending agents, binders, preservatives, tablet disintegrating agents, or an encapsulating material. In powders, the carrier can be a finely divided solid which is a mixture with the finely divided active component. In tablets, the active component generally is mixed with the carrier having the desired binding capacity in suitable proportions and compacted in the shape and size desired. The powders and tablets can contain from about one (1) to about seventy (70) percent of the one or more active agents. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Generally, the one or more active agents can be included at concentration levels ranging from about 0.5%, about 5%, about 10%, about 20%, or about 30% to about 50%, about 60%, about 70%, about 80%, or about 90% by weight of the total composition of oral dosage forms, in an amount sufficient to provide a desired unit of dosage.

Aqueous suspensions for oral use can contain one or more active agents with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

Oils or non-aqueous solvents can be required to bring the one or more active agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. Ligands can also be attached to the liposomes to direct these compositions to particular sites of action.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents can be added, such as the cross-linked polyvinyl pyrrolidone, agar, or alginic acid or a salt thereof such as sodium alginate. The agents can also be formulated as a sustained release preparation.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents can be dissolved or suspended in suitable liquids, such as fatty oils, liquid paraffin, or liquid polyethylene glycols. In addition, stabilizers can be added. All formulations for oral administration can be in dosages suitable for administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or can contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Suitable fillers or carriers with which the compositions can be administered include agar, alcohol, fats, lactose, starch, cellulose derivatives, polysaccharides, polyvinylpyrrolidone, silica, sterile saline and the like, or mixtures thereof used in suitable amounts. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

A syrup or suspension can be made by adding the active compound to a concentrated, aqueous solution of a sugar, e.g., sucrose, to which can also be added any accessory ingredients. Such accessory ingredients can include flavoring, an agent to retard crystallization of the sugar or an agent to increase the solubility of any other ingredient, e.g., as a polyhydric alcohol, for example, glycerol or sorbitol.

When formulating compounds for oral administration, it can be desirable to utilize gastroretentive formulations to enhance absorption from the gastrointestinal (GI) tract. A formulation which is retained in the stomach for several hours can release an active agent slowly and provide a sustained release that can be used herein. Expandable, floating and bioadhesive techniques can be utilized to maximize absorption an active agent.

Formulations for Ophthalmic Administration

In some instances, a composition provided herein can be administered through eyes, e.g. delivered in eye drops. Eye drops can be prepared by dissolving the one or more active agents in a sterile aqueous solution such as physiological saline, buffering solution, etc., or by combining powder compositions to be dissolved before use. Other vehicles can be chosen, as is known in the art, including but not limited to: balance salt solution, saline solution, water soluble poly ethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, cross-linked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose, or other agents known to those skilled in the art).

Other Formulations

In some embodiments, a composition provided herein is administered in otic solutions, suspensions, ointments, or inserts. In some embodiments, a composition described herein, e.g., a vaccine, is formulated for administration as a suppository. For example, a low melting wax, such as a mixture of triglycerides, fatty acid glycerides, Witepsol S55 (trademark of Dynamite Nobel Chemical, Germany), or cocoa butter can be first melted and the active component can be dispersed homogeneously, for example, by stirring. The molten homogeneous mixture can then be poured into convenient sized molds, allowed to cool, and to solidify. In some embodiments, a composition described herein, e.g., a vaccine, is formulated for vaginal administration. In some cases, pessaries, tampons, creams, gels, pastes, foams, or sprays contain one or compositions, e.g., vaccines described herein.

Ingredients, e.g., Carriers, Excipients

A composition provided herein, e.g., a vaccine, can include one or more carriers and excipients (including but not limited to buffers, carbohydrates, mannitol, proteins, peptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In another instance, the composition is substantially free of preservatives. In other embodiments, the composition, e.g., vaccine, contains at least one preservative. General methodology on pharmaceutical dosage forms can be found in Ansel et ah, Pharmaceutical Dosage Forms and Drug Delivery Systems (Lippencott Williams & Wilkins, Baltimore Md. (1999)). It will be recognized that, while any suitable carrier known to those of ordinary skill in the art can be employed to administer the pharmaceutical compositions described herein, the type of carrier can vary depending on the mode of administration. Suitable formulations and additional carriers are described in Remington "The Science and Practice of Pharmacy" ($20^{th}$ Ed., Lippincott Williams & Wilkins, Baltimore Md.), the teachings of which are incorporated by reference in their entirety herein.

Liposomes and Microspheres

A composition provided herein, e.g., a vaccine, can be encapsulated within liposomes. Biodegradable microspheres can also be employed as carriers for the composition.

A composition provided herein, e.g., a vaccine, can be administered in liposomes or microspheres (or microparticles). Methods for preparing liposomes and microspheres for administration to a patient are known to those of skill in the art. For example, U.S. Pat. No. 4,789,734, the contents of which are hereby incorporated by reference, describes methods for encapsulating biological materials in liposomes. The material can be dissolved in an aqueous solution, the appropriate phospholipids and lipids added, along with surfactants if required, and the material dialyzed or sonicated, as desired. Microspheres formed of polymers or proteins are known to those skilled in the art, and can be tailored for passage through the gastrointestinal tract directly into the blood stream. Alternatively, the compound can be incorporated and the microspheres, or composite of microspheres, implanted for slow release over a period of time ranging from days to months.

Preservatives/Sterility

A composition provided herein, e.g., a vaccine, can include material for a single administration (e.g., immunization), or can include material for multiple administrations (e.g., immunizations) (e.g., a "multidose" kit). The composition, e.g., vaccine, can include one or more preservatives such as thiomersal or 2-phenoxyethanol. In some embodiments, the vaccine is substantially free from (e.g., <10 µg/ml) mercurial material e.g., thiomersal-free. In some embodiments, a-Tocopherol succinate is used as an alternative to mercurial compounds. Preservatives can be used to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. In ophthalmic products, e.g., such preservatives can be employed at a level of from 0.004% to 0.02%. In the compositions of the present application the preservative, e.g., benzalkonium chloride, can be employed at a level of from 0.001% to less than 0.01%, e.g., from 0.001% to 0.008%, preferably about 0.005% by weight. A concentration of benzalkonium chloride of 0.005% can be sufficient to preserve a composition provided herein from microbial attack.

As an alternative (or in addition) to including a preservative in multidose compositions, the composition, e.g., vaccine, can be contained in a container having an aseptic adaptor for removal of material.

In some cases, a composition provided herein, e.g., a vaccine, can be sterile. The composition, e.g., vaccine, can be non-pyrogenic e.g., containing <1 EU (endotoxin unit, a standard measure) per dose, and can be <0.1 EU per dose. The composition, e.g., vaccine, can be formulated as a sterile solution or suspension, in suitable vehicles, known in the art. The composition, e.g., vaccine, can be sterilized by conventional, known sterilization techniques, e.g., the composition can be sterile filtered.

Salts/Osmolality

In some embodiments, a composition provided herein, e.g., vaccine, comprises one or more salts. For controlling the tonicity, a physiological salt such as sodium salt can be included a composition provided herein, e.g., vaccine. Other salts can include potassium chloride, potassium dihydrogen phosphate, disodium phosphate, and/or magnesium chloride, or the like. In some embodiments, the composition, e.g., vaccine, is formulated with one or more pharmaceutically acceptable salts. The one or more pharmaceutically acceptable salts can include those of the inorganic ions, such as, for example, sodium, potassium, calcium, magnesium ions, and the like. Such salts can include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid, or maleic acid. If an active agent (e.g., polypeptide) contains a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexylamine, ethanolamine, diethanolamine, triethanolamine, and the like.

A composition, e.g., vaccine, can have an osmolality of between 200 mOsm/kg and 400 mOsm/kg, between 240-360 mOsm/kg, or within the range of 290-310 mOsm/kg.

Buffers/pH

A composition provided herein, e.g., vaccine, can comprise one or more buffers, such as a Tris buffer; a borate buffer; a succinate buffer; a histidine buffer (e.g., with an aluminum hydroxide adjuvant); or a citrate buffer. Buffers, in some cases, are included in the 5-20 mM range.

A composition provided herein, e.g., vaccine, has a pH between about 5.0 and about 8.5, between about 6.0 and about 8.0, between about 6.5 and about 7.5, or between about 7.0 and about 7.8.

Detergents/Surfactants

A composition provided herein, e.g., vaccine, includes one or more detergents and/or surfactants, e.g., polyoxyethylene sorbitan esters surfactants (commonly referred to as "Tweens"), e.g., polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1, 2-ethanediyl) groups, e.g., octoxynol-9 (Triton X-100, or t-octylphenoxypolyethoxyethanol); (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as "SPANs"), such as sorbitan trioleate (Span 85) and sorbitan monolaurate, an octoxynol (such as octoxynol-9 (Triton X-100) or t-octylphenoxypolyethoxyethanol), a cetyl trimethyl ammonium bromide ("CTAB"), or sodium deoxycholate, particularly for a split or surface antigen vaccine. The one or more detergents and/or surfactants can be present only at trace amounts. In some cases, the composition, e.g., vaccine, can include less than 1 mg/ml of each of octoxynol-10 and polysorbate 80. Non-ionic surfactants can be used herein. Surfactants can be classified by their "HLB" (hydrophile/lipophile balance). In some cases, surfactants have a HLB of at least 10, at least 15, and/or at least 16.

In some embodiments, mixtures of surfactants is used in a composition e.g., vaccine, e.g., Tween 80/Span 85 mixtures. A combination of a polyoxyethylene sorbitan ester and an octoxynol can also be suitable. Another combination can comprise laureth 9 plus a polyoxyethylene sorbitan ester and/or an octoxynol. The amounts of surfactants (% by weight) can be: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Adjuvants

A composition provided herein, e.g., vaccine, can comprise one or more adjuvants. An adjuvant can be used to enhance the immune response (humoral and/or cellular) elicited in a subject receiving the vaccine. Sometimes, an adjuvant can elicit a Th1-type response. In some cases, an adjuvant can elicit a Th2-type response. A Th1-type response can be characterized by the production of cytokines such as IFN-γ as opposed to a Th2-type response which can be characterized by the production of cytokines such as IL-4, IL-5, and IL-10.

Lipid-based adjuvants, such as MPL and MDP, can be used with a composition, e.g., vaccine, disclosed herein. Monophosphoryl lipid A (MPL), for example, is an adjuvant that can cause increased presentation of liposomal antigen to specific T Lymphocytes. In addition, a muramyl dipeptide (MDP) can also be used as a suitable adjuvant in conjunction with a composition, e.g., vaccine, described herein.

Adjuvant can also comprise stimulatory molecules such as cytokines. Non-limiting examples of cytokines include: CCL20, a-interferon (IFN-a), β-interferon (IFN-β), γ-interferon, platelet derived growth factor (PDGF), TNFa, TNFp, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHC, CD80, CD86, IL-1, IL-2, IL-4, IL-5, IL-6, IL-10, IL-18, MCP-1, MIP-la, MIP-1-, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC 5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, and TAP2.

Additional adjuvants can include: MCP-1, MIP-la, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, TAP2 and functional fragments thereof.

In some cases, the one or more adjuvants can be a modulator of a toll like receptor. Examples of modulators of toll-like receptors include TLR-9 agonists and TLR-2 agonists and are not limited to small molecule modulators of toll-like receptors such as Imiquimod (R837). Other examples of adjuvants that can be used a composition described herein, e.g., a vaccine, include saponin, CpG ODN and the like.

In some cases, the one or more adjuvants is selected from bacteria toxoids, polyoxypropylene-polyoxyethylene block polymers, aluminum salts, liposomes, CpG polymers, oil-in-water emulsions, or a combination thereof.

Sometimes, the one or more adjuvants can be based on aluminum salts (alum) or derivatives thereof. Exemplary Alums can comprise aluminum hydroxide, aluminum phosphate, potassium aluminum sulfate, sodium aluminum sulfate, ammonium aluminum sulfate, cesium aluminum sulfate, or a mixture of aluminum and magnesium hydroxide. Alum can also comprise crystalline aluminum oxyhydroxide (AIOOH). Sometimes, AIOOH adjuvants can compose of nanolength scale plate-like primary particles that form aggregates, representing the functional subunits in the material. These aggregates can be porous and can have irregular shapes that range from about 1 to about 20 µm in diameter. Upon mixing with antigen, the aggregates can be broken into smaller fragments that can reaggregate to distribute the absorbed antigen throughout the vaccine. In some embodiments, the adjuvant comprises ordered rod-like AlO(OH) nanoparticles.

In some embodiments, the one or more adjuvants are an oil-in-water emulsion. The oil-in-water emulsion can include at least one oil and at least one surfactant, with the oil(s) and surfactant(s) being biodegradable and biocompatible. The oil droplets in the emulsion can be less than 5 µm in diameter, and can even have a sub-micron diameter, with these small sizes being achieved with a microfluidiser to provide stable emulsions. Droplets with a size less than 220 nm can be preferred as they can be subjected to filter sterilization.

The oils used can include such as those from an animal (such as fish) or vegetable source. Sources for vegetable oils can include nuts, seeds, and grains. Peanut oil, soybean oil, coconut oil, and olive oil, the most commonly available, exemplify the nut oils. Jojoba oil can be used e.g., obtained from the jojoba bean. Seed oils include safflower oil, cottonseed oil, sunflower seed oil, sesame seed oil, etc. The grain group can include: corn oil and oils of other cereal grains such as wheat, oats, rye, rice, teff, triticale, and the like. 6-10 carbon fatty acid esters of glycerol and 1,2-propanediol, while not occurring naturally in seed oils, can be prepared by hydrolysis, separation and esterification of the appropriate materials starting from the nut and seed oils. Fats and oils from mammalian milk can be metabolizable and can be used in with the compositions, e.g., vaccines described herein. The procedures for separation, purification, saponification, and other means for obtaining pure oils from animal sources are known in the art. Fish can contain metabolizable oils which can be readily recovered. For example, cod liver oil, shark liver oils, and whale oil such as spermaceti can exemplify several of the fish oils which can be used herein. A number of branched chain oils can be synthesized biochemically in 5-carbon isoprene units and can be generally referred to as terpenoids. Shark liver oil contains a branched, unsaturated terpenoid known as squalene, 2,6,10,15,19,23-hexamethyl-2,6,10,14,18,22-tetracosahexaene. Squalane, the saturated analog to squalene, can also be used. Fish oils, including squalene and squalane, can be readily available from commercial sources or can be obtained by methods known in the art.

Other useful oils include tocopherols, which can be included in a composition described herein, e.g., a vaccine, for use in elderly patients (e.g., aged 60 years or older), as vitamin E can have a positive effect on the immune response in this subject group. Further, tocopherols can have antioxidant properties that can help to stabilize the emulsions. Various tocopherols exist (α, β, γ, δ, ε or ξ); in some cases, a is used. An example of a-tocopherol is DL-a-tocopherol. a-tocopherol succinate can be compatible with compositions provided herein, e.g., influenza vaccines, and can be a useful preservative as an alternative to mercurial compounds. In some embodiments, mixtures of oils can be used e.g., squalene and a-tocopherol. An oil content in the range of 2-20% (by volume) can be used.

Specific oil-in-water emulsion adjuvants include, e.g., a submicron emulsion of squalene, polysorbate 80, and sorbitan trioleate. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as "MF59". The MF59 emulsion advantageously includes citrate ions e.g., 10 mM sodium citrate buffer.

An oil-in water emulsion can be a submicron emulsion of squalene, a tocopherol, and polysorbate 80. These emulsions can have from 2 to 10% squalene, from 2 to 10% tocopherol and from 0.3 to 3% polysorbate 80, and the weight ratio of squalene:tocopherol can be preferably ≤1 (e.g., 0.90) as this can provide a more stable emulsion. Squalene and polysorbate 80 can be present at a volume ratio of about 5:2 or at a weight ratio of about 11:5. One such emulsion can be made by dissolving Tween 80 in PBS to give a 2% solution, then mixing 90 ml of this solution with a mixture of (5 g of DL-a-tocopherol and 5 ml squalene), then microfluidising the mixture. The resulting emulsion has submicron oil droplets e.g., with an average diameter of between 100 and 250 nm, preferably about 180 nm. The emulsion may also include a 3-de-O-acylated monophosphoryl lipid A (3d-MPL). Another useful emulsion of this type can comprise, per human dose, 0.5-10 mg squalene, 0.5-11 mg tocopherol, and 0.1-4 mg polysorbate 80.

An oil-in water emulsion can be an emulsion of squalene, a tocopherol, and a Triton detergent (e.g., Triton X-100). The emulsion can also include a 3d-MPL (see below). The emulsion can contain a phosphate buffer.

An oil-in water emulsion can be an emulsion comprising a polysorbate (e.g., polysorbate 80), a Triton detergent (e.g., Triton X-100) and a tocopherol (e.g., an a-tocopherol succinate). The emulsion can include these three components at a mass ratio of about 75:11:10 (e.g., 750 µ/ml polysorbate 80, 110 u/ml Triton X-100 and 100 µ/ml α-tocopherol succinate), and these concentrations should include any contribution of these components from antigens. The emulsion can also include squalene. The emulsion can also include a 3d-MPL. The aqueous phase can contain a phosphate buffer.

An oil-in water emulsion can be an emulsion of squalane, polysorbate 80, and poloxamer 401 ("Pluronic™ L121"). The emulsion can be formulated in phosphate buffered saline, pH 7.4. This emulsion can be a useful delivery vehicle for muramyl dipeptides, and can be used with threonyl-MDP in the "SAF-1" adjuvant (0.05-1% Thr-MDP, 5% squalane, 2.5% Pluronic L121 and 0.2% polysorbate 80). It can also be used without the Thr-MDP, as in the "AF" adjuvant (5% squalane, 1.25% Pluronic L121 and 0.2% polysorbate 80).

An oil-in water emulsion can be an emulsion comprising squalene, an aqueous solvent, a polyoxyethylene alkyl ether hydrophilic nonionic surfactant (e.g., polyoxyethylene (12) cetostearyl ether) and a hydrophobic nonionic surfactant (e.g., a sorbitan ester or mannide ester, such as sorbitan monoleate or "Span 80"). The emulsion can be thermoreversible and/or has at least 90% of the oil droplets (by volume) with a size less than 200 nm. The emulsion can also include one or more of alditol; a cryoprotective agent (e.g., a sugar, such as dodecylmaltoside and/or sucrose); and/or an alkylpolyglycoside. The emulsion can include a TLR4 agonist. Such emulsions can be lyophilized.

An oil-in water emulsion can be an emulsion of squalene, poloxamer 105 and Abil-Care. The final concentration (weight) of these components in adjuvanted vaccines can be 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An oil-in water emulsion can be an emulsion having from 0.5-50% of an oil, 0.1-10% of a phospholipid, and 0.05-5% of a non-ionic surfactant. Phospholipid components can include phosphatidylcholine, phosphatidylethanolamine, phosphatidylserine, phosphatidylinositol, phosphatidylglycerol, phosphatidic acid, sphingomyelin, and cardiolipin. Submicron droplet sizes can be advantageous.

An oil-in water emulsion can be a submicron oil-in-water emulsion of a non-metabolisable oil (such as light mineral oil) and at least one surfactant (such as lecithin, Tween 80 or Span 80). Additives can include, QuilA saponin, cholesterol, a saponin-lipophile conjugate (such as GPI-OlOO, produced by addition of aliphatic amine to desacylsaponin via the carboxyl group of glucuronic acid), dimethyldioctadecylammonium bromide, and/or N,N-dioctadecyl-N,N-bis(2-hydroxyethyl) propanediamine.

In some embodiments, a composition provided herein, e.g., vaccine, contains adjuvants such as hydrophilic or lipophilic gelling agents, hydrophilic or lipophilic active agents, preserving agents, antioxidants, solvents, fragrances, fillers, sunscreens, odor-absorbers, and dyestuffs. The amounts of these various adjuvants can be those used in the fields considered and, for example, are from about 0.01% to about 20% of the total weight of the composition. Depending on their nature, these adjuvants can be introduced into a fatty phase, into an aqueous phase and/or into lipid vesicles.

A composition provided herein, e.g., a vaccine, comprising one or more active agent such as a peptide, a nucleic acid molecule, an antibody or fragments thereof, an APC, and/or virus described herein, in combination with one or more adjuvants, can be formulated to comprise certain molar ratios. For example, molar ratios of about 99:1 to about 1:99 of an active agent in combination with one or more adjuvants can be used. In some embodiments, the range of molar ratios of an active agent in combination with one or more adjuvants can be selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of an active agent in combination with one or more adjuvants can be about 1:9, and in some cases can be about 1:1. The active agent such as a peptide or polypeptide, a nucleic acid molecule, an antibody or fragments thereof, an APC, and/or virus described herein, in combination with one or more adjuvants can be formulated together, in the same dosage unit e.g., in one vial, suppository, tablet, capsule, an aerosol spray; or each agent, form, and/or compound can be formulated in separate units, e.g., two vials, suppositories, tablets, two capsules, a tablet and a vial, an aerosol spray, and the like.

A composition provided herein, e.g., vaccine, can comprise one or more adjuvants selected from the list Alum, monophosphoryl lipid A (MPL), imiquimod (R837) (a small synthetic antiviral molecule-TLR7 ligand), Pam2Cys, and ordered rod-like AIO(OH) nanoparticles (Rod). In some embodiments, a composition provided herein, e.g., vaccine, comprises Alum. In some embodiments, a composition, e.g., vaccine, provided herein comprises Rod. In some embodiments, a composition provided herein, e.g., vaccine, comprises Rod, MPL, and R837. In some embodiments, a composition provided herein, e.g., vaccine, comprises MPL and R837. In some embodiments, a composition provided herein, e.g., vaccine, comprises Alum, MPL, and R837. In some embodiments, a composition provided herein, e.g., vaccine, comprises Pam2Cys.

Additional Agents

A composition provided herein, e.g., a vaccine, can be administered with an additional active agent. The choice of the additional active agent can depend, at least in part, on the condition being treated. The additional active agent can include, for example, any active agent having a therapeutic effect for a pathogen infection (e.g., viral infection), including, e.g., drugs used to treat inflammatory conditions such as an NSAID, e.g., ibuprofen, naproxen, acetaminophen, ketoprofen, or aspirin. In some embodiments, a formulation for treating or preventing an influenza infection can contain one or more conventional influenza antiviral agents, such as Vitamin D, amantadine, arbidol, laninamivir, rimantadine, zanamivir, peramivir, and oseltamivir. In treatments for retroviral infections, such as HIV, formulations can contain one or more conventional antiviral drugs, such as protease inhibitors (lopinavir/ritonavir (Kaletra®), indinavir (Crixivan®), ritonavir (Norvir®), nelfmavir (Viracept®), saquinavir hard gel capsules (Invirase®), atazanavir (Reyataz®), amprenavir (Agenerase®), fosamprenavir (TelzirR), tipranavir (Aptivus®)), reverse transcriptase inhibitors, including non-Nucleoside and Nucleoside/nucleotide inhibitors (AZT (zidovudine, RetrovirR), ddl (didanosine, Videx®), 3TC (lamivudine, Epivir®), d4T (stavudine, Zerit®), abacavir (Ziagen®), FTC (emtricitabine, Emtriva®), tenofovir (Viread®), efavirenz (Sustiva®) and nevirapine (Viramune®)), fusion inhibitors T20 (enfuvirtide, Fuzeon®), integrase inhibitors (MK-0518 and GS-9137), and maturation inhibitors (PA-457 (Bevirimat®)). As another example, formulations can additionally contain one or more supplements, such as vitamin C, vitamin E, and other vitamins and anti-oxidants.

A composition provided herein, e.g., a vaccine, can include one or more antibiotics (e.g., neomycin, kanamycin, polymyxin B).

In some embodiments, the composition, e.g., a vaccine, can be gluten free.

Co-Solvents

The solubility of the components of a composition provided herein can be enhanced by a co-solvent in the composition. Such co-solvents include polysorbate 20, 60, and 80, Pluronic F68, F-84 and P-103, cyclodextrin, or other agents known to those skilled in the art. Such co-solvents can be employed at a level of from about 0.01% to 2% by weight.

Penetration Enhancers

In some embodiments, a composition provided herein, e.g., a vaccine, can include one or more penetration enhancers. For example, the composition can comprise suitable solid or gel phase carriers or excipients that increase penetration or help delivery of agents or combinations of agents across a permeability barrier, e.g., the skin. Examples of penetration-enhancing compounds include, e.g., water, alcohols (e.g., terpenes like methanol, ethanol, 2-propanol), sulfoxides (e.g., dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl)pyrrolidone), laurocapram, acetone, dimethylacetamide, dimethylformamide, tetrahydrofurfuryl alcohol, L-α-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, a-bisabolol, d-limonene, urea and N,N-diethyl-m-toluamide, and the like. Additional examples include humectants (e.g., urea), glycols (e.g., propylene glycol and polyethylene glycol), glycerol monolaurate, alkanes, alkanols, ORGELASE, calcium carbonate, calcium phosphate, various sugars, starches, cellulose derivatives, gelatin, and/or other polymers. In some embodiments, the compositions will include one or more such penetration enhancers.

Additives for Sustained Release Formulations

In some embodiments, one or more active agents can be attached releasably to biocompatible polymers for use in sustained release formulations on, in or attached to inserts for topical, intraocular, periocular, or systemic administration. The controlled release from a biocompatible polymer can be utilized with a water soluble polymer to form an instillable formulation. The controlled release from a biocompatible polymer, such as PLGA microspheres or nanospheres, can be utilized in a formulation suitable for intra ocular implantation or injection for sustained release administration. Any suitable biodegradable and biocompatible polymer can be used.

Administration Routes

A composition described herein, e.g., a vaccine, can be delivered via a variety of routes to a subject, e.g., a human. Delivery routes can include oral (including buccal and sublingual), rectal, nasal, topical, transdermal, transmucosal, pulmonary, vaginal, suppository, or parenteral (including intramuscular, intra-arterial, intrathecal, intradermal, intraperitoneal, subcutaneous and intravenous) administration or in a form suitable for administration by aerosolization, inhalation or insufflation. The composition, e.g., vaccine, can be administered to muscle, or can be administered via intradermal or subcutaneous injections, or transdermally, such as by iontophoresis. The composition, e.g., vaccine, can be delivered to a subject by epidermal administration.

Therapeutic Regimens

A composition provided herein, e.g., a vaccine, can be administered to a subject in a dosage volume of about 0.1, 0.15, 0.2, 0.25, 0.3, 0.35, 0.4, 0.45, 0.5, 0.55, 0.6, 0.7, 0.8, 0.9, 1.0 mL, or more. A half dose, e.g., about 0.25 mL, can be administered to a child. Sometimes the vaccine can be administered in a higher dose, e.g., about 1 mL.

The composition, e.g., vaccine, can be administered as a 1, 2, 3, 4, 5, 6, 7, 8, 9, 10, or more dose-course regimen. Sometimes, the vaccine can be administered as a 2, 3, or 4 dose-course regimen. Sometimes the vaccine can be administered as a 2 dose-course regimen.

The administration of the first dose and second dose of the 2 dose-course regimen can be separated by about 0 day, 1 day, 2 days, 5 days, 7 days, 14 days, 21 days, 30 days, 2 months, 4 months, 6 months, 9 months, 1 year, 1.5 years, 2 years, 3 years, 4 years, 5 years, 10 years, 20 years, or more. A composition described herein, e.g., vaccine, can be administered to a subject once a year, twice a year, three times a year, every 1, 2, 3, 4, 5, 6, 7, 8, 9, 10, or more years. Sometimes, the composition, e.g., vaccine, can be administered to a subject every 2, 3, 4, 5, 6, 7, or more years. Sometimes, the composition, e.g., vaccine, can be administered every 4, 5, 6, 7, or more years. Sometimes, the composition, e.g., vaccine, can be administered to a subject once. Sometimes, the composition, e.g., vaccine, can be taken by a subject as a multiple dose vaccine over a period of time, e.g., a 2-dose vaccine wherein the second dose can be taken 4-5 years after the first dose. In some cases, a composition, e.g., vaccine, is administered at a time from August to March, from September to February, from October to January, from November to December, e.g. in a region in the North Hemisphere. In some cases, a composition, e.g., vaccine, is administered at a time from March to October, from April to September, from May to August, from June to July, e.g. in a region in the South Hemisphere.

The dosage examples are not limiting and are only used to exemplify particular dosing regiments for administering a composition, e.g., vaccine, described herein. In some embodiments, a "therapeutically effective amount" for use in a human can be determined from an animal model. For example, a dose for a human can be formulated to achieve circulating, liver, topical, and/or gastrointestinal concentrations that have been found to be therapeutically effective in an animal. Based on animal data, and other types of similar data, those skilled in the art can determine a therapeutically effective amount of a composition, e.g., vaccine, appropriate for administration to a human.

A composition described herein, e.g., a vaccine, can be used to treat or prevent seasonal influenza or pandemic influenza. In some embodiments, the methods and compositions described herein can target an influenza virus subtype. Influenza A virus can be subtyped based on hemagglutinin (HA) and neuraminidase (N), two proteins expressed on the surface of the viral envelope. Influenza A virus can display about 18 HA subtypes: H1, H2, H3, H4, H5, H6, H7, H8, H9, H10, H11, H12, H13, H14, H15, H16, H17, and H18; and about eleven N subtypes: N1, N2, N3, N4, N5, N6, N7, N8, N9, N10, and N11. Together, the HA and N subtypes can be combined in any combination. Non-limiting examples of the HA and N subtype combinations that have been observed include: H1N1, H1N2, H1N7, H2N2, H3N2, H3N8, H4N8, H5N1, H5N2, H5N8, H5N9, H6N5, H7N1, H7N2, H7N3, H7N4, H7N7, H7N9, H8N4, H9N2, H10N7, H11N6, H12N5, H13N6, and H14N5. In some embodiments, the vaccines described herein can target an influenza A virus that has a combination of the HA and N subtypes disclosed herein. In some cases, the combination can be represented by HxNy, wherein x represents any H1-H18 subtypes, and y represents any N1-N11 subtypes. For example, in some embodiments, vaccines disclosed herein can target a subtype represented as H1Ny, which is H1 in combination with any N subtype described herein, or a subtype represented as H2Ny, and the like. In some embodiments, a vaccine described herein can target an influenza A virus that has the HA and N subtype combinations H1N1, H1N2, H1N7, H2N2, H3N2, H3N8, H4N8, H5N1, H5N2, H5N8, H5N9, H6N5, H7N1, H7N2, H7N3, H7N4, H7N7, H7N9, H8N4, H9N2, H10N7, H11N6, H12N5, H13N6, or H14N5.

In some embodiments, a composition, e.g., vaccine, described herein can target an influenza B virus. Influenza B viruses can be classified into lineages and strains. An influenza B virus can belong to either the B/Yamagata or the B/Victoria lineage. Exemplary influenza B virus strains include Brisbane/60/2008, Massachusetts/2/2012, and Wisconsin/1/2010.

In some embodiments, a composition, e.g., vaccine, described herein can target an influenza A virus, influenza B virus, and/or an influenza C virus. In some embodiments, a composition, e.g., vaccine, described herein can target strains of influenza A virus, influenza B virus, influenza C virus, or a combination thereof.

In some embodiments, a composition, e.g., vaccine, described herein can be used to treat a patient who has an influenza infection, such as an influenza A virus infection, an influenza B virus infection, or an influenza C virus infection. Sometimes, a composition, e.g., vaccine, described herein can be used as a vaccination method against the infection of influenza A virus, influenza B virus, or influenza C virus. Sometimes, a composition, e.g., vaccine, described herein offers cross-protection against the different strains associated with the influenza A virus, the influenza B virus, and/or the influenza C virus.

The term "therapeutically effective amount" as used herein can mean an amount which is effective to alleviate, ameliorate, or prevent a symptom or sign of a disease or condition to be treated. For example, in some embodiments, a therapeutically effective amount can be an amount which has a beneficial effect in a subject having signs and/or symptoms of a viral infection, e.g., an influenza infection, e.g., an influenza A infection. In some embodiments, a therapeutically effective amount can be an amount which inhibits or reduces signs and/or symptoms of a viral infection, e.g., an influenza infection, e.g., an influenza A infection, as compared to a control. Signs and symptoms of an influenza infection, e.g., an influenza A infection, are well-known in the art and can include fever, cough, sore throat, runny nose, stuffy nose, headache, muscle aches, chills, fatigue (tiredness), nausea, vomiting, diarrhea, pain (e.g., abdominal pain), conjunctivitis, shortness of breath, difficulty breathing, pneumonia, acute respiratory distress, viral pneumonia, respiratory failure, neurologic change (e.g., altered mental status, seizure), or a combination thereof. In some embodiments, the therapeutically effective amount can be one which is sufficient to reduce any of the signs and/or symptoms by about, or at least 10%, 20%, 30%, 40%, 50%, 60%, 70%, 80%, 90%, 95%, or 100% in a subject as compared to a control.

A therapeutically effective amount, when referring to one or more active agents, can be a dose range, mode of administration, formulation, etc., that has been recommended or approved by any of the various regulatory or advisory organizations in the medical or pharmaceutical arts (e.g., FDA, AMA) or by the manufacturer or supplier.

In some aspects of the present disclosure, the composition can comprise a peptide based formulation. The composition comprising a polypeptide described herein can be administered to a subject between about 1 nmol/dose and about 1000 µmol/dose. In some embodiments, the composition can be administered to a subject at a dose about 1 nmol/dose, about 5 nmol/dose, about 10 nmol/dose, about 20 nmol/dose, about 30 nmol/dose, about 40 nmol/dose, about 50 nmol/dose, about 60 nmol/dose, about 70 nmol/dose, about 80 nmol/dose, about 90 nmol/dose, about 100 nmol/dose, about 200 nmol/dose, about 300 nmol/dose, about 400 nmol/dose, about 500 nmol/dose, about 600 nmol/dose, about 700 nmol/dose, about 800 nmol/dose, about 900 nmol/dose, about 1 µmol/dose, about 1 µmol/dose, about 2 µmol/dose, about 3 µmol/dose, about 4 µmol/dose, about 5 µmol/dose, about 6 µmol/dose, about 7 µmol/dose, about 8 µmol/dose, about 9 µmol/dose, about 10 µmol/dose, about 20 µmol/dose, about 50 µmol/dose, about 100 µmol/dose, about 200 µmol/dose, about 300 µmol/dose, about 400 µmol/dose, about 500 µmol/dose, about 750 µmol/dose, about 1000 µmol/dose, or any dose between any two thereof. In some cases, the composition can be administered to a subject at a dose about 50 nmol/dose.

In some aspects of the present disclosure, the composition can comprise a polynucleotide encoding a polypeptide described herein. The composition administered to a subject can comprise the polynucleotide at a dose between about 1 pmol/dose and about 1000 µmol/dose. In some embodiments, the composition administered to a subject can comprise the polynucleotide at a dose between about 1 pmol/dose, about 5 pmol/dose, about 10 pmol/dose, about 20 pmol/dose, about 30 pmol/dose, about 40 pmol/dose, about 50 pmol/dose, about 60 pmol/dose, about 70 pmol/dose, about 80 pmol/dose, about 90 pmol/dose, about 100 pmol/dose, about 200 pmol/dose, about 300 pmol/dose, about 400 pmol/dose, about 500 pmol/dose, about 600 pmol/dose, about 700 pmol/dose, about 800 pmol/dose, about 900 pmol/dose, 1 nmol/dose, about 5 nmol/dose, about 10 nmol/dose, about 20 nmol/dose, about 30 nmol/dose, about 40 nmol/dose, about 50 nmol/dose, about 60 nmol/dose, about 70 nmol/dose, about 80 nmol/dose, about 90 nmol/dose, about 100 nmol/dose, about 200 nmol/dose, about 300 nmol/dose, about 400 nmol/dose, about 500 nmol/dose, about 600 nmol/dose, about 700 nmol/dose, about 800 nmol/dose, about 900 nmol/dose, about 1 µmol/dose, about 1 µmol/dose, about 2 µmol/dose, about 3 µmol/dose, about 4 µmol/dose, about mol/dose, about 6 µmol/dose, about 7 µmol/dose, about 8 µmol/dose, about 9 µmol/dose, about 10 µmol/dose, about 20 µmol/dose, about 50 µmol/dose, about 100 µmol/dose, about 200 µmol/dose, about 300 µmol/dose, about 400 µmol/dose, about 500 µmol/dose, about 750 µmol/dose, about 1000 µmol/dose, or any dose between any two thereof.

In some aspects of the present disclosure, the composition can comprise a recombinant virus containing a polynucleotide encoding a polypeptide as described herein. The composition comprising recombinant virus can be administered to a subject between about $10^3$ and $10^{12}$ viral particles or plaque forming units (PFU), or between about $10^5$ and $10^{10}$ PFU, or between about $10^5$ and $10^8$ PFU, or between about $10^8$ and $10^{10}$ PFU. In some embodiments, the amount of a virus vaccine of this disclosure administered to a subject can be between about $10^3$ and $10^{12}$ viral particles or plaque forming units (PFU), or between about $10^5$ and $10^{10}$ PFU, or between about $10^5$ and $10^8$ PFU, or between about $10^8$ and $10^{10}$ PFU. Sometimes, a virus vaccine of this disclosure administered to a subject can be administered at a dose about $10^3$ PFU/dose to about $10^4$ PFU/dose, about $10^4$ PFU/dose to about $10^5$ PFU/dose, about $10^5$ PFU/dose to about $10^6$ PFU/dose, about $10^7$ PFU/dose to about $10^8$ PFU/dose, about $10^9$ PFU/dose to about $10^{10}$ PFU/dose, about $10^{10}$ PFU/dose to about $10^{11}$ PFU/dose, about $10^{11}$ PFU/dose to about $10^{12}$ PFU/dose, about $10^{12}$ PFU/dose to about $10^{13}$ PFU/dose, about $10^{13}$ PFU/dose to about $10^{14}$ PFU/dose, or about $10^{14}$ PFU/dose to about $10^{15}$ PFU/dose. A virus vaccine of this disclosure administered to a subject can comprise about $2\times10^3$ PFU/dose, $3\times10^4$ PFU/dose, $4\times10^3$ PFU/dose, $5\times10^3$ PFU/dose, $6\times10^3$ PFU/dose, $7\times10^3$ PFU/dose, $8\times10^3$ PFU/dose, $9\times10^3$ PFU/dose, about $10^4$ PFU/dose, about $2\times10^4$ PFU/dose, about $3\times10^4$ PFU/dose, about $4\times10^4$ PFU/dose, about $5\times10^4$ PFU/dose, about $6\times10^4$ PFU/dose, about $7\times10^4$ PFU/dose, about $8\times10^4$ PFU/dose, about $9\times10^4$ PFU/dose, about $10^5$ PFU/dose, $2\times10^5$ PFU/dose, $3\times10^5$ PFU/dose, $4\times10^5$ PFU/dose, $5\times10^5$ PFU/dose, $6\times10^5$ PFU/dose, $7\times10^5$ PFU/dose, $8\times10^5$ PFU/dose, $9\times10^5$ PFU/dose, about $10^6$ PFU/dose, about $2\times10^6$ PFU/dose, about $3\times10^6$ PFU/dose, about $4\times10^6$ PFU/dose, about $5\times10^6$ PFU/dose, about $6\times10^6$ PFU/dose, about $7\times10^6$ PFU/dose, about $8\times10^6$ PFU/dose, about $9\times10^6$ PFU/dose, about $10^7$ PFU/dose, about $2\times10^7$ PFU/dose, about $3\times10^7$ PFU/dose, about $4\times10^7$ PFU/dose, about $5\times10^7$ PFU/dose, about $6\times10^7$ PFU/dose, about $7\times10^7$ PFU/dose, about $8\times10^7$ PFU/dose, about $9\times10^7$ PFU/dose, about $10^8$ PFU/dose, about $2\times10^8$ PFU/dose, about $3\times10^8$ PFU/dose, about $4\times10^8$ PFU/dose, about $5\times10^8$ PFU/dose, about $6\times10^8$ PFU/dose, about $7\times10^8$ PFU/dose, about $8\times10^8$ PFU/dose, about $9\times10^8$ PFU/dose, about $10^9$ PFU/dose, about $2\times10^9$ PFU/dose, about $3\times10^9$ PFU/dose, about $4\times10^9$ PFU/dose, about $5\times10^9$ PFU/dose, about $6\times10^9$ PFU/dose, about $7\times10^9$ PFU/dose, about $8\times10^9$ PFU/dose, about $9\times10^9$ PFU/dose, about $10^{10}$ PFU/dose, about 2×10$^{10}$ PFU/dose, about 3×10$^{10}$ PFU/dose, about 4×10$^{10}$ PFU/dose, about 5×10$^{10}$ PFU/dose, about 6×10$^{10}$ PFU/dose, about 7×10$^{10}$ PFU/dose, about 8×10$^{10}$ PFU/dose, about 9×10$^{10}$ PFU/dose, about 10$^{10}$ PFU/dose, about 2×10$^{10}$ PFU/dose, about 3×10$^{10}$ PFU/dose, about 4×10$^{10}$ PFU/dose, about 5×10$^{10}$ PFU/dose, about 6×10$^{10}$ PFU/dose, about 7×10$^{10}$ PFU/dose, about 8×10$^{10}$ PFU/dose, about 9×10$^{10}$ PFU/dose, about 10$^{11}$ PFU/dose, about 2×10$^{11}$ PFU/dose, about 3×10$^{11}$ PFU/dose, about 4×10$^{11}$ PFU/dose, about 5×10$^{11}$ PFU/dose, about 6×10$^{11}$ PFU/dose, about 7×10$^{11}$ PFU/dose, about 8×10$^{11}$ PFU/dose, about 9×10$^{11}$ PFU/dose, or about 10$^{12}$ PFU/dose, about 10$^{12}$ PFU/dose to about 10$^{13}$ PFU/dose, about 10$^{13}$ PFU/dose to about 10$^{14}$ PFU/dose, or about 10$^{14}$ PFU/dose to about 10$^{15}$ PFU/dose, or any dose between any two thereof.

Sometimes, a virus vaccine of this disclosure administered to a subject can be administered at a dose about 10$^4$ viral particles/dose, about 10$^4$ viral particles/dose to about 10$^5$ viral particles/dose, about 10$^5$ viral particles/dose to about 10$^6$ viral particles/dose, about 10$^7$ viral particles/dose to about 10$^8$ viral particles/dose, about 10$^9$ viral particles/dose to about 10$^{10}$ viral particles/dose, about 10$^{10}$ viral particles/dose to about 10$^{11}$ viral particles/dose, about 10$^{11}$ viral particles/dose to about 10$^{12}$ viral particles/dose, about 10$^{12}$ viral particles/dose to about 10$^{13}$ viral particles/dose, about 10$^{13}$ viral particles/dose to about 10$^{14}$ viral particles/dose, or about 10$^{14}$ viral particles/dose to about 10$^{15}$ viral particles/dose. In some embodiments, a virus vaccine of this disclosure administered to a subject can be administered at a dose about 1×10$^9$ viral particles/dose, about 1.5×10$^9$ viral particles/dose, about 2×10$^9$ viral particles/dose, about 2.5×10$^9$ viral particles/dose, about 3×10$^9$ viral particles/dose, about 3.5×10$^9$ viral particles/dose, about 4×10$^9$ viral particles/dose, about 4.5×10$^9$ viral particles/dose, about 5×10$^9$ viral particles/dose, about 5.5×10$^9$ viral particles/dose, about 6×10$^9$ viral particles/dose, about 6.5×10$^9$ viral particles/dose, about 7×10$^9$ viral particles/dose, about 7.5×10$^9$ viral particles/dose, about 8×10$^9$ viral particles/dose, about 8.5×10$^9$ viral particles/dose, about 9×10$^9$ viral particles/dose, about 1×10$^{10}$ viral particles/dose, about 2×10$^{10}$ viral particles/dose, about 3×10$^{10}$ viral particles/dose, about 4×10$^{10}$ viral particles/dose, about 5×10$^{10}$ viral particles/dose, about 6×10$^{10}$ viral particles/dose, about 7×10$^{10}$ viral particles/dose, about 8×10$^{10}$ viral particles/dose, about 9×10$^{10}$ viral particles/dose, or any dose in between any two thereof. In some embodiments, a virus vaccine of this disclosure administered to a subject can be administered at a dose about 7.5×10$^9$ viral particles/dose.

A composition provided herein, e.g., a vaccine can be administered before, during, or after the onset of a symptom associated with a pathogen infection, e.g., an influenza A infection. Exemplary symptoms can include fever, cough, sore throat, runny nose, stuffy nose, headache, muscle aches, chills, fatigue, nausea, vomiting, diarrhea, pain (e.g., abdominal pain), conjunctivitis, shortness of breath, difficulty breathing, pneumonia, acute respiratory distress, viral pneumonia, respiratory failure, neurologic change (e.g., altered mental status, seizure), or a combination thereof. In some cases, the composition, e.g., vaccine, can be administered to a subject in order to treat a pathogen infection, e.g., influenza infection, e.g., influenza A infection. Sometimes, the composition, e.g., vaccine, can be administered to a subject for a preventive purpose, such as a prophylactic treatment of a pathogen infection, e.g., influenza infection, e.g., influenza A infection. The composition, e.g., vaccine, can be administered to a subject to illicit an immune response from a subject. The composition, e.g., vaccine, can be administered to a subject to illicit an immune response from the subject prior to a pathogen infection, during a pathogen infection, or as a prophylactic measure against a pathogen infection. Following administration of a composition provided herein, e.g., a vaccine, a symptom associated with a pathogen can be reduced about, at least, or at most 5%, 10%, 20%, 30%, 40%, 50%, 60%, 70%, 80%, 90%, or 100%, with about, at least, or at most 1 day, 5 days, 1 week, 2 weeks, 3 weeks, or 1 month.

A complication from an influenza infection, e.g. an influenza A infection, can be, e.g., pneumonia, bronchitis, sinus infection, or an ear infection. In some cases, an influenza infection, e.g., an influenza A infection, can make a chronic health problem worse, e.g., a person with asthma may experience an asthma attack while the person has an influenza infection, or a person with chronic congestive heart failure can experience worsening of this condition while the person has an influenza infection. In some embodiments, a therapeutically effective amount of a composition, e.g., a vaccine described herein, can be administered to a subject with a complication from an influenza infection. In some embodiments, a therapeutically effective amount of a composition, e.g., a vaccine described herein, can be administered to a subject with an influenza infection (e.g., an influenza A infection) and one or more chronic health problems.

A composition provided herein, e.g., a vaccine, or a kit described herein can be stored at between 2° C. and 8° C. Sometimes, the composition, e.g., vaccine, can be stored at room temperature. In some embodiments, the composition, e.g., vaccine, may not be stored frozen. In some embodiments, the composition, e.g., vaccine, can be stored in a temperature such as at −20° C. or −80° C. In some embodiments, the composition, e.g., vaccine, can be stored away from sunlight.

EXAMPLE

The following examples are offered by way of illustration, not by way of limitation.

Example 1

The peptide sequence TYQRTRALV (SEQ ID NO: 37) was selected based on 1) being an experimentally validated BALB/C influenza A virus CD8 T-cell epitope in worldwideweb.fludb.org and 2) having an average invariance ratio (frequency of mutant in final population/frequency in initial population) of <0.08 among all possible mutations in the stretch (generally each residue has 6-7 possible mutations from single nucleotide changes within the codon). Peptide was conjugated to Pam2Cys (a liposomal adjuvant that activates TLR2 and is covalently linked to the peptide) and a CD4 T cell epitope from HA (GALNNRFQIKGVELKS (SEQ ID NO: 115)) (epitopes connected via a central lysine, and Pam2Cys conjugated to central lysine via two serines). (CS Bio, Menlo Park, CA synthesized the lipopeptides) A formulation was made with 50 nmol of Pam2Cys-peptide having the sequence TYQRTRALV (SEQ ID NO: 37) per 20 µL of phosphate buffered saline (PBS) (2.5 µM). A volume of 20 µL of the formulation was administered intranasally to each of 10 BALB/C mice ("Group 2"). A volume of 20 µl of PBS was administered intranasally to each of 10 control BALB/C mice ("Group 1"). Four weeks after the administrations, the mice in both groups were challenged with 100 TCID$_{50}$ PR8 influenza A virus. 60% (6 of 10) of mice in the vaccine group (Group 2) compared to 0% (0 of 10) in the control group (Group 1) survived after 9 days from the lethal challenge of influenza A virus, showing statistically significant protection by vaccine (see FIG. 2).

Example 2

Figure 4:
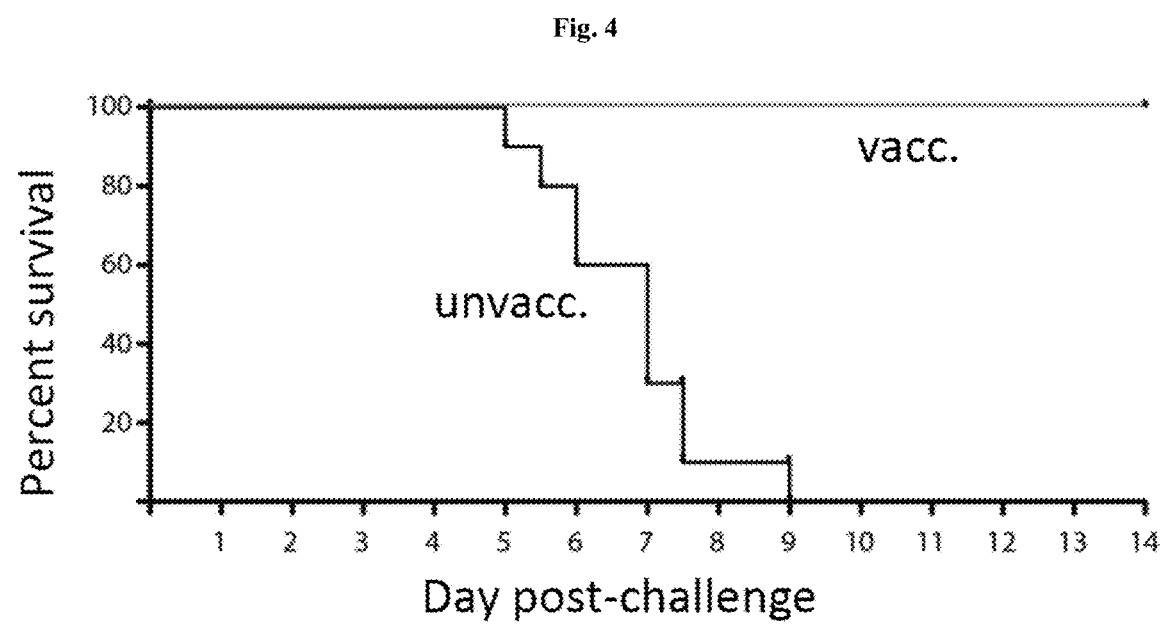
FIG. 4 illustrates percent survival of vaccinated and unvaccinated mice in FIGS. 3A and 3B.

This example describes vaccination with a vaccine comprising 4 influenza virus epitopes. A recombinant adenovirus carrying 4 influenza virus epitopes: ELRSRYWAIRTRSG (NP) (SEQ ID NO: 17), FYIQMCTEL (NP) (SEQ ID NO: 79), TYNAELLVLL (HA) (SEQ ID NO: 80), and TYQRTRALV (NP) (SEQ ID NO: 37) was generated. The recombinant adenovirus contained a single transgene with the four peptides encoded in tandem and separated by the linker RVKR (SEQ ID NO: 110). The sequence of the transgene product is GALNNRFQIKGVELKSKTYQRTRALVRVKRELRSRYWAIRTRSGRVKRFYIQMCTELRVKRTYN AELLVLL (SEQ ID NO: 81). For generating the recombinant adenoviral vector, the transgene was codon optimized for expression in mouse cells. The recombinant adenovirus was administered subcutaneously and intranasally simultaneously to Group 1 mice (10 BALB/C mice) at a dose of $2\times10^7$ pfu (plaque-forming units) in 20 d ($7.5\times10^9$ viral particles to each s.c. and i.n). The mice were challenged 28 days later with a lethal dose of 5-10 LD50 (lethal dose 50) (~100 TCID50 or tissue culture infectious dose 50) of H1N1 flu. All 10 mice in this group survived. 9 out of the 10 mice initially lost weight but regained most of their weight by day 12 post-challenge. See FIG. 3A and FIG. 4.

Figure 3B:
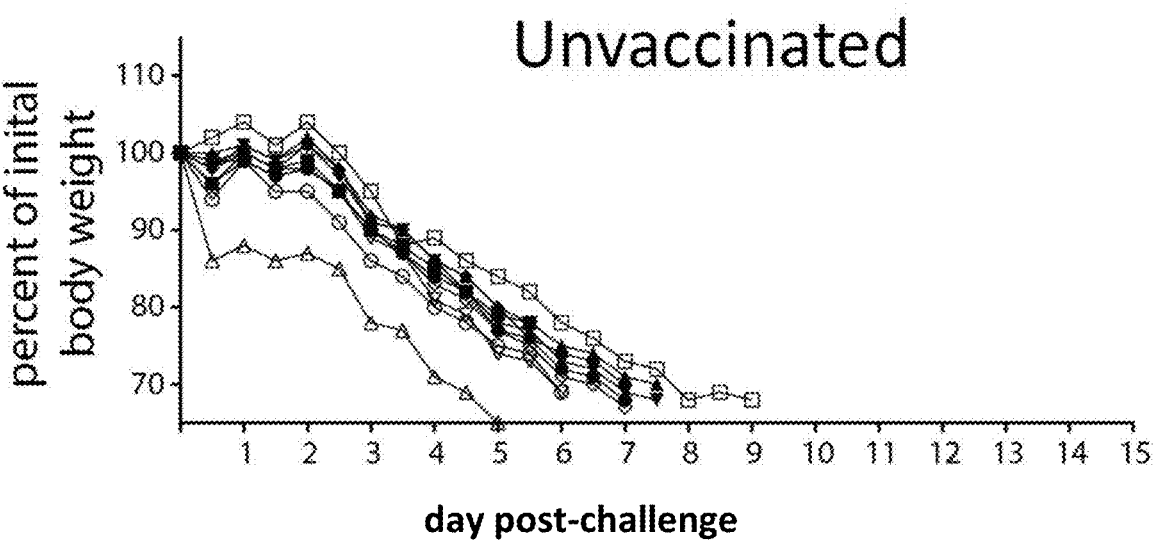
FIG. 3B illustrates the percent of initial body weight of unvaccinated mice.

In a control group (Group 2, unvaccinated, injected with saline s.c. and i.n.), 10 BALB/C mice were challenged with a lethal dose of 5-10 LD50 (lethal dose 50) (~100 TCID50 or tissue culture infectious dose 50) of H1N1 flu. 0 of 10 mice survived, all of the mice died by day 9 post-challenge. See FIG. 3B and FIG. 4.

Figure 3C:
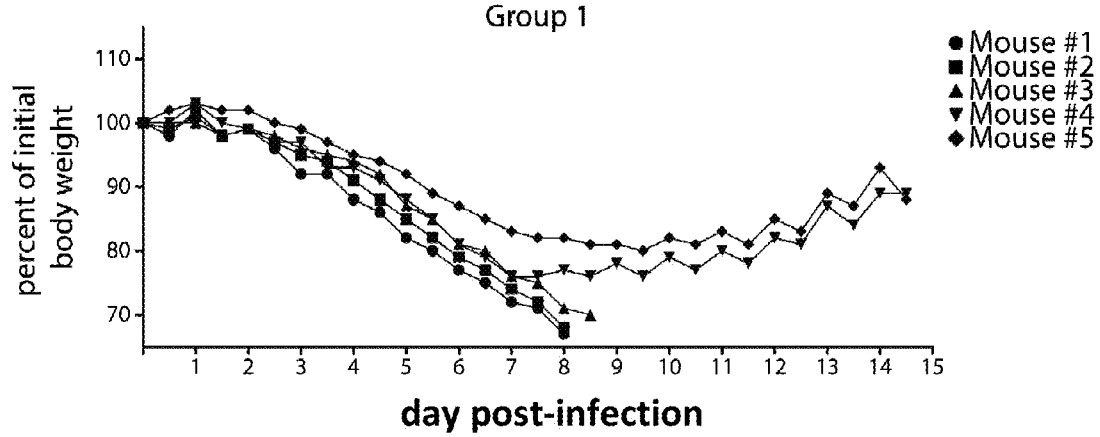
FIG. 3C illustrates the percent of initial body weight of Group 1 (AdCre-injected) mice.
Figure 3D:
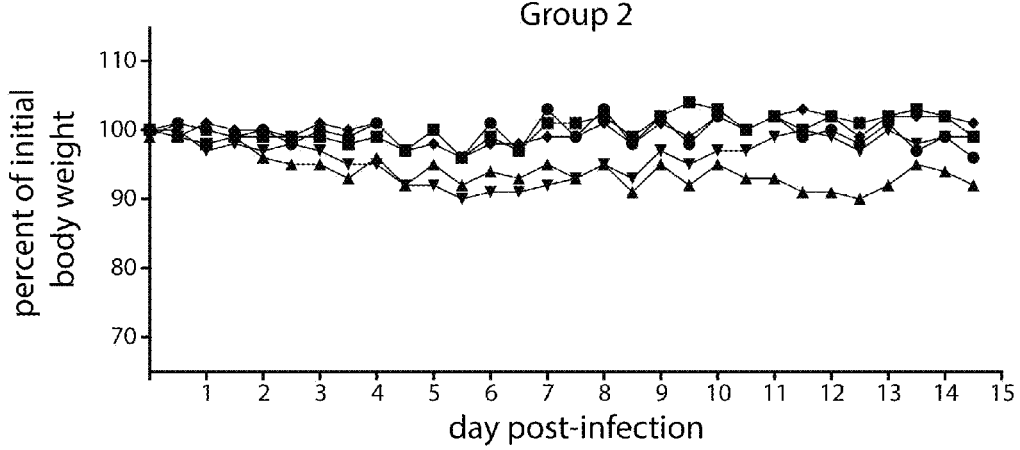
FIG. 3D illustrates the percent of initial body weight of Group 2 vaccinated mice.

In another set of experiments, AdCre-injected mice were used as control group (Group 1 in FIG. 3C) for the Ad vector. AdCre is an adenovirus produced using the same adenoviral vector as the recombinant adenovirus vaccine, but inserted with a Cre recombinase gene instead of the nucleotide sequence expressing the 4 epitopes. As shown in FIG. 3C, 3 of 5 mice in the control group perished, and the other 2 5 mice lost substantial weight. In contrast, in the vaccinated group (Group 2 in FIG. 3D), 0 of 5 mice lost >10% body weight. All 5 mice in AdCre had symptom scores of 3 or greater (not shown), whereas all 5 mice in the vaccine group had no higher than 1.

Example 3

This example describes vaccination with a vaccine comprising 9 influenza virus epitopes. A recombinant adenovirus carrying 9 influenza virus epitopes is generated. A vaccine cocktail of peptides comprising 9 influenza virus epitopes can also be used. Influenza virus epitopes can comprise any combination of the epitopes listed in Table 1.

Vaccination can be performed utilizing HLA-B44-transgenic mice. A prime-boost regimen can be employed. Priming can be with 9 Pam2Cys-adjuvanted peptides. Boosting can be with a recombinant adenovirus carrying 9 influenza virus epitopes or with a universal helper T cell epitope. Following vaccination, mice are challenged with the PR8 strain of influenza virus. Mice are monitored for health, weight, and survival to assess protection conferred by vaccination.

Example 4

This example describes experimental procedures and materials for heterosubtypic protection test of influenza virus.
Kill Curve
A kill curve experiment (a lethal dose curve) can be performed to determine the LD50 (a dose at which 50% of subject animals die), so that a challenge dose of 5-10LD50 can be used for the protection experiment.
Day 1: 3 Mice in Each Group, i.n. In 25 Ul

Vict Id is H3N2, and is $3.2\times10^7$ TCID50/ml

1) Group A: 10 TCID50 Vict Id (H3N2) (Make this 5th: Dilution #5: 50 ul Dilution #4+450 ul PBS)
2) Group B: 100 TCID50 Vict Id (Make this 4th: Dilution #4: 50 ul Dilution #3+450 ul PBS)
3) Group C: 1,000 TCID50 Vict Id (Make this 3rd: Dilution #3: 50 ul Dilution #2+450 ul PBS)
4) Group D: 10,000 TCID50 Vict Id (Make this 2nd: Dilution #2: 50 ul Dilution #1+450 ul PBS)
5) Group E: 100,000 TCID50 Vict Id (Make this 1st: Dilution #1: 100 ul virus stock+700 ul PBS)

Heterosubtypic Protection
Day 1: Immunize Mice:

1) Group 1: 10 mice with 20 ul saline i.n. (intranasal) and 20 ul saline s.c. (subcutaneous)
2) Group 2: 10 mice with $2\times10^7$ pfu in 20 ul AdBALB i.n. and same s.c.
   For $2\times10^7$ pfu AdBALAB: To 3 vials AdBALB, add 115 ul PBS each. Mix vials together (should be 420 ul total, just enough; can also use some from vial in Group 6) and administer above.
3) Group 3: 5 mice with $2\times10^7$ pfu in 20 ul AdBALB5-pep i.n. and same s.c.
   For $2\times10^7$ pfu AdBALABS-pep: To 1 vial AdBALB5-pep, add 230 ul PBS and administer above.
4) Group 4: 5 mice with $7.5\times10^9$ viral particles in 20 ul i.n. and same s.c.
   For $10\times10^9$ pfu AdBALABS-pep: To 1 vial AdBALB5-pep, add 722 ul PBS and administer above.
5) Group 5: 5 mice with 20 ul AdCre i.m. (intramuscular)
   For 20 ul AdCre: To 1 vial AdCre, add 653 ul PBS and administer above.
6) Group 6: 5 mice with 20 ul AdBALB i.m.
   For 20 ul AdBALB: To 1 vial AdBALB, add 115 ul PBS and administer above.

Days 2-15: Monitor Body Weight, Survival, and Clinical Scores
Day 29: Challenge Mice: All i.n. In 20 Ul

1) Groups 1-4: 5-10 LD50 (selected on the basis of kill curve) Vict id
2) Groups 5-6: 100 TCID50 PR8 (Dilute virus stock 1/10,000: 10 ul virus stock+990 ul PBS; 10 ul of this dilution+990 ul PBS for working stock)

Days 30-43: Monitor Body Weight, Survival, and Clinical Scores

Reagents

Total 55 BALB/C 6-12 wk-old female mice.

Adenoviruses: AdBALB (control virus with no epitope sequences); AdBALB5-pep (vaccine carrying 5 different influenza epitope sequences); AdCre (control virus with no epitope sequences but Cre transgene). Influenza viruses: PR8; Vict id (H3N2).

Example 5

This example describes a recombinant adenovirus based vaccine (AdFlu51pep) having 51 different influenza virus epitopes. The recombinant adenovirus is engineered with a single transgene that expresses all 51 epitope sequences in Table 3, which are encoded in tandem and separated by a linker RVKR (SEQ ID NO: 110). The order of the 51 epitope sequences can be random, thereby generating a variety of different transgene sequences. The sequence of one example of the transgene products, or a portion of the transgene product, is as listed in Table 4.

TABLE 4

SEQ ID NO: 106

ELRSRYWAIRTRSGRVKRELRSRHWAIRTRSGRVKRELRSRYWASRTRSGRVKRFMYSDFHFIRVKREMY
SDLHFIRVKRFMYTDPHFIRVKREMFSDFHFIRVKRGTFEFTSFFYRVKRGTFEFTSYFYRVKRILKGKF
QTARVKRIIKGKFQTARVKRILKGKFQIARVKRILRGSIAHKRVKRILRGSVAHKRVKRVLRGSIAHKRV
KRLIFLARSALRVKRLVELARSALRVKRLTFLARSALRVKRYSHGTGTGYRVKRYSHWTGTGYRVKRYSH
GSGTGYRVKRFLARSALILRGSVAHKRVKRFLARSALVLRGSVAHKRVKRIAYERMCNILKGKFQTAARV
KRVAYERMCNILKGKFQTAARVKRVAYERMCNIIKGKFQTAARVKRVAYERMCNILKGKFKTAARVKRVA
YERMCNILKGKFQIAARVKRVAYERMCNILKGKFQTAVRVKRDVVNFVSMEFSLTDPRLRVKRDVVNFVS
MEFSLTYPRLRVKRDVVNFVSMEFSLTDQRLRVKRFLARSALILRGSVAHKSRVKRFLARSALVLRGSVA
HKSRVKRKWGMEMRRCLLQSLQQIRVKRKLGMEMRRCLLQSLQQIRVKRKWGMEMRRCLLQSLQQVRVKR
KWGMELRRCLLQSLQQIRVKRFQGRGVFELRVKRGQISIQPTFSRVKRSQISVQPTFSRVKRGQVSVQPT
FSRVKRGQISVQPTFSRVKRWHSNLNDATYQRTRALVRTGMDPRMRVKRWHSNLNDTTYQRTRALVRTGM
DPRMRVKRWHSNLNDSTYQRTRALVRTGMDPRMRVKRWHSNLNDATYQRKRALVRTGMDPRMRVKRWHSN
LNDATYQRTRSLVRTGMDPRMRVKRWHSNLNDATYQRTRAIVRIGMDPRMRVKRWHSNLNDATYQRTRAL
VRSGMDPRMRVKRWHSNLNDATYQRTRALVRTGRDPRM

The transgene can express the polypeptide linked to one or more copies (e.g., 2, 3, 4, or 5) of influenza B virus NP protein, e.g., SEQ ID NO: 116, 117 or 118, or fragments of the influenza B virus NP protein (e.g., amino acids 2-560 of SEQ ID NO: 116, 117 or 118). In some cases, the vaccine comprises a second adenovirus with a second transgene that can expresses a polypeptide comprising one or more copies (e.g., 2, 3, 4, 5) of influenza B virus NP protein, e.g., SEQ ID NO: 116, 117 or 118, or fragments of influenza B virus NP protein. In some cases, an adenovirus can comprise a transgene that can express a polypeptide comprising SEQ ID NO. 106 and a second polypeptide comprising one or more copies (e.g., 2, 3, 4, or 5) of influenza B virus NP protein, e.g., SEQ ID NO: 116, 117 or 118, or fragments of the influenza B virus NP protein.

Example 6

This example describes production of an adenovirus based influenza vaccine as described in Example 5.

First, shuttle vector (Add2) containing the transgene that expresses SEQ ID NO: 106 can be constructed using conventional molecular cloning techniques. The transgene is driven by CMV promoter. Expression of the transgene can be checked at this point by transfection into 293T cells. Vector construct will be optimized if no polypeptide expression can be observed in transfected 293T cells.

Maxiprep pAdFlu51pep will then be linearized and transfected into 293 cells for generation of adenoviral plaques. A replication defective C68 helper virus or C6 virus will be supplemented to the transfected 293 cells for adenovirus packaging. Viral plaques will form 7-10 days after plating. Plaques can then be picked, frozen for later use, or subject to expansion of the viruses. Laboratory scale expansion of the pAdFlu51pep virus can be performed by serial passage of subconfluent 293 cells through different sizes of cell culture flasks, like T25, T75, or even T150.

Cell culture media and lysed cells will be subject to centrifugation for viral stock. Titering will be performed according to routine virus tittering procedures.

Example 7

This example describes clinical studies for the adenovirus based vaccine as described in Example 5 in human subject.

An open-label, uncontrolled Phase 1 study is carried out to evaluate the adenovirus based vaccine (AdFlu51pep vaccine) containing the 51 different epitope sequences in Table 3 in healthy adults.

Objectives: Evaluate the safety, tolerability and immunogenicity of the AdFlu51pep vaccine in healthy adult volunteers of both sexes between the ages of 18 and 55 years.

Dose

The starting dose for AdFlu51pep vaccine ranges from $3 \times 10^5$ to $1 \times 10^9$ PFU by intramuscular injection into deltoid once, including dose levels at $3 \times 10^5$ PFU, $3 \times 10^6$ PFU, $3 \times 10^7$ PFU, $3 \times 10^8$ PFU, and $1 \times 10^9$ PFU.

Each dose level enrolls between 6 and 12 evaluable healthy adults.

Safety Monitoring

Injection-site and systemic reactogenicity and medication use can be recorded for 7 days after injection and at follow-up (days 14 and 28). Clinical and laboratory evaluations can be performed during each study visit. Laboratory analyses can include a complete blood count and measurements of creatinine, C-reactive protein, and liver function. Adverse events will be listed for each participant.

Immunogenicity

Immunogenicity can be assessed by assaying serum samples of the participants. IFN-γ ELISPOT to assay T cell immunogenicity will be conducted with participants' serum samples collected at baseline (before vaccination) and at 28 and 180 days after injection.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A non-naturally-occurring polypeptide comprising at least a first epitope, a second epitope, and a third epitope, wherein the first epitope, the second epitope, and the third epitope differ from each other;
   wherein the first epitope, the second epitope, and the third epitope are selected from the group consisting of SEQ ID NOs: 40, 58, 61, 43, 51, 93, 22, 49, 82, 88, 34, and a variant of SEQ ID NO: 88 that lacks the N-terminus V residue.

2. The polypeptide of claim 1, wherein:
   the first epitope is SEQ ID NO: 51;
   the second epitope is SEQ ID NO: 58; and
   the third epitope is SEQ ID NO: 93.

3. The polypeptide of claim 2, wherein the polypeptide further comprises a fourth epitope selected from the group consisting of SEQ ID NO: 61, 22, 49, 34, 40, and 82, and wherein the fourth epitope is different from the first epitope, the second epitope, and the third epitope.

4. The polypeptide of claim 2, wherein the polypeptide further comprises epitopes of SEQ ID NOs: 61, 22, 49, 34, 40, 43, and 82.

5. The polypeptide of claim 1, wherein the first epitop and the second epitope are directly linked.

6. The polypeptide of claim 1, wherein at least two of the first, second, and third epitopes are linked by a linker.

7. The polypeptide of claim 6, wherein the linker comprises the sequence RVKR (SEQ ID NO: 110).

8. The polypeptide of claim 1, wherein the first epitope, the second epitope, and the third epitope are SEQ ID NOs: 51, 58, and 93; and wherein the polypeptide further comprises the epitopes of SEQ ID NOs: 61, 22, 49, and 34.

9. A polynucleotide encoding the polypeptide of claim 1.

10. A vector comprising the polynucleotide of claim 9.

11. A virus comprising the polynucleotide of claim 9.

12. The virus of claim 11, wherein the virus is an adenovirus.

13. A pharmaceutical composition comprising the polynucleotide of claim 9, a vector comprising the polynucleotide, or a virus comprising the polynucleotide, and a pharmaceutically acceptable carrier or excipient.

14. A method comprising administering to a subject the pharmaceutical composition of claim 13.

15. The polypeptide of claim 1, wherein the polypeptide further comprises one or more of the following epitopes: SEQ ID NOs: 2, 3, 8, 11, 12, 17, 21, 24, 32, 33, 41, 59, 62, 70, 73-78, 84-86, 92, and 94.

16. A polypeptide, comprising epitopes set forth as SEQ ID NOs: 2, 3, 8, 11, 12, 17, 21, 22, 24, 32-34, 40, 41, 43, 49, 51, 58, 59, 61, 62, 70, 73-78, 82, 84-86, 92-94, and a variant of SEQ ID NO: 88 that lacks the N-terminus V residue.

17. The polypeptide of claim 16, which comprises one or more copies of a linker connecting two consecutive epitopes; and wherein the linker is RVKR (SEQ ID NO: 110).

18. A polynucleotide, comprising a nucleotide sequence encoding the polypeptide of claim 16.

19. The polynucleotide of claim 18, which is located on a vector.

20. A viral particle comprising the polynucleotide of claim 18.

* * * * *

SEQUENCE LISTING

```
Sequence total quantity: 118
SEQ ID NO: 1                moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 1
GPATAQMAL                                                                     9

SEQ ID NO: 2                moltype = AA  length = 10
FEATURE                     Location/Qualifiers
REGION                      1..10
                            note = Description of Artificial Sequence: Synthetic peptide
source                      1..10
                            mol_type = protein
                            organism = synthetic construct
SEQUENCE: 2
GTFEFTSFFY                                                                   10

SEQ ID NO: 3                moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 3
YSHGTGTGY                                                                     9

SEQ ID NO: 4                moltype = AA  length = 18
FEATURE                     Location/Qualifiers
REGION                      1..18
                            note = Description of Artificial Sequence: Synthetic peptide
source                      1..18
                            mol_type = protein
                            organism = synthetic construct
SEQUENCE: 4
GLPVGGNEKK AKLANVVR                                                          18

SEQ ID NO: 5                moltype = AA  length = 17
FEATURE                     Location/Qualifiers
REGION                      1..17
                            note = Description of Artificial Sequence: Synthetic peptide
source                      1..17
                            mol_type = protein
                            organism = synthetic construct
SEQUENCE: 5
GMMMGMFNML STVLGVS                                                           17

SEQ ID NO: 6                moltype = AA  length = 17
FEATURE                     Location/Qualifiers
REGION                      1..17
                            note = Description of Artificial Sequence: Synthetic peptide
source                      1..17
                            mol_type = protein
                            organism = synthetic construct
SEQUENCE: 6
LQLFIKDYRY TYRCHRG                                                           17

SEQ ID NO: 7                moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 7
RRAIATPGM                                                                     9

SEQ ID NO: 8                moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
```

-continued

```
SEQUENCE: 8
FMYSDFHFI                                                                   9

SEQ ID NO: 9            moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 9
MRRNYFTAEV SHCRATEY                                                        18

SEQ ID NO: 10           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 10
QLMWALGENM A                                                               11

SEQ ID NO: 11           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 11
DVVNFVSMEF SLTDPRL                                                         17

SEQ ID NO: 12           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 12
KWGMEMRRCL LQSLQQI                                                         17

SEQ ID NO: 13           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 13
AEIEDLIFLA                                                                 10

SEQ ID NO: 14           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 14
CTELKLSDY                                                                   9

SEQ ID NO: 15           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 15
CTELKLTDQ                                                                   9

SEQ ID NO: 16           moltype = AA  length = 9
FEATURE                 Location/Qualifiers
REGION                  1..9
                        note = Description of Artificial Sequence: Synthetic peptide
```

```
                        source              1..9
                                            mol_type = protein
                                            organism = synthetic construct
SEQUENCE: 16
CTELKLTDY                                                                        9

SEQ ID NO: 17           moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 17
ELRSRYWAIR TRSG                                                                  14

SEQ ID NO: 18           moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 18
ELKSRYWAIR TRSG                                                                  14

SEQ ID NO: 19           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 19
GMDPRMCSL                                                                        9

SEQ ID NO: 20           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 20
ILKGKFQTA                                                                        9

SEQ ID NO: 21           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 21
ILRGSIAHK                                                                        9

SEQ ID NO: 22           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 22
ILRGSVAHK                                                                        9

SEQ ID NO: 23           moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 23
LELRSRYWAI                                                                       10

SEQ ID NO: 24           moltype = AA   length = 9
FEATURE                 Location/Qualifiers
```

```
REGION                  1..9
                        note = Description of Artificial Sequence: Synthetic peptide
source                  1..9
                        mol_type = protein
                        organism = synthetic construct
SEQUENCE: 24
LIFLARSAL                                                                         9

SEQ ID NO: 25           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 25
RGINDRNFW                                                                         9

SEQ ID NO: 26           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 26
FLARSALILR GSVAHK                                                                16

SEQ ID NO: 27           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 27
RMVLSAFDER                                                                       10

SEQ ID NO: 28           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 28
TLELRSGYWA IRTRSGGN                                                              18

SEQ ID NO: 29           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 29
IAYERMCNIL KGKFQTAA                                                              18

SEQ ID NO: 30           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 30
FLARSALILR GSVAHKS                                                               17

SEQ ID NO: 31           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 31
FQGRGVFEL                                                                         9

SEQ ID NO: 32           moltype = AA  length = 10
```

```
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 32
GQISIQPTFS                                                                        10

SEQ ID NO: 33           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 33
WHSNLNDATY QRTRALVRTG MDPRM                                                       25

SEQ ID NO: 34           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 34
WHSNLNDTTY QRTRALVRTG MDPRM                                                       25

SEQ ID NO: 35           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 35
CVNGSCFTV                                                                          9

SEQ ID NO: 36           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 36
RMVLASTTAK                                                                        10

SEQ ID NO: 37           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 37
TYQRTRALV                                                                          9

SEQ ID NO: 38           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 38
CVNGSCYTV                                                                          9

SEQ ID NO: 39           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 39
ELKSRYWAIR TRSG                                                                   14
```

```
SEQ ID NO: 40         moltype = AA   length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 40
FMYSDLHFI                                                                         9

SEQ ID NO: 41         moltype = AA   length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 41
FMYTDFHFI                                                                         9

SEQ ID NO: 42         moltype = AA   length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 42
GRDPRMCSL                                                                         9

SEQ ID NO: 43         moltype = AA   length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 43
GTFEFTSYFY                                                                       10

SEQ ID NO: 44         moltype = AA   length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 44
IIKGKFQTA                                                                         9

SEQ ID NO: 45         moltype = AA   length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 45
ILKGKFQIA                                                                         9

SEQ ID NO: 46         moltype = AA   length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 46
ILRGSVAHK                                                                         9

SEQ ID NO: 47         moltype = AA   length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 47
LQLRSRYWAI                                                                       10
```

```
SEQ ID NO: 48          moltype = AA   length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 48
LELRSRHWAI                                                                  10

SEQ ID NO: 49          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 49
LVFLARSAL                                                                   9

SEQ ID NO: 50          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 50
RWINDRNFW                                                                   9

SEQ ID NO: 51          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 51
YSHWTGTGY                                                                   9

SEQ ID NO: 52          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 52
YSHGSGTGY                                                                   9

SEQ ID NO: 53          moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 53
FLARSALVLR GSVAHK                                                           16

SEQ ID NO: 54          moltype = AA   length = 18
FEATURE                Location/Qualifiers
REGION                 1..18
                       note = Description of Artificial Sequence: Synthetic peptide
source                 1..18
                       mol_type = protein
                       organism = synthetic construct
SEQUENCE: 54
IAYERMCNII KGKFQTAA                                                         18

SEQ ID NO: 55          moltype = AA   length = 18
FEATURE                Location/Qualifiers
REGION                 1..18
                       note = Description of Artificial Sequence: Synthetic peptide
source                 1..18
                       mol_type = protein
                       organism = synthetic construct
```

```
SEQUENCE: 55
IAYERMCNIL KVKFQTAA                                                          18

SEQ ID NO: 56           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 56
IAYERMCNIL KGKFKTAA                                                          18

SEQ ID NO: 57           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 57
IAYERMCNIL KGKFQIAA                                                          18

SEQ ID NO: 58           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 58
DVVNFVSMEF SLTYPRL                                                           17

SEQ ID NO: 59           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 59
DVVNFVSMEF SLTDQRL                                                           17

SEQ ID NO: 60           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 60
FLARSALVLR GSVAHKS                                                           17

SEQ ID NO: 61           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 61
KLGMEMRRCL LQSLQQI                                                           17

SEQ ID NO: 62           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 62
KWGMEMRRCL LQSLQQV                                                           17

SEQ ID NO: 63           moltype = AA  length = 17
FEATURE                 Location/Qualifiers
REGION                  1..17
                        note = Description of Artificial Sequence: Synthetic peptide
```

```
source                  1..17
                        mol_type = protein
                        organism = synthetic construct
SEQUENCE: 63
LQLFIKDFRY TYRCHRG                                                    17

SEQ ID NO: 64           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 64
LQLFIKDYRY TYRCLRG                                                    17

SEQ ID NO: 65           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 65
LQLFIKDYRY TYRCPRG                                                    17

SEQ ID NO: 66           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 66
LQLFIKDYRY TYRCHRV                                                    17

SEQ ID NO: 67           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 67
FQGPGVFEL                                                             9

SEQ ID NO: 68           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 68
SQISIQPTFS                                                            10

SEQ ID NO: 69           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 69
GQVSIQPTFS                                                            10

SEQ ID NO: 70           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 70
GQISVQPTFS                                                            10

SEQ ID NO: 71           moltype = AA  length = 10
FEATURE                 Location/Qualifiers
```

```
REGION                  1..10
                        note = Description of Artificial Sequence: Synthetic peptide
source                  1..10
                        mol_type = protein
                        organism = synthetic construct
SEQUENCE: 71
GQNSIQPTFS                                                                  10

SEQ ID NO: 72           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 72
WHSNLNDTTY QRTRALVRTG MDPRM                                                 25

SEQ ID NO: 73           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 73
WHSNLNDSTY QRTRALVRTG MDPRM                                                 25

SEQ ID NO: 74           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 74
WHSNLNDATY QRKRALVRTG MDPRM                                                 25

SEQ ID NO: 75           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 75
WHSNLNDATY QRTRSLVRTG MDPRM                                                 25

SEQ ID NO: 76           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 76
WHSNLNDATY QRTRAIVRTG MDPRM                                                 25

SEQ ID NO: 77           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 77
WHSNLNDATY QRTRALVRSG MDPRM                                                 25

SEQ ID NO: 78           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 78
WHSNLNDATY QRTRALVRTG RDPRM                                                 25

SEQ ID NO: 79           moltype = AA  length = 9
```

```
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 79
FYIQMCTEL                                                                          9

SEQ ID NO: 80           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 80
TYNAELLVLL                                                                        10

SEQ ID NO: 81           moltype = AA  length = 71
FEATURE                 Location/Qualifiers
REGION                  1..71
                        note = Description of Artificial Sequence: Synthetic
                         polypeptide
source                  1..71
                        mol_type = protein
                        organism = synthetic construct
SEQUENCE: 81
GALNNRFQIK GVELKSKTYQ RTRALVRVKR ELRSRYWAIR TRSGRVKRFY IQMCTELRVK                  60
RTYNAELLVL L                                                                      71

SEQ ID NO: 82           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 82
ELRSRHWAIR TRSG                                                                   14

SEQ ID NO: 83           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 83
ELRSRYWASR TRSG                                                                   14

SEQ ID NO: 84           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 84
FMFSDFHFI                                                                          9

SEQ ID NO: 85           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 85
VLRGSIAHK                                                                          9

SEQ ID NO: 86           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
```

```
SEQUENCE: 86
LTFLARSAL                                                                        9

SEQ ID NO: 87           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 87
VAYERMCNIL KGKFQTAA                                                             18

SEQ ID NO: 88           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 88
VAYERMCNII KGKFQTAA                                                             18

SEQ ID NO: 89           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 89
VAYERMCNIL KGKFKTAA                                                             18

SEQ ID NO: 90           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 90
VAYERMCNIL KGKFQIAA                                                             18

SEQ ID NO: 91           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 91
VAYERMCNIL KGKFQTAV                                                             18

SEQ ID NO: 92           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 92
KWGMELRRCL LQSLQQI                                                              17

SEQ ID NO: 93           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 93
SQISVQPTFS                                                                      10

SEQ ID NO: 94           moltype = AA  length = 10
FEATURE                 Location/Qualifiers
REGION                  1..10
                        note = Description of Artificial Sequence: Synthetic peptide
```

```
source                   1..10
                         mol_type = protein
                         organism = synthetic construct
SEQUENCE: 94
GQVSVQPTFS                                                                   10

SEQ ID NO: 95            moltype = AA  length = 20
FEATURE                  Location/Qualifiers
REGION                   1..20
                         note = Description of Artificial Sequence: Synthetic peptide
source                   1..20
                         mol_type = protein
                         organism = synthetic construct
SEQUENCE: 95
LEAGCKNFFP RSFTSCGSLE                                                        20

SEQ ID NO: 96            moltype = AA  length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 96
CRRRRRREAE AC                                                                12

SEQ ID NO: 97            moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 97
GGGGGGGG                                                                      8

SEQ ID NO: 98            moltype = AA  length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 98
GSAGSAAGSG EF                                                                12

SEQ ID NO: 99            moltype = AA  length = 20
FEATURE                  Location/Qualifiers
REGION                   1..20
                         note = Description of Artificial Sequence: Synthetic peptide
source                   1..20
                         mol_type = protein
                         organism = synthetic construct
SEQUENCE: 99
GGGGSGGGGS GGGGSGGGGS                                                        20

SEQ ID NO: 100           moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 100
ISQAVHAAHA EINEAGR                                                           17

SEQ ID NO: 101           moltype = AA  length = 13
FEATURE                  Location/Qualifiers
REGION                   1..13
                         note = Description of Artificial Sequence: Synthetic peptide
source                   1..13
                         mol_type = protein
                         organism = synthetic construct
SEQUENCE: 101
AKFVAAWTLK AAA                                                               13

SEQ ID NO: 102           moltype = AA  length = 15
FEATURE                  Location/Qualifiers
```

```
REGION                   1..15
                         note = Description of Artificial Sequence: Synthetic peptide
MOD_RES                  3
                         note = L-cyclohexylalanine
MOD_RES                  14
                         note = Aminocaproic acid
source                   1..15
                         mol_type = protein
                         organism = synthetic construct
SEQUENCE: 102
AKXVAAWTLK AAAXC                                                            15

SEQ ID NO: 103           moltype = AA   length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 103
GALNNRFQIK GVELKSK                                                          17

SEQ ID NO: 104           moltype = DNA  length = 36519
FEATURE                  Location/Qualifiers
misc_feature             1..36519
                         note = Description of Artificial Sequence: Synthetic
                          polynucleotide
source                   1..36519
                         mol_type = other DNA
                         organism = synthetic construct
SEQUENCE: 104
ccatcttcaa taatatacct caaacttttt gtgcgcgtta atatgcaaat gaggcgtttg     60
aatttgggga ggaagggcgg tgattggtcg agggatgagc gaccgttagg ggcggggcga    120
gtgacgtttt gatgacgtgg ttgcgaggag gagccagttt gcaagttctc gtgggaaaag    180
tgacgtcaaa cgaggtgtgg tttgaacacg gaaatactca attttcccgc gctctctgac    240
aggaaatgag gtgtttctgg gcggatgcaa gtgaaacgg gccattttcg cgcgaaaact    300
gaatgaggaa gtgaaaatct gagtaatttc gcgtttatgg cagggaggag tatttgccga    360
gggccgagta gactttgacc gattacgtgg gggtttcgat taccgtgttt ttcacctaaa    420
tttccgcgta cggtgtcaaa gtccggtgtt tttacgtagg tgtcagctga tcgccagggt    480
atttaaacct gcgctctcca gtcaagaggc cactcttgag tgccagcgag aagagttttc    540
tcctccgcgc cgcgagtcag atctacactt tgaaagatga ggcacctgag agacctgccc    600
gatgagaaaa tcatcatcgc ttccgggaac gagattctgg aactggtggt aaatgccatg    660
atgggcgacg accctccgga gcccccacc ccatttgaga cacctccgct gcacgatttg    720
tatgatctgg aggtggatgt gcccgaggac gatcccaatg aggaggcggt aaatgatttt    780
tttagcgatg ccgcgctgct agctgccgag gaggcttcga gctctagctc agacagcgac    840
tcttcactgc atacccctag acccggcaga ggtgagaaaa gatcccccga gcttaaaggg    900
gaagagatgg acttgcgctg ctatgaggaa tgcttgcccc cgagcgatga tgaggacgag    960
caggcgatcc agaacgcagc gagccaggga gtgcaagccg ccagcgagag ctttgcgctg   1020
gactgccgc ctctgcccgg acacggctgt aagtcttgtg aatttcatcg catgaatact   1080
ggagataaag ctgtgttgtg tgcactttgc tatatgagag cttacaacca ttgtgtttac   1140
agtaagtgtg attaagttga actttagagg gaggcagaga gcagggtgac tgggcagga   1200
ctggtttatt tatgtatata tgttcttat ataggtcccg tctctgacgc agatgatgag   1260
accccactaa caaagtccac ttcgtcaccc cagaaattg gcacatctcc acctgagaat   1320
attgttagac cagttcctgt tagagccact gggaggagag cagctgtgga atgtttggat   1380
gacttgctac agggtggggt tgaaccttg gacttgtgta cccggaaacg ccccaggcac   1440
taagtgccac acatgtgtgt ttacttgagg tgatgtcagt atttataggg tgtggagtgc   1500
aataaaaaat gtgttgactt taagtgcgtg gtttatgact caggggtggg gactgtgagt   1560
atataagcag gtgcagacct gtgtggttag ctcagagcgg catggagatt tggacggtct   1620
tggaagactt tcacaagact agacagctgc tagagaacgc ctcgaacgga gtctcttacc   1680
tgtggagatt ctgcttcggt ggcgacctag ctaggctagt ctacagggcc aaacaggatt   1740
atagtgaaca atttgaggtt attttgagag agtgttctgg tctttttgac gctcttaact   1800
tgggccatca gtctcacttt aaccagagga tttcgagagc ccttgatttt actactcctg   1860
gcagaaccac tgcagcagta gccttttttg ctttttattct tgacaaatgg agtcaagaaa   1920
cccatttcag caggattac cagctggatt tcttagcagt agcttttgtgg agaacattgg   1980
agtgccagcg cctgaatgca atctccggct acttgccggt acagccgcta gacactctga   2040
ggatcctgaa tctccaggag agtcccaggg cacgccaacg tcgccagcag cagcagcagg   2100
aggaggatca agaagagaac ccgagagccg gcctggaccc tccggcggag gaggaggagt   2160
agctgacctg ttttcctgaac tgcgccgggt gctgactaga tcttcgagtg gtcgggagag   2220
ggggattaag cggtgaggc atgatgagac taatcacaga actgaactga ctgtgggtct   2280
gatgagtcgc aagcgcccag aaacagtgtg gtgcatgag gtgcagtcga ctggcacaga   2340
tgaggtgtcg gtgatgcatg agaggttttc tctagaacaa gtcaagactt gttggttaga   2400
gcctgaggat gattgggagg tagccatcag gaattatgcc aagctggctc tgaggccaga   2460
caagaagtac aagattacta agctgataaa tatcagaaat gcctgctaca tctcaggaa   2520
tggggctgaa gtggagatct gtctccagga aagggtggct ttcagatggt catgatgaa   2580
tatgtacccg ggagtggtgg gcatggatgg ggttaccttt atgaacatga ggttcagggg   2640
agatgggtat aatggcacgg tctttatggc caataccaag ctgacagtcc atggctgctc   2700
cttctttggg tttaataaca cctgcatcga ggctgggg caggtcggtg tgagggctg   2760
cagttttctca gccaactgga tgggggtcgt gggcaggacc aagagtatgc tgtccgtgaa   2820
gaaatgcttg tttgagaggt gccacctggg ggtgatgagc gagggcgaag ccagaatccg   2880
```

```
ccactgcgcc tctaccgaga cgggctgctt tgtgctgtgc aagggcaatg ctaagatcaa 2940
gcataatatg atctgtggag cctcggacga gcgcggctac cagatgctga cctgcgccgg 3000
cgggaacagc catatgctgg ccaccgtaca tgtggcttcc catgctcgca agccctggcc 3060
cgagttcgag cacaatgtca tgaccaggtg caatatgcat ctggggtccc gccgaggcat 3120
gttcatgccc taccagtgca acctgaatta tgtgaaggtg cctggagc ccgatgccat 3180
gtccagagtg agcctgacgg gggtgtttga catgaatgtg gaggtgtgga agattctgaa 3240
atatgatgaa tccaagacca ggtgccgagc ctgcgagtgc ggagggaagc atgccaggtt 3300
ccagcccgtg tgtgtggatg tgacggagga cctgcgaccc gatcatttgg tgttgccctg 3360
caccgggacg gagttcggtt ccagcgggga agaatctgac tagagtgagt agtgttctgg 3420
ggcgggggag gacctgcatg agggccagaa taactgaaat ctgtgcttt ctgtgtgttg 3480
cagcagcatg agcggaagcg gctccttga gggaggggta ttcagccctt atctgacggg 3540
gcgtctcccc tcctgggcgg gagtgcgtca gaatgtgatg ggatccacgg tggacggccg 3600
gcccgtgcag cccgcgaact cttcaaccct gacctatgca acccgagct cttcgtcgtt 3660
ggacgcagct gccgccccag ctgctgcatc tgccgtcgcg cccgtgcgcg gaatggccat 3720
gggcgccggc tactacggca ctctggtggc caactcgagt tccaccaata atcccgccaa 3780
cctgaacgag gagaagctgt tgctgctgat ggccagctc gaggccttga cccagcgcct 3840
gggcgagctg acccagcagg tggctcagct gcaggagcag acgcgggccg cggttgccac 3900
ggtgaaatcc aaataaaaaa tgaatcaata aataacgga cgcggtgtt gattttaaca 3960
cagagtctga atctttattt gattttcg cgcgcggtagg ccctggacca ccggtctcga 4020
tcattgagca cccggtggat cttttccagg acccggtaga ggtgggcttg gatgttgagg 4080
tacatgggca tgagcccgtc ccgggggtgg aggtagctcc attgcagggc ctcgtgctcg 4140
ggggtggtgt tgtaaatcac ccagtcatag caggggcgg tggcatgggtg ttgcacaata 4200
tctttgagga ggagactgat ggccacgggc agcctttgg tgtaggtgtt tacaaatctg 4260
ttgagctggg agggatgcat gcgggggag atgaggtgca tcttgcctg gatcttgaga 4320
ttggcgatgt taccgcccag atcccgcctg gggttcatgt tgtgcaggac caccagcacg 4380
gtgtatccgg tgcacttggg gaatttatca tgcaacttg aagggaagc gtgaaagaat 4440
ttggcgacgc cttttgtgccc gcccaggttt tccatgcact catccatgat gatggcgatg 4500
ggcccgtggg cggcggcctg ggcaaagacg tttcggggt cggacacatc atagttgtgg 4560
tcctgggtga ggtcatcata ggccatttta atgaatttgg ggcggagggt gccggactgg 4620
gggacaaagg taccctcgat cccggggcg tagttcccct cacagatctg catctcccag 4680
gctttgagct cggaggggg gatcatgtcc acctgcggg cgataaagaa cacggtttcc 4740
ggggcgggg agatgagctg ggcgaaagc aagttccgga gcagctggga cttgccgcag 4800
ccggtggggc cgtagatgac cccgatgacc ggctgcaggt ggtagttgag ggagagacag 4860
ctgccgtcct cccggaggag gggggccacc tcgttcatca tctgcgcac gtgcatgttc 4920
tcgcgcacca gttccgccag gaggcgtct cccccaggg ataggagctc ctggagcgag 4980
gcgaagtttt tcagcggctt gagtccgtcg gccatgggca ttttggagag ggtttgttgc 5040
aagagttcca ggcggtccca gagctcgtg atgtgctcta cggcatctcg atccagcaga 5100
cctcctcgtt tcgcggttg ggacggctgc gggagtaggg caccgacga tgggcgtcca 5160
gcgcagccag ggtccggtcc ttccaggtc gcagcgtccg cgtcagggtg gtctccgtca 5220
cggtgaaggg gtgcgcgccg ggctgggcgc ttgcgagggt gcgcttcagg ctcatccggc 5280
tggtcgaaaa ccgctcccga tcggcgccct gcgcgtcggc caggtagcaa ttgaccatga 5340
gttcgtagtt gagcgcctcg gccgcgtggc ctttggcgcg gagcttacct ttggaagtct 5400
gcccgaggc gggacagagg agggacttga ggctgtagag cttgggggcg aggaagacgg 5460
actcgggggc gtaggcgtcc gcgccgcagt gggcgcagac ggtctcgcac tccacgagcc 5520
aggtgaggtc gggctggtcg gggtcaaaaa ccagtttccc gccgttcttt ttgatgcgtt 5580
tcttaccttt ggtctccatg agctcgtgtc ccgctgggg gacaaagagg ctgtccgtgt 5640
ccccgtagac cgactttatg ggccggtcct cgagcggtgg gccgcggtcc tcctcgtaga 5700
ggaaccccgc ccactccgag acgaaagccc gggtccaggc cagcacgaag gaggccacgt 5760
gggacgggta gcgtcgttg tccaccagcg ggtccacctt ttccaggta tgcaaacaca 5820
tgtccccctc gtccacatcc aggaaggtga ttggcttgta agtgtaggcc acgtgaccgg 5880
gggtccggcc cgggggggta taaaagggtg cgggtccctg ctcgtcctca ctgtcttccg 5940
gatcgctgtc caggagcgcc agctgttggg gtaggtattc cctctcgaag gcgggcatga 6000
cctcggcact caggttgtca gtttctagaa acgaggagga tttgatattg acggtgccgg 6060
cggagatgcc tttcaagagc ccctcgtcca tctggtcaga aaagacgatc ttttgttgt 6120
cgagcttggt ggcgaaggag ccgtagaggg cgttggagag gagcttggca atggagcgca 6180
tggtctggtt tttttccttg tcggcgcgct ccttggcggc gatgttgagc tgcacgtact 6240
cgcgcgccac gcacttccat tcggggaaga cggtggtcag ctcgtcgggc acgattctga 6300
cctgccagcc ccgattatgc agggtgatga ggtccacact ggtggccacc tcgccgcgca 6360
ggggctcatt agtccagcag aggcgtccgc ccttgcgcga gcaaaggg ggcaggggt 6420
ccagcatgac ctcgtcgggg gggtcggcat cgatggtgaa gatgccggc aggaggtcgg 6480
ggtcaaagta gctgatggaa gtggccagat cgtccagggc agcttgccat tcgcgcacgg 6540
ccagcgcgcg ctcgtaggga ctgaggggcg tgccccaggg catgggatgg gtaagcgcgg 6600
aggcgtacat gccgcagatg tcgtagacgt agaggggctc ctcgaggatg ccgatgtagg 6660
tggggtagca gcgcccccg cggatgctgg cgcgcacgta gtcatacagc tcgtgccgag 6720
gggcgaggag ccccgggccc aggttggtgc gactgggctt ttcggcgcgg tagacgatct 6780
ggcggaaaat ggcatgcgag ttggaggaga tggtgggcct ttgaagatg ttgaagtggg 6840
cgtggggcag tccgaccgag tcgcggatga agtgggcgta ggagtcttgc agcttggcga 6900
ccgatccggc ggtgactagg acgttccgag cgcagtagtc gagggtctcc tggatgatgt 6960
catacttgag ctgtccttt tgtttccaca gctcgcggtt gagaaggaac tcttcgcggt 7020
ccttccagta ctcttcgagg gggaacccgc cctgatctgc acggtaagac cctagcatgt 7080
agaactggtt gacggccttg taggcgcagc agcccttctc cacggggagg gcgtaggcct 7140
gggcggcctt gcgcagggag gtgtgcgtga gggcgaaagt gtccctgacc atgacccttga 7200
ggaactggtg cttgaagtcg atatcgtcgc agccccctg ctcccagagc tggaagtccg 7260
tgcgcttctt gtaggcgggg ttgggcaaag cgaaagtaac atcgttgaag aggatctgc 7320
ccgcgcgggg cataaagttg cgagtgatgc ggaaaggttg gggcacctcg gcccggttgt 7380
tgatgacctg ggcggcgagc acgatctcgt cgaagccgtt gatgttgtgg cccacgatgt 7440
agagttccac gaatcgcgga cggccctga cgtggggcag tttcttgagc tcctcgtagg 7500
tgagctcgtc ggggtcgctg agcccgtgct gctcgagcgc ccagtcggcg agatgggggt 7560
tggcgcggag gaaggaagtc cagagatcca cggccagggc ggtttgcaga cggtcccggt 7620
```

```
actgacggaa ctgctgcccg acggccattt tttcgggggt gacgcagtag aaggtgcggg   7680
ggtccccgtg ccagcgatcc catttgagct ggagggcgag atcgagggcg agctcgacga   7740
gccggtcgtc cccggagagt ttcatgacca gcatgaaggg gacgagctgc ttgccgaagg   7800
accccatcca ggtgtaggtt tccacatcgt aggtgaggaa gagcctttcg gtgcgaggat   7860
gcgagccgat ggggaagaac tggatctcct gccaccaatt ggaggaatgg ctgttgatgt   7920
gatgaagta gaaatgccga cggcgcgcc aacactcgtg cttgtgttta tacaagcggc   7980
cacagtgctc gcaacgctgc acgggatgca cgtgctgcac gagctgtacc tgagttcctt   8040
tgacgaggaa tttcagtggg aagtggagtc gtggcgcctg catctcgtgc tgtactacgt   8100
cgtggtggtc ggcctggccc tcttctgcct cgatggtggt catgctgacg agcccgcgcg   8160
ggaggcaggt ccagacctcg gcgcgagcgg gtcggagagc gaggacgagg gcgcgcaggc   8220
cggagctgtc cagggtcctg agacgctgcg gagtcaggtc agtgggcagc ggcggcgcgc   8280
ggttgacttg caggagtttt tccagggcgc gcgggaggtc cagatggtac ttgatctcca   8340
ccgcgccatt ggtggcgacg tcgatggctt gcagggtccc gtgccctgg ggtgtgacca   8400
ccgtcccccg tttcttcttg ggcggctggg gcgacggggg cggtgcctct tccatggtta   8460
gaagcggcgg cgaggacgcg cgccgggcgg caggggcggc tcggggcccg gaggcagggg   8520
cggcaggggc acgtcggcgc cgcgcgcggg taggttctgg tactgcgccc ggagaagact   8580
ggcgtgagcg acgacgcgac ggttgacgtc ctggatctga cgcctctggg tgaaggccac   8640
gggacccgtg agtttgaacc tgaaagagag ttcgacagaa tcaatctgga tatcgttgac   8700
ggcggcctgc cgcaggatct cttgcacgtc gcccgagttg tcctggtagg cgatctcggt   8760
catgaactgc tcgatctcct cctcttgaag gtctccgcgg ccggcgcgct ccacggtggc   8820
cgcgaggtcg ttggagatgc ggcccatgag ctgcgagaag cgttcatgc ccgcctcgtt   8880
ccagacgcgg ctgtagacca cgacgccctc gggatcgccg gcgcgcatga ccacctgggc   8940
gaggttgagc tccacgtggc gcgtgaagac cgcgtagttg cagaggcgct ggtagaggta   9000
gttgagcgtg gtggcgatgt gctcggtgac gaagaaatac atgatccagc ggcggagcgg   9060
catctcgctg acgtcgccca cgcctccaa acgttccatg gcctcgtaaa agtccacggc   9120
gaagttgaaa aactgggagt tgcgccgca gacggtcaac tcctcctcca gaagacggat   9180
gagctcggcg atggtggcgc gcacctcgcg ctcgaaggcc cccggagtt cctccacttc   9240
ctcttcttcc tcctccacta acatctcttc tacttcctcc tcaggcggca gtggtggcgg   9300
gggaggggc ctgcgtcgcc ggcggcgcac gggcagacgg tcgatgaagc gctcgatggt   9360
ctcgccgcgc cggcgtcgca tggtctcggt gacggcgcgc ccgtcctcgc ggggccgcag   9420
cgtgaagacg ccgccgcgca tctccaggtg gccgggggg tccccgttgg gcagggagag   9480
ggcgctgacg atgcatctta tcaattgccc cgtagggact ccgcgcaagg acctgagcgt   9540
ctcgagatcc acgggatctg aaaaccgctg aacgaaggct tcgagccagt cgcagtcgca   9600
aggtaggctg agcacgtttt cttctggcgg gtcatgttgg ttgggagcgg ggcgggcgat   9660
gctgctggtg atgaagttga aataggcggt tctgagacgg cggatggtgg cgaggagcac   9720
caggtctttg ggcccggctt gctggatgcg cagacggtcg gccatgcccc aggcgtggtc   9780
ctgacacctg gccaggtcct tgtagtagtc ctgcatgagc cgctccacgg gcacctcctc   9840
ctcgcccgcg cggccgtgca tgcgcgtgag cccgaagccg cgctggggct ggacgagcgc   9900
caggtcggcg acgacgcgct cggcgaggat ggcttgctgg atctgggtga gggtggtctg   9960
gaagtcatca aagtcgacga agcggtggta ggctccggtg ttgatggtgt aggagcagtt  10020
ggccatgacg gaccagttga cggtctggtg gcccggacgc acgagctcgt ggtacttgag  10080
gcgcgagtag gcgcgcgtgt cgaagatgta gtcgttgcag gtgcgcacca ggtactggta  10140
gccgatgagg aagtgcggcg gcggctggcg gtagagccgc catcgctcgg tggcggggcg  10200
gccgggcgcg aggtcctcga gcatggtgcg gtggtagccg tagatgtacc tggacatcca  10260
ggtgatgccg gcggcggtgg tggaggcgcg cgggaactcg cggacgcggt tccagatgtt  10320
gcgcagcggc aggaagtagt tcatggtggg cacggtctgg cccgtgaggc gcgcgcagtc  10380
gtggatgctc tatacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtattg gcactccgt ctcgacccaa gctgcacca accctccagg  10560
atacggaggc gggtcgtttt gcaactttt tttggaggcc ggatgagact agtaagcgcg  10620
gaaagcgacc gaccgcgatg gctcgctgcc gtagtctgga gaagaatcgc cagggttgcg  10680
ttgcggtgtg ccccggttcg aggcggccg gattccgcgg ctaacgaggg cgtggctgcc  10740
ccgtcgtttc caagaccccca tagccagccg acttctccag ttacggagcg agcccctctt  10800
ttgttttgtt tgttttgcc agatgcatcc cgtactgcgg cagatgcgcc cccaccaccc  10860
tccaccgcaa caacagcccc ctccacagcc ggcgcttctg ccccgccc agcagcaact  10920
tccagccacg accgccgcgg ccgccgtgag cggggctgga cagagttatg atcaccagct  10980
ggccttggaa gagggcgagg ggctggcgcg cctggggggcg tcgtcgccgg agcggcaccc  11040
gcgcgtgcag atgaaaaggg acgctcgcga ggcctacgtg cccaagcaga acctgttcag  11100
agacaggagc ggcgaggagc ccgaggagat gcgcgcggcc cggttccacg cggggcggga  11160
gctgcggcgc ggcctggacc gaaagagggt gctgagggac gaggattcg aggcggacga  11220
gctgacgggg atcagccccg cgcgcgcgca cgtggccgcg gccaacctgg tcacggcgta  11280
cgagcagacc gtgaaggagg agagcaactt ccaaaaatcc ttcaacaacc acgtgcgcac  11340
cctgatcgcg cgcgaggagg tgaccctggg cctgatgcac ctgtgggacc tgctggaggc  11400
catcgtgcag aaccccacca gcaagccgct gacggcgcga ctgttcctgg tggtgcccaa  11460
tagtcgggac aacgaagcgt tcagggaggc gctgctgaat atcaccgagc ccgagggccg  11520
ctggctcctg gacctggtga acattctgca gagcatcgtg gtgcaggagc gcgggctgcc  11580
gctgtccgag aagctggcgg ccatcaactt ctcggtgctg agtttgggca agtactacgc  11640
taggaagatc tacaagaccc cgtacgtgcc catagacaag gaggtgaaga tcgacgggtt  11700
ttacatgcgc atgaccctga aagtgctgac cctgagcgac gatctgggg tgtaccgcaa  11760
cgacaggatg caccgtgcgg tgagcgccag caggcggcgc gagctgagcg accaggagct  11820
gatgcatagt ctgcagcggg ccctgaccgg ggccgggacc gaggggagga gctactttga  11880
catgggcgcg gacctgcact ggcagcccag ccgccgggcc ttgaggcgg cggcaggacc  11940
ctacgtagaa gaggtggacg atgaggtgga cgaggagggc gagtacctgg aagactgatg  12000
gcggcgaccgt attttttgcta gatgcaacaa caacagccac ctcctgatcc cgcgatgcgg  12060
gcggcgctgc agagccagcc gtccggcatt aactcctcgg acgattggac ccaggccatg  12120
caacgcatca tggcgctgac gacccgcaac cccgaagcct ttagacagca gccccaggcc  12180
aaccggctct cggccatcct ggaggccgtg gtgcctcgc gctccaaccc cacgcacgag  12240
aaggtcctgg ccatcgtgaa cgcgctggtg gagaacaagg ccatccgcgg cgacgaggcc  12300
ggcctggtgt acaacgcgct gctggagcgc gtggcccgct acaacagcac caacgtgcag  12360
```

```
accaacctgg accgcatggt gaccgacgtg cgcgaggccg tggcccagcg cgagcggttc 12420
caccgcgagt ccaacctggg atccatggtg gcgctgaacg ccttcctcag cacccagccc 12480
gccaacgtgc cccggggcca ggaggactac accaacttca tcagcgccct gcgcctgatg 12540
gtgaccgagg tgcccagag cgaggtgtac cagtccgggc cggactactt cttccagacc 12600
agtcgcagg gcttgcagac cgtgaacctg agccaggctt tcaagaactt gcagggcctg 12660
tggggcgtgc aggcccggt cggggaccgc gcgacggtgt cgagcctgct gacgccgaac 12720
tcgcgcctgc tgctgctgct ggtggccccc ttcacggaca gcggcagcat caaccgcaac 12780
tcgtacctgg gctacctgat taacctgtac cgcgaggcca tcggccaggc gcacgtggac 12840
gagcagacct accaggagat cacccacgtg agccgcgccc tgggccagga cgacccgggc 12900
aacctggaag ccaccctgaa ctttttgctg accaaccggt cgcagaagat cccgccccag 12960
tacgcgctca gcaccgagga ggagcgcatc ctgcgttacg tgcagcagag cgtgggcctg 13020
ttcctgatgc aggagggggc cacccccagc gccgcgctcg acatgaccgc gcgcaacatg 13080
gagcccagca tgtacgccag caaccgcccg ttcatcaata aactgatgga ctacttgcat 13140
cgggcggccg ccatgaactc tgactatttc accaacgcca tcctgaatcc ccactggctc 13200
ccgccgccgg ggttctacac gggcgagtac gacatgcccg accccaatga cgggttcctg 13260
tgggacgatg tggacagcag cgtgttctcc ccccgaccgg gtgctaacga gcgcccttg 13320
tggaagaagg aaggcagcga ccgacgcccg tcctcggcgc tgtccggccg cgagggtgct 13380
gccgcggcgg tgcccgaggc cgccagtcct ttcccgagct tgcccttctc gctgaacagt 13440
atccgcagca gcgagctggg caggatcacg cgcccgcgct tgctgggcga agaggagtac 13500
ttgaatgact cgctgttgag acccgagcgg gagaagaact tccccaataa cgggatagaa 13560
agcctggtgg acaagatgag ccgctggaag acgtatgcgc aggagcacag ggacgatccc 13620
cgggcgtcgc aggggccac gagccggggc agcgccgccc gtaaacgccg gtggcacgac 13680
aggcagcggg gacagatgtg ggacgatgag gactccgccg acgacagcga cgtgttggac 13740
ttgggtggga gtggtaaccc gttcgctcac ctgcgccccc gtatcgggcg catgatgtaa 13800
gagaaaccga aaataaatga tactcaccaa ggccatggcg accagcgtgc gttcgtttct 13860
tctctgttgt tgttgtatct agtatgatga ggcgtgcgta cccggaggt cctcctccct 13920
cgtacgagag cgtgatgcag caggcgatgg cggcggcggc gatgcagccc ccgctggagg 13980
ctccttacgt gcccccgcgg tacctggcgc tacggaggg gcgaacagc attcgttact 14040
cggagctggc acccttgtac gataccaccc ggttgtacct ggtggacaac aagtcggcgg 14100
acatcgcctc gctgaactac cagaacgacc acagcaactt cctgaccacc gtggtgcaga 14160
acaatgactt caccccccacg gaggccagca cccagaccat caactttgac gagcgctcgc 14220
ggtgggggcgg ccagctgaaa accatcatgc acaccaacat gccaacgtg aacgagttca 14280
tgtacagcaa caagttcaag gcgcgggtga tggtctcccg caagaccccc aatggggtga 14340
cagtgacaga ggattatgat ggtagtcagg atgagctgaa gtatgaatgg gtggaatttg 14400
agctgcccga aggcaacttc tcggtgacca tgaccatcga cctgatgaac aacgccatca 14460
tcgacaatta cttggcggtg gggcggcaga acggggtgct ggagagcgac atcggcgtga 14520
agttcgacac taggaacttc aggctgggct gggaccccgt gaccgagctg gtcatgcccg 14580
gggtgtacac caacgaggct ttccatcccg atattgtctt gctgcccggc tgcgggtgg 14640
acttcaccga gagccgcctc agcaacctgc tgggcattcg caagaggcag cccttccagg 14700
aaggcttcca gatcatgtac gaggatctgg aggggggcaa catccccgcg ctcctggatg 14760
tcgacgccta tgagaaagc aaggaggatg cagcagctga agcaactgca gccgtagcta 14820
ccgcctctac cgaggtcagg ggcgataatt ttgcaagcgc cgcagcagtg gcagcggccg 14880
aggcgcggta aaccgaaagt aagatagtca ttcagccggt ggagaaggat agcaagaaca 14940
ggagctacaa cgtactaccg gacaagataa acaccgccta ccgcagctgg tacctagcct 15000
acaactatgg cgaccccgag aagggcgtgc gctcctggac gctgctcacc acctcggacg 15060
tcacctgcgg cgtggagcaa gtctactggt cgctgcccga catgatgcaa gacccggtca 15120
ccttccgctc cacgcgtcaa gttagcaact acccggtggt ggccgcag ctcctgcccg 15180
tctactccaa gagcttcttc aacgagcagg ccgtcactc gcagcagctg cgcgccttca 15240
cctgcttac gcacgtcttc aaccgcttcc ccgagaacca gatcctgtc cgcccgcccg 15300
cgcccaccat taccaccgtc agtgaaaacg ttcctgctct cacagatcac gggaccctgc 15360
cgctgcgcag cagtatccgg ggagtccagc gcgtgaccgt tactgacgcc agacgccgca 15420
cctgccccta cgtctacaag gccctgggca tagtcgcgcc gcgcgtcctc tcgagccgca 15480
ccttctaaat gtccattctc atctcgccca gtaataacac cggttgggc ctgcgcgcgc 15540
ccagcaagat gtacgaggc gctcgccaac gctccacgca acaccccgtg cgcgtgcgcg 15600
ggcacttccg cgctccctgg ggcgccctca agggccgcgt gcggtcgcgc accaccgtcg 15660
acgacgtgat cgaccaggtg gtggccgacg cgcgcaacta cacccccgcc gccgcgcccg 15720
tctccaccgt ggacgccgtc atcgacagcg tggtggcgga cgcgcgccgg tacgcccgcg 15780
ccaagagccg gcgcgcggcg atcgcccggc ggcaccggag caccccgcc atgcgcgcgg 15840
cgcgagcctt gctgcgcagg gccaggccgca cgggacgcag ggccatgctc agggcggca 15900
gacgcgcggc ttcaggcgcc agcgccggca ggaccggag acgcgcggca acggcgggga 15960
cagcggccat cgccagcatg tcccgcccgc ggcgagggaa cgtgtactgg gtgcgcgacg 16020
ccgccaccgg tgtgcgcgtg cccgtgcgca cccgccccc tcgcacttga agatgttcac 16080
ttcgcgatgt tgatgtgtcc cagcggcgag gaggatgtcc aagcgcaaat tcaaggaaga 16140
gatgctccag gtcatcgcgc ctgagatcta cggccctgcg gtggtgaagg aggaaagaaa 16200
gccccgcaaa atcaagcggg tcaaaaagga caaaaaggaa gaagaaagtg atgtggacgg 16260
attggtggag tttgtgcgcg agttcgcccc ccggcggcgc gtgcagtggc gcgggcggaa 16320
ggtgcaaccg tgctgagac ccggcaccac cgtggtcttc acgcccggcg agcgctccgg 16380
caccgcttcc aagcgctcct acgacgaggt gtacgggat gatgatattc tggagcaggc 16440
ggccgagcgc ctgggcgagg ttgcttacgg caagcgcagc cgttccgcac gcaaggcaga 16500
ggcggtgtcc atcccgctgg accacgcaa ccccacgccg agcctcaagc ccgtgacctt 16560
gcagcaggtg ctgccgaccg cggcgccgcg ccggggttc aagcgcgagg gcgaggatct 16620
gtaccccacc atgcagctga tggtgcccaa gcgccagaag ctggaagacg tgctggagac 16680
catgaaggtg gaccccggacg tgcagcccga ggtcaaggtc cggcccatca gcaggtggc 16740
ccggggcggt ggcgtggaca caagattcgc acggagccca tggaaacgca 16800
gaccgagccc atgatcaagc ccagcaccag caccatggga gtgcagacgg atccctggat 16860
gccatcggct cctagtcgaa gaccccggcg caagtacggc gcggccagcc tgctgatgcc 16920
caactacgcg ctgcatcctt ccatcatccc cacgccgggc taccgcggca cgcgcttcta 16980
ccgcggtcat accagcagcc gccgccgcaa gaccaccact cgccgccgcc gtcgccgcac 17040
cgccgctgca accaccctg ccgccctggt gcggagagtg taccgccgcg gccgcgcacc 17100
```

```
tctgaccctg ccgcgcgcgc gctaccaccc gagcatcgcc atttaaactt tcgccagctt    17160
tgcagatcaa tggccctcac atgccgcctt cgcgttccca ttacgggcta ccgaggaaga    17220
aaaccgcgcc gtagaaggct ggcggggaac gggatgcgtc gccaccacca ccggcggcgg    17280
cgcgccatca gcaagcggtt ggggggaggc ttcctgcccg cgctgatccc catcatcgcc    17340
gcggcgatcg gggcgatccc cggcattgct tccgtgcagg tgcaggcctc tcagcgccac    17400
tgagacacac ttggaaacat cttgtaataa acccatggac tctgacgctc ctggtcctgt    17460
gatgtgtttt cgtagacaga tggaagacat caatttttcg tccctggctc cgcgacacgg    17520
cacgcggccg ttcatgggca cctggagcga catcggcacc agccaactga acggggcgc     17580
cttcaattgg agcagtctct ggagcgggct taagaatttc gggtccacgc ttaaaaccta    17640
tggcagcaag gcgtggaaca gcaccacagg gcaggcgctg agggataagc tgaaagagca    17700
gaacttccag cagaaggtgg tcgatgggct cgcctcgggc atcaacgggg tggtggacct    17760
ggccaaccag gccgtgcagc ggcagatcaa cagccgcctg gacccggtgc cgcccgccgg    17820
ctccgtggag atgccgcagg tggaggagga gctgcctccc ctggacaagc ggggcgagaa    17880
gcgaccccgc cccgatgcgg aggagcgct gctgacgcac aggacggagc cgccccgta     17940
cgaggaggcg gtgaaactgg gtctgcccac cacgcggccc atcgcgcccc tggccaccgg    18000
ggtgctgaaa cccgaaaagc ccgcgaccct ggacttgcct cctccccagc cttcccgccc    18060
ctctacagtg gctaagcccc tgccgccggt ggccgtggcc cgcgcgcgac ccgggggcac    18120
cgcccgccct catgcgaact ggcagagcac tctgaacagc atcgtgggtc tgggagtgca    18180
gagtgtgaag cgccgccgct gctattaaac ctaccgtagc gcttaacttg cttgtctgtg    18240
tgtgtatgta ttatgtcgcc gccgccgctg tccaccagaa ggaggagtga agaggcgcgt    18300
cgccgagttg caagatggcc accccatcga tgctgcccca gtgggcgtac atgcacatcg    18360
ccggacagga cgcttcggag tacctgagtc cgggtctggt gcagtttgcc cgcgccacag    18420
acacctactt cagtctgggg aacaagttta ggaaccccac ggtggcgccc acgcacgatg    18480
tgaccaccga ccgcagccag cggctgacgc tgcgcttcgt gcccgtggac cgcgaggaca    18540
acacctactc gtacaaagtg cgctacacgc tggccgtggg cgacaaccgc gtgctggaca    18600
tggccagcac ctactttgac atccgcggcg tgctggatcg gggccctagc ttcaaaccct    18660
actccggcac cgcctacaac agtctggccc ccaaggagc acccaacact tgtcagtgga      18720
catataaagc cgatggtgaa actgccacag aaaaaaccta tacatatgga aatgcacccg    18780
tgcagggcat taacatcaca aaagatggta ttcaacttgg aactgacacc gatgatcagc    18840
caatctacgc agataaaacc tatcagcctg aacctcaagt gggtgatgct gaatggcatg    18900
acatcactgg tactgatgaa aagtatggag gcagagctct taagcctgat accaaaatga    18960
agccttgtta tggttctttt gccaagccta ctaataaaga aggaggtcag gcaaatgtga    19020
aaacaggaac aggcactact aaagaatatg acatagacat ggctttcttt gacaacagaa    19080
gtgcggctgc tgctggccta gctccagaaa ttgttttgta tactgaaaat gtggatttgg    19140
aaactccaga tacccatatt gtatacaaag caggcacaga tgacagcagc tcttctatta    19200
atttgggtca gcaagccatg cccaacgaca ctaactacat tggtttcaga gacaactttg    19260
tcgggctcat gtactacaac agcactgcaa atatgggggt gctggccggt caggcttctc    19320
agctgaatgc tgtggttgac ttgcaagaca gaaacaccga gctgtcctac cagctcttgc    19380
ttgactctct gggtgacaga acccggtatt tcagtatgtg gaatcaggcg gtggacagct    19440
atgatcctga tgtgcgcatt attgaaaatc atggtgtggg agatgaactt cccaactatt    19500
gtttccctct ggatgctgtt ggcagaacag atacttatca gggaattaag gctaatggaa    19560
ctgatcaaac cacatggacc aaagatgaca gtgtcaatga tgctaatgag ataggcaagg    19620
gtaatccatt cgccatggaa atcaacatcc aagccaactc gtggaggaac ttcctctacg    19680
ccaacgtggc cctgtacctg cccgactctt acaagtacac gccggccaat gttaccctgc    19740
ccaccaacac caacacctac gattacatga acggccgggt ggtggcgccc tcgctggtgg    19800
actcctacat caacatcggg gcgcgctggt cgctggatcc catggacaac gtgaacccct    19860
tcaaccacca ccgcaatgcg gggctgcgct accgctccat gctcctgggc aacgggcgct    19920
acgtgccctt ccacatccag gtgccccaga aattttcgc catcaagagc ctcctgctcc      19980
tgcccgggtc ctacacctac gagtggaact tccgcaagga cgtcaacatg atcctgcaga    20040
gctccctcgg caacgacctg cgcacggacg gggcctccat ctccttcacc agcatcaacc    20100
tctacgccac ctttcttccc atggcgcaca acacggcctc cacgctcgag gccatgctgc    20160
gcaacgacac caacgaccag tccttcaacg actacctctc ggcggccaac atgctctacc    20220
ccatcccggc caacgccacc aacgtgccca tctccatccc ctcgcgcaac tgggccgcct    20280
tccgcggctg gtccttcacg cgtctcaaga ccaaggagac gccctcgctg ggctccgggt    20340
tcgaccccta cttcgtctac tcgggctcca tcccctacct cgacggcacc ttctacctca    20400
accacacctt caagaaggtc tccatcacct tcgactcctc cgtcagctgg cccggcaacg    20460
accgctcct gacgccaac gagttcgaaa tcaagcgcac cgtcgacggc gagggctaca     20520
acgtggccca gtgcaacatg accaaggact ggttcctggt ccagatgctg gcccactaca    20580
acatcggcta ccagggcttc tacgtgcccg aggctacaa ggaccgcatg tactccttct     20640
tccgcaactt ccagcccatg agccgccagg tggtggacga ggtcaactac aaggactacc    20700
aggccgtcac cctggcctac cagcacaaca actcggggct cgtcggctac ctcgcgccca    20760
ccatgcgcca gggccagccc tacccgcca actacccta cccgctcatc ggcaagagcg       20820
ccgtcaccag cgtcacccag aaaaagttcc tctgcgacag ggtcatgtgg cgcatccctt    20880
tctccagcaa cttcatgtcc atgggcgcgc tcaccgacct cggccagaat atgctctatg    20940
ccaactccgc ccacgcgcta gacatgaatt tcgaagtcga ccccatggat gagtccaccc    21000
ttctctatgt tgtcttcgaa gtcttcgacg tcgtccgagt gcaccagccc caccgcggcg    21060
tcatcgaggc cgtctacctg cgcaccccct tctcggccgg taacgccacc acctaagctc    21120
ttgcttcttg caagccatgg ccgcgggctc cggcgagcag gagctcaggg ccatcatccg    21180
cgacctggga tgcgggccct acttcctggg caccttcgat aagcgcttcc cgggattcat    21240
ggccccgcac aagctggcct gcgcatcgt caacacgcc ggccgcgaga ccggggcga       21300
gcactggctg gccttcgcct ggaacccgcg ctcgaacacc tgctacctct tcgaccccctt    21360
cgggttctcg gacgagcgcc tcaagcagat ctaccagttc gagtacgagg gctgctgcg      21420
ccgcagcgcc ctggccaccg aggaccgctg cgtcaccctg gaaaagtcca cccagaccgt    21480
gcagggtccg cgctcggccg cctgcggtct cttctgctgg atgttcctgc accgccttcgt    21540
gcactggccc gaccgccca tggacaagaa cccaccatg aacttgctga cggggtgcc        21600
caacggcatg ctccagtcgc cccaggtgga cccaccctg cgccgcaacc aggaggcgct     21660
ctaccgcttc tcaactccc actccgccta ctttcgctcc caccgcgcgc gcatcgaaa       21720
ggccaccgcc ttcgaccgca tgaatcaaga catgtaaacc gtgtgtgtat gttaaatgtc    21780
tttaataaac agcactttca tgttacacat gcatctgaga tgatttattt agaaatcgaa    21840
```

```
agggttctgc cggqtctcgg catggcccgc gggcagggac acgttgcgga actggtactt   21900
ggccagccac ttgaactcgg ggatcagcag tttgggcagc ggggtgtcgg ggaaggagtc   21960
ggtccacagc ttccgcgtca gttgcagggc gcccagcagg tcgggcgcgg agatcttgaa   22020
atcgcagttg ggacccgcgt tctgcgcgcg ggagttgcgg tacacggggt tgcagcactg   22080
gaacaccatc agggccgggt gcttcacgct cgccagcagc gtcgcgtcgg tgatgctctc   22140
cacgtcgagg tcctcggcgt tggccatccc gaagggggtc atcttgcagg tctgccttcc   22200
catggtgggc acgcacccgg gcttgtggtt gcaatcgcag tgcaggggga tcagcatcat   22260
ctgggcctgc tcggcgttca tccccgggta catggccttc atgaaagcct ccaattgcct   22320
gaacgcctgc tgggccttgg ctccctcggt gaagaagacc ccgcaggact tgctagagaa   22380
ctggttggtg gcgcacccgg cgtcgtgcac gcagcagcgc gcgtcgttgt tggccagctg   22440
caccacgctg cgccccagc ggttctgggt gatcttggcc cggtcggggt tctccttcag    22500
cgcgcgctgc ccgttctcgc tcgccacatc catctcgatc atgtgctcct tctggatcat   22560
ggtggtcccg tgcaggcacc gcagcttgcc ctcggcctcg gtgcacccgt gcagccacag   22620
cgcgcaaccg gtgcactccc agttcttgtg ggcgatctgg aatgcgcgct gcacgaagcc   22680
ctgcaggaag cggcccatca tggtggtcag ggtcttgttg ctagtgaagg tcagcggaat   22740
gccgcggtgc tcctcgttga tgtacaggtg gcagatgcgg cggtacacct cgccctgctc   22800
gggcatcagc tggaagttgg cttttcaggtc ggtctccacg cggtagcggt ccatcagcat   22860
agtcatgatt tccatacccct tctcccaggc cgagacgatg gcaggctca tagggttctt    22920
caccatcatc ttagcgctag cagccgcggc caggggtcg ctctcgtcca gggtctcaaa    22980
gctccgcttg ccgtccttct cggtgatccg caccggggg tagctgaagc ccacggccgc    23040
cagctcctcc tcggcctgtc tttcgtcctc gctgtcctgg ctgacgtcct gcaggaccac   23100
atgcttggtc ttgcggggtt tcttcttggg cggcagcggc ggcggagatg ttggagatgg   23160
cgaggggag cgcgagttct cgctcaccac tactatctct tcctcttctt ggtccgaggc    23220
cacgcggcg taggtatgtc tcttcgggg cagaggcgga ggcgacgggc tctgccgcc     23280
gcgacttggc ggatggctgg cagagcccct tccgcgttcg ggggtgcgct cccggcggcg   23340
ctctgactga cttcctccgc ggccggccat tgtgttctct tagggaggaa caacaagcat   23400
ggagactcag ccatcgccaa cctcgccatc tgccccacc gccgacgaga agcagcagca    23460
gcagaatgaa agcttaaccg ccccgccgcc cagccccgcc acctccgacg cggccgtccc   23520
agacatgcaa gagatggagg aatccatcga gattgacctg ggctatgtga cgcccgcgga   23580
gcacgaggag agctggccag tgcgcttttc acaagaagag atacaccaag aacagccaga   23640
gcaggaagca gagaatgagc agagtcaggc tgggctcgag catgacgcg actacctcca     23700
cctgagcggg ggggaggacg cgctcatcaa gcatctggcc cggcaggcca ccatcgtcaa   23760
ggatgcgctg ctcgaccgca ccgaggtgcc cctcagcgtg gaggagctca gccgcgccta   23820
cgagttgaac ctcttctcgc cgcgcgtgcc ccccaagcgc cagccaatg gcacctgcga    23880
gccaacccg cgcctcaact tctacccggt cttcgcggtg cccgaggccg tggccaccta    23940
ccacatcttt ttcaagaacc aaaagatccc cgtctcctgc cgcgcaacc gcacccgcgc    24000
cgacgccctt ttcaacctgg gtcccggcgc ccgcctacct gatatcgcct ccttggaaga   24060
ggttcccaag atcttcgagg gtctgggcag cgacgagact cgggccgcga acgctctgca   24120
aggagaagga ggagacatg agcaccacag cgccctggtc gagttggaag gcgacaacgc    24180
gcggctggcg gtgctcaaac gcacggtcga gctgacccat ttcgcctacc cggctctgaa   24240
cctgcccccc aaagtcatga gcgcggtcat ggaccaggtg ctcatcaagc gcgcgtcgcc   24300
catctccgag gacgagggca tgcaagactc cgaggagggc aagcccgtgg tcagcgacga   24360
gcagctggcc cggtggctgg gtcctaatgc tagtccccag agtttggaag agcggcgcaa   24420
actcatgatg gccgtggtcc tggtgaccgt ggagctggaa tgcctgcgcc gcttcttcgc   24480
cgacgcggag accctgcgca aggtcgagga gaacctgcac tacctcttca ggcacgggtt   24540
cgtgcgccaa ggcctgcaaga tctccaacgt ggagctgacc aacctggtct cctacatggg   24600
catcttgcac gagaaccgcc tggggcagaa cgtgctgcac accaccctgc gcggggaggc   24660
ccggcgcgac tacatccgcg actgcgtcta cctctacctc tgccacacct ggcagacggg   24720
catgggcgtg tggcagcagt gtctggagga gcagaacctg aaaagctct gcaagctcct    24780
gcagaagaac ctcaagggtc tgtggaccgg gttcgacgag cgcaccaccg cctcggacct   24840
ggccgacctc atttttcccg agcgcctcag gctgacgctg gcaacggcc gcgccgcaga    24900
tatgagccaa agcatgttgc aaaactttcg ctctttcatc ctcgaacgct ccggaatcct   24960
gcccgccacc tgctccgcgc tgccctcgga ctttgtgccg ctgaccttcc gcgagtgccc   25020
cccgccgctg tggagccact gctacctgct gcgcctggcc aactacctgg cctaccactg   25080
ggacgtgatc gaggacgtca gcggcgaggg cctgctcgga tgcactgcc gctgcaacct    25140
ctgcacgccg caccgctccc tggcctgcaa cccccagctg ctgagcgaga cccagatcat   25200
cggcaccttc gagttgcaag ggccagcga aggcgagggt tcagccgcca ggggggtct    25260
gaaactcacc ccggggctgt ggacctcggc ctacttgcgc aagttcgtgc ccgaggacta   25320
ccatcccttc gagatcaggt tctacgagga ccaatcccat ccgcccaagg ccagctgtc    25380
ggcctgcgtc atcacccagg gggcgatcct ggcccaattg caagccatcc agaaatcccg   25440
ccaagaattc ttgctgaaaa agggccgcgg ggtctacctc gacccccaga ccggtgagga   25500
gctcaacccc ggcttccccc aggatgcccc gaggaaacaa gaagctgaaa gtggagctgc   25560
cgcccgtgga ggatttggag gaagactggg agaacagcag tcaggcagag gaggaggaga   25620
tggaggaaga ctgggacgag actcaggcag aggaggacg cctgcaagac agtctggagg    25680
aagacgagga ggaggcagag gaggaggtgg aagaagcagc cgccgccaga ccgtcgtcct   25740
cggcggggga gaaagcaagc agcacggata ccatctccgc tccgggtcgg ggtcccgctc   25800
gaccacacag tagatgggac gagaccggac gattcccgaa ccccaccacc cagaccggta   25860
agaaggagcg gcagggatac aagtcctggc gggggcacaa aaacgccatc gtctcctgct   25920
tgcaggcctg cggggcaac atctccttca cccggcgtg cctgctcttc caccgcgggg    25980
tgaactttcc ccgcaacatc ttgcattact accgtcacct ccacagcccc tactacttcc   26040
aagaagaggc agcagcagca gaaaaagacc agcagaaaac cagcagctag aaaatccaca   26100
gcggcggcag caggtggact gaggatcgcg cgaacgagc cggcgcaaac ccgggagctg    26160
aggaaccgga tctttcccac cctctatgcc atcttccagc agagtcgggg gcaggagcag   26220
gaactgaaag tcaagacgga ttctctgcgc tgctgccgc gcagttgtct gtatcacaag    26280
agcgaagacc aacttcagcg cactctcgag gacgccgagg ctctcttcaa caagtactgc   26340
gcgctcactc ttaaagagta gcccgcgccc cccagtcgc agaaaaaggc gggaattacg     26400
tcacctgtgt ccttcgccct agccgcctcc acccatcatc atgagcaaag agattcccac   26460
gccttacatg tggagctacc agcccagat gggcctggcc gccggtgccg cccaggacta    26520
ctccaccccgc atgaattggc tcagcgccgg gcccgcgatg atctcacggg tgaatgacat   26580
```

```
ccgcgcccac cgaaaccaga tactcctaga acagtcagcg ctcaccgcca cgccccgcaa   26640
tcacctcaat ccgcgtaatt ggcccgccgc cctggtgtac caggaaattc cccagcccac   26700
gaccgtacta cttccgcgag acgcccaggc cgaagtccag ctgactaact caggtgtcca   26760
gctggcgggc ggcgccaccc tgtgtcgtca ccgccccgct cagggtataa agcggctggt   26820
gatccggggc agaggcacac agctcaacga cgaggtggtg agctcttcgc tgggtctgcg   26880
acctgacgga gtcttccaac tcgccggatc ggggagatct tccttcacgc ctcgtcaggc   26940
cgtcctgact ttggagagtt cgtcctgcca gccccgctcg ggtggcatcg gcactctcca   27000
gttcgtggag gagttcactc cctcggtcta cttcaacccc ttctccggct cccccggcca   27060
ctaccggac gagttcatcc cgaacttcga cgccatcgac gagtcggtgg acggctacga   27120
ttgaatgtcc catggtggcg cagctgacct agctcggctt cgacacctgg accactgccg   27180
ccgcttccgc tgcttcgctc gggatctcgc cgagtttgcc tactttgagc tgcccgagga   27240
gcaccctcag ggcccggccc acggagtgcg gatcgtcgtc gaaggggggcc tcgactccca   27300
cctgcttcgg atcttcagcc agcgtccgat cctggtcgag cgcgagcaag gacagaccct   27360
tctgactctg tactgcatct gcaaccaccc cggcctgcat gaaagtcttt gttgtctgct   27420
gtgtactgag tataatatcaaa gctgagatca gcgactactc cggacttccg tgtgttcctg   27480
aatccatcaa ccagtctttg ttcttcaccg ggaacgagac cgagctccag ctccagtgta   27540
agccccacaa gaagtacctc acctggctgt tccagggctc cccgatcgcc gttgtcaacc   27600
actgcacaa cgacggagtc ctgctgagcg gcctgccaa ccttacttttt tccacccgca   27660
gaagcaagct ccagctcttc caacccttcc tccccgggac ctatcagtgc gtctcgggac   27720
cctgccatca caccttccac ctgatcccga ataccacagc gtcgctcccc gctactaaca   27780
accaaactaa cctccaccaa cgccaccgtc gcgacctttc tgaatctaat actaccaccc   27840
acaccggagg tgagctccga ggtcaaccaa cctctgggat ttactacggc ccctgggagg   27900
tggttgggtt aatagcgcta ggcctagttg cgggtgggct tttggttctc tgctacctat   27960
acctcccttg ctgttcgtac ttagtggtgc tgtgttgctg gttaagaaa tggggaagat   28020
caccctagtg agctgcggtg cgctggtggc ggtgttgctt tcgattgtgg gactgggcgg   28080
tgcggctgta gtgaaggaga aggccgatcc ctgctgcat ttcaatccca acaaatgcca   28140
gctgagtttt cagcccgatg gcaatccggtg cgcggtactg atcaagtcgg gatgggaatg   28200
cgagaacgtg agaatcgagt acaataacaa gactcggaac aatactcctcg cgtccgtgtg   28260
gcagcccggg gaccccgagt ggtacaccgt ctctgtcccc ggtgctgacg gctccccgcg   28320
caccgtgaat aatactttca tttttgcgca catgtgcgca acgtcatgt ggatgagcaa   28380
gcagtacgat atgtggcccc ccacgaagga gaacatcgtg gtcttctcca tcgcttacag   28440
cctgtgcacg cgctaatca ccgctatcgt gtgcctgagc attcacatgc tcatcgctat   28500
tcgcccagaa aataatgccg aaaaagaaaa acagccataa cgttttttttt cacacccttt   28560
tcagaccatg gcctctgtta aatttttgct tttatttgcc agtctcattg ccgtcattca   28620
tggaatgagt aatgagaaaaa ttactattta cactggcact aatcacacat tgaaaggtcc   28680
agaaaaagcc acagaagttt catggtattg ttattttaat gaatcagatg tatctactga   28740
actctgtgga aacaataaca aaaaaaatga gagcattact ctcatcaagt ttcaatgtgg   28800
atctgactta accctaatta acatcactag agactatgta ggtatgtatt atggaactac   28860
agcaggcatt tcggactgg aattttatca agttctgtg tctgaaccca ccacgcctag   28920
aatgaccaca accacaaaaa ctacacctgt taccactatg cagctcacta ccaataacat   28980
ttttgccatg cgtcaaatgg tcaacaatag cactcaaccc accccaccca gtgaggaaat   29040
tcccaaatcc atgattggca ttattgttgc tgtagtggtg tgcatgttga tcatcgcctt   29100
gtgcatggtg tactatgcct tctgctacag aaagcacaga ctgaacgaca agctggaaca   29160
cttactaagt gttgaatttt aattttttag aaccatgaag atcctaggcc ttttaatttt   29220
ttctatcatt acctctgctc tatgcaattc tgacaatgag gacgttactg tcgttgtcgg   29280
atcaaattat acactgaaag gtccagcgaa gggtatgctt tcgtggtatt gctattttgg   29340
atctgacact acagaaactg aatttatgca tcttaagaat ggcaaaattc aaaattctaa   29400
aattaacaat tatatatgca atggtactga tctgatactc ctcaatatca cgaaatcata   29460
tgctggcagt tacacctgcc ctggagatga tgctgacagt atgattttttt acaaagtaac   29520
tgttgttgat cccactactc cacctccacc accacaact actcacacca cacacagaga   29580
tcaaaccgca gcagaggagg cagcaaagtt agcccttgca ggtccaagaca gttcatttgt   29640
tggcattacc cctacacctg atcagcggtg tccgggggctg ctagtcagcg gcattgtcgg   29700
tgtgctttcg ggattagcag tcataatcat ctgcatgttc attttttgctt gctgctatag   29760
aaggcttcac cgacaaaaat cagacccact gctgaacctc tatgtttaat ttttttccaga   29820
gtcatgaagg cagttagcgc tctagttttt tgttctttga ttggcattgt tttttgcaat   29880
cctattccta aagttagctt tattaaagat gtgaatgtta ctgaggggggg caatgtgaca   29940
ctggtaggtg tagagggtgc tgaaaacacc acctggacaa aataccccct caatgggtgg   30000
aaagatattt gcaattggag tgtattagtt tatacatgtg agggagttaa tcttaccatt   30060
gtcaatgcca cctcagctca aaatgtaga attcaaggac aaagtgtcag tgtatctaat   30120
gggtattta cccaacatac tttatctctat gacgttaaag tcataccact gcctacgcct   30180
agcccaccta gcactaccac acagacaacc cacactacag agacaaccac atacagtaca   30240
ttaaatcagc ctaccaccac tacagcagca gaggttgcca gctcgtctgg ggtccgagtg   30300
gcattttttga tgtgggcccc atctagcagt cccactgcta gtaccaatga gcagactact   30360
gaattttttgt ccactgtcga gagccacacc acagctacct ccagtgcctt ctctagcaco   30420
gccaatctct cctcgctttc ctctacacca atcagtcccg ctactactcc tagcccgct   30480
cctcttccca ctccccctgaa gcaaacagac ggcggcatgc aatggcagat caccctgctc   30540
attgtgatcg ggttggtcat cctggccgtg ttgctctact acatcttctg ccgccgcatt   30600
cccaacgcgc accgcaagcc ggtctacaag cccatcattg tcgggagcca ggagccgcatt   30660
caggtggaag ggggtctaag gaatcttctc ttctcttttta cagtatgggtg attgaactat   30720
gattcctaga caattcttga tcactattct tatctgcctc ctccaagtct gtgccaccct   30780
cgctctggtg gccaacgcca gtccagactg tattgggccc ttcgcctcct acgtgctctt   30840
tgccttcacc acctgcatct gctgctgtag catagtctgc ctgcttatca ccttcttcca   30900
gttcattgac tggatctttg tgcgcatcgc ctacctgcgc caccacccc agtaccgcga   30960
ccagcagtg gcgcggctgc tcaggctcct ctgataagca tgcgggctct gctacttctc   31020
gcgcttctgc tgttagtgct cccccgtccc gtcgacccc ggtcccccac ccagtcccc   31080
gaggaggtcc gcaaatgcaa attccaagaa ccctggaaat tcctcaaatg ctaccgccaa   31140
aaatcagaca tgcatcccag ctggatcatg atcattggga tcgtgaacat tctggcctgc   31200
accctcatct ccttttgtgat ttaccccctgc tttgactttg gttggaactc gccagaggcg   31260
ctctatctcc cgcctgaacc tgacacacca ccacagcaac ctcaggcaca cgcactacca   31320
```

```
ccactacagc ctaggccaca atacatgccc atattagact atgaggccga gccacagcga    31380
cccatgctcc ccgctattag ttacttcaat ctaaccggcg gagatgactg acccactggc    31440
caacaacaac gtcaacgacc ttctcctgga catggacggc cgcgcctcgg agcagcgact    31500
cgcccaactt cgcattcgcc agcagcagga gagagccgtc aaggagctgc aggatgcggt    31560
ggccatccac cagtgcaaga gaggcatctt ctgcctggtg aaacaggcca agatctccta    31620
cgaggtcact ccaaacgacc atcgcctctc ctacgagctc ctgcagcagc gccagaagtt    31680
cacctgcctg gtcggagtca accccatcgt catcacccag cagtctggcg ataccaaggg    31740
gtgcatccac tgctcctgcg actccccccga ctgcgtccac actctgatca agaccctctg    31800
cggcctccgc gacctcctcc ccatgaacta atcaccccct tatccagtga aataaagatc    31860
atattgatga tgattttaca gaaataaaaa ataatcattt gatttgaaat aaagatacaa    31920
tcatattgat gatttgagtt taacaaaaaa ataaagaatc acttacttga aatctgatac    31980
caggtctctg tccatgtttt ctgccaacac cacttcactc ccctcttccc agctctggta    32040
ctgcaggccc cggcgggctg caaacttcct ccacacgctg aaggggatgt caaattcctc    32100
ctgtccctca atcttctttt tatcttctat cagatgtcca aaaagcgcgt ccgggtggat    32160
gatgacttcg accccgtcta cccctacgat gcagacaacg caccgaccgt gcccttcatc    32220
aaccccccct tcgtctcttc agatggattc aagagaagc ccctgggggt gttgtccctg    32280
cgactggccg accccgtcac caccaagaac ggggaaatca ccctcaagct gggagagggg    32340
gtggacctcg attcctcggg aaaactcatc tccaacacgg ccaccaaggc cgccgcccct    32400
ctcagttttt ccaacaacac catttccctt aacatggatc accccttta cactaaagat    32460
ggaaaattat ccttacaagt ttctccacca ttaaatatac tgagaacaag cattctaaac    32520
acactagctt taggttttgg atcaggttta ggactccgtg gctctgcctt ggcagtacag    32580
ttagtctctc cacttacatt tgatactagt ggaaacataa agcttacctt agacagaggt    32640
ttgcatgtta caacaggaga tgcaattgaa agcaacataa gctgggctaa aggtttaaaa    32700
tttgaagatg gagccatagc aaccaacatt ggaaatgggt tagagtttgg aagcagtagt    32760
acagaaacag gtgttgatga tgcttaccca atccaagtta aacttggatc tggccttagc    32820
tttgacagta caggagccat aatggctggt aacaaagaag acgataaact cactttgtgg    32880
acaacacctg atccatcacc aaactgtcaa atactcgcag aaaatgatgc aaaactaaca    32940
ctttgcttga ctaaatgtgg tagtcaaata ctggccactg tgtcagtctt agttgtagga    33000
agtggaaacc taaaccccat tactggcacc gtaagcagtg ctcaggtgtt tctacgtttt    33060
gatgcaaacg tgttcttttt aacagaacat tctacactaa aaaaatactg ggggtatagg    33120
caggagata gcatagatgg cactccatat accaatgctg taggattcat gcccaattta    33180
aaagcttatc caaagtcaca aagttctact actaaaaata atatagtagg gcaagtatac    33240
atgaatggag atgtttcaaa acctatgctt ctcactataa ccctcaatgg tactgatgac    33300
agcaacagta catattcaat gtcattttca tacacctgga ctaatggaag ctatgttgga    33360
gcaacatttg gggctaactc ttataccttc tcatacatcg cccaagaatg aacactgtat    33420
cccaccctgc atgccaaccc ttcccacccc actctgtgga acaaactctg aaacacaaaa    33480
taaaataaag ttcaagtgtt ttattgattc aacagtttta caggattcga gcagttattt    33540
ttcctccacc ctcccaggac atggaataca ccaccctctc cccccgcaca gccttgaaca    33600
tctgaatgcc attggtgatg gacatgcttt tggtctccac gttccacaca gtttcagagc    33660
gagccagtct cgggtcggtc agggagatga aaccctccgg gcactccgc atctgcacct    33720
cacagctcaa cagctgagga ttgtcctcgg tggtcgggat cacggttatc tggaagaagc    33780
agaagagcgg cggtgggaat catagtccgc gaacgggatc ggccggtggt gtcgcatcag    33840
gccccgcagc agtcgctgcc gccgccgctc cgtcaagctg ctgctcaggg ggtccgggtc    33900
cagggactcc ctcagcatga tgcccacggc cctcagcatc agtcgtctgg tgcggcgggc    33960
gcagcagcgc atgcggatct cgctcaggtc gctgcagtac gtgcaacaca gaaccaccag    34020
gttgttcaac agtccatagt tcaacacgct ccagccgaaa ctcatcgcgg gaaggatgct    34080
acccagctgg ccgtcgtacc agatcctcag gtaaatcaag tggtgccccc tccagaaacc    34140
gctgccacg tacatgatct ccttgggcat gtggcggttc accacctccc ggtaccacat    34200
caccctctgt tgaacatgc agccccggat gatcctgcgg aaccacaggg ccagcaccgc    34260
cccgcccgcc atgcagcgaa gagacccccgg gtccggcaa tggcaatgga ggacccaccg    34320
ctcgtaccccg tggatcatct gggagctgaa caagtctatg ttggcacagc acaggcatat    34380
gctcatgcat ctcttcagca ctctcaactc ctcgggggtc aaaaccatat cccagggcac    34440
ggggaactct tgcaggacag cgaacccccgc agaacagggc aatcctgcca cagaacttac    34500
attgtgcatg gacagggtat cgcaatcagg cagcaccggg tgatcctcca ccagagaagc    34560
gtgggtctcg gtctcctcac agcgtggtaa ggggggccgg cgatacggt gatgcgggga    34620
cgcggctgat cgtgttcgcg accgtgtcat gatgcagttg cttttcggaca tttttcgtact    34680
tgctgtagca gaacctggtc cgggcgctgc acaccgatcg ccgcggcgg tctcggcgct    34740
tggaacgctc ggtgttgaaa ttgtaaaaca gccactctct cagaccgtgc agcagatcta    34800
gggcctcagg agtgatgaag atcccatcat gcctgatgcc tctgatcaca tcgaccaccg    34860
tggaatgggc cagacccagc cagatgatgc aattttgttg ggtttcggtg acggcggggg    34920
agggaagaac aggaagaacc atgattaact tttaatccaa acggtctcgg agtacttcaa    34980
aatgaagatc gcggagatgg cacctctcgc ccccgctgtg ttggtggaaa ataacagcca    35040
ggtcaaaggt gatacggttc tcgagatgtt ccacggtggc ttccagcaaa gcctccacgc    35100
gcacatccag aaacaagaca atagcgaaag cgggagggtt ctctaattcc tcaatcatca    35160
tgttacactc ctgcaccatc cccagataat tttcattttt ccagccttga atgattcgaa    35220
ctagttcgtg aggtaaatcc aagccagcca tgataaagag ctcgcgcaga gcgccctcca    35280
ccggcattct taagcacacc ctcataattc caagatattc tgctcctggt tcacctgcag    35340
cagattgaca agcggaatat caaaatctct gccgcgatcc ctgagctcct ccctcagcaa    35400
taactgtaag tactcttca tatcctctcc gaaattttca gccataggac caccaggaat    35460
aagattaggg caagccacag tacagataaa ccgaagtcct cccccagtgag cattgccaaa    35520
tgcaagactg ctataagcat gctgctaga cccggtgata tcttccagat aactggacag    35580
aaaatcgccc aggcaatttt taagaaaatc aacaaaagaa aaatcctcca ggtggacgtt    35640
tagagcctcg ggaacaacga tgaagtaaat gcaagcggtc cgttccagca tggttagtta    35700
gctgatctgt agaaaaaaca aaaatgaaca ttaaaccatg ctagcctggc gaacaggtgg    35760
gtaaatcgtt ctctccagca ccaggcaggc cacggggtct ccggcgcgac cctcgtaaaa    35820
attgtgcta tgattgaaaa ccatcacaga gagacgttcc cggtggcgg cgtgaatgat    35880
tcgacaagat gaatacaccc ccggaacatt ggcgtccgcg agtgaaaaaa agcgcccgag    35940
gaagcaataa ggcactacaa tgctcagtct caagtccagc aaagcgatgc catgcggatg    36000
aagcacaaaa ttctcaggtg cgtacaaaat gtaattactc ccctcctgca caggcagcaa    36060
```

```
agcccccgat ccctccaggt acacatacaa agcctcagcg tccatagctt accgagcagc    36120
agcacacaac aggcgcaaga gtcagagaaa ggctgagctc taacctgtcc acccgctctc    36180
tgctcaatat atagcccaga tctacactga cgtaaaggcc aaagtctaaa aatacccgcc    36240
aaataatcac acacgcccag cacacgccca gaaaccggtg acacactcaa aaaaatacgc    36300
gcacttcctc aaacgcccaa aactgccgtc atttccggtt tcccacgcta cgtcatcaaa    36360
acacgacttt caaattccgt cgaccgttaa aaacgtcacc cgccccgccc ctaacggtcg    36420
cccgtctctc agccaatcag cgccccgcat cccaaattc aaacacctca tttgcatatt    36480
aacgcgcaca aaaagtttga ggtatattat tgatgatgg                          36519

SEQ ID NO: 105          moltype = DNA  length = 36604
FEATURE                 Location/Qualifiers
source                  1..36604
                        mol_type = genomic DNA
                        organism = Simian adenovirus 23
SEQUENCE: 105
catcatcaat aatatacctc aaacttttgg tgcgcgttaa tatgcaaatg agctgtttga      60
atttggggag ggaggaaggt gattggctgc gggagcggcg accgttaggg gcggggcggg     120
tgacgttttg atgacgtggc tatgaggcgg agccggtttg caagttctcg tgggaaaagt     180
gacgtcaaac gaggtgtggt ttgaacacgg aaatactcaa ttttcccgcg ctctctgaca     240
ggaaatgagg tgtttctggg cggatgcaag tgaaaacggg ccattttcgc gcgaaaactg     300
aatgaggaag tgaaaatctg agtaatttcg cgtttatggc agggaggagt atttgccgag     360
ggccgagtag actttgaccg attacgtggg ggtttcgatt accgtatttt tcacctaaat     420
ttccgcgtac ggtgtcaaag tccggtgttt ttacgtaggc gtcagctgat cgccaggagta    480
tttaaacctg cgctctctag tcaagaggcc actcttgagt gccagcgagt agagttttct     540
cctccgcgcc gcgagtcaga tctacacttt gaaagatgag gcacctgaga gacctgcccg     600
gtaatgtttt cctggctact gggaacgaga ttctggaatt ggtggtggac gccatgatgg     660
gtgacgaccc tccagagccc ctaccccat ttgaggcgcc ttcgctgtac gatttgtatg      720
atctggaggt ggatgtgccc gagagcgacc ctaacgagga ggcggtgaat gatttgttta     780
gcgatgccgc gctgctggct gccgagcagg ctaatacgga ctctggctca gacagcgatt     840
cctctctcca taccccgaga cccggacgag gtgagaaaaa gatccccgag cttaaaggag     900
aagagctcga cctgcgctgc tatgaggaat gcttgcctcc gagcgatgat gaggaggacg     960
aggaggcgat tcgagctgcg gtgaaccagg gagtgaaaac tgcgggcgag agctttagcc    1020
tggactgtcc tactctgccc ggacacggct gtaagtcttg tgaatttcat cgcatgaata    1080
ctggagataa gaatctgatg tgtgccctgt gctatatgaa agcttacaac cattgtgttt    1140
acagtaagtg tgattaactt tagttgggaa ggcagagggt gactgggtgc tgactggttt    1200
attttatgtat atgtgtttttt atgtgtaggt cccgtctctg acgtagatga gaccccacct    1260
tcagagtgca tttcatcacc cccagaaatt ggcgaggaac cgcccgaaga tattattcat    1320
agaccagttg cagtgagagt caccggggcg agagcagctg tggagagttt ggatgacttg    1380
ctacagggtg gggatgaacc ttttgacttg tgtacccgga aacgcccag gcactaagtg    1440
ccacacatgt gtgtttactt aaggtgatgt cagtatttat agggtgtgga gtgcaataaa    1500
atccgtgttg acttttaagtg cgtgtttat gactcagggg tgggggactgt gggtatataa    1560
gcaggtgcag acctgtgtgg tcagttcaga gcaggactca tggagatctg gactgtcttg    1620
gaagactttc accagactag acagttgcta gagaactcat cggagggagt ctcttacctg    1680
tggagattct gcttcggtgg gcctctagct aagctagtct ataggggcaa acaggattat    1740
aaggaacaat ttgaggatat tttgagagag tgtcctggta ttttttgactc tctcaacttg    1800
ggccatcagt ctcactttaa ccagagtatt ctgagagccc ttgacttttc tactcctggc    1860
agaactaccg ccgcggtagc cttttttgcc ttattcttg acaaatggag tcaagaaacc    1920
catttcagca gggattaccg tctgactgc ttagcagtag ctttgtggag aacatggagg    1980
tgccagcgcc tgaatgcaat ctccggctac ttgccagtac agccggtaga cacgctgagg    2040
atcctgagtc tccagtcacc ccaggaacac caacgccgcc agcagccgca gcaggagcag    2100
cagcagagag aggaccgaga agagaacccg agagccgagtc tggaccctcc ggtggcggag    2160
gaggaggagt agctgacttg tttcccgagc tgccgccggggt gctgactagg tcttccagtg    2220
gacgggagag ggggattaag cgggagaggc atgaggagac tagccacaga actgaactga    2280
ctgtcagtct gatgagccgc aggcgcccag aatcggtgtg gtggcatgag gtgcagtcgc    2340
agggatgatga tgaggtctcg gtgatgcatg agaaatattc cctagaacaa gtcaagactt    2400
gttggttgga gcccgaggat gattgggagg tagccatcag gaattatgcc aagctggctc    2460
tgaagccaga caagaagtac aagattacca aactgattaa tatcagaaat tcctgctaca    2520
tttcaggaa tggggccgag gtggagatca gtacccagga gagggtggcc ttcagatgtt    2580
gtatgatgaa tatgtaccg ggggtgtgg gcatggaggg agtcaccttt atgaacacga    2640
ggttcagggg tgatgggtat aatgggtgg tctttatgcc caacaccaag ctgacagtcg    2700
acggatgctc cttcttttggc ttcaataaca tgtgcatcga ggcctgggc agtgtttcag    2760
tgagggggatg cagcttttca gccaactgga tggggtcgt gggcagaacc aagagcaagg    2820
tgtcagtgaa gaaatgcctg ttcgagaggt gccacctggg ggtgatgagc gagggcgaag    2880
ccaaagtcaa acactgcgcc tctaccgaga cgggctgtgc tgtgctgatc aaggcaagt    2940
cccaagtcaa gcataacatg atctgtgggg cctcggatga gcgcggctac cagatgctga    3000
cctgcgccgg tgggaacagc catatgctgg ccaccgtgca tgtggcctcg caccccgca    3060
agacatggcc cgagttcgag cacaacgtca tgacccgctg caatgtgcac ctgggctccc    3120
gccgaggcat gttcatgccc tacagtgca acatgcaatt tgtgaaggtg ctgctggagc    3180
ccgatgccat gtccagagtg agcctgacgg gggtgtttga catgaatgtg agctgtggaa    3240
aaattctgag atatgatgaa tccaagacca ggtgccgggc ctgcgaatgc ggaggcaagc    3300
acgcaggct tcagcccgtg tgtgtggagg tgacggagga cctgcgaccc gatcattgg    3360
tgttgtcctg caacgggacg gagttcggct ccagcgggga agaatctgac tagagtgagt    3420
agtgttggg gctgggtgtg agcctgcatg aggggcagaa tgactaaaat ctgtggtttt    3480
ctgtgtgttg cagcagcatg agcggaagcg cctccttga gggagggta ttcagcccatt    3540
atctgacgtg gcgtctcccc tcctgggcgg gagtgcgtca aatgtgatg ggatccacgg    3600
tggacgcccg gcccgtgcag cccgcgaact ttcaaccct gacctacgcg accctgagct    3660
cctcgtccgt ggacgcagct gccgccgcag ctgctgcttc cgccgccagc gccgtgcgcg    3720
gaatggccct gggcgccggc tactacagct ctctggtggc caactcgagt tccaccaata    3780
atccccgcca cctgaacgag gagaagctgc tgctgctgat ggcccagctc gaggccctga    3840
```

```
cccagcgcct gggcgagctg acccagcagg tggctcagct gcaggcgag acgcgggccg   3900
cggttgccac ggtgaaaacc aaataaaaaa tgaatcaata aataaacgga gacggttgtt   3960
gattttaaca cagagtcttg aatctttatt tgattttttcg cgcgcggtag gccctggacc  4020
accggtctcg atcattgagc acccggtgga tcttttccag gacccggtag aggtgggctt   4080
ggatgttgag gtacatgggc atgagcccgt cccgggggtg gaggtagctc cattgcaggg   4140
cctcgtgctc ggggatggtg ttgtaaatca cccagtcata gcaggggcgc agggcgtggg   4200
gctgcacgat gtccttgagg aggagactga tggccacggg cagcccttg gtgtaggtgt    4260
tgacgaacct gttgagctgg gagggatgca tgcgggggga gatgagatgc atcttggcct   4320
ggatcttgag attggcgatg ttcccgccca gatcccgccg ggggttcatg ttgtgcagga   4380
ccaccagcac ggtgtatccg gtgcacttgg ggaatttgtc atgcaacttg gaagggaagg   4440
cgtgaaagaa tttggagacg cccttgtgac cgcccaggtt ttccatgcac tcatccatga   4500
tgatggcgat gggcccgtgg gcggcggcct gggcaaagac gtttcgggg tcggacacat    4560
cgtagttgtg gtcctgggtg agctcgtcat aggccatttt aatgaatttg gggcggaggg   4620
tgcccgactg ggggacgaag gtgccctcga tcccgggtgc gtagttgccc tcgcagatct   4680
gcatctccca ggccttgagc tcggagggggg ggatcatgtc cacctgcggg gcgatgaaaa  4740
aaacggtttc cggggcgggg gagatgagct gggccgaaag caggttccgg agcagctggg   4800
acttgccgca accggtgggg ccgtagatga ccccgatgac cggctgcagg tggtagttga   4860
gggagagaca gctgccgtcc tcgccgagga gggggggccac ctcgttcatc atctcgcgca  4920
catgcatgtt ctcgcgcacg agttccgcca ggaggcgctc gccccccagc gagaggagct   4980
cttgcagcga ggcgaagttt ttcagcggct tgagtccgtc ggccatgggc attttggaga   5040
gggtctgttg caagagttcc agacggtccc agagctcggt gatgtgctct agggcatctc   5100
gatccagcag acctcctcgt ttcgcgggtt ggggcgactg ggggagtagg gcaccagggc   5160
atgggcgtcc agcgaggcca gggtccggtc cttccagggc cgcagggtcc gcgtcagcgt   5220
ggtctccgtc acggtgaagg ggtgcgcgcc gggctgggcg cttgcgaggg tgcgcttcag   5280
gctcatccgc tggtcgaga accgctcccg gtcggcgccc tgcgcgtcgg ccaggtagca    5340
attgagcatg agttcgtagt tgagcgctcg ggccgcggtg cccttggcgc ggagcttacc   5400
tttggaagtg tgtccgcaga cgggacagag gagggacttg agggcgtaga gcttgggggc   5460
gaggaagacg gactcggggg cgtaggcgtc cgcgccgcag ctggcgcaga cggtctcgca   5520
ctccacgagc caggtgaggt cggggcggtt ggggtcaaaa acgaggtttc ctccgtgctt   5580
tttgatgcgt ttcttacctc tggtctccat gagctcgtgt ccccgctgt tgacaaagag    5640
gctgtccgtg tccccgtaga ccgactttat gggccggtcc tcgagcgggg tgccgcggtc   5700
ctcgtcgtag aggaaccccg cccactccga gacgaaggcc cgggtccagg ccagcacgaa   5760
ggaggccacg tgggagggggt agcggtcgtt gtccaccagc gggtccacct tctccagggt  5820
atgcaagcac atgtccccct cgtccacatc caggaaggtg attggcttgt aagtgtaagc   5880
cacgtgaccg gggtccccgg ccgggggggt ataaagggg gcgggcccct gctcgtcctc    5940
actgtcttcc ggatcgctgt ccaggagcgc cagctgttgg ggtaggtatt ccctctcgaa   6000
ggcgggcatg acctcggcac tcaggttgtc agtttctaga aacgaggagg atttgatatt   6060
gacggtgccg ttggagacgc cttttcatgag cccctcgtcc atttggtcag aaaagacgat   6120
cttttttgttg tcgagcttgg tggcgaagga gccgtagagg gcgttgaga gcagcttggc   6180
gatggagcgc atggtctggt tcttttttcctt gtcggcgcgc tccttggcgg cgatgttgag  6240
ctgcacgtac tcgcgcgcca cgcacttcca ttcggggaag acggtggtga gctcgtcggg   6300
cacgattctg acccgccagc cgcggttgtg cagggtgatg aggtccacgc tggtggccac   6360
ctcgcgcgca aggggctcgt tggtccagca gaggcgcccg cccttgcgcg agcagaaggg   6420
gggcagcggg tccagcatga gctcgtcggg ggggtcggcg tccacggtga agatgccggg   6480
caggagctcg gggtcgaagt agctgatgca ggtgcccaga ttgtccagcg ccgcttgcca   6540
gtcgcgcacg gccagcgcgc gctcgtaggg gctgaggggc gtgccccagg gcatgggtg    6600
cgtgagccgg gaggcgtaca tgccgcagat gtcgtagacg tagaggggct cctcgaggac   6660
gccgatgtag gtggggtagc agcgcccccc gcggatgctg gcgcgcacgt agtcgtacag   6720
ctcgtgcgag ggcgcgagga gccccgtgcc gaggtggag cgttgcggct tttcggcgcg    6780
gtagacgatc tggcggaaga tggcgtggga gttggaggag atggtgggcc tttggaagat   6840
gttgaagtgg gcgtggggca ggccgaccga gtccctgatg aagtgggcgt aggagtcctc   6900
cagcttggcg acgagctcgg cggtgacgag gacgtccagg gcgcagtagt cgagggtctc   6960
ttggatgatg tcatacttga gctggcccct ctgcttccac agctcgcggt tgagaaggaa   7020
ctcttcgcgc tccttccagt actcttcgag gggaacccg tcctgatcgg cacggtaaga    7080
gcccaccatg tagaactggt tgacggcctt gtaggcgacg cagcccttct ccacggggag   7140
ggcgtaagct tgcgcggcct tgcgcaggga ggtgtgggtg agggcgaagg tgtcgcgcac   7200
catgaccttg aggaactggt gcttgaagtc gaggtcgtcg cagccgccct gctcccagag   7260
ttggaagtcc gtgcgcttct tgtaggcggg gttaggcaaa gcgaaagtaa catcgttgaa   7320
gaggatcttg cccgcgcggg gcatgaagtt gcgagtcatg cggaaaggct ggggcacctc   7380
ggcccggttg ttgatgacct gggcggcgag gacgatctcg tcgaagccgt tgatgttgtg   7440
cccgacgatg tagagttcca cgaatcgcgg gcggcccttg acgtgggca gcttcttgag   7500
ctcgtcgtag gtgagctcgg cggggtcgct gagcccgtgc tgctcgaggg cccagtcggc   7560
gacgtggggg ttggcgctga ggaaggaagt ccagagatcc acgccaggg cggtctgcaa    7620
gccgtccgtg tactgacgga actgttggcc cacggccatt tttccggggg tgacgcagta   7680
gaaggtgcgg gggtcgccgt gccagcggtc ccacttgagc tggaggggcga ggtcgtgggc  7740
gagctcgacg agcggcgggt ccccggagag tttcatgacc agcatgaagg gacgagctg    7800
cttgccgaag gaccccatcc aggtgtaggt ttccacatcg taggtgagga agagcctttc   7860
ggtgcgagga tgcgagccga tggggaagaa ctggatctcc tgccaccagt tggaggaatg   7920
gctgttgatg tgatggaagt agaaatgccg acggccgcc gagcactcgt gcttgtgttt    7980
atacaagcgt ccgcagtgct cgcaacgctg cacgggatgc acgtgctgca cgagctgtac   8040
ctgggttcct ttggcgagga atttcagtgg gcagtggagc gctggcggct gcatctcgtg   8100
ctgtactacg tcttggccat cggcgtggcc atcgtctgcc tcgatggtgg tcatgctgac   8160
gagcccgcgc gggaggcagg tccagacctc ggctcggacg ggtcggagag cgaggacgag   8220
ggccagg ccgagctgt ccagggtcct gctcggagcg tcgtcggacg cagtgggcga       8280
cggcggcgcg cggttgactt gcaggagctt ttccagggcg cgcggaggt ccagatggta    8340
cttgatctcc acgcgccgt tggtggctac gtccacggct tgcagggtgc cgtgccctg     8400
gggcgccacc accgtgcccc gtttcttctt gggcgctgct tccatgtcgg tcagaagcgg   8460
cggcgaggac gcgcgccggg cggcaggggc ggctcggggc ccggaggcag gggcggcagg   8520
ggcacgtcgg cgccgcgcgc gggcaggttc tggtactgcg cccggagaag actggcgtga   8580
```

```
gcgacgacgc gacggttgac gtcctggatc tgacgcctct gggtgaaggc cacgggaccc  8640
gtgagtttga acctgaaaga gagttcgaca gaatcaatct cggtatcgtt gacggcggcc  8700
tgccgcagga tctcttgcac gtcgcccgag ttgtcctggt aggcgatctc ggtcatgaac  8760
tgctcgatct cctcctcctg aaggtctccg cggccggcgc gctcgacggt ggccgcgagg  8820
tcgttggaga tgcggcccat gagctgcgag aaggcgttca tgccggcctc gttccagacg  8880
cggctgtaga ccacggctcc gtcggggtcg cgcgcgcgca tgaccacctg ggcgaggttg  8940
agctcgacgt ggcgcgtgaa gaccgcgtag ttgcagaggc gctggtagag gtagttgagc  9000
gtggtggcga tgtgctcggt gacgaagaag tacatgatcc agcggcggag cggcatctcg  9060
ctgacgtcgc ccagggcttc caagcgttcc atggcctcgt agaagtccac ggcgaagttg  9120
aaaaactggg agttgcgcgc cgagacggtc aactcctcct ccagaagacg gatgagctcg  9180
gcgatggtgg cgcgcacctc gcgctcgaag gccccggggg gctcctcttc catctcctcc  9240
tcttcctcct ccactaacat ctcttctact tcctcctcag gaggcggtgg cggggagggg  9300
gccctgcgtc gccggcggcg cacgggcaga cggtcgatga agcgctcgat ggtctccccg  9360
cgccggcgac gcatggtctc ggtgacggcg cgcccgtcct cgcggggccg cagcatgaag  9420
acgccgccgc gcatctccag gtggccgccg gggggtcctc cgttgggcag ggagagggcg  9480
ctgacgatgc atcttatcaa ttgacccgta gggactccgc gcaaggacct gagcgtctcg  9540
agatccacgg gatccgaaaa ccgctgaacg aaggcttcga gccagtcgca gtcgcaaggt  9600
aggctgagcc cggtttcttg ttcttcgggt atttggtcgg gaggcgggcg ggcgatgctg  9660
ctggtgatga agttgaagta ggcggtcctg agacggcgga tggtggcgag gagcaccagg  9720
tccttgggcc cggcttgctg gatgcgcaga cggtcggcca tgcccaggcc gtggtcctga  9780
cacctggcga ggtccttgta gtagtcctgc atgagccgct ccacgggcac ctcctcctcg  9840
cccgcggcc cgtgcatgcg cgtgagcccg aacccgcgc gcggctggac gagcgccagg  9900
tcggcgacga cgcgctcggt gaggatggcc tgctggatct gggtgagggt ggtctggaag  9960
tcgtcgaagt cgacgaagcg gtggtaggct ccggtgttga tggtgtagga gcagttggcc  10020
atgacggacc agttgacggt ctggtggccg gtcgcacga gctcgtggta cttgaggcgc  10080
gagtaggcgc gcgtgtcgaa gatgtagtcg ttgcaggcgc gcacgaggta gcggtatccg  10140
acgaggaagt gcggcggcgg ctggcggtag agcggccatc gctcggtggc ggggcgccg  10200
ggcgcgaggt cctcgagcat gaggcggtgg tagccgtaga tgtacctgga catccaggtg  10260
atgccggcgg cggtggtgga ggcgcgcggg aactcgcgga cgcggttcca gatgttgcgc  10320
agcggcagga agtagttcat ggtggccgcg tctggcccg tgaggcgcgc gcagtcgtgg  10380
atgctctaga catacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtactg gcactcccgt ctcgacccaa gctgctaac gaaacctcca  10560
ggatacggag gcgggtcgtt ttttggcctt ggtcgctggt catgaaaaac tagtaagcgc  10620
ggaaagcggc cgccgccgat ggctcgctgc cgtagtctgg agaaagaatc gccaggggttg  10680
cgttgcggtg tgccccggtt cgagcctcag cgctcggcgc cggccggatt ccgcggctaa  10740
cgtgggcgtg gctgccccgt cgtttccaag acccccttagc cagccgactt ctccagttac  10800
ggagcgagcc cctcttttttt tttcttgtgt ttttgccaga tgcatcccgt actgcggcag  10860
atgcgccccc accctccacc acaaccgccc ctaccgcagc agcagcaaca gccgggcgtt  10920
ctgcccccgc cccagcagca gccagccact accgcggcgg ccgccgtgag cggagccggc  10980
gttcagtatg acctggcctt ggaagagggc gaggggctgg cgcggctggg ggcgtcgtcg  11040
ccggagcggc acccgcgcgt gcagatgaaa agggacgctc gcgaggccta cgtgcccaag  11100
cagaacctgt tcagagacag gagcggcgag gagcccgagg agatgcgcgc ctcccgcttc  11160
cacgcggggc gggagctgcg cgcggcctg gaccgaaagc gggtgctgag ggacgaggat  11220
ttcgaggcgg acgagctgac ggggatcagc cccgcgcgcg cgcacgtggc cgcggccaac  11280
ctggtcacgg cgtacgagca gaccgtgaag gaggagagca cttccaaaaa atccttcaac  11340
aaccacgtgc gcacgctgat cgcgccggag gaggtgccga tgggcctgat gcacctgtgg  11400
gacctgctgg aggccatcgt gcagaacccc acgagcaagc cgctgacggc gcagctgttt  11460
ctggtggtgc agcacagtcg ggacaacgag acgttcaggg aggcgctgct gaatatcacc  11520
gagcccgagg gccgctggct cctggacctg gtgaacattt tgcagagcat cgtggtgcag  11580
gagcgcggac tgccgctgtc cgagaagctg gcggccatca acttctcggt ctgagtcttg  11640
ggcaagtact acgctaggaa gatctacaag accccgtacg tgcccataga caaggaggtg  11700
aagatcgacg ggttttacat gcgcatgacc ctgaaagtgc tgaccctgag cgacgatctg  11760
ggggtgtacc gcaacgacag gatgcaccgc gcggtgagcg ccagccgccg gcgcgagctg  11820
agcgaccagg agctgatgca cagcctgcag cgggccctga ccggggccgg gaccgagggg  11880
gagagctact ttgacatggg cgcggacctg cgctggcagc ccagccgccg ggccttggaa  11940
gctgccggcg gttccccta cgtggaggag tggacgatg aggaggagga gggcgagtac  12000
ctggaagact gatggcgcga ccgtatttt gctagatgca gcaacagcca ccgccgccgc  12060
ctcctgatcc cgcgatcgg gcggcgctgc agagccagcc gtccggcatt aactcctcgg  12120
acgattggac ccaggccatg caacgcatca tggcgctgac gacccgcaat cccgaagcct  12180
ttagacagca gcctcaggcc aaccggctct cggccatcct ggaggccgtg gtgccctcgc  12240
gctcgaaccc cacgcacgag aaggtgctgg ccatcgtgaa cgcgctggtg gagaacaagg  12300
ccatccgcgg tgacgaggcc gggctggtgt acaacgcgct gctggagcgc gtggcccgct  12360
acaacagcac caacgtgcag acgaacctgg accgcactgt cgcgaggccg  12420
tgtcgcagcg cgagcggttc caccgcgagt cgaacctggg ctccatggtg gcgctgaacg  12480
ccttcctgag cacgcagccc gccaacgtgc ccggggcca ggaggactac accaacttca  12540
tcagcgcgct gcgctgatg gtggccgagg tgccccagag cgaggtgtac cagtcggggc  12600
cggactactt cttccagacc agtcgccagg gcttgcagac cgtgaacctg agccaggctt  12660
tcaagaactt gcagggactg tggggcgtgc aggccccggt cggggaccgc gcgacggtgg  12720
cgagcctgct gacgccgaac tcgcgcctgc tgctgctgca ggtggcgccc ttcacggaca  12780
gcggcagcgt gagccgcgac tcgtacctgg gctacctgct taacctgtac cgcgaggcca  12840
tcggacaggg gcacgtggac gagcagacct accaggagat cacccacgtg agccgcgcgc  12900
tgggccagga ggacccgggc aacctggagg ccaccctgaa cttcctgctg accaaccggt  12960
gcagagat cccgccccag tacgcgctga gcaccgagga ggcgcatc ctgcgctacg  13020
tgcagcagag cgtggggctg ttcctgatgc aggagggggc cacgcccagc gcggcgctcg  13080
acatgaccgc gcgcaacatg gagcccagca tgtacgcccg caaccgcccg ttcatcaata  13140
agctgatgga ctacttgcat cgggcggccg ccatgaactc ggactacttt accaacgcca  13200
tcttgaaccc gcactggctc ccgccgcccg ggttctacac gggcgagtac gacatgcccg  13260
acccccaacga cgggttcctg tgggacgacg tggacagcag cgtgttctcg ccgcgtccag  13320
```

```
gaaccaatgc cgtgtggaag aaagagggcg gggaccggcg gccgtcctcg gcgctgtccg  13380
gtcgcgcggg tgctgccgcg gcggtgcccg aggccgccag cccccttccc agcctgccct  13440
tttcgctgaa cagcgtgcgc agcagcgagc tgggtcggct gacgcgaccg cgcctgctgg  13500
gcgaggagga gtacctgaac gactccttgt tgaggcccga gcgcgagaag aacttcccca  13560
ataacgggat agagagcctg gtggacaaga tgagccgctc gaagacgtac gcgcacgagc  13620
acagggacga gccccgagct agcagcgcag gcaccgtag acgccagcgg cacgacaggc  13680
agcggggact ggtgtgggac gatgaggatt ccgccgacga cagcagcgtg ttggacttgg  13740
gtgggagtgg tggtaacccg ttcgctcacc tgcgcccccg tatcgggcgc ctgatgtaag  13800
aatctgaaaa aataaaagac ggtactcacc aaggccatgg cgaccagcgt gcgttcttct  13860
ctgttgtttg tagtagtatg atgaggcgcg tgtacccgga gggtcctcct ccctcgtacg  13920
agagcgtgat gcagcaggcg gtggcggcgg cgatgcagcc cccgctggag gcgccttacg  13980
tgcccccgcg gtacctggcg cctacggagg ggcggaacag cattcgttac tcggagctgg  14040
cacccttgta cgataccacc cggttgtacc tggtggacaa caagtcggca gacatcgcct  14100
cgctgaacta ccagaacgac cacagcaact tcctgaccac cgtggtgcag aacaacgatt  14160
tcaccccccac ggaggccagc acccagacca tcaactttga cgagcgctcg cggtggggcg  14220
gccagctgaa aaccatcatg cacaccaaca tgcccaacgt gaacgagttc atgtacagca  14280
acaagttcaa ggcgcgggtg atggtctcgc gcaagacccc caacgggggtg gatgatgatt  14340
atgatggtag tcaggacgag ctgacctacg agtgggtgga gtttgagctg cccgagggca  14400
acttctcggt gaccatgacc atcgatctga tgaacaacgc catcatcgac aactacttgg  14460
cggtggggcg gcagaacggg gtgctggaga gcgacatcgg cgtgaagttc gacacgcgca  14520
acttccggct gggctgggac cccgtgaccg agctggtgat gccgggcgtg tacaccaacg  14580
aggccttcca ccccgacatc tcctgctgc ccggctgcgg cgtggacttc accgagagcc  14640
gcctcagcaa cctgctgggc atccgcaagc ggcagccctt ccaggagggc ttccagatcc  14700
tgtacgagga cctggagggg ggcaacatcc ccgcgctctt ggatgtcgaa gcctacgaga  14760
aaagcaagga ggatagcacc gccgcggcga ccgcagccgt ggccaccgcc tctaccgagg  14820
tgcggggcga taattttgct agcgctgcgg cagcggccga ggcggctgaa accgaaagta  14880
agatagtcat ccagccggtg gagaaggaca gcaaggacag gagctacaac gtgctcgcgg  14940
acaagaaaaa caccgcctac cgcagctggt acctggccta caactacggc gaccccgaga  15000
agggcgtgcg ctcctggacg ctgctcacca cctcggacgt cacctgcggc gtggagcaag  15060
tctactggtc gctgcccgac atgatgcaag acccggtcac cttccgctcc acgcgtcaag  15120
ttagcaacta cccggtggtg ggcgccgagc tcctgcccgt ctactccaag agcttcttca  15180
acgagcaggc cgtctactcg cagcagctgc gcgccttcac ctcgctcacg cacgtcttca  15240
accgcttccc cgagaaccag atcctcgtcc gcccgcccgc gcccaccatt accaccgtca  15300
gtgaaaacgt tcctgctctc acagatcacg ggacccgtcc gctgcgcagc agtatccggg  15360
gagtccagcg cgtgaccgtc actgacgcca gacgccggac ctgcccctac gtctacaagg  15420
ccctgggcgt agtcgcgccg cgcgtcctct cgagccgcac cttctaaaaa atgtccattc  15480
tcatctcgcc cagtaataac accggttggg gcctgcgcgc gcccagcaag atgtacggag  15540
gcgctcgcca acgctccacg caacaccccg tgcgcgtgcg cgggcacttc cgcgctccct  15600
ggggcgccct caagggcgc gtgcgctcgc gcaccaccgt cgacgcgtg atcgaccagg  15660
tggtggccga cgcgcgcaac tacacgcccc ccgccgcgcg cgtctccacc tggacgcccg  15720
tcatcgacag cgtggtggcc gacgcgcgcc ggtacgcccg caccaagagc cggcggcggc  15780
gcatcgcccg gcggcaccgg agcaccccg ccatgcgcgc ggcgcgagcc ttgctgcgca  15840
gggccaggcg cacgggacgc agggccatgc tcagggcgac cagacgcgcg cggctccggca  15900
gcagcagcgc cggcaggacc cgcagacgcg cggccacggc ggcggcggcg gccatcgcca  15960
gcatgtcccg cccgcggcgc ggcaacgtgt actgggtgcg cgacgccgcc accggtgtgc  16020
gcgtgcccgt cgcgcacccg cccccctgca cttgaagatg ctgacttcgc gatgttgatg  16080
tgtccagcg gcgaggagga tgtccaagcg caaatacaag gaagagatgc tccaggtcat  16140
cgcgcctgag atctacgcc ccgcggcggc ggtgaaggag gaaagaaagc cccgcaaact  16200
gaagcgggtc aaaaaggaca aaaaggagga ggaagatgac ggactggtgg agtttgtgcg  16260
cgagttcgcc ccccggcggc gcgtgcagtg gcgcgggcgg aaagtgaaac cggtgctgcg  16320
gcccgcacc acggtggtct tcacgcccgg cgagcgttcc ggctccgcct ccaagcgctc  16380
ctacgacgag gtgtacgggg acgaggacat cctcgagcag gcggtcgagc gtctgggcga  16440
gtttgcgtac ggcaagcgca gccgcccgc gcccttgaaa gaggaggcgg tgtccatccc  16500
gctgaccac ggcaacccca cgccgagcct gaagccggtg accctgcagc aggtgctacc  16560
gagcgcggcg ccgcgccggg gcttcaagcg cgagggcgg gaggatctgt acccgaccat  16620
gcagctgatg gtgcccaagc gccagaagct ggaggacgtg ctggagcaca tgaaggtgga  16680
ccccgaggtg cagcccgagg tcaaggtgcg gcccatcaag caggtggccc cgggcctggg  16740
cgtgcagacc gtggacatca agatccccac ggagcccatg gaaacgcaga ccgagcccgt  16800
gaagcccagc accagcacca tggaggtgca gacggatccc tggatgccag caccagcttc  16860
caccagcact cgccgaagac gcaagtacgg cgccgccagc ctgctgatgc ccaactacgc  16920
gctgcatcct tccatcatcc ccacgccggg ctaccgcggc acgcgcttct accgcggcta  16980
caccagcagc cgccgccgca agaccaccac ccgccgccgt cgtcgcagcc gccgcagcag  17040
caccgcgact tccgccttgg tgcggagagt gtatcgcagc gggcgcgagc ctctgaccct  17100
gccgcgccgc ctgctaccac cgagcatcgc catttaacta ccgcctccta cttgcagata  17160
tggcctcac atgccgcctc cgcgtcccca ttacgggcta ccgaggaaga aagccgcgcc  17220
gtagaaggct gacggggaac gggctgcgtc gccatcacca ccgcggcgg cgcgccatca  17280
gcaagcggtt ggggggaggc ttcctgcccg cgctgatccc catcatcgcc gcggcgatcg  17340
gggcgatccc cggcatagct tccgtggcgg tgcaggcctc tcagcgccac tgagacacaa  17400
aaaagcatgg atttgtaata aaaaaaaaaa tggactgacg ctcctggttc tgtgatgtgt  17460
gttttttagat ggaagacatc aatttttcgt ccctggcacc gcgacacgtg acgcggccgt  17520
ttatgggcac ctggagcgac atcggcaaca gccaactgaa cggggggcgcc ttcaattgga  17580
gcagtctctg gagcgggctt aagaatttcg ggtccacgct caaaacctat ggcaacaagg  17640
cgtggaacag cagcacaggg caggcgctga ggggaaaagct gaaagaacag aacttccagc  17700
agaaggtggt tgatggcctg gcctcaggca tcaacgggggt ggttgacctg gccaaccagg  17760
ccgtgcagaa acagatcaac agccgcctgg acgcggtccc gcccgtgggg tccgtggaga  17820
tgccccaggt ggaggaggag ctgcctcccc tggacaagcg cggcgacaag cgaccgcgtc  17880
ccgacgcgga ggagacgctg ctgacgcaca cggacgagcc gccccgtac gaggaggcgg  17940
tgaaactggg cctgcccacc acgcgggccg tggcgcctct ggccaccgga gtgctgaaac  18000
ccagcagcag ccagcccgcg accctggact tgcctccgcc tcgcccctcc acagtggcta  18060
```

```
agcccctgcc gccggtggcc gtcgcgtcgc gcgccccccg aggccgcccc caggcgaact   18120
ggcagagcac tctgaacagc atcgtgggtc tgggagtgca gagtgtgaag cgccgccgct   18180
gctattaaaa gacactgtag cgcttaactt gcttgtctgt gtgtatatgt atgtccgccg   18240
accagaagga ggagtgtgaa gaggcgcgtc gccgagttgc aagatggcca ccccatcgat   18300
gctgccccag tgggcgtaca tgcacatcgc cggacagggc gcttcggagt acctgagtcc   18360
gggtctggtg cagttcgccc gcgccacaga cacctacttc agtctgggga acaagtttag   18420
gaaccccacg gtggcgccca cgcacgatgt gaccaccgac cgcagccagc ggctgacgct   18480
gcgcttcgtg cccgtggacc gcgaggacaa cacctactcg tacaaagtgc gctacacgct   18540
ggccgtgggc gacaaccgcg tgctggacat ggccagcacc tactttgaca tccgcggcgt   18600
gctggaccgg ggccctagct tcaaaccta ctctggcacc gcctacaaca gcctagctcc   18660
caagggagct cccaattcca gccagtggga gcaagcaaaa acaggcaatg ggggaactat   18720
ggaaacacac acatatggtg tggcccccaat gggcggagag aatattacaa aagatggtct   18780
tcaaattgga actgacgtta cagcgaatca gaataaaacca atttatgccg acaaaacatt   18840
tcaaccagaa ccgcaagtag gagaagaaaa ttggcaagaa actgaaaact tttatgccgg   18900
tagagctctt aaaaaagaca caaacatgaa accttgctat ggctcctatg ctagacccac   18960
caatgaaaaa ggaggtcaag ctaaacttaa agttggagat gatggagttc caaccaaaga   19020
attcgacata gacctggctt tctttgatac tcccggtggc accgtgaacg gtcaagacga   19080
gtataaagca gacattgtca tgtataccga aaacacgtat ttggaaactc cagacacgca   19140
tgtggtatac aaaccaggca aggatgatgc aagttctgaa attaacctgg ttcagcagtc   19200
tatgcccaac agacccaact acattgggtt cagggacaac tttatcggtc ttatgtacta   19260
caacagcact ggcaatatgg gtgtgcttgc tggtcaggcc tcccagctga atgctgtggt   19320
tgatttgcaa gacagaaaca ccgagctgtc ctaccagctc ttgcttgact cttgtgggtga   19380
cagaacccgg tatttcagta tgtggaacca ggccgtggac agttatgacc ccgatgtgca   19440
catcatcgaa aaccatggtg tggaggatga attgccaaac tattgcttcc ccttggacgg   19500
ctctggcact aacgccgcat accaaggtgt gaaagtaaaa gatggtcaag atggtgatgt   19560
tgagagtgaa tgggaaaatg acgatactgt tgcagctcga aatcaattat gtaaaggtaa   19620
catttttcgcc atgagatta atctccaggc taacctgtgg agaagttttcc tctactcgaa   19680
cgtggccctg tacctgcccg actcctacaa gtacacgccg accaacgtca cgctgccgac   19740
caacaccaac acctacgatt acatgaatgg cagagtgaca cctccctcgc tggtagacgc   19800
ctacctcaac atcggggcgc gctggtcgct ggacccccatg gacaacgtca acccccttcaa   19860
ccaccaccgc aacgcgggcc tgcgctaccg ctccatgctc ctgggcaacg ggcgctacgt   19920
gcccttccac atccaggtgc cccaaaagtt tttcgccatc aagagcctcc tgctcctgcc   19980
cgggtcctac acctacgagt ggaacttccg caaggacgtc aacatgatcc tgcagagctc   20040
cctaggcaac gacctgcgca cggacggggc ctccatcgcc ttcaccagca tcaacctcta   20100
cgccaccttc ttccccatgg cgcacaacac cgcctccacg ctcgaggcca tgctgcgcaa   20160
cgacaccaac gaccagtcct tcaacgacta cctctcggcg ccaacatgc tctaccccat   20220
cccggccaac gccaccaacg tgcccatctc catcccctcg cgcaactggg ccgccttccg   20280
cggatggtcc ttcacgcgcc tgaagacccg cgagacgccc tcgctcggct ccgggttcga   20340
ccoctacttc gtctactcgg gctccatccc ctacctagac ggcaccttct acctcaacca   20400
caccttcaag aaggtctcca tcaccttcga ctcctccgtc agctggcccg gcaacgaccg   20460
cctcctgacg cccaacgagt tcgaaatcaa gcgcaccgtc gacggagagg gatcaacgt   20520
ggcccagtgc aacatgacca aggactggtt cctggtccag atgctggccc actacaacat   20580
cggctaccag ggcttctacg tgcccgaggg ctacaaggac cgcatgtact ccttcttccg   20640
caacttccag cccatgagcc gccaggtcgt ggacgaggtc aactacaagg actaccaggc   20700
cgtcaccctg gcctaccagc acaacaactc gggcttcgtc ggctacctcg cgcccaccat   20760
gcgccagggc cagccctacc ccgccaacta ccccctacccg ctcatcggca agagcgccgt   20820
cgccaggtcc acccagaaaa agttcctctg cgaccgggtc atgtggcgca tcccctctc   20880
cagcaacttc atgtccatgg gcgcgctcac cgacctcggc cagaacatgc tctacgccaa   20940
ctccgcccac gcgctagaca tgaatttcga agtcgacccc atggatgagt ccaccccttct   21000
ctatgttgtc ttcgaagtct tcgacgtcgt ccgagtgcac cagccccacc gcggcgtcat   21060
cgaagccgtc tacctgcgca cgcccttctc ggccggcaac gccaccacct aagccgctct   21120
tgcttcttgc aagatgacgg cgggctccgg cgagcaggag ctcagggcca tcctccgcga   21180
cctgggctgc gggccctgct tcctgggcac cttgacaag cgcttccctg gattcatggc   21240
cccgcacaag ctggcctgcg ccatcgtgaa cacggccggc cgcgagaccg gggcgagca   21300
ctggctggcc ttcgcctgga cccgcgctc ccacacatgc tacctcttcg accccttcgg   21360
gttctcggac gagcgcctca agcagatcta ccagttcgag tacgagggcc tgctgcgtcg   21420
cagcgccctg gccaccgagg accgctgcgt cacctggaa aagtccaccc agaccgtgca   21480
gggtccgcgc tcggccgcct gcgggctctt ctgctgcatg ttcctgcacg ccttcgtgca   21540
ctgcccgac cgccccatgg acaagaaccc caccatgaac ttactgggag gggtgcccaa   21600
cggcatgctc cagtcgcccc aggtggaacc caccctgcgc cgcaaccagg aagcgctcta   21660
ccgcttcctc aatgccccact ccgcctactt tcgctcccac cgccgcgcca tcgagaaggc   21720
caccgccttc gaccgcatga atcaagacat gtaaaaaacc ggtgtgtgta tgtgaatgct   21780
ttattcataa taaacagcac atgtttatgc cacttctct gaggctctga ctttatttag   21840
aaatcgaagg ggttctgccg gctctcggca tggcccgcgg gcaggaaac gttgcggaac   21900
tggtacttgg gcagccactt gaactcgggg atcagcagct tgggcacggg gaggtcgggg   21960
aacgagtcgc tccacagctt gcgcgtgagt tgcagggcgc ccagcaggtc gggcgcggag   22020
atcttgaaat cgcagttggg acccgcgttc tgcgcgcgag agttgcggta cacggggttg   22080
cagcactgga acaccatcag ggccgggtgc ttcacgcttg ccagcaccgt cgcgtcggtg   22140
atgccctcca cgtccagatc ctcggcgttg gccatccgca aggggtcat cttgcaggtc   22200
tgccgcccca tgctgggcac gcagccgggc ttgtggttgc aatcgcagtg caggggggatc   22260
agcatcatct gggcctgctc ggagctcatg ccgggtaca tggccttcat gaaagcctcc   22320
agctggcgga aggcctgctg cgccttgccg ccctcgtga agaagacccc gcaggacttg   22380
ctagagaact ggttggtggc gcagcggcg tcgtgcacg agcagcgcgc gtcgttgttg   22440
gccagtgcgc cgcagccgcg ccccacgcg ttctgggtga tcttggccg gttgggggttc   22500
tccttcagcg cgcgctgccc gttctcgctc gccacatcca tctcgatagt gtgctccttc   22560
tggatcatca cggtcccgtg caggcaccgc agcttgccct cggcttcggt gcagccgtgc   22620
agccacagcg cgcagccggt gcactcccag ttcttgtggg cgatctggga gtgcgagtgc   22680
acgaagccct gcaggaagcg gcccatcatc gcggtcaggg tcttgttgct ggtgaaggtc   22740
agcgggatgc cgcggtgctc ctcgttcaca tacaggtggc agatgcggcg gtacacctcg   22800
```

```
ccctgctcgg gcatcagctg gaaggcggac ttcaggtcgc tctccacgcg gtaccggtcc   22860
atcagcagcg tcatcacttc catgcccttc tcccaggccg aaacgatcgg caggctcagg   22920
gggttcttca ccgccattgt catcttagtc gccgccgccg aggtcagggg gtcgttctcg   22980
tccagggtct caaacactcg cttgccgtcc ttctcgatga tgcgcacggg gggaaagctg   23040
aagccacgg ccgccagctc ctcctcggcc tgcctttcgt cctcgctgtc ctggctgatg   23100
tcttgcaaag gcacatgctt ggtcttgcgg ggtttctttt tgggcggcag aggcggcggc   23160
gatgtgctgg gagagcgcga gttctcgttc accacgacta tttcttcttc ttggccgtcg   23220
tccgagacca cgcggcggta ggcatgcctc ttctggggca gaggcggagg cgacgggctc   23280
tcgcggttcg gcgggcggct ggcagagccc cttccgcgtt cggggtgcg ctcctggccg   23340
cgctgctctg actgacttcc tccgcggccg gccattgtgt tctcctaggg agcaacaaca   23400
agcatggaga ctcagccatc gtcgccaaca tcgccatctg cccccgccgc caccgccgac   23460
gagaaccagc agcagaatga aagcttaacc gccccgccgc ccagcccac ctccgacgcc   23520
gcggccccag acatgcaaga gatggaggaa tccatcgaga ttgacctggg ctacgtgacg   23580
cccgcgggac acgaggagga gctggcagcg cgcttttcag ccccggaaga gaaccaccaa   23640
gagcagccaa gcaggaagc agagaacgag cagaaccagg ctgggcacga gcatggcgac   23700
tacctgagcg gggcagagga cgtgctcatc aagcatctgg cccgccaatg catcatcgtc   23760
aaggacgcgc tgctcgaccg cgccgagtg cccctcagcg tggcggagct cagccgcgcc   23820
tacgagcgca acctcttctc gccgcgcgtg ccccccaagg gccagcccaa cggcacctgt   23880
gagcccaacc cgcgcctcaa cttctacccg gtcttgcgg tgcccgaggc cctggccacc   23940
taccacctct ttttcaagaa ccaaaggatc ccgtctcct gccgcgccaa ccgcacccgc   24000
gccgacgccc tgctcaacct gggccccggc gcccgcctac ctgatatcac ctccttggaa   24060
gaggttccca agatcttcga gggtctgggc agcgacgaga ctcgggccgc gaacgctctg   24120
caaggaagcg gagaggagca tgagcaccac agcgccctgg tggagttgga aggcgacaac   24180
gcgcgcctgg cggtcctcaa gcgcacggtc gagctgaccc acttcgccta cccggcgctc   24240
aacctgcccc ccaaggtcat gagcgccgtc atggaccagg tgctcatcaa gcgcgcctcg   24300
cccctctcgg aggaggagat gcaggacccc gagagttcag agctgaccaa ccgcgtggtc   24360
agcgacgagc agctgcgcg ctggctggga gcgagtagca cccccagag cctggaagag   24420
cggcgcaagc tcatgatggc cgtggtcctg gtgaccgtgg agctggagtg tctgcgccgc   24480
ttctttgccg acgcggagac cctgcgcaag gtcgaggaga acctgcacta cctcttcagg   24540
cacggggttcg tgccgccagg cctgcaagatc tccaacgtgg agctgaccaa cctggtctcc   24600
tacatgggca tcctgcacga gaaccgcctg gggcaaaacg tgctgcacac caccctgcgc   24660
ggggaggccc gccgcgacta catccgcgac tgcgtctacc tgtacctctg ccacacctgg   24720
cagacgggca tgggcgtgtg gcagcagtgc ctggaggagc agaacctgaa agagctctgc   24780
aagctcctgc agaagaacct caaggccctg tggaccgggt tcgacgagcg taccaccgc   24840
tcggacctgg ccgacctcat cttccccgag cgcctgcggc tgacgctgcg cactggcc   24900
cccgacttta tgagccaaag catgttgcaa aactttcgct ctttcatcct cgaacgctcc   24960
gggatcctgc ccgccacctg ctccgcgctg ccctcggact tcgtgccgct gaccttccgc   25020
gagtgccccc cgccgctctg gagccactgc tacttgctgc gcctggccaa ctaccggcc   25080
taccactcgg acgtgatcga ggacgtcagc ggcgagggtc tgctggagtg ccactgccgc   25140
tgcaacctct gcacgccgca ccgctccctg gcctgcaacc cccagctgct gagcgagacc   25200
cagatcatcg gcaccttcga gttgcaaggc cccggcgacg gcgagggcaa gggggtctg   25260
aaaactcaccc cgggctgtg gacctcggcc tacttgcgca gttcgtgcc cgaggactac   25320
catcccttcg agatcaggtt ctacgaggac caatcccagc cgcccaaggc cgagctgtcg   25380
gcctgcgtca tcacccaggg ggccatcctg gcccaattgc aagccatcca gaaatcccgc   25440
caagaatttc tgctgaaaaaa gggccacggg gtctacttgg acccccagac cggagaggag   25500
ctcaaccca gcttcccca ggatgccccg aggaagcagc aagaagctga aagtggagct   25560
gccgccgccg gaggatttgg aggaagactg gagagcagt caggcagagg aggagagat   25620
ggaagactgg gacagcactc aggcagagga ggacagcctg caagacagtc tggaggagga   25680
agacgaggtg gaggaggcag aggaagaagc agccgccgcc agaccgtcgt cctcggcgga   25740
gaaagcaagc agcacggata ccatctccgc tccgggtcgg ggtcgcggcg gccgggccca   25800
cagtaggtgg gacgagaccg ggcgcttccc gaacccacc acccagaccg gtaagaagga   25860
gcggcaggga tacaagtcct ggcgggggca caaaaacgcc atcgtctcct gcttgcaagc   25920
ctgcgggggc aacatctcct tcacccgcg ctacctgctc ttccaccgcg gggtgaactt   25980
cccccgcaac atcttgcatt actaccgtca cctccacagc cctactact gtttccaaga   26040
agaggcagaa acccagcagc agcagaaaac cagcggcagc agcagctaga aaatccacag   26100
cggcggcagg tggactgagg atcgcggcga acgagccggc gcagaccggg agctgagga   26160
accggatctt tccaccctc tatgccatct tccagcagag tcgggggcag gagcaggaac   26220
tgaaagtcaa gaaccgttct ctgcgctcgc tcacccgcag ttgtctgtat cacaagagcg   26280
aagaccaact tcagcgcact ctcgaggctc ccgaggctct cttcaacaag tactgcgcgc   26340
tcactcttaa agagtagccc gcgcccgccc acacacggaa aaaggcggga attacgtcac   26400
cacctgcgcc cttcgcccga ccatcatgag caaagagatt cccacgcctt acatgtggag   26460
ctaccagccc cagatgggcc tggccgccgg cgccgcccag gactactcca cccgcatgaa   26520
ctggctcagt gccgggcccg cgatgatctc acgggtgaat gacatccgcg cccaccgaaa   26580
ccagatactc ctagaacagt cagcgatcac cgccacgccc cgccatcacc ttaatccgca   26640
taattggccc gccgccctgg tgtaccagga aattccccag cccacgaccg tactacttcc   26700
gcgagacgcc caggccgaag tccagctgac taactcaggt gtccagctgg ccggcggcgc   26760
cgccctgtgt cgtcaccgcc ccgctcaggg tataaagcgg ctggtgatcc gaggcagagg   26820
cacacagctc aacgacgagg tggtgagctc ttcgctgggt ctgcgacctg acggagtctt   26880
ccaactcgcc ggatcgggga gatcttcctt cacgcctcgt caggccgtcc tgactttgga   26940
gagttcgtcc tcgcagcccc gctcgggcgg catcggcact ctccagttcg tggaggagtt   27000
cactccctcg gtctacttca acccccttctc cggctccccc ggccactacc cggacgagtt   27060
catcccgaac ttcgacgcca tcagcgagtc ggtggacggc tacgattgaa tgtcccatgg   27120
tggcgcagct gacctagctc ggcttcgaca cctggaccac tgccgccgct tccgctgctt   27180
cgctcgggat ctcgcgagt ttgccttactt tgagctgccc gaggagcctc tcagggccg   27240
agccacgaa gtgcgatca tcgtcgaagg gggcctcgac tcccaccctgc ttcggatctt   27300
cagccagcga ccgatcctgg tcgagcgcga acaaggacag acccttctta ctttgtactg   27360
catctgcaac caccccggcc tgcatgaaag tctttgttgt ctgctgtgta ctgagtataa   27420
taaaagctga gatcagcgac tactccggac tcgattgtgg tgttcctgct atcaaccggt   27480
ccctgttctt caccgggaac gagaccgagc tccagctcca gtgtaagccc cacaagaagt   27540
```

```
acctcacctg gctgttccag ggctccccga tcgccgttgt caaccactgc gacaacgacg    27600
gagtcctgct gagcggccct gccaaccttt cttttccac ccgcagaagc aagctccagc    27660
tcttccaacc cttcctcccc gggacctatc agtgcgtctc aggaccctgc catcacacct    27720
tccacctgat cccgaatacc acagcgccgc tccccgctac taacaaccaa actacccacc    27780
aacgccaccg tcgcgacctt tcctctgaat ctaatacgac taccggaggt ggctccgag    27840
gtcgaccaac ctctgggatt tactacggcc cctgggaggt ggtggggtta atagcgctag    27900
gcctagttgc gggtgggctt ttggttctct gctacctata cctcccttgc tgttcgtact    27960
tagtggtgct gtgttgctgg tttaagaaat ggggaagatc accctagtga gctgcggtgc    28020
gctggtggcg gtgttgcttt cgattgtggg actgggcggc gcggctgtag tgaaggagaa    28080
ggccgatccc tgcttgcatt tcaatcccaa caaatgccag ctgagttttc agcccgatga    28140
caatcggtgc gcggtactga tcaagtgcgg atgggaatgc gagaacgtga gaatcgagta    28200
caataacaag actcggaaca atactctcgc gtccgtgtgg cagcccgggg accccgagtg    28260
gtacaccgtc tctgtcccg gtgctgacgg ctccccgcgc accgtgaata atactttcat    28320
ttttgcgcac atgtgcaaca cggtcatgtg gatgagcaag cagtacgata tgtggccccc    28380
cacgaaggag aacatcgtgg tcttctccat cgcttacagc ctgtgcacgg cgctaatcac    28440
cgctatcgtg tgcctgagca ttcacatgct catcgctatt cgcccagaa ataatgccga    28500
gaaagagaaa cagccataac acgttttttc acacaccttg tttttacaga caatgcgtct    28560
gttaaatttt ttaaacattg tgctcagtat tgcttatgcc tctggttatg caaacataca    28620
gaaaacccctt tatgtaggat ctgatggtac actagagggt acccaatcac aagccaaggt    28680
tgcatggtat ttttatagaa ccaacactga tccagttaaa ctttgtaagg gtgaattgcc    28740
gcgtacacat aaaactccac ttacatttag ttgcagcaat aataatctta cacttttttc    28800
aattacaaaa caatatactg ttacttatta cagtacaaac tttcatacag gacaagataa    28860
atattatact gttaaggtag aaaatcctac cactcctaga actaccacca ccaccactac    28920
tgcaaagccc actgtgaaaa ctacaactag gaccaccaca actacagaaa ccaccaccag    28980
cacaacactt gctgcaacta cacacacaca cactaagcta accttacaga ccactaatga    29040
tttgatcgcc ctgctgcaaa agggggataa cagcaccact tccaatgagg agataccaa    29100
atccatgatt ggcattattg ttgctgtagt ggtgtgcatg ttgatcatcg ccttgtgcat    29160
ggtgtactat gccttctgct acagaaagca cagactgaac gacaagctgg aacacttact    29220
aagtgttgaa ttttaatttt ttagaaccat gaagatccta ggcctttta gttttttctat    29280
cattacctct gctctttgtg aatcagtgga tagagatgtt actattacca ctggttctaa    29340
ttatacactg aaagggccac cctcaggtat gctttcgtgg tattgctatt ttggaactga    29400
cactgatcaa actgaattat gcaattttca aaaaggcaaa acctcaaact ctaaaatctc    29460
taattatcaa tgcaatggca ctgatctgat actactcaat gtcacgaaag catatggtgg    29520
cagttattat tgccctggac aaaacactga agaaatgatt ttttacaaag tggaagtggt    29580
tgatcccact acaccaccca ccaccacaca tattcatacc acacacacag aacaaacacc    29640
agaggcaaca gaagcagagt tggccttcca ggttcacgga gattcctttg ctgtcaatac    29700
ccctacaccc gatcagcggt gtccggggcc gctagtcagc ggcattgtcg gtgtgctttc    29760
gggattagca gtcataatca tctgcatgtt catttttgct tgctgctata gaaggcttta    29820
ccgacaaaaa tcagacccac tgctgaacct ctatgtttaa tttttccag agccatgaag    29880
gcagttagcg ctctagtttt ttgttctttg attggcattg tttttaatag taaaattacc    29940
agagttagct ttattaaaca tgttaatgta actgaaggag ataacatcac actagcaggt    30000
gtagaaggtg ctcaaaacac cacctggaca aaataccatc taggatggag agatatttgc    30060
acctggaatg taacttatta ttgcatagga gttaatctta ccattgttaa cgctaaccaa    30120
tctcagaatg ggttaattaa aggacagagt gttagtgtga ccagtgatgg gtactatacc    30180
cagcatagtt ttaactacaa cattactgtc ataccactgc ctacgcctag cccacctagc    30240
actaccacac agacaaccac atacagtaca tcaaatcagc ctaccaccac tacagcagca    30300
gaggttgcca gctcgtctgg ggtccggagtg gcattttga tgttggcccc atctagcagt    30360
cccactgcta gtaccaatga gcagactact gaatttttgt ccactgtcga gagccacacc    30420
acagctacct ccagtgcctt ctctagcacc gccaatgtct cctcgctttc ctctacacca    30480
atcagccccg ctactactcc tagccccgct cctcttccca ctccctgaa gcaaacagac    30540
ggcggcatgc aatggcagat caccctgctc attgtgatcg ggttggtcat cctggccgtg    30600
ttgctctact acatcttctg ccgccgcatt cccaacgcgc accgcaagcc ggcctacaag    30660
cccatcgtta tcgggcagcc ggagccgctt caggtggaag ggggtctaag gaatcttctc    30720
ttctcttttta cagtatggtg attgaactat gattcctaga caattcttga tcactattct    30780
tatctgcctc ctccaagtct gtgccaccct cgctctgctg gccaacgcca gtccagactg    30840
tattgggccc ttcgcctcct acgtgctctt tgccttcgtc acctgcatct gctgctgtag    30900
catagtctgc ctgcttatca ccttcttcca gttcattgac tggatctttg tgcgcatcgc    30960
ctacctgcgc caccaccccc agtaccgcga ccagcgagtg gcgcagctgc tcaggctcct    31020
ctgataagca tgcgggctct gctacttctc gcgcttctgc tgttagtgct ccccgtccc    31080
gtcgaccccc ggtccccac tcagtccccc gaggaggttc gcaaatgcaa attccaagaa    31140
ccctggaaat tcctcaaatg ctaccgcaa aaatcagaca tgcatcccag ctggatcatg    31200
atcattggga tcgtgaacat tctggcctgc accctcatct cctttgtgat ttaccccctgc    31260
tttgactttg gttggaactc gccagaggcg ctctatctcc cgcctgaacc tgacacacca    31320
ccacagcagc aacctcaggc acacgcacta ccaccaccac agccaccagc acaatacatg    31380
cccatattag actatgaggc cgagccacac cgacccatgc tccccgctat tagttacttc    31440
aatctaaccg gcggagatga ctgacccact ggccaataac aacgtcaacg accttctcct    31500
ggacatggac ggccgcgcct cggagcagcg actcgcccaa cttcgcattc gtcagcagca    31560
ggagagagcc gtcaaggagc tgcaggacgg catagccatc caccagtcga agagaggcat    31620
cttctgcctg gtgaaacagg ccaagatctc ctacgaggtc acccagaccg accatcgact    31680
ctcctacgag ctcctgcagc agcgccagaa gttcacctgc ctggtcggag tcaaccccat    31740
cgtcatcacc cagcagtcgg gcgataccaa ggggtgcatc cactgctcct gcgactcccc    31800
cgactgcgtc cacactctga tcaagaccct ctgcggcctc cgcgacctcc tcccatgaa    31860
ctaatcaccc ccttatccag tgaaataaag atcatattga tgatgattta ataaaaaaaa    31920
ataatcattt gatttgaaat aaagatacaa tcatattgat gatttgagtt taacaaaaat    31980
aaagaatcac ttacttgaaa tctgatacca ggtctctgtc catgtttttct gccaacacca    32040
cctcactccc ctcttcccag ctctggtact gcaggcccg gcgggctgca aacttcctcc    32100
acacgctgaa ggggatgtca aattcctcct gtccctcaat cttcatttta tcttctatca    32160
gatgtccaaa aagcgcgtcc gggtggatga tgacttcgac cccgtctacc cctacgatgc    32220
agacaacgca ccgaccgtgc ccttcatcaa cccccccttc gtctcttcag atggattcca    32280
```

```
agagaagccc ctgggggtgt tgtccctgcg actggctgac cccgtcacca ccaagaacgg   32340
ggaaatcacc ctcaagctgg gagagggggt ggacctcgac tcgtcgggaa aactcatctc   32400
caacacggcc accaaggccg ccgcccctct cagtatttca aacaacacca tttcccttaa   32460
aactgctgcc cctttctaca acaacaatgg aactttaagc ctcaatgtct ccacaccatt   32520
agcagtattt cccacattta acactttagg cataagtctt ggaaacggtc ttcagacttc   32580
aaataagttg ttgactgtac aactaactca tcctcttaca ttcagctcaa atagcatcac   32640
agtaaaaaca gacaaagggc tatatattaa ctccagtgga aacagaggac ttgaggctaa   32700
tataagccta aaaagaggac tagtttttga cggtaatgct attgcaacat atattggaaa   32760
tggcttagac tatggatctt atgatagtga tggaaaaaca agacccgtaa ttaccaaaat   32820
tggagcagga ttaaattttg atgctaacaa agcaatagct gtcaaactag gcacaggttt   32880
aagtttttgac tccgctggtg ccttgacagc tggaaacaaa caggatgaca agctaacact   32940
ttggactacc cctgacccaa gccctaattg tcaattactt tcagacagag atgccaaatt   33000
tactctctgt cttacaaaat gcggtagtca aatactaggc actgtggcag tggcggctgt   33060
tactgtagga tcagcactaa atccaattaa tgacacagtc aaaagcgcca tagttttcct   33120
tagatttgat tccgatggtg tactcatgtc aaactcatca atggtaggtg attactggaa   33180
ctttagggag ggacagacca ctcaaagtgt agcctataca aatgctgtgg gattcatgcc   33240
aaatataggt gcatatccaa aaacccaaag taaaacacct aaaaatagca tagtcagtca   33300
ggtatattta actggagaaa ctactatgcc aatgacacta accataactt tcaatggcac   33360
tgatgaaaaa gacacaaccc cagttagcac ctactctatg acttttacat ggcagtggac   33420
tggagactat aaggacaaaa atattacctt tgctaccaac tcattctctt tttcctacat   33480
cgcccaggaa taatcccacc cagcaagcca ccccttttc ccaccacctt tgtctatatg    33540
gaaactctga aacagaaaaa taaagttcaa gtgtttatt gaatcaacag ttttacagga    33600
ctcgagcagt tattttttcct ccaccctccc aggacatgga atacaccacc ctctcccccc   33660
gcacagcctt gaacatctga atgccattgg tgatggacat gcttttggtc tccacgttcc   33720
acacagtttc agagcgagcc agtctcggat cggtcaggga gatgaaaccc tccgggcact   33780
cccgcatctg cacctcacag ctcaacagct gaggattgtc ctcggtggtc gggatcacgg   33840
ttatctggaa gaagcagaag agcggcggtg ggaatcatag tccgcgaacg ggatcggccg   33900
gtggtgtcgc atcaggcccc gcagcagtcg ctgccgccgc cgtccgtca agctgctgct    33960
caggggggttc gggtccaggg actccctcag catgatgccc acggccctca gcatcagtcg   34020
tctggtgcgg cgggcgcagc agcgcatgcg aatctcgctc aggtcactgc agtacgtgca   34080
acacaggacc accaggttgt tcaacagtcc atagttcaac acgctccagc cgaaactcat    34140
cgcgggaagg atgctaccca cgtggccgtc gtaccagatc ctcaggtaaa tcaagtggcg   34200
ctccctccag aagacgctgc ccatgtacat gatctccttg ggcatgtggc ggttcaccac    34260
ctcccggtac cacatcaccc tctggttgaa catgcgaccc cggatgatcc tgcggaacca   34320
cagggccagc accgcccgc cggccatgca gcgaagagac cccggatccc ggcaatgaca    34380
atggaggacc caccgctcgt acccgtggat catctgggag ctgaacaagt ctatgttggc    34440
acagcacagg catatgctca tgcatctctt cagcactctc agctcctcgg gggtcaaaac    34500
catatcccag ggcacgggga actcttgcag gacagcgaac cccgcagaac agggcaatcc    34560
tcgcacataa cttacattgt gcatggacag ggtatcgcaa tcaggcagca ccgggtgatc    34620
ctccaccaga gaagcgcggg tctcggtctc ctcacagcgt ggtaagggg ccggccgata    34680
cgggtgatgg cgggacgcgg ctgatcgtgt tctcgaccgt gtcatgatgc agttgctttc    34740
ggacattttc gtacttgctg tagcagaacc tggtccgggc gctgcacacc gatcgccggc    34800
ggcggtctcg gcgcttggaa cgctcggtgt taaagttgta aaacagccac tctctcagac    34860
cgtgcagcag atctagggcc tcaggagtga tgaagatccc atcatgcctg atagctctga    34920
tcacatcgac caccgtggaa tgggccaggc ccagccagat gatgcaattt tgttgggttt   34980
cggtgacggc gggggaggga agaacaggaa gaaccatgat taacttttaa tccaaacggt   35040
ctcggagcac ttcaaaatga aggtcacgga gatggcacct ctcgccccg ctgtgttggt   35100
ggaaaataac agccaggtca aaggtgatac ggttctcgag atgttccacg gtggcttcca   35160
gcaaagcctc cacgcgcaca tccagaaaca agacaatagc gaaagcggga gggttctcta   35220
attcctcaac catcatgtta cactcctgca ccatccccag ataattttca ttttccagc    35280
cttgaatgat tcgaactagt tcctgaggta aatccaagcc agccatgata aaaagctcgc    35340
gcagagcacc ctccaccggc attcttaagc acaccctcat aattccaaga tattctgtc    35400
ctggttcacc tgcagcagat tgacaagcgg aatatcaaaa tctctgccgc gatccctgag   35460
ctcctccctc agcaataact gtaagtactc tttcatatcg tctccgaaat ttttagccat    35520
aggaccccca ggaataagag aagggcaagc cacattacag ataaaccgaa gtcccccca    35580
gtgagcattg ccaaatgtaa gattgaaata agcatgctgg ctagaccgg tgtatcttc    35640
cagataactg gacagaaaat cgggtaagca attttaaga aaatcaacaa aagaaaaatc   35700
ttccaggtgc acgtttaggg cctcgggaac aacgatggag taagtgcaag gggtgcgttc    35760
cagcatgtt agttagctga tctgtaaaaa aacaaaaaat aaaacattaa accatgctag    35820
cctggcgaac aggtgggtaa atcgttctct ccagcaccag gcaggccacg gggtctccgg    35880
cgcgaccctc gtaaaaattg tcgctatgat tgaaaaccat cacagagaga cgttcccggt   35940
ggccggcgtg aatgattcga gaagaagcat acacccccgg aacattggag tccgtgagtg   36000
aaaaaaagcg gccgaggaag caatgaggca ctacaacgct cactctcaag tccagcaaag   36060
cgatgccatg cggatgaagc acaaaatttt caggtgcgta aaaaatgtaa ttactcccct   36120
cctgcacagg cagcgaagct cccgatccct ccagatacac atacaaagcc tcagcgtcca    36180
tagcttaccg agcggcagca gcagcggcac acaacaggcg caagagtcag agaaaagact    36240
gagctctaac ctgtccgccc gctctctgct caatatatag cccagatct acactgacgt     36300
aaaggccaaa gtctaaaaat acccgccaaa taatcacaca cgcccagcac acgcccagaa    36360
accggtgaca cactcagaaa aatacgcgca cttcctcaaa cggccaaact gccgtcattt    36420
ccgggttccc acgctacgtc atcaaaacac gactttcaaa ttcgtcgac cgttaaaaac     36480
atcacccgcc ccgcccctaa cggtcgccgc tcccgcagcc aatcaccttc ctccctcccc   36540
aaattcaaac agctcatttg catattaacg cgcaccaaaa gtttgaggta tattattgat    36600
gatg                                                                36604
```

SEQ ID NO: 106          moltype = AA   length = 948
FEATURE                 Location/Qualifiers
REGION                  1..948
                        note = Description of Artificial Sequence: Synthetic
                        polypeptide

```
source                  1..948
                        mol_type = protein
                        organism = synthetic construct
SEQUENCE: 106
ELRSRYWAIR TRSGRVKREL RSRHWAIRTR SGRVKRELRS RYWASRTRSG RVKRFMYSDF     60
HFIRVKRFMY SDLHFIRVKR FMYTDFHFIR VKRFMFSDFH FIRVKRGTFE FTSFFYRVKR    120
GTFEFTSYFY RVKRILKGKF QTARVKRIIK GKFQTARVKR ILKGKFQIAR VKRILRGSIA    180
HKRVKRILRG SVAHKRVKRV LRGSIAHKRV KRLIFLARSA LRVKRLVFLA RSALRVKRLT    240
FLARSALRVK RYSHGTGTGY RVKRYSHWTG TGYRVKRYSH GSGTGYRVKR FLARSALILR    300
GSVAHKRVKR FLARSALVLR GSVAHKRVKR IAYERMCNIL KGKFQTAARV KRVAYERMCN    360
ILKGKFQTAA RVKRVAYERM CNIIKGKFQT AARVKRVAYE RMCNILKGKF KTAARVKRVA    420
YERMCNILKG KFQIAARVKR VAYERMCNIL KGKFQTAVRV KRDVVNFVSM EFSLTDPRLR    480
VKRDVVNFVS MEFSLTYPRL RVKRDVVNFV SMEFSLTDQR LRVKRFLARS ALILRGSVAH    540
KSRVKRFLAR SALVLRGSVA HKSRVKRKWG MEMRRCLLQS LQQIRVKRKL GMEMRRCLLQ    600
SLQQIRVKRK WGMEMRRCLL QSLQQVRVKR KWGMELRRCL LQSLQQIRVK RFQGRGVFEL    660
RVKRGQISIQ PTFSRVKRSQ ISVQPTFSRV KRGQVSVQPT FSRVKRGQIS VQPTFSRVKR    720
WHSNLNDATY QRTRALVRTG MDPRMRVKRW HSNLNDTTYQ RTRALVRTGM DPRMRVKRWH    780
SNLNDSTYQR TRALVRTGMD PRMRVKRWHS NLNDATYQRT RALVRTGMDP RMRVKRWHSN    840
LNDATYQRTR SLVRTGMDPR MRVKRWHSNL NDATYQRTRA IVRTGMDPRM RVKRWHSNLN    900
DATYQRTRAL VRSGMDPRMR VKRWHSNLND ATYQRTRALV RTGRDPRM               948

SEQ ID NO: 107          moltype = AA  length = 50
FEATURE                 Location/Qualifiers
REGION                  1..50
                        note = Description of Artificial Sequence: Synthetic
                        polypeptide
REGION                  1..50
                        note = MISC_FEATURE - This sequence may encompass 1-10 'Gly
                        Gly Gly Gly Ser' repeating units
source                  1..50
                        mol_type = protein
                        organism = synthetic construct
SEQUENCE: 107
GGGGSGGGGS GGGGSGGGGS GGGGSGGGGS GGGGSGGGGS GGGGSGGGGS                50

SEQ ID NO: 108          moltype = AA  length = 100
FEATURE                 Location/Qualifiers
REGION                  1..100
                        note = Description of Artificial Sequence: Synthetic
                        polypeptide
REGION                  1..100
                        note = MISC_FEATURE - This sequence may encompass 1-20 'Glu
                        Ala Ala Ala Lys' repeating units
source                  1..100
                        mol_type = protein
                        organism = synthetic construct
SEQUENCE: 108
EAAAKEAAAK EAAAKEAAAK EAAAKEAAAK EAAAKEAAAK EAAAKEAAAK EAAAKEAAAK     60
EAAAKEAAAK EAAAKEAAAK EAAAKEAAAK EAAAKEAAAK                         100

SEQ ID NO: 109          moltype = AA  length = 40
FEATURE                 Location/Qualifiers
REGION                  1..40
                        note = Description of Artificial Sequence: Synthetic
                        polypeptide
REGION                  1..40
                        note = MISC_FEATURE - This sequence may encompass 1-20 'Xaa
                        Pro' repeating units
source                  1..40
                        mol_type = protein
                        organism = synthetic construct
SEQUENCE: 109
XPXPXPXPXP XPXPXPXPXP XPXPXPXPXP XPXPXPXPXP                           40

SEQ ID NO: 110          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 110
RVKR                                                                   4

SEQ ID NO: 111          moltype = AA  length = 6
FEATURE                 Location/Qualifiers
REGION                  1..6
                        note = Description of Artificial Sequence: Synthetic peptide
```

```
MOD_RES                       1
                              note = S-[2,3-bis(palmitoyloxy)-(2-R,S)-propyl]-N-palmitoyl
                              -(R)-cysteine
source                        1..6
                              mol_type = protein
                              organism = synthetic construct
SEQUENCE: 111
CSKKKK                                                                           6

SEQ ID NO: 112                moltype = AA   length = 5
FEATURE                       Location/Qualifiers
REGION                        1..5
                              note = Description of Artificial Sequence: Synthetic peptide
MOD_RES                       1
                              note = Tripalmitoyl-S-glyceryl-cysteine
source                        1..5
                              mol_type = protein
                              organism = synthetic construct
SEQUENCE: 112
CSSNA                                                                            5

SEQ ID NO: 113                moltype = AA   length = 6
FEATURE                       Location/Qualifiers
REGION                        1..6
                              note = Description of Artificial Sequence: Synthetic peptide
MOD_RES                       1
                              note = Tripalmitoyl-S-glyceryl-cysteine
source                        1..6
                              mol_type = protein
                              organism = synthetic construct
SEQUENCE: 113
CSKKKK                                                                           6

SEQ ID NO: 114                moltype = AA   length = 6
FEATURE                       Location/Qualifiers
REGION                        1..6
                              note = Description of Artificial Sequence: Synthetic peptide
MOD_RES                       1
                              note = Dipalmitoyl-S-glyceryl-cysteine
source                        1..6
                              mol_type = protein
                              organism = synthetic construct
SEQUENCE: 114
CSKKKK                                                                           6

SEQ ID NO: 115                moltype = AA   length = 16
FEATURE                       Location/Qualifiers
REGION                        1..16
                              note = Description of Artificial Sequence: Synthetic peptide
source                        1..16
                              mol_type = protein
                              organism = synthetic construct
SEQUENCE: 115
GALNNRFQIK GVELKS                                                               16

SEQ ID NO: 116                moltype = AA   length = 560
FEATURE                       Location/Qualifiers
source                        1..560
                              mol_type = protein
                              organism = Influenza B virus
SEQUENCE: 116
MSNMDIDGIN TGTIDKTPEE ITSGTSGTTR PIIRPATLAP PSNKRTRNPS PERATTSSED   60
DVGRKTQKKQ TPTEIKKSVY NMVVKLGEFY NQMMVKAGLN DDMERNLIQN AHAVERILLA  120
ATDDKKTEFQ KKKNARDVKE GKEEIDHNKT GGTFYKMVRD DKTIYFSPIR ITFLKEEVKT  180
MYKTTMGSDG FSGLNHIMIG HSQMNDVCFQ RSKALKRVGL DPSLISTFAG STVPRRSGAT  240
GVAIKGGGTL VAEAIRFIGR AMADRGLLRD IKAKTAYEKI LLNLKNKCSA PQQKALVDQV  300
IGSRNPGIAD IEDLTLLARS MVVVRPSVAS KVVLPISIYA KIPQLGFNVE EYSMVGYEAM  360
ALYNMATPVS ILRMGDDAKD KSQLFFMSCF GAAYEDLRVL SALTGTEFKP RSALKCKGFH  420
VPAKEQVEGM GAALMSIKLQ FWAPMTRSGG NEVGGDGGSG QISCSPVFAV ERPIALSKQA  480
VRRMLSMNIE GRDADVKGNL LKMMNDSMAK KTSGNAFIGK KMFQISDKNK TNPIEIPIKQ  540
TIPNFFFGRD TAEDYDDLDY                                             560

SEQ ID NO: 117                moltype = AA   length = 560
FEATURE                       Location/Qualifiers
source                        1..560
                              mol_type = protein
                              organism = Influenza B virus
```

```
SEQUENCE: 117
MSNMDIDGIN TGTIDKTPEE ITSGTSGTTR PIIRPATLAP PSNKRTRNPS PERATTSSEA   60
DVGRKTQKKQ TPTEIKKSVY NMVVKLGEFY NQMMVKAGLN DDMERNLIQN AHAVERILLA  120
ATDDKKTEFQ KKKNARDVKE GKEEIDHNKT GGTFYKMVRD DKTIYFSPIR ITFLKEEVKT  180
MYKTTMGSDG FSGLNHIMIG HSQMNDVCFQ RSKALKRVGL DPSLISTFAG STLPRRSGAT  240
GVAIKGGGTL VAEAIRFIGR AMADRGLLRD IKAKTAYEKI LLNLKNKCSA PQQKALVDQV  300
IGSRNPGIAD IEDLTLLARS MVVVRPSVAS KVVLPISIYA KIPQLGFNVE EYSMVGYEAM  360
ALYNMATPVS ILRMGDDAKD KSQLFFMSCF GAAYEDLRVL SALTGTEFKP RSALKCKGFH  420
VPAKEQVEGM GAALMSIKLQ FWAPMTRSGG NEVGGDGGSG QISCSPVFAV ERPIALSKQA  480
VRRMLSMNIE GRDADVKGNL LKMMNDSMAK KTNGNAFIGK KMFQISDKNK TNPVEIPIKQ  540
TIPNFFFGRD TAEDYDDLDY                                             560

SEQ ID NO: 118          moltype = AA  length = 560
FEATURE                 Location/Qualifiers
source                  1..560
                        mol_type = protein
                        organism = Influenza B virus
SEQUENCE: 118
MSNMDIDGIN TGTIDKTPEE ITSGTSGTTR PIIRPATLAP PSNKRTRNPS PERATTSSED   60
DVGRKTQKKQ TPTEIKKSVY NMVVKLGEFY NQMMVKAGLN DDMERNLIQN AYAVERILLA  120
ATDDKKTEFQ KKKNARDVKE GKEEIDHNKT GGTFYKMVRD DKTIYFSPIR ITFLKEEVKT  180
MYKTTMGSDG FSGLNHIMIG HSQMNDVCFQ RSKALKRVGL DPSLISTFAG STVPRRSGAT  240
GVAIKGGGTL VAEAIRFIGR AMADRGLLRD IKAKTAYEKI LLNLKNKCSA PQQKALVDQV  300
IGSRNPGIAD IEDLTLLARS MVVVRPSVAS KVVLPISIYA KIPQLGFNVE EYSMVGYEAM  360
ALYNMATPVS ILRMGDDAKD KSQLFFMSCF GAAYEDLRVL SALTGTEFKP RSALKCKGFH  420
VPAKEQVEGM GAALMSIKLQ FWAPMTRSGG NEAGGDGGSG QISCSPVFAV ERPIALSKQA  480
VRRMLSMNIE GRDADVKGNL LKMMNDSMAK KTSGNAFIGK KMFQISDKNK TNPIEIPIKQ  540
TIPNFFFGRD TAEDYDDLDY                                             560
```